(12) United States Patent
Arnold et al.

(10) Patent No.: US 7,060,822 B1
(45) Date of Patent: Jun. 13, 2006

(54) 2-PYRAZOLIN-5-ONES

(75) Inventors: Lee Arnold, Westborough, MA (US); Marina Moran Moset, Madrid (ES); Jose Maria Castellano Berlanga, Madrid (ES); Isabel Fernandez, Madrid (ES); David J. Calderwood, Framingham, MA (US); Paul Rafferty, Nottingham (GB)

(73) Assignee: Abbott GmbH & Co. KG, Wiesbaden (DE)

(*) Notice: Subject to any disclaimer, the term of this patent is extended or adjusted under 35 U.S.C. 154(b) by 0 days.

(21) Appl. No.: 09/621,468

(22) Filed: Jul. 24, 2000

Related U.S. Application Data

(60) Provisional application No. 60/146,563, filed on Jul. 30, 1999.

(51) Int. Cl.
   C07D 413/00 (2006.01)
   C07D 401/00 (2006.01)
   C07D 403/00 (2006.01)
   C07D 411/00 (2006.01)
   C07D 231/02 (2006.01)

(52) U.S. Cl. ................ 544/120; 544/238; 544/333; 544/371; 544/405; 548/364.1

(58) Field of Classification Search ............ 548/364.1, 548/364.4, 364.7, 365.1, 365.7, 366.1, 366.4, 548/366.7, 367.1, 367.4, 367.7, 368.1, 368.7, 548/370.1, 370.4; 544/120, 238, 333, 371, 544/405

See application file for complete search history.

(56) References Cited

U.S. PATENT DOCUMENTS

| 4,369,310 A | 1/1983 | Postle ................ 542/442 |
| 5,393,648 A | 2/1995 | Toda et al. ............ 430/522 |
| 5,709,983 A * | 1/1998 | Brick et al. ............ 430/519 |
| 6,107,487 A * | 8/2000 | Blum et al. ............ 546/209 |
| 6,455,525 B1 * | 9/2002 | Singh et al. ............ 514/241 |

FOREIGN PATENT DOCUMENTS

| EP | 0211363 A2 | 2/1987 |
| EP | 0 430 186 A1 | 6/1991 |
| EP | 0460616 A1 | 12/1991 |
| EP | 0 583 004 A1 | 2/1994 |
| EP | 0 587 230 A2 | 3/1994 |
| EP | 0 594 973 A1 | 5/1994 |
| JP | 63104234 A2 | 5/1988 |
| JP | 02278257 A2 | 11/1990 |
| JP | 03216643 A2 | 9/1991 |
| WO | WO 93/11458 | 6/1993 |

OTHER PUBLICATIONS

Mitra et al. (Acta Cienc. Indica, Chem. (1985), 11(4), 267-72) Abstract.*

Barnikow et al. (Chemische Berichte (1967), 100(5), 1661-6. Abstarct.*

Misawa et al. (JP 52051366), Apr. 25, 1999, Abstract.*

Ege et al. (Journal of the chemical Society, Perkin Transactions 1: Organic and Bio-Organic Chemistry (1972-1999) (1983), (2), 325-31). Abstract.*

Dubau et al. (Chemische Berichte (1983), 116(7), 2714-16). Abstract.*

Schmidt et al. (Journal of Organic Chemistry (1983), 48(23), 4367-70). Abstarct.*

Imai et al. (JP 62029570). Feb. 7, 1987 Abstract.*

Fathy et al. (Journal of Chemical and Engineering Data (1988), 33(2), 218-19). Abstract.*

Selim et al. (Oriental Journal of Chemistry (1994), 10(3), 199-204). Abstract.*

Imai, N. et al., "Diisopropylbenzylidene-substituted heterocycles," Database CHEMABS Online, No. XP-002158250, (From Abstract of Japanese Patent 62029570, (1987).

Jain, S. M. et al., "Synthesis and antiinflammatory activity of some glycosidated 4-benzylidene-3-methylpyrazolin-5-(4H) -ones," From Database CHEMABS Online, No. XP-002158249 (1989). (From Indian J. Chem., Sec. B, 27B(11):1019-1023 (1988)).

Mach-Phuoc-Sinh et al., "Analgesic and antiinflammatory compounds in the 1-phenyl-5-pyrazolone series," From Database CHEMABS Online, No. XP-002158251, (1968). (From Chim. Ther., 3(1):17-33 (1968)).

Barnikow, G. et al., "Thionocarboxylic acidesters. II. Reactions of monothionomalonic acid esters with amino compounds," From Database CHEMABS Online, No. XP-002158252, (1967). (From Chem. Ber., 100(5):1661-1666 (1967)).

(Continued)

Primary Examiner—Bruck Kifle
(74) Attorney, Agent, or Firm—John D. Conway; Gayle B. O'Brien

(57) ABSTRACT

Chemical compounds having structural formula I

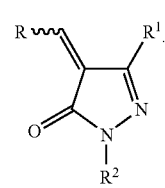

and physiologically acceptable salts thereof, are inhibitors of serine/threonine and tyrosine kinase activity. Several of the tyrosine kinases, whose activity is inhibited by these chemical compounds, are involved in angiogenic processes. Thus, these chemical compounds can ameliorate disease states where angiogenesis or endothelial cell hyperproliferation is a factor. These compounds can be used to treat cancer and hyperproliferative disorders.

11 Claims, No Drawings

OTHER PUBLICATIONS

Selim, M. A. et al., "Activated nitriles in heterocyclic synthesis: synthesis of pyrano [2, 3-c] pyrazole derivatives," From Database CHEMABS Online, No. XP-002158253, (1995). (From Orient. J. Chem, 10(3):199-204 (1994)).

Abdelrazek, F. M. et al., "Substituted acrylonitriles in heterocyclic synthesis. The reaction of .alpha.-substituted .beta.-(2-furyl) acrylonitriles with some active methylene heterocycles," From Database CHEMABS Online, No. XP-002158262 (1986). (From Synthesis, 4:432-434 (1985)).

Schmidt, D. G. et al., "Substituted .gamma.-butyrolactones. Part 32. Ring construction using 3-(arylemthylene) -2,4(3H,5H)-furandione: synthesis of pyrazolones and furo[3,4-c] [1,5]benzothiazepinones," From Database CHEMABS Online, No. XP-002158263 (1983). (From J. Org. Chem, 48(23):4367-4370 (1983)).

Hiremath, S.P., et al., "Synthesis of Various Pyrazole-1-carbonyl-indoles," *Indian J. of Chem.*, 27B:758-762 (1988).

Belezheva, V.S., et al., "Synthesis and Properties of Some Lewis and Brönsted Acids of the Indole Series," Plenum Publishing Corporation (1979).

* cited by examiner

2-PYRAZOLIN-5-ONES

RELATED APPLICATION(S)

This application claims the benefit of U.S. Provisional Application No.: 60/146,563, filed Jul. 30, 1999, the entire teachings of which are incorporated herein by reference.

This invention relates to certain 2-pyrazolin-5-ones which are inhibitors of protein kinases, particularly tyrosine kinases and serine/threonine kinases, of which some are novel compounds, to pharmaceutical compositions containing these pyrazolinones and to processes for preparing these pyrazolinones.

BACKGROUND OF THE INVENTION

There are at least 400 enzymes identified as protein kinases. These enzymes catalyze the phosphorylation of target protein substrates. The phosphorylation is usually a transfer reaction of a phosphate group from ATP to the protein substrate. The specific structure in the target substrate to which the phosphate is transferred is a tyrosine, serine or threonine residue. Since these amino acid residues are the target structures for the phosphoryl transfer, these protein kinase enzymes are commonly referred to as tyrosine kinases or serine/threonine kinases.

The phosphorylation reactions, and counteracting phosphatase reactions, at the tyrosine, serine and threonine residues are involved in countless cellular processes that underlie responses to diverse intracellular signals (typically mediated through cellular receptors), regulation of cellular functions, and activation or deactivation of cellular processes. A cascade of protein kinases often participate in intracellular signal transduction and are necessary for the realization of these cellular processes. Because of their ubiquity in these processes, the protein kinases can be found as an integral part of the plasma membrane or as cytoplasmic enzymes or localized in the nucleus, often as components of enzyme complexes. In many instances, these protein kinases are an essential element of enzyme and structural protein complexes that determine where and when a cellular process occurs within a cell.

Protein Tyrosine Kinases. Protein tyrosine kinases (PTKs) are enzymes which catalyze the phosphorylation of specific tyrosine residues in cellular proteins. This post-translational modification of these substrate proteins, often enzymes themselves, acts as a molecular switch regulating cell proliferation, activation or differentiation (for review, see Schlessinger and Ulrich, 1992, *Neuron* 9:383–391). Aberrant or excessive PTK activity has been observed in many disease states including benign and malignant proliferative disorders as well as diseases resulting from inappropriate activation of the immune system (e.g., autoimmune disorders), allograft rejection, and graft vs. host disease. In addition, endothelial-cell specific receptor PTKs such as KDR and Tie-2 mediate the angiogenic process, and are thus involved in supporting the progression of cancers and other diseases involving inappropriate vascularization (e.g., diabetic retinopathy, choroidal neovascularization due to age-related macular degeneration, psoriasis, arthritis, retinopathy of prematurity, infantile hemangiomas).

Tyrosine kinases can be of the receptor-type (having extracellular, transmembrane and intracellular domains) or the non-receptor type (being wholly intracellular).

Receptor Tyrosine Kinases (RTKs). The RTKs comprise a large family of transmembrane receptors with diverse biological activities. At present, at least nineteen (19) distinct RTK subfamilies have been identified. The receptor tyrosine kinase (RTK) family includes receptors that are crucial for the growth and differentiation of a variety of cell types (Yarden and Ullrich, *Ann. Rev. Biochem.* 57:433–478, 1988; Ullrich and Schlessinger, *Cell* 61:243–254, 1990). The intrinsic function of RTKs is activated upon ligand binding, which results in phosphorylation of the receptor and multiple cellular substrates, and subsequently in a variety of cellular responses (Ullrich & Schlessinger, 1990, *Cell* 61:203–212). Thus, receptor tyrosine kinase mediated signal transduction is initiated by extracellular interaction with a specific growth factor (ligand), typically followed by receptor dimerization, stimulation of the intrinsic protein tyrosine kinase activity and receptor trans-phosphorylation. Binding sites are thereby created for intracellular signal transduction molecules and lead to the formation of complexes with a spectrum of cytoplasmic signaling molecules that facilitate the appropriate cellular response. (e.g., cell division, differentiation, metabolic effects, changes in the extracellular microenvironment) see Schlessinger and Ullrich, 1992, *Neuron* 9:1–20.

Proteins with SH2 (src homology –2) or phosphotyrosine binding (PTB) domains bind activated tyrosine kinase receptors and their substrates with high affinity to propagate signals into cell. Both of the domains recognize phosphotyrosine. (Fantl et al., 1992, *Cell* 69:413–423; Songyang et al., 1994, *Mol. Cell. Biol.* 14:2777–2785; Songyang et al., 1993, *Cell* 72:767–778; and Koch et al., 1991, *Science* 252:668–678; Shoelson, *Curr. Opin. Chem. Biol.* (1997), 1(2), 227–234; Cowburn, *Curr. Opin. Struct. Biol.* (1997), 7(6), 835–838). Several intracellular substrate proteins that associate with receptor tyrosine kinases (RTKs) have been identified. They may be divided into two principal groups: (1) substrates which have a catalytic domain; and (2) substrates which lack such a domain but serve as adapters and associate with catalytically active molecules (Songyang et al., 1993, *Cell* 72:767–778). The specificity of the interactions between receptors or proteins and SH2 or PTB domains of their substrates is determined by the amino acid residues immediately surrounding the phosphorylated tyrosine residue. For example, differences in the binding affinities between SH2 domains and the amino acid sequences surrounding the phosphotyrosine residues on particular receptors correlate with the observed differences in their substrate phosphorylation profiles (Songyang et al., 1993, *Cell* 72:767–778). Observations suggest that the function of each receptor tyrosine kinase is determined not only by its pattern of expression and ligand availability but also by the array of downstream signal transduction pathways that are activated by a particular receptor as well as the timing and duration of those stimuli. Thus, phosphorylation provides an important regulatory step which determines the selectivity of signaling pathways recruited by specific growth factor receptors, as well as differentiation factor receptors.

Several receptor tyrosine kinases such as FGFR-1, PDGFR, and c-Met, and growth factors that bind thereto, have been suggested to play a role in angiogenesis, although some may promote angiogenesis indirectly (Mustonen and Alitalo, *J. Cell Biol.* 129:895–898, 1995). One such receptor tyrosine kinase, known as "fetal liver kinase 1" (FLK-1), is a member of the type III subclass of RTKs. An alternative designation for human FLK-1 is "kinase insert domain-containing receptor" (KDR) (Terman et al., *Oncogene* 6:1677–83, 1991). Another alternative designation for FLK-1/KDR is "vascular endothelial cell growth factor receptor 2" (VEGFR-2) since it binds VEGF with high affinity. The murine version of FLK-1/VEGFR-2 has also been called NYK (Oelrichs et al, *Oncogene* 8(1):11–15, 1993). DNAs encoding mouse, rat and human FLK-1 have been isolated, and the nucleotide and encoded amino acid sequences reported (Matthews et al., *Proc. Natl. Acad. Sci. USA,* 88:9026–30, 1991; Terman et al., 1991, supra; Terman et al., *Biochem. Biophys. Res. Comm.* 187:1579–86, 1992; Sarzani et al., supra; and Millauer et al., *Cell* 72:835–846, 1993). Numerous studies such as those reported in Millauer et al., supra, suggest that VEGF and FLK-1/KDR/VEGFR-2 are a ligand-receptor pair that play an important role in the proliferation of vascular endothelial cells, and formation and sprouting of blood vessels, termed vasculogenesis and angiogenesis, respectively.

Another type III subclass RTK designated "fms-like tyrosine kinase-1" (Flt-1) is related to FLK-1/KDR (DeVries et al. *Science* 255;989–991, 1992; Shibuya et al., *Oncogene* 5:519–524, 1990). An alternative designation for Flt-1 is "vascular endothelial cell growth factor receptor 1" (VEGFR-1). To date, members of the FLK-1/KDR/VEGFR-2 and Flt-1/VEGFR-1 subfamilies have been found expressed primarily on endothelial cells. These subclass members are specifically stimulated by members of the vascular endothelial cell growth factor (VEGF) family of ligands (Klagsburn and D'Amore, *Cytokine & Growth Factor Reviews* 7: 259–270, 1996). Vascular endothelial cell growth factor (VEGF) binds to Flt-1 with higher affinity than to FLK-1/KDR and is mitogenic toward vascular endothelial cells (Terman et al., 1992, supra; Mustonen et al. supra; DeVries et al., supra). Flt-1 is believed to be essential for endothelial organization during vascular development. Flt-1 expression is associated with early vascular development in mouse embryos, and with neovascularization during wound healing (Mustonen and Alitalo, supra). Expression of Flt-1 in adult organs such as kidney glomeruli suggests an additional function for this receptor that is not related to cell growth (Mustonen and Alitalo, supra).

As previously stated, recent evidence suggests that VEGF plays a role in the stimulation of both normal and pathological angiogenesis (Jakeman et al., *Endocrinology* 133: 848–859, 1993; Kolch et al., *Breast Cancer Research and Treatment* 36: 139–155, 1995; Ferrara et al., *Endocrine Reviews* 18(1); 4–25, 1997; Ferrara et al., Regulation of Angiogenesis (ed. L. D. Goldberg and E. M. Rosen), 209–232, 1997). In addition, VEGF has been implicated in the control and enhancement of vascular permeability (Connolly, et al., *J. Biol. Chem.* 264: 20017–20024, 1989; Brown et al., *Regulation of Angiogenesis* (ed. L. D. Goldberg and E. M. Rosen), 233–269, 1997).

Different forms of VEGF arising from alternative splicing of mRNA have been reported, including the four species described by Ferrara et al. (*J. Cell. Biochem.* 47:211–218, 1991). Both secreted and predominantly cell-associated species of VEGF have been identified by Ferrara et al. supra, and the protein is known to exist in the form of disulfide linked dimers.

Several related homologues of VEGF have recently been identified. However, their roles in normal physiological and disease processes have not yet been elucidated. In addition, the members of the VEGF family are often coexpressed with VEGF in a number of tissues and are, in general, capable of forming heterodimers with VEGF. This property likely alters the receptor specificity and biological effects of the heterodimers and further complicates the elucidation of their specific functions as illustrated below (Korpelainen and Alitalo, *Curr. Opin. Cell Biol.,* 159–164, 1998 and references cited therein).

Placenta growth factor (PlGF) has an amino acid sequence that exhibits significant homology to the VEGF sequence (Park et al., *J. Biol. Chem.* 269:25646–54, 1994; Maglione et al. *Oncogene* 8:925–31, 1993). As with VEGF, different species of PlGF arise from alternative splicing of mRNA, and the protein exists in dimeric form (Park et al., supra). PlGF-1 and PlGF-2 bind to Flt-1 with high affinity, and PlGF-2 also avidly binds to neuropilin-1 (Migdal et al, *J. Biol. Chem.* 273 (35): 22272–22278), but neither binds to FLK-1/KDR (Park et al., supra). PlGF has been reported to potentiate both the vascular permeability and mitogenic effect of VEGF on endothelial cells when VEGF is present at low concentrations (purportedly due to heterodimer formation) (Park et al., supra).

VEGF-B is produced as two isoforms (167 and 185 residues) that also appear to bind Flt-1/VEGFR-1. It may play a role in the regulation of extracellular matrix degradation, cell adhesion, and migration through modulation of the expression and activity of urokinase type plasminogen activator and plasminogen activator inhibitor 1 (Pepper et al, *Proc. Natl. Acad. Sci. U.S.A.* (1998), 95(20): 11709–11714).

VEGF-C was originally cloned as a ligand for VEGFR-3/Flt-4 which is primarily expressed by lymphatic endothelial cells. In its fully processed form, VEGF-C can also bind KDR/VEGFR-2 and stimulate proliferation and migration of endothelial cells in vitro and angiogenesis in in vivo models (Lymboussaki et al, *Am. J. Pathol*. (1998), 153(2): 395–403; Witzenbichler et al, *Am. J. Pathol.* (1998), 153(2), 381–394). The transgenic overexpression of VEGF-C causes proliferation and enlargement of only lymphatic vessels, while blood vessels are unaffected. Unlike VEGF, the expression of VEGF-C is not induced by hypoxia (Ristimaki et al, *J. Biol. Chem.* (1998), 273(14), 8413–8418).

The most recently discovered VEGF-D is structurally very similar to VEGF-C. VEGF-D is reported to bind and activate at least two VEGFRs, VEGFR-3/Flt-4 and KDR/VEGFR-2. It was originally cloned as a c-fos inducible mitogen for fibroblasts and is most prominently expressed in the mesenchymal cells of the lung and skin (Achen et al, *Proc. Natl. Acad. Sci. U.S.A.* (1998), 95(2), 548–553 and references therein).

As for VEGF, VEGF-C and VEGF-D have been claimed to induce increases in vascular permeability in vivo in a Miles assay when injected into cutaneous tissue (PCT/US97/14696; WO98/07832, Witzenbichler et al., supra). The physiological role and significance of these ligands in modulating vascular hyperpermeability and endothelial responses in tissues where they are expressed remains uncertain.

There has been recently reported a virally encoded, novel type of vascular endothelial growth factor, VEGF-E (NZ-7 VEGF), which preferentially utilizes KDR/Flk-1 receptor and carries a potent mitotic activity without heparin-binding domain (Meyer et al, *EMBO J.* (1999), 18(2), 363–374; Ogawa et al, *J. Biol. Chem.* (1998), 273(47), 31273–31282.). VEGF-E sequences possess about 25% homology to mammalian VEGF and are encoded by the parapoxvirus Orf virus (OV). This parapoxvirus that affects sheep and goats and occasionally, humans, to generate lesions with angiogenesis. VEGF-E is a dimer of about 20 kDa with no basic domain nor affinity for heparin, but has the characteristic cysteine knot motif present in all mammalian VEGFs, and was surprisingly found to possess potency and bioactivities similar to the heparin-binding VEGF165 isoform of VEGF-A, i.e. both factors stimulate the release of tissue factor (TF), the proliferation, chemotaxis and sprouting of cultured vascular endothelial cells in vitro and angiogenesis in vivo. Like VEGF165, VEGF-E was found to bind with high affinity to VEGF receptor-2 (KDR) resulting in receptor autophosphorylation and a biphasic rise in free intracellular Ca2+ concentrations, while in contrast to VEGF165, VEGF-E did not bind to VEGF receptor-1 (Flt-1).

Based upon emerging discoveries of other homologues of VEGF and VEGFRs and the precedents for ligand and receptor heterodimerization, the actions of such VEGF homologues may involve formation of VEGF ligand heterodimers, and/or heterodimerization of receptors, or binding to a yet undiscovered VEGFR (Witzenbichler et al., supra). Also, recent reports suggest neuropilin-1 (Migdal et al, supra) or VEGFR-3/Flt-4 (Witzenbichler et al., supra), or receptors other than KDR/VEGFR-2 may be involved in the induction of vascular permeability (Stacker, S. A., Vitali, A., Domagala, T., Nice, E., and Wilks, A. F., "Angiogenesis and Cancer" Conference, Amer. Assoc. Cancer Res., January 1998, Orlando, Fla.; Williams, *Diabetelogia* 40: S118–120 (1997)). Until now, no direct evidence for the essential role of KDR in VEGF-mediated vascular hyperpermeability has been disclosed.

The Non-Receptor Tyrosine Kinases. The non-receptor tyrosine kinases represent a collection of cellular enzymes which lack extracellular and transmembrane sequences. At present, over twenty-four individual non-receptor tyrosine kinases, comprising eleven (11) subfamilies (Src, Frk, Btk, Csk, Abl, Zap70, Fes/Fps, Fak, Jak, Ack and LIMK) have been identified. At present, the Src subfamily of non-receptor tyrosine kinases is comprised of the largest number of PTKs and include Src, Yes, Fyn, Lyn, Lck, Blk, Hck, Fgr and Yrk. The Src subfamily of enzymes has been linked to oncogenesis and immune responses. A more detailed discussion of non-receptor tyrosine kinases is provided in Bolen, 1993, *Oncogene* 8:2025–2031, which is incorporated herein by reference.

Many of the tyrosine kinases, whether an RTK or non-receptor tyrosine kinase, have been found to be involved in cellular signaling pathways involved in numerous pathogenic conditions, including cancer, psoriasis, and other hyperproliferative disorders or hyper-immune responses.

Development of Compounds to Modulate the PTKs. In view of the surmised importance of PTKs to the control, regulation, and modulation of cell proliferation, the diseases and disorders associated with abnormal cell proliferation, many attempts have been made to identify receptor and non-receptor tyrosine kinase "inhibitors" using a variety of approaches, including the use of mutant ligands (U.S. Application No. 4,966,849), soluble receptors and antibodies (Application No. WO 94/10202; Kendall & Thomas, 1994, *Proc. Nat. Acad. Sci* 90:10705–09; Kim et al., 1993, *Nature* 362:841–844), RNA ligands (Jellinek, et al., *Biochemistry* 33:10450–56; Takano, et al., 1993, *Mol. Bio. Cell* 4:358A; Kinsella, et al. 1992, *Exp. Cell Res.* 199:56–62; Wright, et al., 1992, *J. Cellular Phys.* 152:448–57) and tyrosine kinase inhibitors (WO 94/03427; WO 92/21660; WO 91/15495; WO 94/14808; U.S. Pat. No. 5,330,992; Mariani, et al., 1994, *Proc. Am. Assoc. Cancer Res.* 35:2268).

More recently, attempts have been made to identify small molecules which act as tyrosine kinase inhibitors. For example, bis monocyclic, bicyclic or heterocyclic aryl compounds (PCT WO 92/20642) and vinylene-azaindole derivatives (PCT WO 94/14808) have been described generally as tyrosine kinase inhibitors. Styryl compounds (U.S. Pat. No. 5,217,999), styryl-substituted pyridyl compounds (U.S. Pat. No. 5,302,606), certain quinazoline derivatives (EP Application No. 0 566 266 A1; *Expert Opin. Ther. Pat.* (1998), 8(4): 475–478), selenoindoles and selenides (PCT WO 94/03427), tricyclic polyhydroxylic compounds (PCT WO 92/21660) and benzylphosphonic acid compounds (PCT WO 91/15495) have been described as compounds for use as tyrosine kinase inhibitors for use in the treatment of cancer. Anilinocinnolines (PCT WO97/34876) and quinazoline derivative compounds (PCT WO97/22596; PCT WO97/42187) have been described as inhibitors of angiogenesis and vascular permeability.

In addition, attempts have been made to identify small molecules which act as serine/threonine kinase inhibitors. For example, bis(indolylmaleimide) compounds have been described as inhibiting particular PKC serine/threonine kinase isoforms whose signal transducing function is associated with altered vascular permeability in VEGF-related diseases (PCT WO97/40830; PCT WO97/40831).

Plk-1 Kinase Inhibitors

Plk-1 is a serine/threonine kinase which is an important regulator of cell cycle progression. It plays critical roles in the assembly and the dynamic function of the mitotic spindle apparatus. Plk-1 and related kinases have also been shown to be closely involved in the activation and inactivation of other cell cycle regulators, such as cyclin-dependent kinases. High levels of Plk-1 expression are associated with cell proliferation activities. It is often found in malignant tumors of various origins. Inhibitors of Plk-1 are expected to block cancer cell proliferation by disrupting processes involving mitotic spindles and inappropriately activated cyclin-dependent kinases.

Cdc2/Cyclin B Kinase Inhibitors (Cdc2 is Also Known as cdk1)

Cdc2/cyclin B is another serine/threonine kinase enzyme which belongs to the cyclin-dependent kinase (cdks) family. These enzymes are involved in the critical transition between various phases of cell cycle progression. It is believed that uncontrolled cell proliferation, which is the hallmark of cancer is dependent upon elevated cdk activities in these cells. The inhibition of elevated cdk activities in cancer cells by cdc2/cyclin B kinase inhibitors could suppress proliferation and may restore the normal control of cell cycle progression.

The identification of effective small compounds which specifically inhibit signal transduction and cellular proliferation by modulating the activity of receptor and non-receptor tyrosine and serine/threonine kinases to regulate and modulate abnormal or inappropriate cell proliferation, differentiation, or metabolism is therefore desirable. In particular, the identification of methods and compounds that specifically inhibit the function of a tyrosine kinase which is essential for angiogenic processes or the formation of vascular hyperpermeability leading to edema, ascites, effusions, exudates, and macromolecular extravasation and matrix deposition as well as associated disorders would be beneficial.

SUMMARY OF THE INVENTION

This invention is directed to compounds of the formula

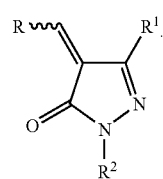

and physiologically acceptable salts thereof, wherein, R is a substituted or unsubstituted aliphatic, aromatic, heterocyclic or aralkyl group, and $R^2$ is a hydrogen, lower alkyl group or aryl group. R¹ is hydrogen or -A-Z, wherein A is —(CH₂)ₙ—, —(CH₂)ₙNH—, —(CH₂)ₙO—, —(CH₂)ₙS—, —(CH₂)ₙS(O)— or —(CH₂)ₙS(O)₂—; and Z is —H, a lower alkyl, aralkyl, trihalomethyl, R³CO—, trihalomethylcarbonyl, R³OC(O)—, —NR⁴R⁵, —C(O)NR⁴R⁵, R³O—, or a ring system selected from the group consisting of a C₃–C₆ cycloalkane, benzene, pyrrole, isoxazole, isothiazole, indole, pyridine, pyrazine, pyrimidine, thiophene, imidazole, furan, benzimidazole, pyridazine, quinoxaline, pyrazole, oxazole, thiazole, benzothiazole, tetrahydrofuran, triazine and the applicable N-oxides thereof which can be optionally substituted with one or more halogens, a lower alkyl, R³O—, HO—, HOC(O)—, R³OC(O)—, trihalomethyl, nitro, aryl, —CN, —C(O)NR⁴R⁵ or —NR⁴R⁵. R³ for each occurrence is, independently, selected from the group consisting of substituted or unsubstituted: lower alkyl group, lower alkoxy lower alkyl group, an aromatic group, a (C₃–C₆)cycloalkyl group, a heterocyclic group, an aralkyl group, a (C₃–C₆)cycloalkyl-alkyl group and a heterocyclylalkyl group. R⁴ and R⁵ for each occurrence are each, independently, hydrogen or are selected from the group of substituted or unsubstituted: a lower alkyl group, an aromatic group, a (C₃–C₆)cycloalkylalkyl group, a heterocyclic group, an aralkyl group, a (C₃–C₆)cycloalkyl-alkyl group and a heterocyclyl-alkyl group; optionally, R⁴ and R⁵ together with the nitrogen to which they are attached represent morpholino, pyrrolidino, piperidino, imidazol-1-yl, piperazino, thiamorpholino, azepino or perhydro-1,4-diazepin-1-yl groups each optionally substituted with one or more moieties selected from the group consisting of lower alkyl, hydroxy, lower alkoxy lower alkyl, an aromatic group, a (C₃–C₆)cycloalkyl group, a heterocyclic group, an aralkyl group, a (C₃–C₆)cycloalkyl-alkyl group and a heterocyclylalkyl group; Numerical index n is an integer from 0 to 3.

Suitable substitutents for R include halogens, lower alkyl groups, R³O—, hydroxy, HOC(O)—, R³OC(O)—, R³OC(O)R⁶—, R³OR⁶—, trihalomethyl, trihalomethylcarbonyl, nitro, —C(O)NR⁴R⁵, —NR⁴R⁵, R³CO—, —(CH₂)ₙ—R⁷, —C(O)(CH₂)ₙ—R⁷, —C(O)—(CH₂)ₙ—C(O)—R⁷, —O(CH₂)ₙR⁷, —C(O)NR⁴(CH₂)ₙR⁷, —C(O)O(CH₂)ₙR⁷, —OC(O)(CH₂)ₙR⁷, —NR⁴C(O)(CH₂)ₙR⁷, —R⁶NR⁴R⁵, —R⁶N(R⁴)—R⁶—R⁷, —R⁶N[R⁶—R⁷]₂, —R⁶C(O)NR⁴(CH₂)ₙR⁷, —R⁶C(O)O(CH₂)ₙR⁷, —R⁶OC(O)(CH₂)ₙR⁷, —R⁶NR⁴C(O)(CH₂)ₙR⁷, —R⁶CH[C(O)OR⁴][NR⁵C(O)R⁴] or a substituted aryl or aralkyl group, wherein the substituent is selected from the group consisting of halogen, trihalomethyl, hydroxy, —NR⁴R⁵, nitro, —CONR⁴R⁵, lower alkyl group, R³O—, —C(O)OR⁴ or —OC(O)R³. R⁶ is a lower alkyl group or an aryl group. R⁷ is alkoxy, haloalkyl, lower alkyl piperazine, hydroxy, R³O—, R³C(O)— or —NR⁴R⁵.

Suitable substituents for R³, R⁴ and R⁵ include one or more moieties selected from the group consisting of halogens, lower alkyl, hydroxy, lower alkoxy, carboxy, lower alkyl ester, trihalomethyl preferrably trifluoromethyl, nitro, phenyl, phenyl-lower alkyl, (C₃–C₆)cycloalkyl, (C₃–C₆)cycloalkyl-alkyl, CN, amino, alkylamino, dialkylamino, —C(O)NH₂, —C(O)NH(alkyl) and —C(O)N(alkyl)₂.

Aliphatic groups include straight chained or branched C₁–C₁₈ hydrocarbons, or cyclic C₃–C₁₈ hydrocarbons which are completely saturated or which contain one or more units of unsaturation. Lower alkyl groups are straight chained or branched C₁–C₆ hydrocarbons or C₃–C₆ cyclic hydrocarbons which are completely saturated.

Aromatic groups, as used herein, include carbocyclic ring systems (e.g. benzyl and cinnamylidene) and fused polycyclic aromatic ring systems (e.g. naphthyl). In addition, aromatic groups includes heteroaryl ring systems (e.g. pyridine, thiophene, furan, pyrrole, imidazole, oxazole, thiazole, pyrazole, triazole, pyrimidine and pyrazine) and heteroaryl ring systems in which a carbocyclic aromatic ring, carbocyclic nonaromatic ring or heteroaryl ring is fused to one or more other heteroaryl rings (e.g. benzimidazole, benzothiazole, indole, tetrahydroindole, azaindole, indazole, isoxazole, isothiazole, imidazole and quinoline). An aryl group, as used herein, refer to an aromatic group having five or six atoms. An aralkyl group is an aromatic substituent that is linked to a compound by an aliphatic group having from one to six carbon atoms. A heterocyclic group, as used herein, refers to a mono-, bi- or tri-cyclic heterocyclic group that is not aromatic or has a degree of unsaturation wherein the unsaturation does not make the group an aromatic group.

Tautomers, stereoisomers, enantiomers and mixtures of these compounds are included in this invention. Pharmaceutically acceptable addition salts of these compounds are also included in this invention.

In one embodiment, R² is hydrogen, and R is, preferably, a substituted indole, or a substituted or unsubstituted imidazole, 1,2,3-triazole, 1,2,4-triazole, benzimidazole, pyrrole, pyrazole, 4,5,6,7-tetrahydroindole, benzoindole, azaindole, indazole, pyridine, quinoline, pyrimidine, benzene or pyrazine.

In a preferred embodiment, R² is hydrogen, n is zero, and Z is a cyclopropyl, 3-pyridyl or pyrazinyl group. In another preferred embodiment, R² is hydrogen, A is —O—, n is 0 and Z is ethyl, propyl or isopropyl. In yet another preferred embodiment, R² is hydrogen, A is CH₂, n is 2 and Z is benzene which is optionally substituted with halogen, trihalomethyl, hydroxy, —NR⁴R⁵, nitro, —C(O)NR⁴R⁵, lower alkyl group, R³O—, —C(O)OR⁴ or —OC(O)R³.

In a preferred embodiment, the present invention is directed to a compound represented by the following formula:

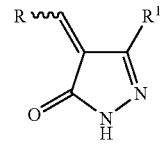

and physiologically acceptable salts thereof, wherein:

R is selected from the group consisting of substituted or unsubstituted: indole, imidazole, 1,2,3-triazole, 1,2,4-triazole, benzimidazole, 4,5,6,7-tetrahydroindole, benzoindole, azaindole, indazole, pyridine, quinoline, pyrimidine, benzene, pyrazine, pyrrole, pyrazole, oxazole and thiazole;

R¹ is hydrogen or -A-Z;

A is —(CH₂)ₙ—, —(CH₂)ₙNH—, —(CH₂)ₙO—, —(CH₂)ₙS—, —(CH₂)ₙS(O)— or —(CH₂)ₙS(O)₂—;

Z is —H, a lower alkyl, aralkyl, trihalomethyl, trihalomethylcarbonyl, R³OC(O)—, —NR⁴R⁵, —C(O)NR⁴R⁵, R³CO—, R³O—, or a ring system selected from the group consisting of a C₃–C₆ cycloalkane, isoxazole, isothiazole, imidazole, benzene, pyrrole, indole, pyridine, pyrazine, pyrimidine, benzothiazole, tetrahydrofuran, thiophene, imidazole, furan, triazine, benzimidazole, pyridazine, quinoxaline, pyrazole, oxazole, thiazole and the N-oxides thereof wherein said ring system can be optionally substituted with one or more moieties selected from the group consisting of halogens, lower alkyl, R³O—, HO—, HOC(O)—, R³OC(O)—, trihalomethyl, nitro, an aromatic group, a (C₃–C₆) cycloalkyl group, a heterocyclic group, an aralkyl group, a (C$_3$–C$_6$)cycloalkyl-alkyl group, a heterocyclyl-alkyl group, —CN, —C(O)NR$^4$R$^5$ or —NR$^4$R$^5$;

R$^3$ for each occurrence is, independently, selected from the group consisting of substituted or unsubstituted: lower alkyl group, lower alkoxy lower alkyl group, aromatic group, (C$_3$–C$_6$)cycloalkyl group, heterocyclic group, aralkyl group, (C$_3$–C$_6$)cycloalkyl-alkyl group, and heterocyclyl-alkyl group;

R$^4$ and R$^5$ for each occurrence are each, independently, hydrogen, or are selected from the group consisting of substituted or unsubstituted: lower alkyl group, aromatic group, (C$_3$–C$_6$)cycloalkyl group, heterocyclic group, aralkyl group, (C$_3$–C$_6$)cycloalkyl-alkyl group, and heterocyclyl-alkyl group;

optionally, R$^4$ and R$^5$ together with the nitrogen atom to which they are attached represent morpholino, pyrrolidino, piperidino, imidazol-1-yl, piperazino, thiamorpholino, azepino or perhydro-1,4-diazepin-1-yl groups each optionally substituted by one or more moieties selected from the group consisting of lower alkyl, hydroxy, lower alkoxy lower alkyl, an aromatic group, a (C$_3$–C$_6$)cycloalkyl group, a heterocyclic group, an aralkyl group, a (C$_3$–C$_6$)cycloalkyl-alkyl group and a heterocyclyl-alkyl group; and n is an integer from 0 to 3; provided that when R is an unsubstituted indol-3-yl then R$^1$ is not —NH$_2$.

In another preferred embodiment, the present invention is directed to a compound represented by the following structural formula:

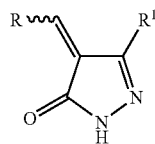

and physiologically acceptable salts thereof, wherein:

R is selected from the group consisting of substituted or unsubstituted: indole, imidazole, 1,2,3-triazole, 1,2,4-triazole, benzimidazole, 4,5,6,7-tetrahydroindole, benzoindole, azaindole, indazole, pyridine, quinoline, pyrimidine, benzene, pyrazine, pyrrole, pyrazole, oxazole and thiazole;

R$^1$ is hydrogen or -A-Z;

A is —(CH$_2$)$_n$—, —(CH$_2$)$_n$NH—, —(CH$_2$)$_n$O—, —(CH$_2$)$_n$S—, —(CH$_2$)$_n$S(O)— or —(CH$_2$)$_n$S(O)$_2$—;

Z is —H, a lower alkyl, aralkyl, trihalomethyl, trihalomethylcarbonyl, R$^3$OC(O)—, —NR$^4$R$^5$, —C(O)NR$^4$R$^5$, R$^3$CO—, R$^3$O—, or a ring system selected from the group consisting of a C$_3$–C$_6$ cycloalkane, isoxazole, isothiazole, imidazole, benzene, pyrrole, indole, pyridine, pyrazine, pyrimidine, benzothiazole, tetrahydrofuran, thiophene, imidazole, furan, triazine, benzimidazole, pyridazine, quinoxaline, pyrazole, oxazole, thiazole and the N-oxides thereof wherein said ring system can be optionally substituted with one or more moieties selected from the group consisting of halogens, lower alkyl, R$^3$O—, HO—, HOC(O)—, R$^3$OC(O)—, trihalomethyl, nitro, an aromatic group, a (C$_3$–C$_6$) cycloalkyl group, a heterocyclic group, an aralkyl group, a (C$_3$–C$_6$)cycloalkyl-alkyl group, a heterocyclyl-alkyl group, —CN, —C(O)NR$^4$R$^5$ or —NR$^4$R$^5$;

R$^3$ for each occurrence is, independently, selected from the group consisting of substituted or unsubstituted: lower alkyl group, lower alkoxy lower alkyl group, an aromatic group, a (C$_3$–C$_6$)cycloalkyl group, a heterocyclic group, an aralkyl group, a (C$_3$–C$_6$)cycloalkyl-alkyl group and a heterocyclyl-alkyl group;

R$^4$ and R$^5$ for each occurrence are each, independently, hydrogen or is selected from the group consisting of substituted or unsubstituted: a lower alkyl group, an aromatic group, a (C$_3$–C$_6$)cycloalkyl group, a heterocyclic group, an aralkyl group, a (C$_3$–C$_6$)cycloalkyl-alkyl group and a heterocyclyl-alkyl group; optionally, R$^4$ and R$^5$ together with the nitrogen to which they are attached represent morpholino, pyrrolidino, piperidino, imidazol-1-yl, piperazino, thiamorpholino, azepino or perhydro-1,4-diazepin-1-yl groups each optionally substituted with one or more moieties selected from the group consisting of lower alkyl, hydroxy, lower alkoxy lower alkyl, an aromatic group, a (C$_3$–C$_6$)cycloalkyl group, a heterocyclic group, an aralkyl group, a (C$_3$–C$_6$)cycloalkyl-alkyl group and a heterocyclyl-alkyl group; and n is an integer from 0 to 3;

provided that:

when R is unsubstituted indol-3-yl then R$^1$ is not —NH$_2$; and when R is a substituted or unsubstituted benzene or an unsubstituted imidazole, 1,2,3-triazole, 1,2,4-triazole, pyridine, pyrimidine, pyrazine, pyrrole, pyrazole, oxazole or thiazole; then R$^1$ is not a lower alkyl, a (C$_3$–C$_6$)cycloalkyl, benzene, or —C(O)NR$^4$R$^5$, wherein R$^4$ and R$^5$ are each independently H, a lower alkyl or a carbocyclic aryl.

In another preferred embodiment, the present invention is directed to a compound represented by the following structural formula:

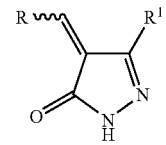

and physiologically acceptable salts thereof, wherein:

R is selected from the group consisting of substituted or unsubstituted: indole, imidazole, 1,2,3-triazole, 1,2,4-triazole, benzimidazole, 4,5,6,7-tetrahydroindole, benzoindole, azaindole, indazole, pyridine, quinoline, pyrimidine, benzene, pyrazine, pyrrole, pyrazole, oxazole and thiazole;

R$^1$ is hydrogen or -A-Z;

A is —(CH$_2$)$_n$—, —(CH$_2$)$_n$NH—, —(CH$_2$)$_n$O—, —(CH$_2$)$_n$S—, —(CH$_2$)$_n$S(O)— or —(CH$_2$)$_n$S(O)$_2$—;

Z is —H, a lower alkyl, aralkyl, trihalomethyl, trihalomethylcarbonyl, R$^3$OC(O)—, —NR$^4$R$^5$, —C(O)NR$^4$R$^5$, R$^3$CO—, R$^3$O—, or a ring system selected from the group consisting of a C$_3$–C$_6$ cycloalkane, isoxazole, isothiazole, imidazole, benzene, pyrrole, indole, pyridine, pyrazine, pyrimidine, benzothiazole, tetrahydrofuran, thiophene, imidazole, furan, triazine, benzimidazole, pyridazine, quinoxaline, pyrazole, oxazole, thiazole and the N-oxides thereof wherein said ring system can be optionally substituted with one or more moieties selected from the group consisting of halogens, lower alkyl, R$^3$O—, HO—, HOC(O)—, R$^3$OC(O)—, trihalomethyl, nitro, an aromatic group, a (C$_3$–C$_6$) cycloalkyl group, a heterocyclic group, an aralkyl group, a (C$_3$–C$_6$)cycloalkyl-alkyl group, a heterocyclyl-alkyl group, —CN, —C(O)NR$^4$R$^5$ or —NR$^4$R$^5$;

R$^3$ for each occurrence is, independently, selected from the group consisting of a substituted or unsubstituted: lower alkyl group, lower alkoxy lower alkyl group, aromatic group, $(C_3–C_6)$cycloalkyl group, heterocyclic group, aralkyl group, a $(C_3–C_6)$cycloalkyl-alkyl group, and heterocyclyl-alkyl group;

$R^4$ and $R^5$ for each occurrence are each, independently, hydrogen or are selected from the group consisting of substituted or unsubstituted: lower alkyl group, aromatic group, $(C_3–C_6)$cycloalkyl group, heterocyclic group, aralkyl group, $(C_3–C_6)$cycloalkyl-alkyl group, and heterocyclyl-alkyl group;

optionally, $R^4$ and $R^5$ together with the nitrogen atom to which they are attached represent morpholino, pyrrolidino, piperidino, imidazol-1-yl, piperazino, thiamorpholino, azepino or perhydro-1,4-diazepin-1-yl groups each optionally substituted by one or more moieties selected from the group consisting of lower alkyl, hydroxy, lower alkoxy lower alkyl, an aromatic group, a $(C_3–C_6)$cycloalkyl group, a heterocyclic group, an aralkyl group, a $(C_3–C_6)$cycloalkyl-alkyl group and a heterocyclyl-alkyl group; and n is an integer from 0 to 3; provided that:

a) R is not pyrrol-3-yl or pyrrol-3-yl substituted with an alkyl or a carbocyclic aryl group;
b) R is not indol-3-yl or indol-3-yl substituted with an alkyl or a carbocyclic aryl group; and
c) R is not azaindole or azaindole substituted at the 2-position with an alkyl or a carbocyclic aryl group.

In another preferred embodiment, the present invention is directed to a compound represented by the following structural formula:

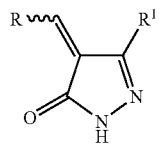

and physiologically acceptable salts thereof, wherein:

R is substituted pyrrole or is selected from the group consisting of substituted or unsubstituted: indole, imidazole, 1,2,3-triazole, 1,2,4-triazole, benzimidazole, 4,5,6,7-tetrahydroindole, benzoindole, azaindole, indazole, pyridine, quinoline, pyrimidine, benzene, pyrazine, pyrazole, oxazole and thiazole;

$R^1$ is hydrogen or -A-Z;

A is $—(CH_2)_n—$, $—(CH_2)_nNH—$, $—(CH_2)_nO—$, $—(CH_2)_nS—$, $—(CH_2)_nS(O)—$ or $—(CH_2)_nS(O)_2—$;

Z is —H, a lower alkyl, aralkyl, trihalomethyl, trihalomethylcarbonyl, $R^3OC(O)—$, $—NR^4R^5$, $—C(O)NR^4R^5$, $R^3CO—$, $R^3O—$, or a ring system selected from the group consisting of a $C_3–C_6$ cycloalkane, isoxazole, isothiazole, imidazole, benzene, pyrrole, indole, pyridine, pyrazine, pyrimidine, benzothiazole, tetrahydrofuran, thiophene, imidazole, furan, triazine, benzimidazole, pyridazine, quinoxaline, pyrazole, oxazole, thiazole and the N-oxides thereof wherein said ring system can be optionally substituted with one or more moieties selected from the group consisting of halogens, lower alkyl, $R^3O—$, $HO—$, $HOC(O)—$, $R^3OC(O)—$, trihalomethyl, nitro, an aromatic group, a $(C_3–C_6)$ cycloalkyl group, a heterocyclic group, an aralkyl group, a $(C_3–C_6)$cycloalkyl-alkyl group, a heterocyclyl-alkyl group, $—CN$, $—C(O)NR^4R^5$ or $—NR^4R^5$;

$R^3$ for each occurrence is, independently, selected from the group consisting of: lower alkyl group, lower alkoxy lower alkyl group, aromatic group, $(C_3–C_6)$cycloalkyl group, heterocyclic group, aralkyl group, $(C_3–C_6)$cycloalkyl-alkyl group, and heterocyclyl-alkyl group;

$R^4$ and $R^5$ for each occurrence are each, independently, hydrogen or are selected from the group consisting of substituted or unsubstituted: lower alkyl group, aromatic group, $(C_3–C_6)$cycloalkyl group, heterocyclic group, aralkyl group, $(C_3–C_6)$cycloalkyl-alkyl group, and heterocyclyl-alkyl group;

optionally, $R^4$ and $R^5$ together with the nitrogen atom to which they are attached represent morpholino, pyrrolidino, piperidino, imidazol-1-yl, piperazino, thiamorpholino, azepino or perhydro-1,4-diazepin-1-yl groups each optionally substituted by one or more moieties selected from the group consisting of lower alkyl, hydroxy, lower alkoxy lower alkyl, an aromatic group, a $(C_3–C_6)$cycloalkyl group, a heterocyclic group, an aralkyl group, a $(C_3–C_6)$cycloalkyl-alkyl group and a heterocyclyl-alkyl group; and n is an integer from 0 to 3;

provided that:

a) when R is substituted pyrrole, the pyrrole is substituted with $R^3OC(O)R^6$, $R^3OR^6—$, trihalomethyl, trihalomethylcarbonyl, $—(CH_2)_p—R^7$, $—O(CH_2)_pR^7$, $—C(O)N(R^4)(CH_2)_pR^7$, $—C(O)O(CH_2)_pR^7$, $—OC(O)(CH_2)_pR^7$, $—N(R^4)C(O)(CH_2)_pR^7$, $—R^6NR^4R^5$, $—R^6N(R^4)—R^6—R^7$, $—R^6N(R^6—R^7)_2$, $—R^6C(O)N(R^4)(CH_2)_pR^7$, $—R^6C(O)O(CH_2)_pR^7$, $—R^6OC(O)(CH_2)_pR^7$, $—R^6N(R^4)C(O)(CH_2)_pR^7$, $—R^6CH(C(O)OR^4)(N(R^4)C(O)R^4)$, a substituted aryl or aralkyl group, wherein: $R^6$ for each occurrence is independently a lower alkyl group or an aryl group; $R^7$ for each occurrence is independently an alkoxy, haloalkyl, lower alkylpiperazine, hydroxy, $R^3O—$, $R^3C(O)—$ or $NR^4R^5$; and p is an integer from 1–3;

b) when R is indol-3-yl, the indol-3-yl is substituted with $R^3OC(O)R^6$, $R^3OR^6—$, trihalomethyl, trihalomethylcarbonyl, $—(CH_2)_p—R^7$, $—O(CH_2)_pR^7$, $—C(O)N(R^4)(CH_2)_pR^7$, $—C(O)O(CH_2)_pR^7$, $—OC(O)(CH_2)_pR^7$, $—N(R^4)C(O)(CH_2)_pR^7$, $—R^6NR^4R^5$, $—R^6N(R^4)—R^6—R^7$, $—R^6N(R^6—R^7)_2$, $—R^6C(O)N(R^4)(CH_2)_pR^7$, $—R^6C(O)O(CH_2)_pR^7$, $—R^6OC(O)(CH_2)_pR^7$, $—R^6N(R^4)C(O)(CH_2)_pR^7$, $—R^6CH(C(O)OR^4)(N(R^4)C(O)R^4)$ or a substituted aryl or aralkyl group; and c) when R is pyrazol-3-yl, the pyrazol-3-yl is substituted with $R^3OC(O)R^6$, $R^3OR^6—$, trihalomethyl, trihalomethylcarbonyl, $—(CH_2)_p—R^7$, $—O(CH_2)_pR^7$, $—C(O)N(R^4)(CH_2)_pR^7$, $—C(O)O(CH_2)_pR^7$, $—OC(O)(CH_2)_pR^7$, $—N(R^4)C(O)(CH_2)_pR^7$, $—R^6NR^4R^5$, $—R^6N(R^4)—R^6R^7$, $—R^6N(R^6—R^7)_2$, $—R^6C(O)N(R^4)(CH_2)_pR^7$, $—R^6C(O)O(CH_2)_pR^7$, $—R^6OC(O)(CH_2)_pR^7$, $—R^6N(R^4)C(O)(CH_2)_pR^7$, $—R^6CH(C(O)OR^4)(N(R^4)C(O)R^4)$ or a substituted aryl or aralkyl group.

In another preferred embodiment, the present invention is directed to a compound represented by the following structural formula:

and physiologically acceptable salts thereof, wherein:

R is substituted pyrrole or is selected from the group consisting of substituted or unsubstituted: indole, imidazole, 1,2,3-triazole, 1,2,4-triazole, benzimidazole, 4,5,6,7-tetrahydroindole, benzoindole, azaindole, indazole, pyridine, quinoline, pyrimidine, benzene, pyrazine, pyrazole, oxazole and thiazole;

$R^1$ is hydrogen or -A-Z;

A is —$(CH_2)_n$—, —$(CH_2)_n NH$—, —$(CH_2)_n O$—, —$(CH_2)_n S$—, —$(CH_2)_n S(O)$— or —$(CH_2)_n S(O)_2$—;

Z is —H, a lower alkyl, aralkyl, trihalomethyl, trihalomethylcarbonyl, $R^3 OC(O)$—, —$NR^4 R^5$, —$C(O)NR^4 R^5$, $R^3 CO$—, $R^3 O$—, or a ring system selected from the group consisting of a $C_3$–$C_6$ cycloalkane, isoxazole, isothiazole, imidazole, benzene, pyrrole, indole, pyridine, pyrazine, pyrimidine, benzothiazole, tetrahydrofuran, thiophene, imidazole, furan, triazine, benzimidazole, pyridazine, quinoxaline, pyrazole, oxazole, thiazole and the N-oxides thereof wherein said ring system can be optionally substituted with one or more moieties selected from the group consisting of halogens, lower alkyl, $R^3 O$—, HO—, HOC(O)—, $R^3 OC(O)$—, trihalomethyl, nitro an aromatic group, a ($C_3$–$C_6$) cycloalkyl group, a heterocyclic group, an aralkyl group, a ($C_3$–$C_6$)cycloalkyl-alkyl group, a heterocyclyl-alkyl group, —CN, —$C(O)NR^4 R^5$ or —$NR^4 R^5$;

$R^3$ for each occurrence is, independently, selected from the group consisting of substituted or unsubstituted: lower alkyl group, lower alkoxy lower alkyl group, aromatic group, ($C_3$–$C_6$)cycloalkyl group, heterocyclic group, aralkyl group, ($C_3$–$C_6$)cycloalkyl-alkyl group, and heterocyclyl-alkyl group;

$R^4$ and $R^5$ for each occurrence are each, independently, hydrogen or are selected from the group consisting of substituted or unsubstituted: lower alkyl group, aromatic group, ($C_3$–$C_6$)cycloalkyl group, heterocyclic group, aralkyl group, ($C_3$–$C_6$)cycloalkyl-alkyl group, and heterocyclyl-alkyl group;

optionally, $R^4$ and $R^5$ together with the nitrogen atom to which they are attached represent morpholino, pyrrolidino, piperidino, imidazol-1-yl, piperazino, thiamorpholino, azepino or perhydro-1,4-diazepin-1-yl groups each optionally substituted by one or more moieties selected from the group consisting of lower alkyl, hydroxy, lower alkoxy lower alkyl, an aromatic group, a ($C_3$–$C_6$)cycloalkyl group, a heterocyclic group, an aralkyl group, a ($C_3$–$C_6$)cycloalkyl-alkyl group and a heterocyclyl-alkyl group; and n is an integer from 0 to 3;

provided that:

a) when R is an unsubstituted indol-3-yl then $R^1$ is not —$NH_2$;

b) when R is a substituted or unsubstituted benzene or an unsubstituted imidazole, 1,2,3-triazole, 1,2,4-triazole, pyridine, pyrimidine, pyrazine, pyrrole, pyrazole, oxazole or thiazole; then $R^1$ is not a lower alkyl, a ($C_3$–$C_6$) cycloalkyl, benzene, or —$C(O)NR^4 R^5$, wherein $R^4$ and $R^5$ are each independently H, a lower alkyl or a carbocyclic aryl;

c) R is not pyrrol-3-yl or pyrrol-3-yl substituted with an alkyl or a carbocyclic aryl group;

d) R is not indol-3-yl or indol-3-yl substituted with an alkyl or a carbocyclic aryl group;

e) R is not azaindole or azaindole substituted at the 2-position with an alkyl or a carbocyclic aryl group f) when R is substituted pyrrole, the pyrrole is substituted with $R^3 OC(O)R^6$, $R^3 OR^6$—, trihalomethyl, trihalomethylcarbonyl, —$(CH_2)_p$—$R^7$, —$O(CH_2)_p R^7$, —$C(O)N(R^4)(CH_2)_p R^7$, —$C(O)O(CH_2)_p R^7$, —$OC(O)(CH_2)_p R^7$, —$N(R^4)C(O)(CH_2)_p R^7$, —$R^6 NR^4 R^5$, —$R^6 N(R^4)$—$R^6$—$R^7$, —$R^6 N(R^6$—$R^7)_2$, —$R^6 C(O)N(R^4)(CH_2)_p R^7$, —$R^6 C(O)O(CH_2)_p R^7$, —$R^6 OC(O)(CH_2)_p R^7$, —$R^6 N(R^4)C(O)(CH_2)_p R^7$, —$R^6 CH(C(O)OR^4)(N(R^4)C(O)R^4)$, a substituted aryl or aralkyl group, wherein: $R^6$ for each occurrence is independently a lower alkyl group or an aryl group; $R^7$ for each occurrence is independently an alkoxy, haloalkyl, lower alkylpiperazine, hydroxy, $R^3 O$—, $R^3 C(O)$— or $NR^4 R^5$; and p is an integer from 1–3;

g) when R is indol-3-yl, the indol-3-yl is substituted with $R^3 OC(O)R^6$, $R^3 OR^6$—, trihalomethyl, trihalomethylcarbonyl, —$(CH_2)_p$—$R^7$, —$O(CH_2)_p R^7$, —$C(O)N(R^4)(CH_2)_p R^7$, —$C(O)O(CH_2)_p R^7$, —$OC(O)(CH_2)_p R^7$, —$N(R^4)C(O)(CH_2)_p R^7$, —$R^6 NR^4 R^5$, —$R^6 N(R^4)$—$R^6$—$R^7$, —$R^6 N(R^6$—$R^7)_2$, —$R^6 C(O)N(R^4)(CH_2)_p R^7$, —$R^6 C(O)O(CH_2)_p R^7$, —$R^6 OC(O)(CH_2)_p R^7$, —$R^6 N(R^4)C(O)(CH_2)_p R^7$, —$R^6 CH(C(O)OR^4)(N(R^4)C(O)R^4)$ or a substituted aryl or aralkyl group; and h) when R is pyrazol-3-yl, the pyrazol-3-yl is substituted with $R^3 OC(O)R^6$, $R^3 OR^6$—, trihalomethyl, trihalomethylcarbonyl, —$(CH_2)_p$—$R^7$, —$O(CH_2)_p R^7$, —$C(O)N(R^4)(CH_2)_p R^7$, —$C(O)O(CH_2)_p R^7$, —$OC(O)(CH_2)_p R^7$, —$N(R^4)C(O)(CH_2)_p R^7$, —$R^6 NR^4 R^5$, —$R^6 N(R^4)$—$R^6$—$R^7$, —$R^6 N(R^6$—$R^7)_2$, —$R^6 C(O)N(R^4)(CH_2)_p R^7$, —$R^6 C(O)O(CH_2)_p R^7$, —$R^6 OC(O)(CH_2)_p R^7$, —$R^6 N(R^4)C(O)(CH_2)_p R^7$, —$R^6 CH(C(O)OR^4)(N(R^4)C(O)R^4)$ or a substituted aryl or aralkyl group.

In a more preferred embodiment, the present invention is directed to any of the foregoing compounds wherein A is —NH—, —O—, —S—, —S(O)— or —$S(O)_2$—; and Z is cyclopropyl, 3-pyridyl or pyrazinyl.

In yet another more preferred embodiment, the present invention is directed to any of the foregoing compounds wherein A is —O—; and Z is ethyl, n-propyl or isopropyl.

In still another more preferred embodiment, the present invention is directed to any of the foregoing compounds wherein A is —$CH_2$—; and Z is phenyl, wherein said phenyl is optionally substituted with one or more moieties selected from the group consisting of halogens, trihalomethyl, hydroxy, —$NR^4 R^5$, nitro, —$CONR^4 R^5$, lower alkyl group, $R^3 O$—, —$C(O)OR^4$ and —$OC(O)R^4$.

In still another preferred embodiment, the present invention is directed to any of the foregoing compounds wherein R is substituted with one or more substituents, each independently selected from the group consisting of halogens, lower alkyl groups, $R^3 O$—, hydroxy, HOC(O)—, $R^3 OC(O)$—, $R^3 OC(O)R^6$—, $R^3 OR^6$—, trihalomethyl, trihalomethylcarbonyl, nitro, —$C(O)NR^4 R^5$, —$NR^4 R^5$, $R^3 CO$—, —$(CH_2)_n$—$R^7$, —$C(O)(CH_2)_n$—$R^7$, —$C(O)$—$(CH_2)_n$—$C(O)$—$R^7$, —$O(CH_2)_n R^7$, —$C(O)NR^4(CH_2)_n R^7$, —$C(O)O(CH_2)_n R^7$, —$OC(O)(CH_2)_n R^7$, —$NR^4 C(O)(CH_2)_n R^7$, —$R^6 NR^4 R^5$, —$R^6 N(R^4)$—$R^6$—$R^7$, —$R^6 N(R^6$—$R^7)_2$, —$R^6 C(O)NR^4(CH_2)_n R^7$, —$R^6 C(O)O(CH_2)_n R^7$, —$R^6 OC(O)(CH_2)_n R^7$, —$R^6 NR^4 C(O)(CH_2)_n R^7$, —$R^6 CH(C(O)OR^4)(NR^5 C(O)R^4)$, an optionally substituted aryl and an optionally substituted aralkyl group. The optionally substituted aryl and optionally substituted aralkyl groups are optionally substituted with one or more substituents selected from the group consisting of halogen, trihalomethyl, hydroxy, —$NR^4 R^5$, nitro, —$CONR^4 R^5$, lower alkyl group, $R^3 O$—, —$C(O)OR^4$ and —$OC(O)R^3$. $R^6$ is a lower alkyl group or an aryl group. $R^7$ is alkoxy, haloalkyl, lower alkyl piperazine, hydroxy, $R^3 O$—, $R^3 C(O)$— or —$NR^4 R^5$. In one aspect of this embodiment, R is pyrrolyl, indolyl, azaindolyl, phenyl, pyrazolyl, imidazolyl, thienyl, 4,5,6,7-tetrahydroindolyl, or quinolinyl. In another aspect of this embodiment, R is pyrrol-2-yl, pyrrol-3-yl, indol-2-yl, indol-3-yl, azaindol-3-yl, pyrazol-4-yl, imidazol-2-yl, imidazol-4-yl, thien-2-yl or quinolin-5-yl.

In still another preferred embodiment, the present invention is directed to any of the foregoing compounds wherein $R^1$ is trifluoromethyl, amino, cyclopropylamino, methyl, ethyl, propyl, isopropyl, cyclopropyl, 2-methylcyclopropyl, 2,2,3,3-tetramethylcyclopropyl, 2-phenylcyclopropyl, cyclobutyl, cyclopentyl, cyclohexyl, —$(CH_2)_p$—O-phenyl, —$(CH_2)_p$—O-(4-methoxyphenyl), —$(CH_2)_p$—O-(4-chlorophenyl), —$(CH_2)_p$—O-(4-methylphenyl), —$(CH_2)_p$—O-(3-methylphenyl), —$(CH_2)_p$—O-(4-phenylphenyl), —$(CH_2)_p$—O-(4-hydroxyphenyl), —$(CH_2)_p$—O-(4-nitrophenyl), —$(CH_2)_p$—O-(4-aminophenyl), —$(CH_2)_p$—O-(4-carbamoylphenyl), —$(CH_2)_p$—O-(4-methoxycarbonylphenyl), —NH-phenyl, —NH-(4-methoxyphenyl), —NH-(4-chlorophenyl), —NH-(4-fluorophenyl), —NH—(4-isopropylphenyl), isopropoxy, ethoxy, cyclopentyloxy, —$(CH_2)_p$-indolyl, —$(CH_2)_p$-pyridyl, —$(CH_2)_p$-benzothiazolyl, —$(CH_2)_p$-pyrrolyl, —$(CH_2)_p$-tetrahydrofuryl, —$(CH_2)_p$-pyrazinyl, —$(CH_2)_p$-furyl, —$(CH_2)_p$-thienyl, —$(CH_2)_p$-phenyl, —$(CH_2)_p$-isoxazolyl, —$(CH_2)_p$-(5-methylisoxazolyl), —$(CH_2)_p$-pyrimidinyl, —$(CH_2)_p$-pyridazinyl, —$(CH_2)_n$—C(O)—OMe, —$(CH_2)_n$—C(O)-OEt or benzyl optionally substituted with one or more of Cl, F, OMe, methyl or amino. p is an integer from 1 to 3. In one aspect of this embodiment, R is optionally substituted with one or more moieties selected from the group consisting of Br, Cl, F, aminomethyl, N,N-dimethylaminomethyl, carboxy, carboxymethyl, carboxyethyl, carbonylmethyl, carbonylethyl, methoxycarbonyl, ethoxycarbonyl, phenyl, 4-morpholinomethyl, —C(O)—O—$(CH_2)_2$—$N(Me)_2$, —C(O)—O—$(CH_2)_2$—$N(Et)_2$, —C(O)—O—$CH_2$—$N(Me)_2$, —C(O)—O—$(CH_2)_2$—$N(Me)_2$, —C(O)—NH—$(CH_2)_2$—$N(Me)_2$, —$CH_2$—NH—C(O)—$CF_3$ and an optionally substituted moiety selected from the group consisting of methyl, ethyl, propyl, isopropyl, butyl and phenyl, where the optionally substituted moiety is optionally substituted with one or more of Br, Cl, F, hydroxy, nitro, amino or lower alkyl.

In another aspect, the present invention provides a pharmaceutical composition comprising any one or more of the compounds of the present invention, as defined herein, and a pharmaceutically acceptable carrier or diluent.

In another aspect, the present invention provides a method of inhibiting one or more protein kinase activity comprising the administration of a compound represented by the formula:

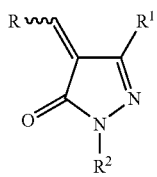

and physiologically acceptable salts and biologically active metabolites thereof, wherein:

R is selected from the group consisting of a substituted or unsubstituted: aliphatic group, aromatic group, a $(C_3-C_6)$cycloalkyl group, a heterocyclic group, an aralkyl group, a $(C_3-C_6)$cycloalkyl-alkyl group and a heterocyclyl-alkyl group;

$R^1$ is hydrogen or -A-Z;

$R^2$ is hydrogen or is selected from the group consisting of a substituted or unsubstituted: lower alkyl group, an aromatic group, a $(C_3-C_6)$cycloalkyl group, a heterocyclic group, an aralkyl group, a $(C_3-C_6)$cycloalkyl-alkyl group, a heterocyclyl-alkyl group;

A is —$(CH_2)_n$—, —$(CH_2)_n$NH—, —$(CH_2)_n$O—, —$(CH_2)_n$S—, —$(CH_2)_n$S(O)— or —$(CH_2)_n$S(O)_2$—;

Z is —H, a lower alkyl, aralkyl, trihalomethyl, trihalomethylcarbonyl, $R^3$CO—, $R^3$OC(O)—, —$NR^4R^5$, —C(O)$NR^4R^5$, $R^3$O—, or a ring system selected from the group consisting of a $(C_3-C_6)$cycloalkyl, benzene, pyrrole, isoxazole, isothiazole, indole, pyridine, pyrazine, pyrimidine, benzothiazole, tetrahydrofuran, thiophene, triazine, imidazole, furan, benzimidazole, pyridazine, quinoxaline, pyrazole, oxazole, thiazole and the N-oxides thereof wherein said ring system can be optionally substituted with one or more moieties selected from the group consisting of halogens, lower alkyl, $R^3$O—, HO—, HOC(O)—, $R^3$OC(O)—, trihalomethyl, nitro, aryl, —CN, —C(O)$NR^4R^5$ and —$NR^4R^5$;

$R^3$ for each occurrence is, independently, selected from the group consisting of substituted or unsubstituted: lower alkyl group, lower alkoxy lower alkyl group, an aromatic group, a $(C_3-C_6)$cycloalkyl group, a heterocyclic group, an aralkyl group, a $(C_3-C_6)$cycloalkyl-alkyl group and a heterocyclyl-alkyl group;

$R^4$ and $R^5$ for each occurrence are each, independently, hydrogen or are selected from the group consisting of substituted or unsubstituted: a lower alkyl group, an aromatic group, a $(C_3-C_6)$cycloalkyl group, a heterocyclic group, an aralkyl group, a $(C_3-C_6)$cycloalkyl-alkyl group and a heterocyclyl-alkyl group; optionally, $R^4$ and $R^5$ together with the nitrogen to which they are attached represent morpholino, pyrrolidino, piperidino, imidazol-1-yl, piperazino, thiamorpholino, azepino or perhydro-1,4-diazepin-1-yl groups each optionally substituted with one or more moieties selected from the group consisting of lower alkyl, hydroxy, lower alkoxy lower alkyl, an aromatic group, a $(C_3-C_6)$cycloalkyl group, a heterocyclic group, an aralkyl group, a $(C_3-C_6)$cycloalkyl-alkyl group and a heterocyclyl-alkyl group; and n is an integer from 0 to 3.

A preferred method of the foregoing method is where the inhibition of the protein kinase is in a recipient in need thereof.

A preferred method of any of the foregoing methods is where the compound is a mixture of stereoisomers.

A preferred method of any of the foregoing methods is where the stereoisomers are enantiomers.

A preferred method of any of the foregoing methods is where the stereoisomers are E and Z isomers.

A preferred method of any of the foregoing methods is where the compound is a mixture of structural isomers.

A preferred method of any of the foregoing methods is where the structural isomers are tautomers.

A preferred method of any of the foregoing methods is where said protein kinase is either a receptor tyrosine kinase or a non-receptor tyrosine kinase.

A preferred method of any of the foregoing methods is where said tyrosine kinase is selected from the group consisting of KDR, Flt-1, TIE-2, FGFR, PDGFR, IGF-1-R, c-Met, Lck, Src, fyn, Lyn, Blk, and yes.

In another aspect, the present invention is directed to a method of treating or essentially inhibiting hyperproliferative disorders or inflammatory diseases in a recipient in need thereof comprising the administration to said recipient of any of the compounds of the present invention as defined herein.

In another aspect, the present invention is directed to a method of treating or inhibiting angiogenesis in a recipient in need thereof comprising the administration to said recipient of any of the compounds of the present invention as defined herein.

In another aspect, the present invention is directed to a method of inducing an anti-angiogenic effect in a recipient in need thereof comprising the administration to said recipient of any of the compounds of the present invention as defined herein.

In another aspect, the present invention is directed to a method of treating or inhibiting the progression of a disease or condition in a recipient in need thereof comprising the administration to said recipient of any of the compounds of the present invention, as defined herein, where said disease or condition is selected from the group consisting of cancer, arthritis, atherosclerosis, restenosis, psoriasis, hemangioma, myocardial angiogenesis, coronary and cerebral collaterals, ischemic limb angiogenesis, corneal disease, rubeosis, neovascular glaucoma, macular degeneration, wound healing, peptic ulcer, *Helicobacter* related diseases, virally induced angiogenic disorders, fractures, diabetic retinopathy, Crohn's disease, inflammatory bowel disorder, cat scratch fever, retinopathy or prematurity, ulcers, thyroid hyperplasia, burns, trauma, acute lung injury, chronic lung disease, stroke, polyps, cysts, synovitis, chronic and allergic inflammation, ovarian hyperstimulation syndrome, pulmonary and cerebral edema, keloid, fibrosis, cirrhosis, carpal tunnel syndrome, sepsis, adult respiratory distress syndrome, multiple-organ dysfunction syndrome, ascites and tumor-associated effusions and edema.

In another aspect, the present invention is directed to a method of affecting vascular hyperpermeability or the production of edema in a recipient in need thereof comprising the administration to said recipient of any of the compounds of the present invention, as defined herein. A preferred method of the immediately foregoing method is where the effect on the production of edema is antiedematous.

A preferred method of any of the foregoing methods is where the protein kinase is a serine kinase.

A preferred method of any of the foregoing methods is where the protein kinase is a threonine kinase.

Particularly preferred compounds of the present invention are:

3-Cyclopropyl-4-{[(3,5-dimethyl-4-(4-methy-1-piperazinylmethyl)pyrrol-2-yl]methylene}-2-pyrazolin-5-one,
3-Cyclopropyl-4-[(3,5-dimethyl-4-(1-pyrrolidinylmethylpyrrol-2-yl)methylene]-2-pyrazolin-5-one,
3-Cyclopropyl-4-[(4-diethylaminomethyl-3,5-dimethylpyrrol-2-yl)methylene]-2-pyrazolin-5-one,
3-Cyclopropyl-4-[(3,5-dimethyl-4-piperidinomethylpyrrol-2-yl)methylene]-2-pyrazolin-5-one,
3-Cyclopropyl-4-[(4-diethanolaminomethyl-3,5-dimethylpyrrol-2-yl)methylene]-2-pyrazolin-5-one,
3-Cyclopropyl-4-[(3-dimethylaminomethyl-4,5-tetramethylenepyrrol-2-yl)methylene]-2-pyrazolin-5-one,
3-Cyclopropyl-4-[(3-morpholinomethyl-4,5-tetramethylenepyrrol-2-yl)methylene]-2-pyrazolin-5-one,
3-Cyclopropyl-4-[(3-diethylaminomethyl-4,5-tetramethylenepyrrol-2-yl)methylene]-2-pyrazolin-5-one,
3-Cyclopropyl-4-{[3-(4-methyl-1-piperazinylmethyl)-4,5-tetramethylenepyrrol-2-yl]methylene}-2-pyrazolin-5-one,
3-Cyclopropyl-4-{[3-(1-pyrrolidinyl)methyl-4,5-tetramethylenepyrrol-2-yl]methylene}-2-pyrazolin-5-one,
3-Cyclopropyl-4-[(3-piperidinomethyl-4,5-tetramethylenepyrrol-2-yl)methylene]-2-pyrazolin-5-one,
3-Cyclopropyl-4-[(4-dimethylamino-4,5,6,7-tetrahydroindol-2-yl)methylene]-2-pyrazolin-5-one,
3-Cyclopropyl-4-[(4-diethylaminoethyl-3,5-dimethylpyrrol-2-yl)methylene]-2-pyrazolin-5-one,
3-Cyclopropyl-4-(3,5-dibromo-4-hydroxybenzylidene)-2-pyrazolin-5-one,
3-Cyclopropyl-4-[(4-oxo-1,5,6,7-tetrahydroindol-2-yl)methylene]-2-pyrazolin-5-one,
3-Cyclopropyl-4-[(4-dimethylaminomethyl-5-methylpyrrol-2-yl)methylene]-2-pyrazolin-5-one,
4-[(5-Chloropyrrol-2-yl)methylene]-3-cyclopropyl-2-pyrazolin-5-one,
3-Cyclopropyl-4-[(5-trifluoromethylpyrrol-2-yl)methylene]-2-pyrazolin-5-one,
3-Cyclopropyl-4-[4-(2-dimethylaminoethoxycarbonylpyrrol-2-yl)methylene]-2-pyrazolin-5-one,
3-Cyclopropyl-4-[4-(2-dimethylaminoethylaminocarbonylpyrrol-2-yl)methylene]-2-pyrazolin-5-one,
3-Cyclopropyl-4-[(3-ethoxycarbonylindol-2-yl)methylene]-2-pyrazolin-5-one,
3-Cyclopropyl-4-[3-(2-dimethylaminoethoxycarbonylindol-2-yl)methylene]-2-pyrazolin-5-one,
3-Cyclopropyl-4-[3-(2-dimethylaminoethylaminocarbonylindol-2-yl)methylene]-2-pyrazolin-5-one,
3-Cyclopropyl-4-[4-(4-morpholinoethoxycarbonylpyrrol-2-yl)methylene]-2-pyrazolin-5-one,
3-Cyclopropyl-4-[4-(4-morpholinoethylaminocarbonylpyrrol-2-yl)methylene]-2-pyrazolin-5-one,
3-Cyclopropyl-4-[3-(4-morpholinoethoxycarbonylindol-2-yl)methylene]-2-pyrazolin-5-one,
3-Cyclopropyl-4-[3-(4-morpholinoethylaminocarbonylindol-2-yl)methylene]-2-pyrazolin-5-one,
3-Cyclopropyl-4-[(3,4-Diethoxycarbonylpyrrol-2-yl)methylene]-2-pyrazolin-5-one,
4-{[3-(2-Amino-2-carboxyethyl)indol-2-yl]methylene}-3-cyclopropyl-2-pyrazolin-5-one,
3-Cyclopropyl-4-[(5-ethoxy-4-methoxycarbonylmethyl-3-methoxycarbonylpyrrol-2-yl)methylene]-2-pyrazolin-5-one,
3-Cyclopropyl-4-[(5-chloro-4-methoxycarbonylmethyl-3-methoxycarbonylpyrrol-2-yl)methylene]-2-pyrazolin-5-one,
4-[(3,5-Dimethyl-4-morpholinomethylpyrrol-2-yl)methylene]-3-(3-pyridyl)-2-pyrazolin-5-one,
4-{[(3,5-Dimethyl-4-[(4-methyl-1-piperazinylmethyl)pyrrol-2-yl]methylene}-3-(3-pyridyl)-2-pyrazolin-5-one,
4-[(3,5-Dimethyl-4-[(1-pyrrolidinylmethylpyrrol-2-yl)methylene]-3-(3-pyridyl)-2-pyrazolin-5-one,
4-[(4-Diethylaminomethyl-3,5-dimethylpyrrol-2-yl)methylene]-3-(3-pyridyl)-2-pyrazolin-5-one,
4-[(3,5-Dimethyl-4-piperidinomethylpyrrol-2-yl)methylene]-3-(3-pyridyl)-2-pyrazolin-5-one,
4-[(4-Diethanolaminomethyl-3,5-dimethylpyrrol-2-yl)methylene]-3-(3-pyridyl)-2-pyrazolin-5-one,
4-[(3-Dimethylaminomethyl-4,5-tetramethylenepyrrol-2-yl)methylene]-3-(3-pyridyl)-2-pyrazolin-5-one,
4-[(3-Morpholinomethyl-4,5-tetramethylenepyrrol-2-yl)methylene]-3-(3-pyridyl)-2-pyrazolin-5-one,
4-[(3-Diethylaminomethyl-4,5-tetramethylenepyrrol-2-yl)methylene]-3-(3-pyridyl)-2-pyrazolin-5-one,
4-{[3-(4-Methyl-1-piperazinylmethyl)-4,5-tetramethylenepyrrol-2-yl]methylene}-3-(3-pyridyl)-2-pyrazolin-5-one,
3-(3-Pyridyl)-4-{[3-(1-pyrrolidinyl)methyl-4,5-tetramethylenepyrrol-2-yl]methylene}-2-pyrazolin-5-one,
4-[(3-Piperidinomethyl-4,5-tetramethylenepyrrol-2-yl)methylene]-3-(3-pyridyl)-2-pyrazolin-5-one,
4-[(4-Dimethylamino-4,5,6,7-tetrahydroindol-2-yl)methylene]-3-(3-pyridyl)-2-pyrazolin-5-one, 4-[(4-Diethylaminoethyl-3,5-dimethylpyrrol-2-yl)methylene]-3-(3-pyridyl)-2-pyrazolin-5-one,
4-(3,5-Dibromo-4-hydroxybenzylidene)-3-(3-pyridyl)-2-pyrazolin-5-one,
4-[(4-Oxo-1,5,6,7-tetrahydroindol-2-yl)methylene]-3-(3-pyridyl)-2-pyrazolin-5-one,
4-[(4-Dimethylaminomethyl-5-methylpyrrol-2-yl)methylene]-3-(3-pyridyl)-2-pyrazolin-5-one,
4-[(4-Bromopyrrol-2-yl)methylene]-3-(3-pyridyl)-2-pyrazolin-5-one,
4-[(4-Chloropyrrol-2-yl)methylene]-3-(3-pyridyl)-2-pyrazolin-5-one,
4-[(5-Chloropyrrol-2-yl)methylene]-3-(3-pyridyl-2-pyrazolin-5-one,
3-(3-Pyridyl)-4-[(5-trifluoromethylpyrrol-2-yl)methylene]-2-pyrazolin-5-one,
4-[(4-Ethoxycarbonylpyrrol-2-yl)methylene]-3-(3-pyridyl)-2-pyrazolin-5-one,
4-[4-(2-Dimethylaminoethoxycarbonylpyrrol-2-yl)methylene]-3-(3-pyridyl)-2-pyrazolin-5-one,
4-[4-(2-Dimethylaminoethylaminocarbonylpyrrol-2-yl)methylene]-3-(3-pyridyl)-2-pyrazolin-5-one,
4-[(3-Ethoxycarbonylindol-2-yl)methylene]-3-(3-pyridyl)-2-pyrazolin-5-one,
4-[3-(2-Dimethylaminoethoxycarbonylindol-2-yl)methylene]-3-(3-pyridyl)-2-pyrazolin-5-one,
4-[3-(2-Dimethylaminoethylaminocarbonylindol-2-yl)methylene]-3-(3-pyridyl)-2-pyrazolin-5-one,
4-[4-(4-Morpholinoethoxycarbonylpyrrol-2-yl)methylene]-3-(3-pyridyl)-2-pyrazolin-5-one,
4-[4-(4-Morpholinoethylaminocarbonylpyrrol-2-yl)methylene]-3-(3-pyridyl)-2-pyrazolin-5-one,
4-[3-(4-Morpholinoethoxycarbonylindol-2-yl)methylene)-3-(3-pyridyl)-2-pyrazolin-5-one,
4-[3-(4-Morpholinoethylaminocarbonylindol-2-yl)methylene]-3-(3-pyridyl)-2-pyrazolin-5-one,
4-[(3,4-Diethoxycarbonylpyrrol-2-yl)methylene]-3-(3-pyridyl)-2-pyrazolin-5-one,
4-{[3-(2-Acetamido-2-methoxycarbonylethyl)indol-2-yl]methylene}-3-(3-pyridyl)-2-pyrazolin-5-one,
4-{[3-(2-Amino-2-carboxyethyl)indol-2-yl]methylene}-3-(3-pyridyl)-2-pyrazolin-5-one,
4-[(5-Ethoxy-4-methoxycarbonylmethyl-3-methoxycarbonylpyrrol-2-yl)methylene]-3-(3-pyridyl)-2-pyrazolin-5-one,
4-[(5-Chloro-4-methoxycarbonylmethyl-3-methoxycarbonylpyrrol-2-yl)methylene]-3-(3-pyridyl)-2-pyrazolin-5-one,
4-[(3,5-Dimethyl-4-morpholinomethylpyrrol-2-yl)methylene]-3-isopropoxy-2-pyrazolin-5-one,
4-[(3,5-Dimethyl-4-{[(4-methyl-1-piperazinylmethyl)pyrrol-2-yl]methylene}-3-isopropoxy-2-pyrazolin-5-one,
4-[(3,5-Dimethyl-4-[(1-pyrrolidinylmethylpyrrol-2-yl)methylene]-3-isopropoxy-2-pyrazolin-5-one,
4-[(4-Diethylaminomethyl-3,5-dimethyl-pyrrol-2-yl)methylene]-3-isopropoxy-2-pyrazolin-5-one,
4-[(3,5-Dimethyl-4-(piperidinomethylpyrrol-2-yl)methylene]-3-isopropoxy-2-pyrazolin-5-one,
4-[(4-Diethanolaminomethyl-3,5-dimethylpyrrol-2-yl)methylene]-3-isopropoxy-2-pyrazolin-5-one,
4-[(3-Dimethylaminomethyl-4,5-tetramethylenepyrrol-2-yl)methylene]-3-isopropoxy-2-pyrazolin-5-one,
3-Isopropoxy-4-[(3-morpholinomethyl-4,5-tetramethylenepyrrol-2-yl)methylene]-2-pyrazolin-5-one,
4-[(3-Diethylaminomethyl-4,5-tetramethylenepyrrol-2-yl)methylene]-3-isopropoxy-2-pyrazolin-5-one,
3-Isopropoxy-4-{[3-(4-methyl-1-piperazinyl)methyl-4,5-tetramethylenepyrrol-2-yl]methylene}-2-pyrazolin-5-one,
3-Isopropoxy-4-{[3-(1-pyrrolidinyl)methyl-4,5-tetramethylenepyrrol-2-yl]methylene}-2-pyrazolin-5-one,
3-Isopropoxy 4-[(3-piperidinomethyl-4,5-tetramethylenepyrrol-2-yl)methylene]--2-pyrazolin-5-one,
4-[(4-Dimethylamino-4,5,6,7-tetrahydroindol-2-yl)methylene]-3-isopropoxy-2-, pyrazolin-5-one,
4-[(4-Diethylaminoethyl-3,5-dimethylpyrrol-2-yl)methylene]-3-isopropoxy-2-pyrazolin-5-one,
4-(3,5-Dibromo-4-hydroxybenzylidene)-3-isopropoxy-2-pyrazolin-5-one,
3-Isopropoxy-4-[(4-oxo-1,5,6,7-tetrahydroindol-2-yl)methylene]-2-pyrazolin-5-one,
4-[(4-Dimethylaminomethyl-5-methylpyrrol-2-yl)methylene]-3-isopropoxy-2-pyrazolin-5-one,
4-[(4-Bromopyrrol-2-yl)methylene]-3-isopropoxy-2-pyrazolin-5-one,
4-[(4-Chloropyrrol-2-yl)methylene]-3-isopropoxy-2-pyrazolin-5-one,
4-[(5-Chloropyrrol-2-yl)methylene]-3-isopropoxy-2-pyrazolin-5-one,
3-Isopropoxy-4-[(5-trifluoromethylpyrrol-2-yl)methylene]-2-pyrazolin-5-one,
4-[(4-Ethoxycarbonylpyrrol-2-yl)methylene]-3-isopropoxy-2-pyrazolin-5-one,
4-[4-(2-Dimethylaminoethoxycarbonylpyrrol-2-yl)methylene]-3-isopropoxy-2-pyrazolin-5-one,
4-[4-(2-Dimethylaminoethylaminocarbonylpyrrol-2-yl)methylene]-3-isopropoxy-2-pyrazolin-5-one,
4-[(3-Ethoxycarbonylindol-2-yl)methylene]-3-isopropoxy-2-pyrazolin-5-one,
4-[3-(2-Dimethylaminoethoxycarbonylindol-2-yl)methylene]-3-isopropoxy-2-pyrazolin-5-one,
4-[3-(2-Dimethylaminoethylaminocarbonylindol-2-yl)methylene]-3-isopropoxy-2-pyrazolin-5-one,
3-Isopropoxy-4-[4-(4-morpholinoethoxycarbonylpyrrol-2-yl)methylene]-2-pyrazolin-5-one,
3-Isopropoxy-4-[4-(4-morpholinoethylaminocarbonylpyrrol-2-yl)methylene]-2-pyrazolin-5-one,
3-Isopropoxy-4-[3-(4-morpholinoethoxycarbonylindol-2-yl)methylene]-2-pyrazolin-5-one,
3-Isopropoxy-4-[3-(4-morpholinoethylaminocarbonylindol-2-yl)methylene]-2-pyrazolin-5-one,
4-[(3,4-Diethoxycarbonylpyrrol-2-yl)methylene]-3-isopropoxy-2-pyrazolin-5-one,
4-{[3-(2-Amino-2-carboxyethyl)indol-2-yl]methylene}-3-isopropoxy-2-pyrazolin-5-one,
4-[(5-Ethoxy-4-methoxycarbonylmethyl-3-methoxycarbonylpyrrol-2-yl)methylene]-3-isopropoxy-2-pyrazolin-5-one,
4-[(5-Chloro-4-methoxycarbonylmethyl-3-methoxycarbonylpyrrol-2-yl)methylene]-3 isopropoxy-2-pyrazolin-5-one,
4-[(3,5-Dimethyl-4-morpholinomethylpyrrol-2-yl)methylene]-3-ethoxy-2-pyrazolin-5-one,
4-[(3,5-Dimethyl-4-{[(4-methyl-1-piperazinylmethyl)pyrrol-2-yl]methylene}-3-ethoxy-2-pyrazolin-5-one,
4-[(3,5-Dimethyl-4-[(1-pyrrolidinylmethylpyrrol-2-yl)methylene]-3-ethoxy-2-pyrazolin-5-one,
4-[(4-Diethylaminomethyl-3,5-dimethyl-pyrrol-2-yl)methylene]-3-ethoxy-2-pyrazolin-5-one,
4-[(3,5-Dimethyl-4-(piperidinomethylpyrrol-2-yl)methylene]-3-ethoxy-2-pyrazolin-5-one,
4-[(4-Diethanolaminomethyl-3,5-dimethyl-pyrrol-2-yl)methylene]-3-ethoxy-2-pyrazolin-5-one, 4-[(3-Dimethylaminomethyl-4,5-tetramethylenepyrrol-2-yl) methylene]-3-ethoxy-2-pyrazolin-5-one,
3-Ethoxy-4-[(3-morpholinomethyl-4,5-tetramethylenepyrrol-2-yl)methylene]-2-pyrazolin-5-one,
4-[(3-Diethylaminomethyl-4,5-tetramethylenepyrrol-2-yl) methylene]-3-ethoxy-2-pyrazolin-5-one,
3-Ethoxy-4-{[3-(4-methyl-1-piperazinyl)methyl-4,5-tetramethylenepyrrol-2-yl]methylene}-2-pyrazolin-5-one,
3-Ethoxy-4-{[3-(1-pyrrolidinyl)methyl-4,5-tetramethylenepyrrol-2-yl]methylene}-2-pyrazolin-5-one,
3-Ethoxy-4-[(3-piperidinomethyl-4,5-tetramethylenepyrrol-2-yl)methylene]-2-pyrazolin-5-one,
4-[(4-Dimethylamino-4,5,6,7-tetrahydroindol-2-yl)methylene]-3-ethoxy-2-pyrazolin-5-one,
4-[(4-Diethylaminoethyl-3,5-dimethylpyrrol-2-yl)methylene]-3-ethoxy-2-pyrazolin-5-one,
4-(3,5-Dibromo-4-hydroxybenzylidene)-3-ethoxy-2-pyrazolin-5-one,
4-[(3,5-Dimethyl-4-dimethylaminomethylpyrrol-2-yl)methylene]-3-ethoxy-2-pyrazolin-5-one,
3-Ethoxy-4-[(4-oxo-1,5,6,7-tetrahydroindol-2-yl)methylene]-2-pyrazolin-5-one,
4-[(4-Dimethylaminomethyl-5-methylpyrrol-2-yl)methylene]-3-ethoxy-2-pyrazolin-5-one,
3-Ethoxy-4-[(5-trifluoromethylpyrrol-2-yl)methylene]-2-pyrazolin-5-one,
4-[4-(2-Dimethylaminoethoxycarbonylpyrrol-2-yl)methylene]-3-ethoxy-2-pyrazolin-5-one,
4-[4-(2-Dimethylaminoethylaminocarbonylpyrrol-2-yl)methylene]-3-ethoxy-2-pyrazolin-5-one,
4-[(3-Ethoxycarbonylindol-2-yl)methylene]-3-ethoxy-2-pyrazolin-5-one,
4-[3-(2-Dimethylaminoethylaminocarbonylindol-2-yl)methylene]-3-ethoxy-2-pyrazolin-5-one,
4-[3-(2-Dimethylaminoethylaminocarbonylindol-2-yl)methylene]-3-ethoxy-2-pyrazolin-5-one,
3-Ethoxy-4-[4-(4-morpholinoethoxycarbonylpyrrol-2-yl) methylene]-2-pyrazolin-5-one,
3-Ethoxy-4-[4-(4-morpholinoethylaminocarbonylpyrrol-2-yl)methylene]-2-pyrazolin-5-one,
3-Ethoxy-4-[3-(4-morpholinoethoxycarbonylindol-2-yl)methylene]-2-pyrazolin-5-one,
3-Ethoxy-4-[(5-methoxyindol-2-yl)methylene]-2-pyrazolin-5-one,
4-{[3,5-Dimethyl-4-(2-dimethylaminoethoxycarbonyl)pyrrol-2-yl]methylene}-3-ethoxy-2-pyrazolin-5-one,
3-Ethoxy-4-[(indol-3-yl)methylene]-2-pyrazolin-5-one,
4-{[3-(2-Acetamido-2-methoxycarbonylethyl)indol-2-yl] methylene}-3-ethoxy-2-pyrazolin-5-one,
4-{[3-(2-Amino-2-carboxyethyl)indol-2-yl]methylene}-3-ethoxy-2-pyrazolin-5-one,
4-[(5-Ethoxy-4-methoxycarbonylmethyl-3-methoxycarbonylpyrrol-2-yl)methylene]-3-ethoxy-2-pyrazolin-5-one,
4-[(3-Dimethylaminomethyl-4,5-tetramethylenepyrrol-2-yl) methylene]-3-pyrazinyl-2-pyrazolin-5-one,
4-[(3-Morpholinomethyl-4,5-tetramethylenepyrrol-2-yl) methylene]-3-pyrazinyl-2-pyrazolin-5-one,
4-[(3-Diethylaminomethyl-4,5-tetramethylenepyrrol-2-yl) methylene]-3-pyrazinyl-2-pyrazolin-5-one,
4-{[3-(4-Methyl-1-piperazinylmethyl)-4,5-tetramethylenepyrrol-2-yl]methylene}-3-pyrazinyl-2-pyrazolin-5-one,
3-Pyrazinyl-4-{[3-(1-pyrrolidinyl)methyl-4,5-tetramethylenepyrrol-2-yl]methylene}-2-pyrazolin-5-one,
4-[(3-Piperidinomethyl-4,5-tetramethylenepyrrol-2-yl)methylene]-3-pyrazinyl-2-pyrazolin-5-one,
4-[(4-Dimethylamino-4,5,6,7-tetrahydroindol-2-yl)methylene]-3-pyrazinyl-2-pyrazolin-5-one,
4-[(4-Diethylaminoethyl-3,5-dimethylpyrrol-2-yl)methylene]-3-pyrazinyl-2-pyrazolin-5-one,
4-(3,5-Dibromo-4-hydroxybenzylidene)-3-pyrazinyl-2-pyrazolin-5-one,
4-[(4-Bromopyrrol-2-yl)methylene]-3-pyrazinyl-2-pyrazolin-5-one,
4-[(4-Chloropyrrol-2-yl)methylene]-3-pyrazinyl-2-pyrazolin-5-one,
4-[(5-Chloropyrrol-2-yl)methylene]-3-pyrazinyl-2-pyrazolin-5-one,
3-Pyrazinyl-4-[(5-trifluoromethylpyrrol-2-yl)methylene]-2-pyrazolin-5-one,
4-[(4-Ethoxycarbonylpyrrol-2-yl)methylene]-3-pyrazinyl-2-pyrazolin-5-one,
4-[4-(2-Dimethylaminoethoxycarbonylpyrrol-2-yl)methylene]-3-pyrazinyl-2-pyrazolin-5-one,
4-[4-(2-Dimethylaminoethylaminocarbonylpyrrol-2-yl)methylene]-3-pyrazinyl-2-pyrazolin-5-one,
4-[(3-Ethoxycarbonylindol-2-yl)methylene]-3-pyrazinyl-2-pyrazolin-5-one,
4-[3-(2-Dimethylaminoethoxycarbonylindol-2-yl)methylene]-3-pyrazinyl-2-pyrazolin-5-one,
4-[3-(2-Dimethylaminoethylaminocarbonylindol-2-yl)methylene]-3-pyrazinyl-2-pyrazolin-5-one,
4-[4-(4-Morpholinoethoxycarbonylpyrrol-2-yl)methylene]-3-pyrazinyl-2-pyrazolin-5-one,
4-[4-(4-Morpholinoethylaminocarbonylpyrrol-2-yl)methylene]-3-pyrazinyl-2-pyrazolin-5-one,
4-[3-(4-Morpholinoethoxycarbonylindol-2-yl)methylene]-3-pyrazinyl-2-pyrazolin-5-one,
4-[3-(4-Morpholinoethylaminocarbonylindol-2-yl)methylene]-3-pyrazinyl-2-pyrazolin-5-one,
4-[(3,5-Dimethyl-4-ethoxycarbonylpyrrol-2-yl)methylene]-3-pyrazinyl-2-pyrazolin-5-one,
4-{[3,5-Dimethyl-4-(2-dimethylaminoethylaminocarbonyl) pyrrol-2-yl]methylene}-3-pyrazinyl-2-pyrazolin-5-one,
4-[(Indol-3-yl)methylene]-3-pyrazinyl-2-pyrazolin-5-one,
4-[(1-Methylindol-3-yl)methylene]-3-pyrazinyl-2-pyrazolin-5-one,
3-Pyrazinyl-4-[(pyrrol-2-yl)methylene]-2-pyrazolin-5-one,
4-[(Indol-2-yl)methylene]-3-pyrazinyl-2-pyrazolin-5-one,
4-[(3,4-Diethoxycarbonylpyrrol-2-yl)methylene]-3-pyrazinyl-2-pyrazolin-5-one,
4-{[3-(2-Acetamido-2-methoxycarbonylethyl)indol-2-yl] methylene}-3- pyrazinyl-2-pyrazolin-5-one,
4-{[3-(2-Amino-2-carboxyethyl)indol-2-yl]methylene}-3-pyrazinyl-2-pyrazolin-5-one,
4-[(5-Ethoxy-4-methoxycarbonylmethyl-3-methoxycarbonylpyrrol-2-yl)methylene]-3-pyrazinyl-2-pyrazolin-5-one,
4-[(5-Chloro-4-methoxycarbonylmethyl-3-methoxycarbonylpyrrol-2-yl)methylene]-3-pyrazinyl-2-pyrazolin-5-one,
4-[(4-Bromopyrrol-2-yl)methylene]-3-(imidazol-2-yl)-2-pyrazolin-5-one,
4-[(4-Chloropyrrol-2-yl)methylene]-3-(imidazol-2-yl)-2-pyrazolin-5-one,
4-[(5-Chloropyrrol-2-yl)methylene]-3-(imidazol-2-yl)-2-pyrazolin-5-one,
3-(Imidazol-2-yl)-4-[(5-trifluoromethylpyrrol-2-yl)methylene]-2-pyrazolin-5-one,
3-(Imidazol-2-yl)-4-[(4-ethoxycarbonylpyrrol-2-yl)methylene]-2-pyrazolin-5-one,
4-[4-(2-Dimethylaminoethoxycarbonylpyrrol-2-yl)methylene]-3-(imidazol-2-yl)-2-pyrazolin-5-one,
4-[4-(2-Dimethylaminoethylaminocarbonylpyrrol-2-yl)methylene]-3-(imidazol-2-yl)-2-pyrazolin-5-one, 4-[(3-Ethoxycarbonylindol-2-yl)methylene]-3-(imidazol-2-yl)-2-pyrazolin-5-one,
4-[3-(2-Dimethylaminoethoxycarbonylindol-2-yl)methylene]-3-(imidazol-2-yl)-2-pyrazolin-5-one,
4-[3-(2-Dimethylaminoethylaminocarbonylindol-2-yl)methylene]-3-(imidazol-2-yl)-2-pyrazolin-5-one,
3-(Imidazol-2-yl)-4-[4-(4-morpholinoethoxycarbonylpyrrol-2-yl)methylene]-2-pyrazolin-5-one,
3-(Imidazol-2-yl)-4-[4-(4-morpholinoethylaminocarbonylpyrrol-2-yl)methylene]-2-pyrazolin-5-one,
3-(Imidazol-2-yl)-4-[3-(4-morpholinoethoxycarbonylindol-2-yl)methylene]-2-pyrazolin-5-one,
3-(Imidazol-2-yl)-4-[3-(4-morpholinoethylaminocarbonylindol-2-yl)methylene]-2-pyrazolin-5-one,
4-[(3,5-Dimethyl-4-ethylpyrrol-2-yl)methylene]-3-(imidazol-2-yl)-2-pyrazolin-5-one,
3-(Imidazol-2-yl)-4-[(1-methylindol-3-yl)methylene]-2-pyrazolin-5-one,
4-[3,5-Dimethyl-4-ethoxycarbonylpyrrol-2-yl)methylene]-3-(imidazol-2-yl)-2-pyrazolin-5-one,
3-(Imidazol-2-yl)-4-[(5-methoxyindol-2-yl)methylene]-2-pyrazolin-5-one,
3-(Imidazol-2-yl)-4-[(4,5-tetramethylenepyrrol-2-yl)methylene]-2-pyrazolin-5-one,
4-{[3,5-Dimethyl-4-(2-dimethylaminoethoxycarbonyl)pyrrol-2-yl]methylene}-3-(imidazol-2-yl)-2-pyrazolin-5-one,
4-{[3,5-Dimethyl-4-(2-dimethylaminoethylaminocarbonyl)pyrrol-2-yl]methylene}-3-(imidazol-2-yl)-2-pyrazolin-5-one,
3-(Imidazol-2-yl)-4-[(indol-3-yl)methylene]-2-pyrazolin-5-one,
3-(Imidazol-2-yl)-4-[(pyrrol-2-yl)methylene]-2-pyrazolin-5-one,
3-(Imidazol-2-yl)-4-[(indol-2-yl)methylene]-2-pyrazolin-5-one,
4-[(3,4-Diethoxycarbonylpyrrol-2-yl)methylene]-3-(imidazol-2-yl))-2-pyrazolin-5-one,
4-{[3-(2-Acetamido-2-methoxycarbonylethyl)indol-2-yl]methylene}-3-(imidazol-2-yl)-2-pyrazolin-5-one,
4-{[3-(2-Amino-2-carboxyethyl)indol-2-yl]methylene}-3-(imidazol-2-yl)-2-pyrazolin-5-one,
4-[(5-Ethoxy-4-methoxycarbonylmethyl-3-methoxycarbonylpyrrol-2-yl)methylene]-3-(imidazol-2-yl)-2-pyrazolin-5-one,
4-[(5-Chloro-4-methoxycarbonylmethyl-3-methoxycarbonylpyrrol-2-yl)methylene]-3-(imidazol-2-yl)-2-pyrazolin-5-one,
4-[(4-Bromopyrrol-2-yl)methylene]-3-(1-methylcyclopropyl)-2-pyrazolin-5-one,
4-[(4-Chloropyrrol-2-yl)methylene]-3-(1-methylcyclopropyl)-2-pyrazolin-5-one,
4-[(5-Chloropyrrol-2-yl)methylene]-3-(1-methylcyclopropyl)-2-pyrazolin-5-one,
3-(1-Methylcyclopropyl)-4-[(5-trifluoromethylpyrrol-2-yl)methylene]-2-pyrazolin-5-one,
4-[(4-Ethoxycarbonylpyrrol-2-yl)methylene]-3-(1-methylcyclopropyl)-2-pyrazolin-5-one,
4-[4-(2-Dimethylaminoethoxycarbonylpyrrol-2-yl)methylene]-3-(1-methylcyclopropyl)-2-pyrazolin-5-one,
4-[4-(2-Dimethylaminoethylaminocarbonylpyrrol-2-yl)methylene]-3-(1-methylcyclopropyl)-2-pyrazolin-5-one,
4-[(3-Ethoxycarbonylindol-2-yl)methylene]-3-(1-methylcyclopropyl)-2-pyrazolin-5-one,
4-[3-(2-Dimethylaminoethoxycarbonylindol-2-yl)methylene]-3-(1-methylcyclopropyl)-2-pyrazolin-5-one,
4-[3-(2-Dimethylaminoethylaminocarbonylindol-2-yl)methylene]-3-(1-methylcyclopropyl)-2-pyrazolin-5-one,
3-(1-Methylcyclopropyl)-4-[4-(4-morpholinoethoxycarbonylpyrrol-2-yl)methylene]-2-pyrazolin-5-one,
3-(1-Methylcyclopropyl)-4-[4-(4-morpholinoethylaminocarbonylpyrrol-2-yl)methylene]-2-pyrazolin-5-one,
3-(1-Methylcyclopropyl)-4-[3-(4-morpholinoethoxycarbonylindol-2-yl)methylene]-2-pyrazolin-5-one,
3-(1-Methylcyclopropyl)-4-[3-(4-morpholinoethylaminocarbonylindol-2-yl)methylene]-2-pyrazolin-5-one,
4-[(3,5-Dimethyl-4-ethylpyrrol-2-yl)methylene]-3-(1-methylcyclopropyl)-2-pyrazolin-5-one,
3-(1-Methylcyclopropyl)-4-[(1-methylindol-3-yl)methylene]-2-pyrazolin-5-one,
4-[3,5-Dimethyl-4-ethoxycarbonylpyrrol-2-yl)methylene]-3-(1-methylcyclopropyl)-2-pyrazolin-5-one,
4-[(5-Methoxyindol-2-yl)methylene]-3-(1-methylcyclopropyl)-2-pyrazolin-5-one,
3-(1-Methylcyclopropyl)-4-[(4,5-tetramethylenepyrrol-2-yl)methylene]-2-pyrazolin-5-one,
4-{[3,5-Dimethyl-4-(2-dimethylaminoethoxycarbonyl)pyrrol-2-yl]methylene}-3-(1-methylcyclopropyl)-2-pyrazolin-5-one,
4-{[3,5-Dimethyl-4-(2-dimethylaminoethylaminocarbonyl)pyrrol-2-yl]methylene}-3-(1-methylcyclopropyl)-2-pyrazolin-5-one,
4-[(Indol-3-yl)methylene]-3-(1-methylcyclopropyl)-2-pyrazolin-5-one,
4-[(Pyrrol-2-yl)methylene]-3-(1-methylcyclopropyl)-2-pyrazolin-5-one,
4-[(Indol-2-yl)methylene]-3-(1-methylcyclopropyl)-2-pyrazolin-5-one,
4-[(3,4-Diethoxycarbonylpyrrol-2-yl)methylene]-3-(1-methylcyclopropyl))-2-pyrazolin-5-one,
4-{[3-(2-Acetamido-2-methoxycarbonylethyl)indol-2-yl]methylene}-3-(1-methylcyclopropyl)-2-pyrazolin-5-one,
4-{[3-(2-Amino-2-carboxyethyl)indol-2-yl]methylene}-3-(1-methylcyclopropyl)-2-pyrazolin-5-one,
4-[(5-Ethoxy-4-methoxycarbonylmethyl-3-methoxycarbonylpyrrol-2-yl)methylene]-3-(1-methylcyclopropyl)-2-pyrazolin-5-one,
4-[(5-Chloro-4-methoxycarbonylmethyl-3-methoxycarbonylpyrrol-2-yl)methylene]-3-(1-methylcyclopropyl)-2-pyrazolin-5-one,
4-[(3,5-Dimethyl-4-morpholinomethylpyrrol-2-yl)methylene]-3-(2-yl)-2-pyrazolin-5-one,
4-{[3,5-Dimethyl-4-(4-methyl-1-piperazinylmethyl)pyrrol-2-yl]methylene}-3-(2-furyl)-2-pyrazolin-5-one,
4-{[3,5-Dimethyl-4-(1-pyrrolidinylmethyl)pyrrol-2-yl]methylene}-3-(2-furyl)-2-pyrazolin-5-one,
4-[(4-Diethylaminomethyl-3,5-dimethylpyrrol-2-yl)methylene]-3-(2-furyl)-2-pyrazolin-5-one,
4-[(3,5-Dimethyl-4-piperidinomethylpyrrol-2-yl)methylene]-3-(2-furyl)-2-pyrazolin-5-one,
4-[(4-Diethanolaminomethyl-3,5-dimethylpyrrol-2-yl)methylene]-3-(2-furyl)-2-pyrazolin-5-one,
4-[(3-Dimethylaminomethyl-4,5-tetramethylenepyrrol-2-yl)methylene]-3-(2-furyl)-2-pyrazolin-5-one,
3-(2-Furyl)-4-[(3-morpholinomethyl-4,5-tetramethylenepyrrol-2-yl)methylene]-2-pyrazolin-5-one,
4-[(3-Diethylaminoethyl-4,5-tetramethylenepyrrol-2-yl)methylene]-3-(2-furyl)-2-pyrazolin-5-one,
3-(2-Furyl)-4-{[3-(4-methyl-1-piperazinylmethyl)-4,5-tetramethylenepyrrol-2-yl]methylene}-2-pyrazolin-5-one,
3-(2-Furyl)-4-{[3-(1-pyrrolidinyl)methyl-4,5-tetramethylenepyrrol-2-yl]methylene}-2-pyrazolin-5-one, 3-(2-Furyl)-4-[(3-piperidinomethyl-4,5-tetramethylenepyrrol-2-yl)methylene]-2-pyrazolin-5-one,
4-[(4-Dimethylamino-4,5,6,7-tetrahydroindol-2-yl)methylene]-3-(2-furyl)-2-pyrazolin-5-one,
4-[(4-Diethylaminoethyl-3,5-dimethylpyrrol-2-yl)methylene]-3-(2-furyl)-2-pyrazolin-5-one,
4-(3,5-Dibromo-4-hydroxybenzylidene)-3-(2-furyl)-2-pyrazolin-5-one,
3-(2-Furyl)-4-[(4-Oxo-1,5,6,7-tetrahydroindol-2-yl)methylene]-2-pyrazolin-5-one,
3-(2-Furyl)-4-[(4-Dimethylaminomethyl-5-methylpyrrol-2-yl)methylene]-2-pyrazolin-5-one,
4-[(4-Bromopyrrol-2-yl)methylene]-3-(2-furyl)-2-pyrazolin-5-one,
4-[(4-Chloropyrrol-2-yl)methylene]-3-(2-furyl)-2-pyrazolin-5-one,
4-[(5-Chloropyrrol-2-yl)methylene]-3-(2-furyl)-2-pyrazolin-5-one,
3-(2-Furyl)-4-[(5-trifluoromethylpyrrol-2-yl)methylene]-2-pyrazolin-5-one,
4-[(4-Ethoxycarbonylpyrrol-2-yl)methylene]-3-(2-furyl)-2-pyrazolin-5-one,
4-[4-(2-Dimethylaminoethoxycarbonylpyrrol-2-yl)methylene]-3-(2-furyl)-2-pyrazolin-5-one,
4-[4-(2-Dimethylaminoethylaminocarbonylpyrrol-2-yl)methylene]-3-(2-furyl)-2-pyrazolin-5-one,
4-[(3-Ethoxycarbonylindol-2-yl)methylene]-3-(2-furyl)-2-pyrazolin-5-one,
4-[3-(2-Dimethylaminoethoxycarbonylindol-2-yl)methylene]-3-(2-furyl)-2-pyrazolin-5-one,
4-[3-(2-Dimethylaminoethylaminocarbonylindol-2-yl)methylene]-3-(2-furyl)-2-pyrazolin-5-one,
3-(2-Furyl)-4-[4-(4-morpholinoethoxycarbonylpyrrol-2-yl)methylene]-2-pyrazolin-5-one,
3-(2-Furyl)-4-[4-(4-morpholinoethylaminocarbonylpyrrol-2-yl)methylene]-2-pyrazolin-5-one,
3-(2-Furyl)-4-[3-(4-morpholinoethoxycarbonylindol-2-yl)methylene]-2-pyrazolin-5-one,
3-(2-Furyl)-4-[3-(4-morpholinoethylaminocarbonylindol-2-yl)methylene]-2-pyrazolin-5-one,
4-[(3,5-Dimethyl-4-ethylpyrrol-2-yl)methylene]-3-(2-furyl)-2-pyrazolin-5-one,
3-(2-Furyl)-4-[(1-methylindol-3-yl)methylene]-2-pyrazolin-5-one,
4-[3,5-Dimethyl-4-ethoxycarbonylpyrrol-2-yl)methylene]-3-(2-furyl)-2-pyrazolin-5-one,
3-(2-Furyl)-4-[(5-methoxyindol-2-yl)methylene]-2-pyrazolin-5-one,
3-(2-Furyl)-4-[(4,5-tetramethylenepyrrol-2-yl)methylene]-2-pyrazolin-5-one,
4-{[3,5-Dimethyl-4-(2-dimethylaminoethoxycarbonyl)pyrrol-2-yl]methylene}-3-(2-furyl)-2-pyrazolin-5-one,
4-{[3,5-Dimethyl-4-(2-dimethylaminoethylaminocarbonyl)pyrrol-2-yl]methylene}-3-(2-furyl)-2-pyrazolin-5-one,
3-(2-Furyl)-4-[(indol-3-yl)methylene]-2-pyrazolin-5-one,
3-(2-Furyl)-4-[(pyrrol-2-yl)methylene]-2-pyrazolin-5-one,
3-(2-Furyl)-4-[(indol-2-yl)methylene]-2-pyrazolin-5-one,
4-[(3,4-Diethoxycarbonylpyrrol-2-yl)methylene]-3-(3-(2-furyl))-2-pyrazolin-5-one,
4-{[3-(2-Acetamido-2-methoxycarbonylethyl)indol-2-yl]methylene}-3-(2-furyl)-2-pyrazolin-5-one,
4-{[3-(2-Amino-2-carboxyethyl)indol-2-yl]methylene}-3-(2-furyl)-2-pyrazolin-5-one,
4-[(5-Ethoxy-4-methoxycarbonylmethyl-3-methoxycarbonylpyrrol-2-yl)methylene]-3-(2-furyl)-2-pyrazolin-5-one,
4-[(5-Chloro-4-methoxycarbonylmethyl-3-methoxycarbonylpyrrol-2-yl)methylene]-3-(2-furyl)-2-pyrazolin-5-one,
4-[(3,5-Dimethyl-4-[(morpholinomethylpyrrol-2-yl)methylene]-3-(2-thienyl)-2-pyrazolin-5-one,
4-[(3,5-Dimethyl-4-(4-methyl-1-piperazinyl)methylpyrrol-2-yl]methylene}-3-(2-thienyl)-2-pyrazolin-5-one,
4-[(3,5-Dimethyl-4-(1-pyrrolidinylmethylpyrrol-2-yl)methylene]-3-(2-thienyl)-2-pyrazolin-5-one,
4-[(4-Diethylaminomethyl-3,5-dimethylpyrrol-2-yl)methylene]-3-(2-thienyl)-2-pyrazolin-5-one,
4-[(3,5-Dimethyl-4-piperidinomethylpyrrol-2-yl)methylene]-3-(2-thienyl)-2-pyrazolin-5-one,
4-[(4-Diethanolaminomethyl-3,5-dimethylpyrrol-2-yl)methylene]-3-(2-thienyl)-2-pyrazolin-5-one,
4-[(3-Dimethylaminomethyl-4,5-tetramethylenepyrrol-2-yl)methylene]-3-(2-thienyl)-2-pyrazolin-5-one,
4-[(3-Morpholinomethyl-4,5-tetramethylenepyrrol-2-yl)methylene]-3-(2-thienyl)-2-pyrazolin-5-one,
4-[(3-Diethylaminomethyl-4,5-tetramethylenepyrrol-2-yl)methylene]-3-(2-thienyl)-2-pyrazolin-5-one,
4-{[3-(4-Methyl-1-piperazinylmethyl)-4,5-tetramethylenepyrrol-2-yl]methylene}-3-(2-thienyl)-2-pyrazolin-5-one,
4-{[3-(1-Pyrrolidinylmethyl)-4,5-tetramethylenepyrrol-2-yl]methylene}-3-(2-thienyl)-2-pyrazolin-5-one,
4-[(3-Piperidinomethyl-4,5-tetramethylenepyrrol-2-yl)methylene]-3-(2-thienyl)-2-pyrazolin-5-one,
4-[(4-Dimethylamino-4,5,6,7-tetrahydroindol-2-yl)methylene]-3-(2-thienyl)-2-pyrazolin-5-one,
4-[(4-Diethylaminoethyl-3,5-dimethylpyrrol-2-yl)methylene]-3-(2-thienyl)-2-pyrazolin-5-one,
4-(3,5-Dibromo-4-hydroxybenzylidene)-3-(2-thienyl)-2-pyrazolin-5-one,
4-[(4-Oxo-4,5,6,7-tetrahydroindol-2-yl)methylene]-3-(2-thienyl)-2-pyrazolin-5-one,
4-[(4-Dimethylaminomethyl-5-methylpyrrol-2-yl)methylene]-3-(2-thienyl)-2-pyrazolin-5-one,
4-[(4-Bromopyrrol-2-yl)methylene]-3-(2-thienyl)-2-pyrazolin-5-one,
4-[(4-Chloropyrrol-2-yl)methylene]-3-(2-thienyl)-2-pyrazolin-5-one,
4-[(5-Chloropyrrol-2-yl)methylene]-3-(2-thienyl)-2-pyrazolin-5-one,
3-(2-Thienyl)-4-[(5-trifluoromethylpyrrol-2-yl)methylene]-2-pyrazolin-5-one,
4-[(4-Ethoxycarbonylpyrrol-2-yl)methylene]-3-(2-thienyl)-2-pyrazolin-5-one,
4-[4-(2-Dimethylaminoethoxycarbonylpyrrol-2-yl)methylene]-3-(2-thienyl)-2-pyrazolin-5-one,
4-[4-(2-Dimethylaminoethylaminocarbonylpyrrol-2-yl)methylene]-3-(2-thienyl)-2-pyrazolin-5-one,
4-[(3-Ethoxycarbonylindol-2-yl)methylene]-3-(2-thienyl)-2-pyrazolin-5-one,
4-[3-(2-Dimethylaminoethoxycarbonylindol-2-yl)methylene]-3-(2-thienyl)-2-pyrazolin-5-one,
4-[3-(2-Dimethylaminoethylaminocarbonylindol-2-yl)methylene]-3-(2-thienyl)-2-pyrazolin-5-one,
4-[4-(4-Morpholinoethoxycarbonylpyrrol-2-yl)methylene]-3-(2-thienyl)-2-pyrazolin-5-one,
4-[4-(4-Morpholinoethylaminocarbonylpyrrol-2-yl)methylene]-3-(2-thienyl)-2-pyrazolin-5-one,
4-[3-(4-Morpholinoethoxycarbonylindol-2-yl)methylene]-3-(2-thienyl)-2-pyrazolin-5-one,
4-[3-(4-Morpholinoethylaminocarbonylindol-2-yl)methylene]-3-(2-thienyl)-2-pyrazolin-5-one,
4-[(3,5-Dimethyl-4-ethylpyrrol-2-yl)methylene]-3-(2-thienyl)-2-pyrazolin-5-one,
4-[(1-Methylindol-3-yl)methylene]-3-(2-thienyl)-2-pyrazolin-5-one, 4-[3,5-Dimethyl-4-ethoxycarbonylpyrrol-2-yl)methylene]-3-(2-thienyl)-2-pyrazolin-5-one,
4-[(5-Methoxyindol-2-yl)methylene]-3-(2-thienyl)-2-pyrazolin-5-one,
4-[(4,5-Tetramethylenepyrrol-2-yl)methylene]-3-(2-thienyl)-2-pyrazolin-5-one,
4-{[3,5-Dimethyl-4-(2-dimethylaminoethoxycarbonyl)pyrrol-2-yl]methylene}-3-(2-thienyl)-2-pyrazolin-5-one,
4-{[3,5-Dimethyl-4-(2-dimethylaminoethylaminocarbonyl)pyrrol-2-yl]methylene}-3-(2-thienyl)-2-pyrazolin-5-one,
4-[(Indol-3-yl)methylene]-3-(2-thienyl)-2-pyrazolin-5-one,
4-[(Pyrrol-2-yl)methylene]-3-(2-thienyl)-2-pyrazolin-5-one,
4-[(Indol-2-yl)methylene]-3-(2-thienyl)-2-pyrazolin-5-one,
4-[(3,4-Diethoxycarbonylpyrrol-2-yl)methylene]-3-(2-thienyl)-2-pyrazolin-5-one,
4-{[3-(2-Acetamido-2-methoxycarbonylethyl)indol-2-yl]methylene}-3-(2-thienyl)-2-pyrazolin-5-one,
4-{[3-(2-Amino-2-carboxyethyl)indol-2-yl]methylene}-3-(2-thienyl)-2-pyrazolin-5-one,
4-[(5-Ethoxy-4-methoxycarbonylmethyl-3-methoxycarbonylpyrrol-2-yl)methylene]-3-(2-thienyl)-2-pyrazolin-5-one,
4-[(5-Chloro-4-methoxycarbonylmethyl-3-methoxycarbonylpyrrol-2-yl)methylene]-3-(2-thienyl)-2-pyrazolin-5-one,
4-[(4-Bromopyrrol-2-yl)methylene]-3-cyclopropoxy-2-pyrazolin-5-one,
4-[(4-Chloropyrrol-2-yl)methylene]-3-cyclopropoxy-2-pyrazolin-5-one,
4-[(5-Chloropyrrol-2-yl)methylene]-3-cyclopropoxy-2-pyrazolin-5-one,
3-Cyclopropoxy-4-[(5-trifluoromethylpyrrol-2-yl)methylene]-2-pyrazolin-5-one,
3-Cyclopropoxy-4-[(4-ethoxycarbonylpyrrol-2-yl)methylene]-2-pyrazolin-5-one,
3-Cyclopropoxy-4-[4-(2-dimethylaminoethoxycarbonylpyrrol-2-yl)methylene]-2-pyrazolin-5-one,
3-Cyclopropoxy-4-[4-(2-dimethylaminoethylaminocarbonylpyrrol-2-yl)methylene]-2-pyrazolin-5-one,
3-Cyclopropoxy-4-[(3-ethoxycarbonylindol-2-yl)methylene]-2-pyrazolin-5-one,
3-Cyclopropoxy-4-[3-(2-dimethylaminoethoxycarbonylindol-2-yl)methylene]-2-pyrazolin-5-one,
3-Cyclopropoxy-4-[3-(2-dimethylaminoethylaminocarbonylindol-2-yl)methylene]-2-pyrazolin-5-one,
3-Cyclopropoxy-4-[4-(4-morpholinoethoxycarbonylpyrrol-2-yl)methylene]-2-pyrazolin-5-one,
3-Cyclopropoxy-4-[4-(4-morpholinoethylaminocarbonylpyrrol-2-yl)methylene]-2-pyrazolin-5-one,
3-Cyclopropoxy-4-[3-(4-morpholinoethoxycarbonylindol-2-yl)methylene]-2-pyrazolin-5-one,
3-Cyclopropoxy-4-[3-(4-morpholinoethylaminocarbonylindol-2-yl)methylene]-2-pyrazolin-5-one,
3-Cyclopropoxy-4-[(3,5-dimethyl-4-ethylpyrrol-2-yl)methylene]-2-pyrazolin-5-one,
3-Cyclopropoxy-4-[(1-methylindol-3-yl)methylene]-2-pyrazolin-5-one,
3-Cyclopropoxy-4-[3,5-dimethyl-4-ethoxycarbonylpyrrol-2-yl)methylene]-2-pyrazolin-5-one,
3-Cyclopropoxy-4-[(5-methoxyindol-2-yl)methylene]-2-pyrazolin-5-one,
3-Cyclopropoxy-4-[(4,5-tetramethylenepyrrol-2-yl)methylene]-2-pyrazolin-5-one,
3-Cyclopropoxy-4-{[3,5-dimethyl-4-(2-dimethylaminoethoxycarbonyl)pyrrol-2-yl]methylene}-2-pyrazolin-5-one,
3-Cyclopropoxy-4-{[3,5-Dimethyl-4-(2-dimethylaminoethylaminocarbonyl)pyrrol-2-yl)methylene]-2-pyrazolin-5-one,
3-Cyclopropoxy-4-[(indol-3-yl)methylene]-2-pyrazolin-5-one,
3-Cyclopropoxy-4-[(pyrrol-2-yl)methylene]-2-pyrazolin-5-one,
3-Cyclopropoxy-4-[(Indol-2-yl)methylene]-2-pyrazolin-5-one,
3-Cyclopropoxy-4-[(3,4-diethoxycarbonylpyrrol-2-yl)methylene]-2-pyrazolin-5-one,
4-{[3-(2-Acetamido-2-methoxycarbonylethyl)indol-2-yl]methylene}-3-cyclopropoxy-2-pyrazolin-5-one,
4-{[3-(2-Amino-2-carboxyethyl)indol-2-yl]methylene}-3-cyclopropoxy-2-pyrazolin-5-one,
3-Cyclopropoxy-4-[(5-Ethoxy-4-methoxycarbonylmethyl-3-methoxycarbonylpyrrol-2-yl)methylene]-2-pyrazolin-5-one,
4-[(5-Chloro-4-methoxycarbonylmethyl-3-methoxycarbonylpyrrol-2-yl)methylene]-3-cyclopropoxy-2-pyrazolin-5-one,
4-[(4-Bromopyrrol-2-yl)methylene]-3-[2-(5-pyrimidinylethyl)]-2-pyrazolin-5-one,
4-[(4-Chloropyrrol-2-yl)methylene]-3-[2-(5-pyrimidinylethyl)]-2-pyrazolin-5-one,
4-[(5-Chloropyrrol-2-yl)methylene]-3-[2-(5-pyrimidinylethyl)]-2-pyrazolin-5-one,
3-[2-(5-pyrimidinylethyl)]-4-[(5-trifluoromethylpyrrol-2-yl)methylene]-2-pyrazolin-5-one,
4-[(4-Ethoxycarbonylpyrrol-2-yl)methylene]-3-[2-(5-pyrimidinylethyl)]-2-pyrazolin-5-one,
4-[4-(2-Dimethylaminoethoxycarbonylpyrrol-2-yl)methylene]-3-[2-(5-pyrimidinylethyl)]-2-pyrazolin-5-one,
4-[4-(2-Dimethylaminoethylaminocarbonylpyrrol-2-yl)methylene]-3-[2-(5-pyrimidinylethyl)]-2-pyrazolin-5-one,
4-[(3-Ethoxycarbonylindol-2-yl)methylene]-3-[2-(5-pyrimidinylethyl)]-2-pyrazolin-5-one,
4-[3-(2-Dimethylaminoethoxycarbonylindol-2-yl)methylene]-3-[2-(5-pyrimidinylethyl)]-2-pyrazolin-5-one,
4-[3-(2-Dimethylaminoethylaminocarbonylindol-2-yl)methylene]-3-[2-(5-pyrimidinylethyl)]-2-pyrazolin-5-one,
4-[4-(4-Morpholinoethoxycarbonylpyrrol-2-yl)methylene]-3-[2-(5-pyrimidinylethyl)]-2-pyrazolin-5-one,
4-[4-(4-Morpholinoethylaminocarbonylpyrrol-2-yl)methylene]-3-[2-(5-pyrimidinylethyl)]-2-pyrazolin-5-one,
4-[3-(4-Morpholinoethoxycarbonylindol-2-yl)methylene]-3-[2-(5-pyrimidinylethyl)]-2-pyrazolin-5-one,
4-[3-(4-Morpholinoethylaminocarbonylindol-2-yl)methylene]-3-[2-(5-pyrimidinylethyl)]-2-pyrazolin-5-one,
4-[(3,5-Dimethyl-4-ethylpyrrol-2-yl)methylene]-3-[2-(5-pyrimidinylethyl)]-2-pyrazolin-5-one,
4-[(1-Methylindol-3-yl)methylene]-3-[2-(5-pyrimidinylethyl)]-2-pyrazolin-5-one,
4-[3,5-Dimethyl-4-ethoxycarbonylpyrrol-2-yl)methylene]-3-[2-(5-pyrimidinylethyl)]-2-pyrazolin-5-one,
4-[(5-Methoxyindol-2-yl)methylene]-3-[2-(5-pyrimidinylethyl)]-2-pyrazolin-5-one,
3-[2-(5-pyrimidinylethyl)]-4-[(4,5-tetramethylenepyrrol-2-yl)methylene]-2-pyrazolin-5-one,
4-{[3,5-Dimethyl-4-(2-dimethylaminoethoxycarbonyl)pyrrol-2-yl]methylene}-3-[2-(5-pyrimidinylethyl)]-2-pyrazolin-5-one,
4-{[3,5-Dimethyl-4-(2-dimethylaminoethylaminocarbonyl)pyrrol-2-yl]methylene}-3-[2-(5-pyrimidinylethyl)]-2-pyrazolin-5-one,
4-[(Indol-3-yl)methylene]-3-[2-(5-pyrimidinylethyl)]-2-pyrazolin-5-one, 3-[2-(5-pyrimidinylethyl)]-4-[(pyrrol-2-yl)methylene]-2-pyrazolin-5-one,
4-[(Indol-2-yl)methylene]-3-[2-(5-pyrimidinylethyl)]-2-pyrazolin-5-one,
4-[(3,4-Diethoxycarbonylpyrrol-2-yl)methylene]-3-[2-(5-pyrimidinylethyl)]-2-pyrazolin-5-one,
4-{[3-(2-Acetamido-2-methoxycarbonylethyl)indol-2-yl]methylene}-3-[2-(5-pyrimidinylethyl)]-2-pyrazolin-5-one,
4-{[3-(2-Amino-2-carboxyethyl)indol-2-yl]methylene}-3-[2-(5-pyrimidinylethyl)]-2-pyrazolin-5-one,
4-[(5-Ethoxy-4-methoxycarbonylmethyl-3-methoxycarbonylpyrrol-2-yl)methylene]-3-[2-(5-pyrimidinylethyl)]-2-pyrazolin-5-one,
4-[(5-Chloro-4-methoxycarbonylmethyl-3-methoxycarbonylpyrrol-2-yl)methylene]-3-[2-(5-pyrimidinylethyl)]-2-pyrazolin-5-one,
4-[(4-Bromopyrrol-2-yl)methylene]-3-(2-phenylethyl)-2-pyrazolin-5-one,
4-[(4-Chloropyrrol-2-yl)methylene]-3-(2-phenylethyl)-2-pyrazolin-5-one,
4-[(5-Chloropyrrol-2-yl)methylene]-3-(2-phenylethyl)-2-pyrazolin-5-one,
3-(2-phenylethyl)-4-[(5-trifluoromethylpyrrol-2-yl)methylene]-2-pyrazolin-5-one,
4-[(4-Ethoxycarbonylpyrrol-2-yl)methylene]-3-(2-phenylethyl)-2-pyrazolin-5-one,
4-[4-(2-Dimethylaminoethoxycarbonylpyrrol-2-yl)methylene]-3-(2-phenylethyl)-2-pyrazolin-5-one,
4-[4-(2-Dimethylaminoethylaminocarbonylpyrrol-2-yl)methylene]-3-(2-phenylethyl)-2-pyrazolin-5-one,
4-[(3-Ethoxycarbonylindol-2-yl)methylene]-3-(2-phenylethyl)-2-pyrazolin-5-one,
4-[3-(2-Dimethylaminoethoxycarbonylindol-2-yl)methylene]-3-(2-phenylethyl)-2-pyrazolin-5-one,
4-[3-(2-Dimethylaminoethylaminocarbonylindol-2-yl)methylene]-3-(2-phenylethyl)-2-pyrazolin-5-one,
4-[4-(4-Morpholinoethoxycarbonylpyrrol-2-yl)methylene]-3-(2-phenylethyl)-2-pyrazolin-5-one,
4-[4-(4-Morpholinoethylaminocarbonylpyrrol-2-yl)methylene]-3-(2-phenylethyl)-2-pyrazolin-5-one,
4-[3-(4-Morpholinoethoxycarbonylindol-2-yl)methylene]-3-(2-phenylethyl)-2-pyrazolin-5-one,
4-[3-(4-Morpholinoethylaminocarbonylindol-2-yl)methylene]-3-(2-phenylethyl)-2-pyrazolin-5-one,
4-[(1-Methylindol-3-yl)methylene]-3-(2-phenylethyl)-2-pyrazolin-5-one,
4-[3,5-Dimethyl-4-ethoxycarbonylpyrrol-2-yl)methylene]-3-(2-phenylethyl)-2-pyrazolin-5-one,
4-[(5-Methoxyindol-2-yl)methylene]-3-(2-phenylethyl)-2-pyrazolin-5-one,
3-(2-phenylethyl)-4-[(4,5-tetramethylenepyrrol-2-yl)methylene]-2-pyrazolin-5-one,
4-{[3,5-Dimethyl-4-(2-dimethylaminoethoxycarbonyl)pyrrol-2-yl]methylene}-3-(2-phenylethyl)-2-pyrazolin-5-one,
4-{[3,5-Dimethyl-4-(2-dimethylaminoethylaminocarbonyl)pyrrol-2-yl)methylene]-3-(2-phenylethyl)-2-pyrazolin-5-one,
4-[(Indol-2-yl)methylene]-3-(2-phenylethyl)-2-pyrazolin-5-one,
4-[(3,4-Diethoxycarbonylpyrrol-2-yl)methylene]-3-(2-phenylethyl)-2-pyrazolin-5-one,
4-{[3-(2-Acetamido-2-methoxycarbonylethyl)indol-2-yl]methylene}-3-(2-phenylethyl)-2-pyrazolin-5-one,
4-{[3-(2-Amino-2-carboxyethyl)indol-2-yl]methylene}-3-(2-phenylethyl)-2-pyrazolin-5-one,
4-[(5-Ethoxy-4-methoxycarbonylmethyl-3-methoxycarbonylpyrrol-2-yl)methylene]-3-(2-phenylethyl)-2-pyrazolin-5-one,
4-[(5-Chloro-4-methoxycarbonylmethyl-3-methoxycarbonylpyrrol-2-yl)methylene]-3-(2-phenylethyl)-2-pyrazolin-5-one,
4-[(4-Bromopyrrol-2-yl)methylene]-3-[2-(4-hydroxyphenyl)ethyl]-2-pyrazolin-5-one,
4-[(4-Chloropyrrol-2-yl)methylene]-3-[2-(4-hydroxyphenyl)ethyl]-2-pyrazolin-5-one,
4-[(5-Chloropyrrol-2-yl)methylene]-3-[2-(4-hydroxyphenyl)ethyl]-2-pyrazolin-5-one,
3-[2-(4-hydroxyphenyl)ethyl]-4-[(5-trifluoromethylpyrrol-2-yl)methylene]-2-pyrazolin-5-one,
4-[(4-Ethoxycarbonylpyrrol-2-yl)methylene]-3-[2-(4-hydroxyphenyl)ethyl]-2-pyrazolin-5-one,
4-[4-(2-Dimethylaminoethoxycarbonylpyrrol-2-yl)methylene]-3-[2-(4-hydroxyphenyl)ethyl]-2-pyrazolin-5-one,
4-[4-(2-Dimethylaminoethylaminocarbonylpyrrol-2-yl)methylene]-3-[2-(4-hydroxyphenyl)ethyl]-2-pyrazolin-5-one,
4-[(3-Ethoxycarbonylindol-2-yl)methylene]-3-[2-(4-hydroxyphenyl)ethyl]-2-pyrazolin-5-one,
4-[3-(2-Dimethylaminoethoxycarbonylindol-2-yl)methylene]-3-[2-(4-hydroxyphenyl)ethyl]-2-pyrazolin-5-one,
4-[3-(2-Dimethylaminoethylaminocarbonylindol-2-yl)methylene]-3-[2-(4-hydroxyphenyl)ethyl]-2-pyrazolin-5-one,
3-[2-(4-hydroxyphenyl)ethyl]-4-[4-(4-morpholinoethoxycarbonylpyrrol-2-yl)methylene]-2-pyrazolin-5-one,
3-[2-(4-hydroxyphenyl)ethyl]-4-[4-(4-morpholinoethylaminocarbonylpyrrol-2-yl)methylene]-2-pyrazolin-5-one,
3-[2-(4-hydroxyphenyl)ethyl]-4-[3-(4-morpholinoethoxycarbonylindol-2-yl)methylene]-2-pyrazolin-5-one,
3-[2-(4-hydroxyphenyl)ethyl]-4-[3-(4-morpholinoethylaminocarbonylindol-2-yl)methylene]-2-pyrazolin-5-one,
4-[3,5-Dimethyl-4-ethoxycarbonylpyrrol-2-yl)methylene]-3-[2-(4-hydroxyphenyl)ethyl]-2-pyrazolin-5-one,
3-[2-(4-hydroxyphenyl)ethyl]-4-[(5-methoxyindol-2-yl)methylene]-2-pyrazolin-5-one,
3-[2-(4-hydroxyphenyl)ethyl]-4-[(4,5-tetramethylenepyrrol-2-yl)methylene]-2-pyrazolin-5-one,
4-{[3,5-Dimethyl-4-(2-dimethylaminoethoxycarbonyl)pyrrol-2-yl]methylene}-3-[2-(4-hydroxyphenyl)ethyl]-2-pyrazolin-5-one,
4-{[3,5-Dimethyl-4-(2-dimethylaminoethylaminocarbonyl)pyrrol-2-yl)methylene]-3-[2-(4-hydroxyphenyl)ethyl]-2-pyrazolin-5-one,
4-[(3,4-Diethoxycarbonylpyrrol-2-yl)methylene]-3-[2-(4-hydroxyphenyl)ethyl]-2-pyrazolin-5-one,
4-{[3-(2-Acetamido-2-methoxycarbonylethyl)indol-2-yl]methylene}-3-[2-(4-hydroxyphenyl)ethyl]-2-pyrazolin-5-one,
4-{[3-(2-Amino-2-carboxyethyl)indol-2-yl]methylene}-3-[2-(4-hydroxyphenyl)ethyl]-2-pyrazolin-5-one,
4-[(5-Ethoxy-4-methoxycarbonylmethyl-3-methoxycarbonylpyrrol-2-yl)methylene]-3-[2-(4-hydroxyphenyl)ethyl]-2-pyrazolin-5-one,
4-[(5-Chloro-4-methoxycarbonylmethyl-3-methoxycarbonylpyrrol-2-yl)methylene]-3-[2-(4-hydroxyphenyl)ethyl]-2-pyrazolin-5-one,
3-[2-(4-aminophenyl)ethyl]-4-[(4-bromopyrrol-2-yl)methylene]-2-pyrazolin-5-one,
3-[2-(4-aminophenyl)ethyl]-4-[(4-chloropyrrol-2-yl)methylene]-2-pyrazolin-5-one,
3-[2-(4-aminophenyl)ethyl]-4-[(5-chloropyrrol-2-yl)methylene]-2-pyrazolin-5-one, 3-[2-(4-aminophenyl)ethyl]-4-[(5-trifluoromethylpyrrol-2-yl)methylene]-2-pyrazolin-5-one,
3-[2-(4-aminophenyl)ethyl]-4-[(4-ethoxycarbonylpyrrol-2-yl)methylene]-2-pyrazolin-5-one,
3-[2-(4-aminophenyl)ethyl]-4-[4-(2-dimethylaminoethoxycarbonylpyrrol-2-yl)methylene]-2-pyrazolin-5-one,
3-[2-(4-aminophenyl)ethyl]-4-[4-(2-dimethylaminoethylaminocarbonylpyrrol-2-yl)methylene]-2-pyrazolin-5-one,
3-[2-(4-aminophenyl)ethyl]-4-[(3-ethoxycarbonylindol-2-yl)methylene]-2-pyrazolin-5-one,
3-[2-(4-aminophenyl)ethyl]-4-[3-(2-dimethylaminoethoxycarbonylindol-2-yl)methylene]-2-pyrazolin-5-one,
3-[2-(4-aminophenyl)ethyl]-4-[3-(2-dimethylaminoethylaminocarbonylindol-2-yl)methylene]-2-pyrazolin-5-one,
3-[2-(4-aminophenyl)ethyl]-4-[4-(4-morpholinoethoxycarbonylpyrrol-2-yl)methylene]-2-pyrazolin-5-one,
3-[2-(4-aminophenyl)ethyl]-4-[4-(4-morpholinoethylaminocarbonylpyrrol-2-yl)methylene]-2-pyrazolin-5-one,
3-[2-(4-aminophenyl)ethyl]-4-[3-(4-morpholinoethoxycarbonylindol-2-yl)methylene]-2-pyrazolin-5-one,
3-[2-(4-aminophenyl)ethyl]-4-[3-(4-morpholinoethylaminocarbonylindol-2-yl)methylene]-2-pyrazolin-5-one,
3-[2-(4-aminophenyl)ethyl]-4-[(5-methoxyindol-2-yl)methylene]-2-pyrazolin-5-one
3-[2-(4-aminophenyl)ethyl]-4-[(4,5-tetramethylenepyrrol-2-yl)methylene]-2-pyrazolin-5-one,
3-[2-(4-aminophenyl)ethyl]-4-{[3,5-dimethyl-4-(2-dimethylaminoethoxycarbonyl)pyrrol-2-yl]methylene}-2-pyrazolin-5-one,
3-[2-(4-aminophenyl)ethyl]-4-{[3,5-dimethyl-4-(2-dimethylaminoethylamino carbonyl)pyrrol-2-yl]methylene}-2-pyrazolin-5-one,
3-[2-(4-aminophenyl)ethyl]-4-[(pyrrol-2-yl)methylene]-2-pyrazolin-5-one,
3-[2-(4-aminophenyl)ethyl]-4-[(Indol-2-yl)methylene]-2-pyrazolin-5-one,
3-[2-(4-aminophenyl)ethyl]-4-[(3,4-diethoxycarbonylpyrrol-2-yl)methylene]-2-pyrazolin-5-one,
4-{[3-(2-Acetamido-2-methoxycarbonylethyl)indol-2-yl]methylene}-3-[2-(4-aminophenyl)ethyl]-2-pyrazolin-5-one,
4-{[3-(2-Amino-2-carboxyethyl)indol-2-yl]methylene}-3-[2-(4-aminophenyl)ethyl]-2-pyrazolin-5-one,
3-[2-(4-aminophenyl)ethyl]-4-[(5-ethoxy-4-methoxycarbonylmethyl-3-methoxycarbonylpyrrol-2-yl)methylene]-2-pyrazolin-5-one,
3-[2-(4-aminophenyl)ethyl]-4-[(5-chloro-4-methoxycarbonylmethyl-3-methoxycarbonylpyrrol-2-yl)methylene]-2-pyrazolin-5-one,
4-[(3,5-Dimethyl-4-morpholinomethylpyrrol-2-yl)methylene]-3-(4-pyrimidinyl)-2-pyrazolin-5-one,
4-[(3,5-Dimethyl-4-{[(4-methyl-1-piperazinylmethyl)pyrrol-2-yl]methylene}-3-(4-pyrimidinyl)-2-pyrazolin-5-one,
4-[(3,5-Dimethyl-4-(1-pyrrolidinylmethylpyrrol-2-yl)methylene]-3-(4-pyrimidinyl)-2-pyrazolin-5-one,
4-[(4-Diethylaminomethyl-3,5-dimethylpyrrol-2-yl)methylene]-3-(4-pyrimidinyl)-2-pyrazolin-5-one,
4-[(3,5-Dimethyl-4-(piperidinomethylpyrrol-2-yl)methylene]-3-(4-pyrimidinyl)-2-pyrazolin-5-one,
4-[(4-Diethanolaminomethyl-3,5-dimethylpyrrol-2-yl)methylene]-3-(4-pyrimidinyl)-2-pyrazolin-5-one,
4-[(3-Dimethylaminomethyl-4,5-tetramethylenepyrrol-2-yl)methylene]-3-(4-pyrimidinyl)-2-pyrazolin-5-one,
4-[(3-Morpholinomethyl-4,5-tetramethylenepyrrol-2-yl)methylene]-3-(4-pyrimidinyl)-2-pyrazolin-5-one,
4-[(3-Diethylaminomethyl-4,5-tetramethylenepyrrol-2-yl)methylene]-3-(4-pyrimidinyl)-2-pyrazolin-5-one,
4-{[3-(4-Methyl-1-piperazinyl)methyl-4,5-tetramethylenepyrrol-2-yl]methylene}-3-(4-pyrimidinyl)-2-pyrazolin-5-one,
3-(4-Pyrimidinyl)-4-{[3-(1-pyrrolidinyl)methyl-4,5-tetramethylenepyrrol-2-yl]methylene}-2-pyrazolin-5-one,
4-[(3-Piperidinomethyl-4,5-tetramethylenepyrrol-2-yl)methylene]-3-(4-pyrimidinyl)-2-pyrazolin-5-one,
4-[(4-Dimethylamino-4,5,6,7-tetrahydroindol-2-yl)methylene]-3-(4-pyrimidinyl)pyrazolin-5-one,
4-[(4-Diethylaminoethyl-3,5-dimethylpyrrol-2-yl)methylene]-3-(4-pyrimidinyl)-2-pyrazolin-5-one,
4-(3,5-Dibromo-4-hydroxybenzylidene)-3-(4-pyrimidinyl)-2-pyrazolin-5-one,
4-[(3,5-Dimethyl-4-dimethylaminomethylpyrrol-2-yl)methylene]-3-(4-pyrimidinyl)-2-pyrazolin-5-one,
4-[(4-Oxo-1,5,6,7-tetrahydroindol-2-yl)methylene]-3-(4-pyrimidinyl)-2-pyrazolin-5-one,
4-[(4-Dimethylaminomethyl-5-methylpyrrol-2-yl)methylene]-3-(4-pyrimidinyl)-2-pyrazolin-5-one,
4-[(3,5-Dimethyl-4-morpholinomethylpyrrol-2-yl)methylene]-3-(5-pyrimidinyl)-2-pyrazolin-5-one,
4-[(3,5-Dimethyl-4-{[(4-methyl-1-piperazinylmethyl)pyrrol-2-yl]methylene}-3-(5-pyrimidinyl)-2-pyrazolin-5-one,
4-[(3,5-Dimethyl-4-(1-pyrrolidinylmethylpyrrol-2-yl)methylene]-3-(5-pyrimidinyl)-2-pyrazolin-5-one,
4-[(3,5-Dimethyl-4-diethylaminomethylpyrrol-2-yl)methylene]-3-(5-pyrimidinyl)-2-pyrazolin-5-one,
4-[(3,5-Dimethyl-4-(piperidinomethylpyrrol-2-yl)methylene]-3-(5-pyrimidinyl)-2-pyrazolin-5-one,
4-[(4-Diethanolaminomethyl-3,5-dimethylpyrrol-2-yl)methylene]-3-(5-pyrimidinyl)-2-pyrazolin-5-one,
4-[(3-Dimethylaminomethyl-4,5-tetramethylenepyrrol-2-yl)methylene]-3-(5-pyrimidinyl)-2-pyrazolin-5-one,
4-[(3-Morpholinomethyl-4,5-tetramethylenepyrrol-2-yl)methylene]-3-(5-pyrimidinyl)-2-pyrazolin-5-one,
4-[(3-Diethylaminomethyl-4,5-tetramethylenepyrrol-2-yl)methylene]-3-(5-pyrimidinyl)-2-pyrazolin-5-one,
4-{[3-(4-Methyl-1-piperazinyl)methyl-4,5-tetramethylenepyrrol-2-yl]methylene}-3-(5-pyrimidinyl)-2-pyrazolin-5-one,
3-(5-Pyrimidinyl)-4-{[3-(1-pyrrolidinyl)methyl-4,5-tetramethylenepyrrol-2-yl]methylene}-2-pyrazolin-5-one,
4-[(3-Piperidinomethyl-4,5-tetramethylenepyrrol-2-yl)methylene]-3-(5-pyrimidinyl)-2-pyrazolin-5-one,
4-[(4-Dimethylamino-4,5,6,7-tetrahydroindol-2-yl)methylene]-3-(5-pyrimidinyl)-2-pyrazolin-5-one,
4-[(4-Diethylaminoethyl-3,5-dimethylpyrrol-2-yl)methylene]-3-(5-pyrimidinyl)-2-pyrazolin-5-one,
4-(3,5-Dibromo-4-hydroxybenzylidene)-3-(5-pyrimidinyl)-2-pyrazolin-5-one,
4-[(3,5-Dimethyl-4-dimethylaminomethylpyrrol-2-yl)methylene]-3-(5-pyrimidinyl)-2-pyrazolin-5-one,
4-[(4-Oxo-1,5,6,7-tetrahydroindol-2-yl)methylene]-3-(5-pyrimidinyl)-2-pyrazolin-5-one,
4-[(4-Dimethylaminomethyl-5-methylpyrrol-2-yl)methylene]-3-(5-pyrimidinyl)-2-pyrazolin-5-one,
4-[(3,5-Dimethyl-4-morpholinomethylpyrrol-2-yl)methylene]-3-(2-pyrimidinyl)-2-pyrazolin-5-one,
4-[(3,5-Dimethyl-4-{[(4-methyl-1-piperazinylmethyl)pyrrol-2-yl]methylene}-3-(2-pyrimidinyl)-2-pyrazolin-5-one, 4-[(3,5-Dimethyl-4-(1-pyrrolidinylmethylpyrrol-2-yl)methylene]-3-(2-pyrimidinyl)-2-pyrazolin-5-one,
4-[(4-Diethylaminomethyl-3,5-dimethylpyrrol-2-yl)methylene]-3-(2-pyrimidinyl)-2-pyrazolin-5-one,
4-[(3,5-Dimethyl-4-(piperidinomethylpyrrol-2-yl)methylene]-3-(2-pyrimidinyl)-2-pyrazolin-5-one,
4-[(4-Diethanolaminomethyl-3,5-dimethylpyrrol-2-yl)methylene]-3-(2-pyrimidinyl)-2-pyrazolin-5-one,
4-[(3-Dimethylaminomethyl-4,5-tetramethylenepyrrol-2-yl)methylene]-3-(2-pyrimidinyl)-2-pyrazolin-5-one,
4-[(3-Morpholinomethyl-4,5-tetramethylenepyrrol-2-yl)methylene]-3-(2-pyrimidinyl)-2-pyrazolin-5-one,
4-[(3-Diethylaminomethyl-4,5-tetramethylenepyrrol-2-yl)methylene]-3-(2-pyrimidinyl)-2-pyrazolin-5-one,
4-{[3-(4-Methyl-1-piperazinyl)methyl-4,5-tetramethylenepyrrol-2-yl]methylene}-3-(2-pyrimidinyl)-2-pyrazolin-5-one,
3-(2-Pyrimidinyl)-4-{[3-(1-pyrrolidinyl)methyl-4,5-tetramethylenepyrrol-2-yl]methylene}-2-pyrazolin-5-one,
4-[(3-Piperidinomethyl-4,5-tetramethylenepyrrol-2-yl)methylene]-3-(2-pyrimidinyl)-2-pyrazolin-5-one,
4-[(4-Dimethylamino-4,5,6,7-tetrahydroindol-2-yl)methylene]-3-(2-pyrimidinyl)-2-pyrazolin-5-one,
4-[(4-Diethylaminoethyl-3,5-dimethylpyrrol-2-yl)methylene]-3-(2-pyrimidinyl)-2-pyrazolin-5-one,
4-(3,5-Dibromo-4-hydroxybenzylidene)-3-(2-pyrimidinyl)-2-pyrazolin-5-one,
4-[(3,5-Dimethyl-4-dimethylaminomethylpyrrol-2-yl)methylene]-3-(2-pyrimidinyl)-2-pyrazolin-5-one,
4-[(4-Oxo-1,5,6,7-tetrahydroindol-2-yl)methylene]-3-(2-pyrimidinyl)-2-pyrazolin-5-one,
4-[(4-Dimethylaminomethyl-5-methylpyrrol-2-yl)methylene]-3-(2-pyrimidinyl)-2-pyrazolin-5-one,
4-[(3,5-Dimethyl-4-morpholinomethylpyrrol-2-yl)methylene]-3-(3-pyridazinyl)-2-pyrazolin-5-one,
4-[(3,5-Dimethyl-4-{[(4-methyl-1-piperazinylmethyl)pyrrol-2-yl]methylene}-3-(3-pyridazinyl)-2-pyrazolin-5-one,
4-[(3,5-Dimethyl-4-(1-pyrrolidinylmethylpyrrol-2-yl)methylene]-3-(3-pyridazinyl)-2-pyrazolin-5-one,
4-[(4-Diethylaminomethyl-3,5-dimethylpyrrol-2-yl)methylene]-3-(3-pyridazinyl)-2-pyrazolin-5-one,
4-[(3,5-Dimethyl-4-piperidinomethylpyrrol-2-yl)methylene]-3-(3-pyridazinyl)-2-pyrazolin-5-one,
4-[(4-Diethanolaminomethyl-3,5-dimethylpyrrol-2-yl)methylene]-3-(3-pyridazinyl)-2-pyrazolin-5-one,
4-[(3-Dimethylaminomethyl-4,5-tetramethylenepyrrol-2-yl)methylene]-3-(3-pyridazinyl)-2-pyrazolin-5-one,
4-[(3-Morpholinomethyl-4,5-tetramethylenepyrrol-2-yl)methylene]-3-(3-pyridazinyl)-2-pyrazolin-5-one,
4-[(3-Diethylaminomethyl-4,5-tetramethylenepyrrol-2-yl)methylene]-3-(3-pyridazinyl)-2-pyrazolin-5-one,
4-{[3-(4-Methyl-1-piperazinyl)methyl-4,5-tetramethylenepyrrol-2-yl]methylene}-3-(3-pyridazinyl)-2-pyrazolin-5-one,
3-(3-Pyridazinyl)-4-{[3-(1-pyrrolidinyl)methyl-4,5-tetramethylenepyrrol-2-yl]methylene}-2-pyrazolin-5-one,
4-[(3-Piperidinomethyl-4,5-tetramethylenepyrrol-2-yl)methylene]-3-(3-pyridazinyl)-2-pyrazolin-5-one,
4-[(4-Dimethylamino-4,5,6,7-tetrahydroindol-2-yl)methylene]-3-(3-pyridazinyl)-2-pyrazolin-5-one,
4-[(4-Diethylaminoethyl-3,5-dimethylpyrrol-2-yl)methylene]-3-(3-pyridazinyl)-2-pyrazolin-5-one,
4-(3,5-Dibromo-4-hydroxybenzylidene)-3-(3-pyridazinyl)-2-pyrazolin-5-one,
4-[(3,5-Dimethyl-4-dimethylaminomethylpyrrol-2-yl)methylene]-3-(3-pyridazinyl)-2-pyrazolin-5-one,
4-[(4-Oxo-1,5,6,7-tetrahydroindol-2-yl)methylene]-3-(3-pyridazinyl)-2-pyrazolin-5-one,
4-[(4-Dimethylaminomethyl-5-methylpyrrol-2-yl)methylene]-3-(3-pyridazinyl)-2-pyrazolin-5-one,
4-[(3,5-Dimethyl-4-morpholinomethylpyrrol-2-yl)methylene]-3-(4-pyridazinyl)-2-pyrazolin-5-one,
4-[(3,5-Dimethyl-4-{[(4-methyl-1-piperazinylmethyl)pyrrol-2-yl]methylene}-3-(4-pyridazinyl)-2-pyrazolin-5-one,
4-[(3,5-Dimethyl-4-(1-pyrrolidinylmethylpyrrol-2-yl)methylene]-3-(4-pyridazinyl)-2-pyrazolin-5-one,
4-[(4-Diethylaminomethyl-3,5-dimethylpyrrol-2-yl)methylene]-3-(4-pyridazinyl)-2-pyrazolin-5-one,
4-[(3,5-Dimethyl-4-(piperidinomethylpyrrol-2-yl)methylene]-3-(4-pyridazinyl)-2-pyrazolin-5-one,
4-[(4-Diethanolaminomethyl-3,5-dimethyl-pyrrol-2-yl)methylene]-3-(4-pyridazinyl)-2-pyrazolin-5-one,
4-[(3-Dimethylaminomethyl-4,5-tetramethylenepyrrol-2-yl)methylene]-3-(4-pyridazinyl)-2-pyrazolin-5-one,
4-[(3-Morpholinomethyl-4,5-tetramethylenepyrrol-2-yl)methylene]-3-(4-pyridazinyl)-2-pyrazolin-5-one,
4-[(3-Diethylaminomethyl-4,5-tetramethylenepyrrol-2-yl)methylene]-3-(4-pyridazinyl)-2-pyrazolin-5-one,
4-{[3-(4-Methyl-1-piperazinyl)methyl-4,5-tetramethylenepyrrol-2-yl]methylene}-3-(4-pyridazinyl)-2-pyrazolin-5-one,
3-(4-Pyridazinyl)-4-{[3-(1-pyrrolidinyl)methyl-4,5-tetramethylenepyrrol-2-yl]methylene}-2-pyrazolin-5-one,
4-[(3-Piperidinomethyl-4,5-tetramethylenepyrrol-2-yl)methylene]-3-(4-pyridazinyl)-2-pyrazolin-5-one,
4-[(4-Dimethylamino-4,5,6,7-tetrahydroindol-2-yl)methylene]-3-(4-pyridazinyl)-2-pyrazolin-5-one,
4-[(4-Diethylaminoethyl-3,5-dimethylpyrrol-2-yl)methylene]-3-(4-pyridazinyl)-2-pyrazolin-5-one,
4-(3,5-Dibromo-4-hydroxybenzylidene)-3-(4-pyridazinyl)-2-pyrazolin-5-one,
4-[(3,5-Dimethyl-4-dimethylaminomethylpyrrol-2-yl)methylene]-3-(4-pyridazinyl)-2-pyrazolin-5-one,
4-[(4-Oxo-1,5,6,7-tetrahydroindol-2-yl)methylene]-3-(4-pyridazinyl)-2-pyrazolin-5-one,
4-[(4-Dimethylaminomethyl-5-methylpyrrol-2-yl)methylene]-3-(4-pyridazinyl)-2-pyrazolin-5-one,
4-[(3,5-Dimethyl-4-morpholinomethylpyrrol-2-yl)methylene]-3-(5-isoxazolyl)-2-pyrazolin-5-one,
4-[(3,5-Dimethyl-4-{[(4-methyl-1-piperazinylmethyl)pyrrol-2-yl]methylene}-3-(5-isoxazolyl)-2-pyrazolin-5-one,
4-[(3,5-Dimethyl-4-[(1-pyrrolidinylmethylpyrrol-2-yl)methylene]-3-(5-isoxazolyl)-2-pyrazolin-5-one,
4-[(4-Diethylaminomethyl-3,5-dimethylpyrrol-2-yl)methylene]-3-(5-isoxazolyl)-2-pyrazolin-5-one,
4-[(4-Diethanolaminomethyl-3,5-Dimethylpyrrol-2-yl)methylene]-3-(5-isoxazolyl)-2-pyrazolin-5-one,
4-[(3-Dimethylaminomethyl-4,5-tetramethylenepyrrol-2-yl)methylene]-3-(5-isoxazolyl)-2-pyrazolin-5-one,
3-(5-Isoxazolyl)-4-[(3-morpholinomethyl-4,5-tetramethylenepyrrol-2-yl)methylene]-2-pyrazolin-5-one,
4-[(3-Diethylaminomethyl-4,5-tetramethylenepyrrol-2-yl)methylene]-3-(5-isoxazolyl)-2-pyrazolin-5-one,
3-(5-Isoxazolyl)4-{[3-(4-methyl-1-piperazinyl)methyl-4,5-tetramethylenepyrrol-2-yl]methylene}--2-pyrazolin-5-one,
3-(5-isoxazolyl)-4-{[3-(1-pyrrolidinyl)methyl-4,5-tetramethylenepyrrol-2-yl]methylene}-2-pyrazolin-5-one,
3-(5-Isoxazolyl)-4-[(3-piperidinomethyl-4,5-tetramethylenepyrrol-2-yl)methylene]-2-pyrazolin-5-one,
4-[(4-Dimethylamino-4,5,6,7-tetrahydroindol-2-yl)methylene]-3-(5-isoxazolyl)-2-pyrazolin-5-one, 4-[(4-Diethylaminoethyl-3,5-dimethylpyrrol-2-yl)methylene]-3-(5-isoxazolyl)-2-pyrazolin-5-one,
4-(3,5-Dibromo-4-hydroxybenzylidene)-3-(5-isoxazolyl)-2-pyrazolin-5-one,
4-[(4-Oxo-1,5,6,7-tetrahydroindol-2-yl)methylene]-3-(5-isoxazolyl)-2-pyrazolin-5-one,
4-[(4-Dimethylaminomethyl-5-methylpyrrol-2-yl)methylene]-3-(5-isoxazolyl)-2-pyrazolin-5-one,
4-[(3,5-Dimethyl-4-morpholinomethylpyrrol-2-yl)methylene]-3-(5-methyl-3-isoxazolyl)-2-pyrazolin-5-one,
4-[(3,5-Dimethyl-4-{[(4-methyl-1-piperazinylmethyl)pyrrol-2-yl]methylene}-3-(5-methyl-3-isoxazolyl)-2-pyrazolin-5-one,
4-[(3,5-Dimethyl-4-[(1-pyrrolidinylmethylpyrrol-2-yl)methylene]-3-(5-methyl-3-isoxazolyl)-2-pyrazolin-5-one,
4-[(4-Diethylaminomethyl-3,5-dimethylpyrrol-2-yl)methylene]-3-(5-methyl-3-isoxazolyl)-2-pyrazolin-5-one,
4-[(3,5-Dimethyl-4-piperidinomethylpyrrol-2-yl)methylene]-3-(5-methyl-3-isoxazolyl)-2-pyrazolin-5-one,
4-[(4-Diethanolaminomethyl-3,5-dimethyl-pyrrol-2-yl)methylene]-3-(5-methyl-3-isoxazolyl)-2-pyrazolin-5-one,
4-[(3-Dimethylaminomethyl-4,5-tetramethylenepyrrol-2-yl)methylene]-3-(5-methyl-3-isoxazolyl)-2-pyrazolin-5-one,
3-(5-Methyl-3-isoxazolyl)-4-[(3-morpholinomethyl-4,5-tetramethylenepyrrol-2-yl)methylene]-2-pyrazolin-5-one,
4-[(3-Diethylaminomethyl-4,5-tetramethylenepyrrol-2-yl)methylene]-3-(5-methyl-3-isoxazolyl)-2-pyrazolin-5-one,
3-(5-Methyl-3-isoxazolyl)4-{[3-(4-methyl-1-piperazinyl)methyl-4,5-tetramethylenepyrrol-2-yl]methylene}-2-pyrazolin-5-one,
3-(5-Methyl-3-isoxazolyl)-4-{[3-(1-pyrrolidinyl)methyl-4,5-tetramethylenepyrrol-2-yl]methylene}-2-pyrazolin-5-one,
3-(5-Methyl-3-isoxazolyl)4-[(3-piperidinomethyl-4,5-tetramethylenepyrrol-2-yl)methylene]-2-pyrazolin-5-one,
4-[(4-Dimethylamino-4,5,6,7-tetrahydroindol-2-yl)methylene]-3-(5-methyl-3-isoxazolyl)-2-pyrazolin-5-one,
4-[(4-Diethylaminoethyl-3,5-dimethylpyrrol-2-yl)methylene]-3-(5-methyl-3-isoxazolyl)-2-pyrazolin-5-one,
4-(3,5-Dibromo-4-hydroxybenzylidene)-3-(5-methyl-3-isoxazolyl)-2-pyrazolin-5-one,
4-[(3,5-Dimethyl-4-dimethylaminomethylpyrrol-2-yl)methylene]-3-(5-methyl-3-isoxazolyl)-2-pyrazolin-5-one,
3-(5-Methyl-3-isoxazolyl)-4-[(4-oxo-1,5,6,7-tetrahydroindol-2-yl)methylene]-2-pyrazolin-5-one,
4-[(4-Dimethylaminomethyl-5-methylpyrrol-2-yl)methylene]-3-(5-methyl-3-isoxazolyl)-2-pyrazolin-5-one,
3-cyclopropyl-4-(1-3-[(dimethylamino)methyl]-4,5,6,7-tetrahydro-1H-2-indolylmethylidene)-4,5-dihydro-1H-5-pyrazolone,
3-cyclopropyl-4-(1-4-[(1,1-dimethylammonio)methyl]-3,5-dimethyl-1H-2-pyrrolylmethylidene)-4,5-dihydro-1H-5-pyrazolone maleate,
4-[1-(4-[[2-(dimethylamino)ethyl](methyl)amino]methyl-3,5-dimethyl-1H-2-pyrrolyl)methylidene]-3-(2-pyrazinyl)-4,5-dihydro-1H-5-pyrazolone
4-(1-4-[2-(diethylamino)ethyl]-3,5-dimethyl-1H-2-pyrrolylmethylidene)-3-(2-pyrazinyl)-4,5-dihydro-1H-5-pyrazolone,
4-1-[4-(3-chloropropanoyl)-3,5-dimethyl-1H-2-pyrrolyl]methylidene-3-(2-pyrazinyl)-4,5-dihydro-1H-5-pyrazolone,
4-(1-3-[(dimethylamino)methyl]-4,5,6,7-tetrahydro-1H-2-indolylmethylidene)-3-(2-pyrazinyl)-4,5-dihydro-1H-5-pyrazolone,
4-(1-4-[(dimethylamino)methyl]-3,5-dimethyl-1H-2-pyrrolylmethylidene)-3-(5-methyl-3-isoxazolyl)-4,5-dihydro-1H-5-pyrazolone,
3-Cyclopropyl-4-[(4,5-dimethylpyrrol-2-yl)methylene]-2-pyrazolin-5-one,
3-Benzyl-4-[(pyrrol-2-yl)methylene]-2-pyrazolin-5-one,
3-(4-Methoxyphenyloxymethyl)-4-[(pyrrol-2-yl)methylene]-2-pyrazolin-5-one,
3-Phenyloxymethyl-4-[(pyrrol-2-yl)methylene]-2-pyrazolin-5-one,
3-(4-Chlorophenyloxymethyl)-4-[(pyrrol-2-yl)methylene]-2-pyrazolin-5-one,
3-(4-Methoxybenzyl)-4-[(pyrrol-2-yl)methylene]-2-pyrazolin-5-one,
3-Benzyl-4-{[4-(2-carboxyethyl)-3-methylpyrrol-2-yl]methylene}-2-pyrazolin-5-one,
3-Benzyl-4-{[3-(2-carboxyethyl)-4-methylpyrrol-2-yl]methylene}-2-pyrazolin-5-one,
3-(4-Methylphenyloxymethyl)-4-[(pyrrol-2-yl)methylene]-2-pyrazolin-5-one,
2-Amino-4-[)pyrrol-2-yl)methylene]-2-pyrazolin-5-one,
3-Isopropoxy-4-[(pyrrol-2-yl)methylene]-2-pyrazolin-5-one,
3-Phenylethyl-4-[(pyrrol-2-yl)methylene]-2-pyrazolin-5-one,
3-Phenylamino-4-[(pyrrol-2-yl)methylene]-2-pyrazolin-5-one,
3-(4-Methylbenzyl)-4-[(pyrrol-2-yl)methylene]-2-pyrazolin-5-one,
3-(4-Methylphenylamino)-4-[(pyrrol-2-yl)methylene]-2-pyrazolin-5-one,
3-(4-Methoxyphenylamino)-4-[(pyrrol-2-yl)methylene]-2-pyrazolin-5-one,
3-(4-Chlorobenzyl)-4-[(pyrrol-2-yl)methylene]-2-pyrazolin-5-one,
3-(4-Chlorophenylamino)-4-[(pyrrol-2-yl)methylene]-2-pyrazolin-5-one,
3-(3-Chlorophenyloxymethyl)-4-[(pyrrol-2-yl)methylene]-2-pyrazolin-5-one,
3-(Indol-3-yl)-4-[(pyrrol-2-yl)methylene]-2-pyrazolin-5-one,
3-(3-Methoxybenzyl)-4-[(pyrrol-2-yl)methylene]-2-pyrazolin-5-one,
3-(3,4-Dimethoxybenzyl)-4-[(pyrrol-2-yl)methylene]-2-pyrazolin-5-one,
3-(4-Methoxyphenylethyl)-4-[(pyrrol-2-yl)methylene]-2-pyrazolin-5-one,
3-(4-Phenylphenyloxymethyl)-4-[(pyrrol-2-yl)methylene]-2-pyrazolin-5-one,
3-(2-Phenylpropyl)-4-[(pyrrol-2-yl)methylene]-2-pyrazolin-5-one,
3-(3-Phenylpropyl)-4-[(pyrrol-2-yl)methylene]-2-pyrazolin-5-one,
3-(4-Hydroxyphenylethyl)-4-[(pyrrol-2-yl)methylene]-2-pyrazolin-5-one,
4-[(3,5-Dimethylpyrrol-2-yl)methylene]-3-phenylethyl-2-pyrazolin-5-one,
3-(4-Methylphenylethyl)-4-[(pyrrol-2-yl)methylene]-2-pyrazolin-5-one,
4-[(3,5-Dimethylpyrrol-2-yl)methylene]-3-isopropoxy-2-pyrazolin-5-one,
3-Ethoxy-4-[(pyrrol-2-yl)methylene]-2-pyrazolin-5-one,
3-(4-Nitrophenylethyl)-4-[(pyrrol-2-yl)methylene]-2-pyrazolin-5-one,
3-(4-Fluorophenylamino)-4-[(pyrrol-2-yl)methylene]-2-pyrazolin-5-one, 3-(4-Chlorophenylethyl)-4-[(pyrrol-2-yl)methylene]-2-pyrazolin-5-one,
4-[(4,5-Dimethylpyrrol-2-yl)methylene]-3-isopropoxy-2-pyrazolin-5-one,
4-[(3,5-Dimethyl-4-ethylpyrrol-2-yl)methylene]-3-isopropoxy-2-pyrazolin-5-one,
4-[(3,5-Dimethyl-4-ethylpyrrol-2-yl)methylene]-3-phenylethyl-2-pyrazolin-5-one,
4-{[1-(4-Hydroxybutyl)pyrrol-2-yl]methylene}-3-isopropoxy-2-pyrazolin-5-one,
3-Cyclopentyloxy-4-[(pyrrol-2-yl)methylene]-2-pyrazolin-5-one,
3-Tert-butylureido-4-[(pyrrol-2-yl)methylene]-2-pyrazolin-5-one,
3-Isopropoxy-4-[(4-methylpyrrol-2-yl)methylene]-2-pyrazolin-5-one,
3-(4-Aminophenylethyl)-4-[(4-methylpyrrol-2-yl)methylene]-2-pyrazolin-5-one,
3-Isopropoxy-4-[(1-methylpyrrol-2-yl)methylene]-2-pyrazolin-5-one,
3-Isopropoxy-4-[(5-methylpyrrol-2-yl)methylene]-2-pyrazolin-5-one,
3-(4-Aminophenylethyl)-4-[(3,5-dimethyl-4-ethylpyrrol-2-yl)methylene]-2-pyrazolin-5-one,
3-Ethoxy-4-[(5-methylpyrrol-2-yl)methylene]2-pyrazolin-5-one,
3-(4-Carbamoylphenylethyl)-4-[(3,5-dimethyl-4-ethylpyrrol-2-yl)methylene]-2-pyrazolin-5-one,
4-[(3,5-Dimethyl-4-ethylpyrrol-2-yl)methylene]-3-(4-methoxycarbonylphenylethyl-2-pyrazolin-5-one,
4-[(3,5-Dimethyl-4-ethoxycarbonylpyrrol-2-yl)methylene]-3-isopropoxy-2-pyrazolin-5-one,
3-(4-Aminophenylethyl)-4-[(3,5-dimethyl-4-ethoxycarbonylpyrrol-2-yl)methylene]-2-pyrazolin-5-one,
4-[(5-Ethylpyrrol-2-yl)methylene]-3-isopropoxy-2-pyrazolin-5-one,
4-[(3,5-Dimethyl-4-ethylpyrrol-2-yl)methylene]-3-(4-hydroxyphenylethyl)-2-pyrazolin-5-one,
3-(Ethoxycarbonylmethyl)-4-[(pyrrol-2-yl)methylene]-2-pyrazolin-5-one,
3-(4-Methoxyphenylaminocarbonylmethyl)-4-[(pyrrol-2-yl)methylene]-2-pyrazolin-5-one,
4-{(3-(2-Carboxyethyl)-4-methylpyrrol-2-yl]methylene}-3-isopropyl-2-pyrazolin-5-one,
3-Cyclopropyl-4-[(pyrrol-2-yl)methylene]-2-ppyrazolin-5-one,
3-Cyclobutyl-4-[(pyrrol-2-yl)methylene]-2-pyrazolin-5-one,
3-(3-Pyridil)-4-[(pyrrol-2-yl)methylene]-2-pyrazolin-5-one,
3-Cyclopropyl-4-[[1-(3,5-dichlorophenyl)pyrrol-2-yl)methylene]-2-pyrazolin-5-one,
4-[(Pyrrol-2-yl)methylene]-3-(2,2,3,3-tetramethylcyclopropyl)-2-pyrazolin-5-one,
3-Cyclopropyl-4-[(3,5-dimethylpyrrol-2-yl)methylene]-2-pyrazolin-5-one,
3-Cyclopentyl-4-[(pyrrol-2-yl)methylene]-2-pyrazolin-5-one,
3-(2-Methylcyclopropyl)-4-[(pyrrol-2-yl)methylene]-2-pyrazolin-5-one,
4-(Benzothiazol-2-yl)-4-[(pyrrol-2-yl)methylene]-2-pyrazolin-5-one,
4-[(4,5-Dimethylpyrrol-2-yl)methylene]-4-(3-pyridyl)]-2-pyrazolin-5-one,
3-Cyclopropyl-4[(3,5-dimethyl-4-ethylpyrrol-2-yl)methylene]-2-pyrazolin-5-one,
3-(Pyrrol-2-yl)-4-[(pyrrol-2-yl)methylene]-2-pyrazolin-5-one,
3-Cyclopropyl-4-[(4-methylpyrrol-2-yl)methylene]-2-pyrazolin-5-one,
3-(Benzothiazol-2-yl)-4-[(4-methylpyrrol-2-yl)methylene]-2-pyrazolin-5-one,
4-[(3,5-Dimethylpyrrol-2-yl)methylene]-3-(3-pyridyl)-2-pyrazolin-5-one,
4-[3,5-Dimetyl-4-ethylpyrrol-2-yl)methylene]-3-(3-pyridyl)-2-pyrazolin-5-one,
3-Cyclopropyl-4-[(5-methylpyrrol-2-yl)methylene]-2-pyrazolin-5-one,
4-[(5-Methylpyrrol-2-yl)methylene]-3-(–3-pyridyl)-2-pyrazolin-5-one,
3-Cyclopropyl-4-[(5-ethylpyrrol-2-yl)methylene]-2-pyrazolin-5-one,
3-Cyclopropyl-4-[(3,5-dimethyl-4-ethoxycarbonylpyrrol-2-yl)methylene]-2-pyrazolin-5-one,
3-Isopropoxy-4-[(5-phenylpyrrol-2-yl)methylene]-2-pyrazolin-5-one,
3-Propyl-4-[(pyrrol-2-yl)methylene]-2-pyrazolin-5-one,
3-Methyl-4-[(pyrrol-2-yl)methylene]-2-pyrazolin-5-one,
3-(4-Isopropylphenylamino)-4-[(pyrrol-2-yl)methylene]-2-pyrazolin-5-one,
3-(3-Phenylamino)-4-[(pyrrol-2-yl)methylene]-2-pyrazolin-5-one,
3-Cyclopropyl-4-{[1-(4-hydroxybutyl)pyrrol-2-yl]methylene]-2-pyrazolin-5-one,
4-{[4-(2-Carboxyethyl)-3-methylpyrrol-2-yl]methylene}-3-isopropoxy-2-pyrazolin-5-one,
4-[(4-Carboxy-3,5-dimethylpyrrol-2-yl)methylene]-3-isopropoxy-2-pyrazolin-5-one,
3-Isopropoxy-4-[(4,5-tetramethylenepyrrol-2-yl)methylene]-2-pyrazolin-5-one,
4-[(3,5-Dimethyl-4-morpholinomethylpyrrol-2-yl)methylene]-3-isopropoxy-2-pyrazolin-5-one,
4-[(3,5-Dimethyl-4-dimethylaminomethylpyrrol-2-yl)methylene]-3-isopropoxy-2-pyrazolin-5-one,
4-[(4-Acetyl-3,5-dimethylpyrrol-2-yl)methylene]-3-isopropoxy-2-pyrazolin-5-one,
4-{[3,5-Dimethyl-4-(2-dimetylaminoethyloxycarbonyl)pyrrol-2-yl]methylene}-3-isopropoxy-2-pyrazolin-5-one,
4-{[3,5-Dimethyl-4-(2-dimetylaminoethylaminocarbonyl)pyrrol-2-yl]methylene}-3-isopropoxy-2-pyrazolin-5-one,
4-[(5-Ethoxycarbonylpyrrol-2-yl)methylene]-3-isopropoxy-2-pyrazolin-5-one,
4-[(5-Carboxypyrrol-2-yl)methylene]-3-isopropoxy-2-pyrazolin-5-one,
3-(4-Chlorophenylaminocarbonylmethyl)-4-[(pyrrol-2-yl)methylene]-2-pyrazolin-5-one,
3-Cyclopropyl-4-[(5-phenylpyrrol-2-yl)methylene]-2-pyrazolin-5-one,
4-[(3,5-Dimethyl-4-ethylpyrrol-2-yl)methylene]-3-(tetrahydrofuran-3-yl)-2-pyrazolin-5-one,
4-[(4-Carboxy-3,5-dimethylpyrrol-2-yl)methylene]-3-cyclopropyl-2-pyrazolin-5-one,
4-[(3,5-dimethyl-4-ethoxycarbonylpyrrol-2-yl)methylene]-3-(3-pyridyl)-2-pyrazolin-5-one,
3-Cyclopropyl-4-[(3,5-dimethyl-4-morpholinomethylpyrrol-2-yl)methylene]-2-pyrazolin-5-one,
4-[(3,4-dimethylpyrrol-2-yl)methylene]-3-pyrazinyl-2-pyrazolin-5-one,
4-{[4-(2-Carboxyethyl)-3-methylpyrrol-2-yl]methylene}-3-cyclopropyl-2-pyrazolin-5-one,
3-Cyclopropyl-4-[(3,5-dimethyl-4-dimethylaminomethylpyrrol-2-yl)methylene]-2-pyrazolin-5-one,
3-Cyclopropyl-4-[(5-ethoxycarbonylpyrrol-2-yl)methylene]-2-pyrazolin-5-one, 3-Cyclopropyl-4-[(4,5-tetramethylenepyrrol-2-yl)methylene]-2-pyrazolin-5-one,
3-(2-Methoxycarbonylethyl)-4-[(pyrrol-2-yl)methylene]-2-pyrazolin-5-one,
3-Ethoxycarbonyl-4-[(pyrrol-2-yl)methylene]-2-pyrazolin-5-one,
3-Isopropyl-4-[(pyrrol-2-yl)methylene]-2-pyrazolin-5-one,
3-(trans-2-phenylcyclopropyl)-4-[(pyrrol-2-yl)methylene]-2-pyrazolin-5-one,
3-Cyclohexyl-4-[(pyrrol-2-yl)methylene]-2-pyrazolin-5-one,
3-Cyclopropylamino-4-[(4,5-tetramethylenepyrrol-2-yl)methylene]-2-pyrazolin-5-one,
3-Cyclopropyl-4-[(5-morpholinomethylpyrrol-2-yl)methylene]-2-pyrazolin-5-one,
4-[(5-Carboxypyrrol-2-yl)methylene]-3-cyclopropyl-2-pyrazolin-5-one,
4-[(4-Chloropyrrol-2-yl)methylene]-3-ethoxy-2-pyrazolin-5-one,
4-[(4-Bromopyrrol-2-yl)methylene]-3-ethoxy-2-pyrazolin-5-one,
4-[(5-Chloropyrrol-2-yl)methylene]-3-ethoxy-2-pyrazolin-5-one,
4[(4-Chloropyrrol-2-yl)methylene]-3-cyclopropyl-2-pyrazolin-5-one,
4-[(4-Bromopyrrol-2-yl)methylene]-3-cyclopropyl-2-pyrazolin-5-one,
3-Pyrazinyl-4-[(4,5-tetramethylenepyrrol-2-yl)methylene]-2-pyrazolin-5-one,
3-(3-Pyridyl)-4-[(4,5-tetramethylenepyrrol-2-yl)methylene]-2-pyrazolin-5-one,
4-[(4-Carboxy-3,5-dimethylpyrrol-2-yl)methylene]-3-pyrazinyl-2-pyrazolin-5-one,
3-Cyclopropyl-4-{[3,5-dimethyl-4-(2-dimethylaminoethyloxycarbonyl)pyrrol-2-yl]methylene}-2-pyrazolin-5-one,
4-{[3,5-Dimethyl-4(2-dimethylaminoethyloxycarbonyl)pyrrol-2-yl]methylene}-3-pyrazinyl-2-pyrazolin-5-one,
4-[(3,5-Dimethyl-4-dimethylaminomethylpyrrol-2-yl)methylene]-3-pyrazinyl-2-pyrazolin-5-one,
4-[(3,5-Dimethyl-4-dimethylaminomethylpyrrol-2-yl)methylene]-3-pyrazinyl-2-pyrazolin-5-one maleate,
4-{[3,5-Dimethyl-4-(2-morpholinoethylaminocarbonyl)pyrrol-2-yl]methylene-3-pyrazinyl-2-pyrazolin-5-one,
4-[(3,5-Dimethylpyrrol-2-yl)methylene]-3-(2-pyridyl)-2-pyrazolin-5-one,
4-[(3,5-Dimethyl-4-ethylpyrrol-2-yl)methylene]-3-(2-pyridyl)-2-pyrazolin-5-one,
4-[(4,5-tetramethylenepyrrol-2-yl)methylene]-3-(2-pyridyl)-2-pyrazolin-5-one,
4-[(3,5-dimethylpyrrol-2-yl)methylene]-3-(2-furyl)-2-pyrazolin-5-one,
4-[(3,5-dimethyl-4-morpholinomethylpyrrol-2-yl)methylene]-3-pyrazinyl-2-pyrazolin-5-one,
4-[(3,5-dimethylpyrrol-2-yl)methylene]-3-(2-thienyl)-2-pyrazolin-5-one,
3-Cyclopropyl-4-[(4-ethoxycarbonylpyrrol-2-yl)methylene]-2-pyrazolin-5-one,
3-Cyclopropyl-4-[(3,5-dimethyl-4-trifluoroacetamidomethylpyrrol-2-yl)methylene]-2-pyrazolin-5-one,
3-Cyclopropyl-4-[(4-aminomethyl-3,5-dimethylpyrrol-2-yl)methylene]-2-pyrazolin-5-one,
3-(Benzothiazol-2-yl)-4-[(3,5-dimethylpyrrol-2-yl)methylene]-2-pyrazolin-5-one,
3-(Benzothiazol-2-yl)-4-[(3,5-dimethyl-4-morpholinomethylpyrrol-2-yl)methylene]-2-pyrazolin-5-one,
4-[(3,5-Dimethyl-4-ethylpyrrol-2-yl)methylene]-3-pyrazinyl-2-pyrazolin-5-one,
4-[(4-Ethoxycarbonylpyrrol-2-yl)methylene]-3-pyrazinyl-2-pyrazolin-5-one,
4-[(4-Carboxypyrrol-2-yl)methylene]-3-pyrazinyl-2-pyrazolin-5-one,
4-[(3,5-Dimethyl-4-diethanolaminomethylpyrrol-2-yl)methylene]-3-pyrazinyl-2-pyrazolin-5-one,
4-[(3,5-Dimethyl-4-trifluoroacetamidomethylpyrrol-2-yl)methylene]-3-pyrazinyl-2-pyrazolin-5-one,
3-Cyclopropyl-4-[(4-ethoxycarbonyl-3-phenylpyrrol-2-yl)methylene]-2-pyrazolin-5-one,
4-{[3,5-Dimethyl-4-(1-pyrrolidinylmethyl)pyrrol-2-yl]methylene}-3-pyrazinyl-2-pyrazolin-5-one,
4-[(3,5-Dimethyl-4-dimethylaminomethylpyrrol-2-yl)methylene]-3-(2-furyl)-2-pyrazolin-5-one,
4-[(3,5-Dimethyl-4-dimethylaminomethylpyrrol-2-yl)methylene]-3-(2-thienyl)-2-pyrazolin-5-one,
4-[(3,5-Dimethyl-4-dimethylaminomethylpyrrol-2-yl)methylene]-3-(3-pyridyl)-2-pyrazolin-5-one,
4-[(3,5-Dimethyl-4-ethoxycarbonylpyrrol-2-yl)methylene]-3-phenyl-2-pyrazolin-5-one,
4-[(3,5-Dimethyl-4-ethylpyrrol-2-yl)methylene]-3-phenyl-2-pyrazolin-5-one,
4-[(3,4-Di(ethoxycarbonyl)pyrrol-2-yl)methylene]-3-ethoxy-2-pyrazolin-5-one,
3-Ethoxy-4-[(4-ethoxycarbonylpyrrol-2-yl)methylene]-2-pyrazolin-5-one,
4-[(3,5-Dimethyl-4-ethoxycarbonylpyrrol-2-yl)methylene]-3-(2-pyridylethyl)-2-pyrazolin-5-one,
4-[(3,5-Dimethyl-4-ethoxycarbonylpyrrol-2-yl)methylene]-3-(1-methyl-2-phenylethyl)-2-pyrazolin-5-one,
4-[(4-Carboxy-3,5-dimethylpyrrol-2-yl)methylene]-3-ethoxy-2-pyrazolin-5-one,
3-Ethoxy-4-[(5-nitropyrrol-2-yl)methylene]-2-pyrazolin-5-one,
3-Ethoxy-4-[(4-nitropyrrol-2-yl)methylene]-2-pyrazolin-5-one,
4-[(4-Carboxypyrrol-2-yl)methylene]-3-ethoxy-2-pyrazolin-5-one,
4-{[3,5-Dimethyl-4-(2-dimethylaminoethylaminocarbonyl)pyrrol-2-yl]methylene}-3-ethoxy-2-pyrazolin-5-one,
4-[(5-Chloro-3-methoxycarbonyl-4-methoxycarbonylmethylpyrrol-2-yl)methylene]-3-ethoxy-2-pyrazolin-5-one,
4-{[3-(2-Carboxyethyl)-4-methylpyrrol-2-yl]methylene}-3-ethoxy-2-pyrazolin-5-one,
4-[(3,5-Dimethyl-4-ethoxycarbonylpyrrol-2-yl)methylene]-3-ethoxy-2-pyrazolin-5-one,
3-Ethoxy-4-[(4,5-tetramethylenepyrrol-2-yl)methylene]-2-pyrazolin-5-one,
4-[(3,5-Dimethyl-4-ethoxycarbonylpyrrol-2-yl)methylene]-3-trifluoromethyl-2-pyrazolin-5-one,
4-[(3,5-Dimethyl-4-ethoxycarbonylpyrrol-2-yl)methylene]-3-(5-isoxazolyl)-2-pyrazolin-5-one,
3-(3-Aminophenyl)-4-[(3,5-Dimethyl-4-ethoxycarbonylpyrrol-2-yl)methylene]-2-pyrazolin-5-one,
3-Ethoxy-4-{[2-(4-morpholinoethyl)aminocarbonylpyrrol-2-yl]methylene}-2-pyrazolin-5-one,
4-[(4-Ethoxycarbonyl-3-phenylpyrrol-2-yl)methylene]-3-pyrazinyl-2-pyrazolin-5-one,
4-{[4-(4-Methyl-1-pyperazinylmethyl)-3,5-dimethylpyrrol-2-yl]methylene}-3-pyrazinyl-2-pyrazolin-5-one,
4-[(4-Diethylaminomethyl-3,5-dimethylpyrrol-2-yl)methylene]-3-pyrazinyl-2-pyrazolin-5-one,
4-[(3,5-Dimethyl-4-piperidinomethylpyrrol-2-yl)methylene]-3-pyrazinyl-2-pyrazolin-5-one,
4-[(3,5-Dimethyl-4-piperidinomethylpyrrol-2-yl)methylene]-3-(5-isoxazolyl)-2-pyrazolin-5-one, 4-[(3,5-Dimethyl-4-dimethylaminomethylpyrrol-2-yl)methylene]-3-(5-isoxazolyl)-2-pyrazolin-5-one,
4-[(5-Methyl-4-dimethylaminomethylpyrrol-2-yl)methylene]-3-pyrazinyl-2-pyrazolin-5-one,
4-{{3,5-Dimethyl-4-[N-(2-dimethylaminoethyl)-N-methylaminomethylpyrrol-2-yl}methylene}-3-pyrazinyl-2-pyrazolin-5-one,
3-Cyclopropyl-4-[(3-dimethylaminomethyl-4,5-tetramethylenepyrrol-2-yl)methylene]-2-pyrazolin-5-one,
4-[(3-Dimethylaminomethyl-4,5-tetramethylenepyrrol-2-yl)methylene]-3-pyrazinyl-2-pyrazolin-5-one,
3-Cyclopropyl-4-[(3,5-dimethyl-4-dimethylaminomethylpyrrol-2-yl)methylene]-2-pyrazolin-5-one maleate,
4-{[4-(3-Chloropropionyl)-3,5-dimethylpyrrol-2-yl]methylene}-3-pyrazinyl-2-pyrazolin-5-one,
4-{[4-(2-Diethylaminoethyl)-3,5-dimethylpyrrol-2-yl]methylene}-3-pyrazinyl-2-pyrazolin-5-one,
4-[(3,5-Dimethyl-4-dimethylaminomethylpyrrol-2-yl)methylene]-3-(5-methyl-3-isoxazolyl)-2-pyrazolin-5-one,
4-{[3,5-Dimethyl-4-(4-hydroxypiperidinomethyl)pyrrol-2-yl]methylene}-3-pyrazinyl-2-pyrazolin-5-one,
4-[(4-Aminomethyl-3,5-dimethylpyrrol-2-yl)methylene]-3-pyrazinyl-2-pyrazolin-5-one maleate,
4-{[4-(4-Benzylpiperidino)methylpyrrol-2-yl]methylene}-3-pyrazinyl-2-pyrazolin-5-one,
4-{[3,5-Dimethyl-4-(2-hydroxyethyl)pyrrol-2-yl]methylene}-3-pyrazinyl-2-pyrazolin-5-one,
4-{{3,5-Dimethyl-4-[2-(1-pyrrolidinylethyl)]pyrrol-2-yl}methylene}-3-pyrazinyl-2-pyrazolin-5-one,
3-Cyclopropyl-4-{{3,5-Dimethyl-4-[2-(1-pyrrolidinylethyl)]pyrrol-2-yl}methylene}-2-pyrazolin-5-one,
3-Cyclopropyl-4-{[3,5-Dimethyl-4-(2-hydroxyethyl)pyrrol-2-yl]methylene}-2-pyrazolin-5-one,
4-{[3,5-Dimethyl-4-(2-ethylaminoethyl)pyrrol-2-yl]methylene}-3-pyrazinyl-2-pyrazolin-5-one,
4-{[4-(3-Diethylaminopropyl)-3,5-dimethylpyrrol-2-yl]methylene}-3-pyrazinyl-2-pyrazolin-5-one,
4-{[3,5-Dimethyl-4-(3-hydroxypropyl)pyrrol-2-yl]methylene}-3-pyrazinyl-2-pyrazolin-5-one,
4-[(3,5-Dimethyl-4-dimethylaminoacetylpyrrol-2-yl)methylene]-3-pyrazinyl-2-pyrazolin-5-one hydrochloride,
4-[(3,5-Dimethyl-4-dimethylaminoacetylpyrrol-2-yl)methylene]-3-ethoxy-2-pyrazolin-5-one,
3-Cyclopropyl-4-{[(2-diethylaminoethyl)-3,5-dimethyl-4-pyrrol-2-yl]methylene}-2-pyrazolin-5-one,
4-{[3,5-Dimethyl-4-(2-dimethylaminoethyl)pyrrol-2-yl]methylene}-3-pyrazinyl-2-pyrazolin-5-one,
4-{[3,5-Dimethyl-4-(4-hydroxybutyl)pyrrol-2-yl]methylene}-3-pyrazinyl-2-pyrazolin-5-one,
4-{[4-(4-Diethylaminobutyl)-3,5-dimethylpyrrol-2-yl]methylene}-3-pyrazinyl-2-pyrazolin-5-one,
4-{[4-(2-Diethylaminoethyl-N-oxide)-3,5-dimethylpyrrol-2-yl]methylene}-3-pyrazinyl-2-pyrazolin-5-one,
4-{[3,5-dimethyl-4-(1-pyrrolidinylacetyl)pyrrol-2-yl]methylene}-3-pyrazinyl-2-pyrazolin-5-one,
4-[(4-Diethylaminoacetyl-3,5-dimethylpyrrol-2-yl)methylene]-3-pyrazinyl-2-pyrazolin-5-one,
4-[(3-Isopropyl-5-methylpyrrol-2-yl)methylene]-3-pyrazinyl-2-pyrazolin-5-one,
4-{[3,5-Dimethyl-4-[3-(1-pyrrolidinylpropyl)]pyrrol-2-yl]methylene}-3-pyrazinyl-2-pyrazolin-5-one,
4-[(Dimethylaminomethyl-3-isopropyl-5-methylpyrrol-2-yl)methylene]-3-pyrazinyl-2-pyrazolin-5-one,
3-Cyclopropyl-4-[(dimethylaminomethyl-3-isopropyl-5-methylpyrrol-2-yl)methylene]-2-pyrazolin-5-one,
4-{[3,5-Dimethyl-4-(2-ethoxyoxalyl)pyrrol-2-yl]methylene}-3-pyrazinyl-2-pyrazolin-5-one,
3-Benzyl-4-[(indol-3-yl)methylene]-2-pyrazolin-5-one,
3-Benzyl-4-{[1-(4-hydroxybutyl)indol-3-yl]methylene}-2-pyrazolin-5-one,
4-[(Indol-3-yl)methylene]-3-(4-methoxyphenyloxymethyl)-2-pyrazolin-5-one,
4-[(Indol-3-yl)methylene]-3-phenyloxymethyl-2-pyrazolin-5-one,
3-(4-Chlorophenyloxymethyl)-4-[(indol-3-yl)methylene]-2-pyrazolin-5-one,
4-[(Indol-3-yl)methylene]-3-(4-methoxybenzyl)-2-pyrazolin-5-one,
4-[(Indol-3-yl)methylene]-3-(4-methylphenyloxymethyl)-2-pyrazolin-5-one,
4-[(Indol-3-yl)methylene]-3-phenylethyl-2-pyrazolin-5-one,
4-[(Indol-3-yl)methylene]-3-isopropoxy-2-pyrazolin-5-one,
4-[(Indol-3-yl)methylene]-3-(4-methylbenzyl)-2-pyrazolin-5-one,
4-[(Indol-3-yl)methylene]-3-phenylamino-2-pyrazolin-5-one,
4-[(Indol-3-yl)methylene]-3-(4-methylphenylamino)-2-pyrazolin-5-one,
4-[(Indol-3-yl)methylene]-3-(4-methoxyphenylamino)-2-pyrazolin-5-one,
3-(4-Chlorobenzyl)-4-[(indol-3-yl)methylene]-2-pyrazolin-5-one,
4-{[1-(4-hydroxybutyl)indol-3-yl]methylene}-3-(4-methoxybenzyl)-2-pyrazolin-5-one,
3-(4-Chlorophenylamino)-4-[(indol-3-yl)methylene]-2-pyrazolin-5-one,
4-[(Indol-3-yl)methylene]-3-(3-methoxybenzyl)-2-pyrazolin-5-one,
3-(3,4-dimethoxybenzyl)-4-[(indol-3-yl)methylene]-2-pyrazolin-5-one,
3-(4-hydroxybenzyl)-4-[(indol-3-yl)methylene]-2-pyrazolin-5-one,
3-(3-Chlorophenyloxymethyl)-4-[(indol-3-yl)methylene]-2-pyrazolin-5-one,
3-(Indol-3-yl)-4-[(indol-3-yl)methylene]-2-pyrazolin-5-one,
4-[(Indol-3-yl)methylene]-3-(4-methoxyphenylethyl)-2-pyrazolin-5-one,
4-[(Indol-3-yl)methylene]-3-(4-phenylphenyloxymethyl)-2-pyrazolin-5-one,
4-[(Indol-3-yl)methylene]-3-(2-phenylpropyl)-2-pyrazolin-5-one,
4-[(Indol-3-yl)methylene]-3-(3-phenylpropyl)-2-pyrazolin-5-one,
3-(4-Hydroxyphenylethyl)-4-[(indol-3-yl)methylene]-2-pyrazolin-5-one,
4-[(Indol-3-yl)methylene]-3-(4-methylphenylethyl)-2-pyrazolin-5-one,
3-Ethoxy-4-[(indol-3-yl)methylene]-2-pyrazolin-5-one,
4-{[1-(4-Hydroxybutyl)indol-3-yl]methylene}-3-isopropoxy-2-pyrazolin-5-one,
4-{[1-(4-Hydroxybutyl)indol-3-yl]methylene}-3-phenylethyl-2-pyrazolin-5-one,
4-[(Indol-3-yl)methylene]-3-(4-nitrophenylethyl)-2-pyrazolin-5-one,
4-[(Indol-3-yl)methylene]-3-propoxy-2-pyrazolin-5-one,
3-(4-Fluorophenylamino)4-[(indol-3-yl)methylene]--2-pyrazolin-5-one,
3-(4-Aminophenylethyl)-4-[(indol-3-yl)methylene]-2-pyrazolin-5-one,
3-Isopropoxy-4-[(2-methylindol-3-yl)methylene]-2-pyrazolin-5-one, 3-Isopropoxy-4-[(7-methylindol-3-yl)methylene]-2-pyrazolin-5-one,
4-[(7-Methylindol-3-yl)methylene]-3-phenylethyl-2-pyrazolin-5-one,
3-Cyclopentyl-4-[(indol-3-yl)methylene]-2-pyrazolin-5-one,
3-Isopropoxy-4-[(1-methylindol-3-yl)methylene]-2-pyrazolin-5-one,
4-[(Indol-3-yl)methylene]-3-(4-methoxycarbonylphenylethyl)-2-pyrazolin-5-one,
3-Isopropoxy-4-[(1-isopropylindol-3-yl)methylene]-2-pyrazolin-5-one,
3-(4-Hydroxyphenylethyl)-4-[(1-methylindol-3-yl)methylene]-2-pyrazolin-5-one,
3-Isopropyl-4-[(indol-3-yl)methylene]-2-pyrazolin-5-one,
3-(4-Chlorophenylaminocarbonylmethyl)-4-[(indol-3-yl)methylene]-2-pyrazolin-5-one,
3-Ethoxycarbonylmethyl-4-[(indol-3-yl)methylene]-2-pyrazolin-5-one,
4-[(Indol-3-yl)methylene]-3-(4-methoxyphenylaminocarbonylmethyl)-2-pyrazolin-5-one,
3-Cyclopropyl-4-[(indol-3-yl)methylene]-2-pyrazolin-5-one,
4-[(Indol-3-yl)methylene]-3-(3-pyridyl)-2-pyrazolin-5-one,
3-(2-Aminocarbonylethyl)-4-[(indol-3-yl)methylene]-2-pyrazolin-5-one,
3-Cyclobutyl-4-[(indol-3-yl)methylene]-2-pyrazolin-5-one,
3-(2-Dimethylaminocarbonylethyl)-4-[(indol-3-yl)methylene]-2-pyrazolin-5-one,
3-Cyclopropyl-4-{[1-(4-hydroxybutyl)indol-3-yl]methylene}-2-pyrazolin-5-one,
4-[(Indol-3-yl)methylene]-3-(4-pyridyl)-2-pyrazolin-5-one,
3-Cyclopentyl-4-[(indol-3-yl)methylene]-2-pyrazolin-5-one,
4-[(Indol-3-yl)methylene]-3-(2,2,3,3-tetramethylcyclopropyl)-2-pyrazolin-5-one,
4-[(Indol-3-yl)methylene]-3-(2-methylcyclopropyl)-2-pyrazolin-5-one,
3-Cyclohexyl-4-{[1-(4-hydroxybutyl)indol-3-yl]methylene}-2-pyrazolin-5-one,
4-{[1-(4-Hydroxybutyl)indol-3-yl]methylene}-3-(4-pyridyl)-2-pyrazolin-5-one,
3-(Benzothiazol-2-yl)-4-[(indol-3-yl)methylene]-2-pyrazolin-5-one,
4-[(Indol-3-yl)methylene]-3-(2-pyridyl)-2-pyrazolin-5-one,
3-Dimethylamino-4-[(indol-3-yl)methylene]-2-pyrazolin-5-one,
4-[(Indol-3-yl)methylene]-3-(pyrrol-2-yl)-2-pyrazolin-5-one,
4-[(Indol-3-yl)methylene]-3-(6-methoxybenzothiazol-2-yl)-2-pyrazolin-5-one,
3-Cyclopropyl-4-[(1-methylindol-3-yl)methylene]-2-pyrazolin-5-one,
3-Cyclopropyl-4-[(7-methylindol-3-yl)methylene]-2-pyrazolin-5-one,
4-[(1-Methylindol-3-yl)methylene]-3-(3-pyridyl)-2-pyrazolin-5-one,
4-[(Indol-3-yl)methylene]-3-propyl-2-pyrazolin-5-one,
4-[(Indol-3-yl)methylene]-3-methyl-2-pyrazolin-5-one,
4-[(Indol-3-yl)methylene]-3-trifluoromethyl-2-pyrazolin-5-one,
4-{[1-(4-Hydroxybutyl)indol-3-yl]methylene}-2-pyrazolin-5-one,
4-{[1-(4-Hydroxybutyl)indol-3-yl]methylene}-3-methyl-2-pyrazolin-5-one,
4-{[1-(4-Hydroxybutyl)indol-3-yl]methylene}-3-trifluoromethyl-2-pyrazolin-5-one,
4-{[1-(4-Hydroxybutyl)indol-3-yl]methylene}-3-(tert-butyl)-2-pyrazolin-5-one,
3-Ethoxycarbonyl-4-[(indol-3-yl)methylene]-2-pyrazolin-5-one,
4-[(Indol-3-yl)methylene]-3-(2-methoxycarbonylethyl)-2-pyrazolin-5-one,
4-[(Indol-3-yl)methylene]-3-(trans-2-phenyl-1-cyclopropyl)-2-pyrazolin-5-one,
3-Cyclobutyl-4-{[1-(4-hydroxybutyl)indol-3-yl]methylene}-2-pyrazolin-5-one,
4-[(6-Carboxy-1-methylindol-3-yl)methylene]-3-cyclopropyl-2-pyrazolin-5-one,
3-Cyclopropyl-4-[(5-methoxy-1-methylindol-3-yl)methylene]-2-pyrazolin-5-one,
4-[(1-Methylindol-3-yl)methylene]-3-pyrazinyl-2-pyrazolin-5-one,
3-Cyclopropyl-4-[(1,7-dimethylindol-3-yl)methylene]-2-pyrazolin-5-one,
4-[(1-Methylindol-3-yl)methylene]-3-(tetrahydrofuran-3-yl)-2-pyrazolin-5-one,
3-Cyclopropylamino-4-[(1-methylindol-3-yl)methylene]-2-pyrazolin-5-one,
4-[(6-Carboxy-1-methylindol-3-yl)methylene]-3-isopropoxy-2-pyrazolin-5-one,
4-[(1,7-Dimethylindol-3-yl)methylene]-3-isopropoxy-2-pyrazolin-5-one,
3-Isopropoxy-4-[(5-methoxy-1-methylindol-3-yl)methylene]-2-pyrazolin-5-one,
3-(4-Fluorophenylamino)-4-[(1-methylindol-3-yl)methylene]-2-pyrazolin-5-one,
4-[(1-Methylindol-3-yl)methylene]-3-trifluoroacetamido-2-pyrazolin-5-one,
3-(4-Aminophenylethyl)-4-[(1-methylindol-3-yl)methylene]-2-pyrazolin-5-one,
3-Amino-4-[(1-methylindol-3-yl)methylene]-2-pyrazolin-5-one,
3-(4-Chlorophenylethyl)-4-[(indol-3-yl)methylene]-2-pyrazolin-5-one,
3-Ethoxy-4-[(1-methylindol-3-yl)methylene]-2-pyrazolin-5-one,
3-(5-Isoxazolyl)-4-[(1-methylindol-3-yl)methylene]-2-pyrazolin-5-one,
4-[(1-Methylindol-3-yl)methylene]-3-tert-butyl-2-pyrazolin-5-one,
4-[(6-Carboxy-1-methylindol-3-yl)methylene]-3-pyrazinyl-2-pyrazolin-5-one,
4-{{1-Methyl-6-[2-(4-morpholino)ethyl]aminocarbonylindol-3-yl}methylene}-3-pyrazinyl-2-pyrazolin-5-one,
4-[(Indol-2-yl)methylene]-3-isopropoxy-2-pyrazolin-5-one,
3-(4-Hydroxyphenylethyl)-4-[(indol-2-yl)methylene]-2-pyrazolin-5-one,
3-(4-Aminophenylethyl)-4-[(indol-2-yl)methylene]-2-pyrazolin-5-one,
3-(4-Methoxycarbonylphenylethyl]-4-[(indol-2-yl)methylene]-2-pyrazolin-5-one,
3-(4-Carbamoylphenylethyl)-4-[(indol-2-yl)methylene]-2-pyrazolin-5-one,
3-Cyclopropyl-4-[(indol-2-yl)methylene]-2-pyrazolin-5-one,
3-Cyclopropyl-4-[(3-dimethylaminomethylindol-2-yl)methylene]-2-pyrazolin-5-one,
4-[(Indol-2-yl)methylene]-3-(3-pyridyl)-2-pyrazolin-5-one,
3-Isopropoxy-4-[(5-methoxyindol-2-yl)methylene]-2-pyrazolin-5-one,
3-Isopropoxy-4-[(1-methylindol-2-yl)methylene]-2-pyrazolin-5-one, 4-[(Indol-2-yl)methylene]-3-(tetrahydrofuran-3-yl)-2-pyrazolin-5-one,
3-Cyclopropyl-4-[(5-methoxyindol-2-yl)methylene]-2-pyrazolin-5-one,
3-Cyclopropyl-4-[(5-nitroindol-2-yl)methylene]-2-pyrazolin-5-one,
4-[(Indol-2-yl)methylene]-3-isopropylamino-2-pyrazolin-5-one,
3-(4-Carboxyphenylethyl)-4-[(indol-2-yl)methylene]-2-pyrazolin-5-one,
4-[(Indol-2-yl)methylene]-3-phenyl-2-pyrazolin-5-one,
3-Isopropoxy-4-[(3-methylindol-2-yl)methylene]-2-pyrazolin-5-one,
3-Isopropoxy-4-{[3-(2-methoxycarbonyl-2-acetamidoethyl)indol-2-yl]methylene}-2-pyrazolin-5-one,
3-Ethoxy-4-[(indol-2-yl)methylene]-2-pyrazolin-5-one,
3-Ethoxy-4-{[3-(4-morpholinomethyl)indol-2-yl]methylene}-2-pyrazolin-5-one,
3-Cyclopropyl-4-{[3-(4-morpholinomethyl)indol-2-yl]methylene}-2-pyrazolin-5-one,
4-[(5-Methoxyindol-2-yl)methylene]-3-pyrazinyl-2-pyrazolin-5-one,
4-[(5-Methoxyindol-2-yl)methylene]-3-(2-pyridyl)-2-pyrazolin-5-one,
4-[(4-Chloro-6,7-dihydroindol-2-yl)methylene]-3-ethoxy-2-pyrazolin-5-one,
4-[(4-Chloro-6,7-dihydroindol-2-yl)methylene]-3-pyrazinyl-2-pyrazolin-5-one,
4-[(4-Oxo-1,5,6,7-dihydroindol-2-yl)methylene]-3-pyrazinyl-2-pyrazolin-5-one,
4-[(3-Dimethylaminomethylindol-2-yl)methylene]-3-ethoxy-2-pyrazolin-5-one,
4-[(7-Azaindol-3-yl)methylene]-3-benzyl-2-pyrazolin-5-one,
3-Benzyl-4-{[1-(4-hydroxybutyl)-7-azaindol-3-yl]methylene}-2-pyrazolin-5-one,
4-[(7-Azaindol-3-yl)methylene]-3-(4-methoxyphenyloxymethyl)-2-pyrazolin-5-one,
4-[(7-Azaindol-3-yl)methylene]-3-isopropoxy-2-pyrazolin-5-one,
3-Amino-4-[(7-azaindol-3-yl)methylene]-2-pyrazolin-5-one,
4-[(7-Azaindol-3-yl)methylene]-3-(4-methoxybenzyl)-2-pyrazolin-5-one,
4-[(7-Azaindol-3-yl)methylene]-3-phenylamino-2-pyrazolin-5-one,
4-[(7-Azaindol-3-yl)methylene]-3-(4-methylbenzyl)-2-pyrazolin-5-one,
4-[(7-Azaindol-3-yl)methylene]-3-(4-hydroxyphenylethyl)-2-pyrazolin-5-one,
4-{[1-(4-Hydroxybutyl)-7-azaindol-3-yl]methylene}-3-(4-hydroxyphenylethyl)-2-pyrazolin-5-one,
4-[(7-Azaindol-3-yl)methylene]-3-isopropyl-2-pyrazolin-5-one,
4-[(7-Azaindol-3-yl)methylene]-3-cyclopropyl-2-pyrazolin-5-one,
4-[(7-Azaindol-3-yl)methylene]-3-cyclobutyl-2-pyrazolin-5-one,
4-[(7-Azaindol-3-yl)methylene]-3-(3-pyridyl)-2-pyrazolin-5-one,
4-[(7-Azaindol-3-yl)methylene]-3-phenyl-2-pyrazolin-5-one,
4-[(7-Azaindol-3-yl)methylene]-3-(4-fluorophenylamino)-2-pyrazolin-5-one,
4-[(7-Azaindol-3-yl)methylene]-3-propyl-2-pyrazolin-5-one,
4-[(7-Azaindol-3-yl)methylene]-3-methyl-2-pyrazolin-5-one,
4-[(7-Azaindol-3-yl)methylene]-3-trifluoromethyl-2-pyrazolin-5-one,
4-[(7-Azaindol-3-yl)methylene]-3-(tert-butyl)-2-pyrazolin-5-one,
4-{[1-(4-Hydroxybutyl)-7-azaindol-3-yl]methylene}-3-trifluoromethyl-2-pyrazolin-5-one,
4-[(7-Azaindol-3-yl)methylene]-3-(4-isopropylphenylamino)-2-pyrazolin-5-one,
4-[(7-Azaindol-3-yl)methylene]-3-(3-methylphenylamino)-2-pyrazolin-5-one,
4-{[1-(4-Hydroxybutyl)-7-azaindol-3-yl]methylene}-3-(3-methylphenylamino)-2-pyrazolin-5-one,
4-[(7-Azaindol-3-yl)methylene]-3-phenylethyl-2-pyrazolin-5-one,
3-Benzyl-4-[(4-dimethylaminophenyl)methylene]-2-pyrazolin-5-one,
4-[(4-Dimethylaminophenyl)methylene]-3-isopropoxy-2-pyrazolin-5-one,
4-[(4-Dimethylaminophenyl)methylene]-3-phenylethyl-2-pyrazolin-5-one,
3-Cyclopropyl-4-[(4-dimethylaminophenyl)methylene]-2-pyrazolin-5-one,
3-Isopropoxy-4-[(3-methylpyrazol-4-yl)methylene]-2-pyrazolin-5-one,
3-Cyclopropyl-4-[(3-methylpyrazol-4-yl)methylene]-2-pyrazolin-5-one,
4-[(Imidazol-2-yl)methylene]-3-isopropoxy-2-pyrazolin-5-one,
3-Cyclopropyl-4-[(imidazol-2-yl)methylene]-2-pyrazolin-5-one,
4-[(Imidazol-4-yl)methylene]-3-isopropoxy-2-pyrazolin-5-one,
3-Cyclopropyl-4-[(thien-2-yl)methylene]-2-pyrazolin-5-one,
4[(Indol-3-yl)methylene]-3-isopropyl-1-methyl-2-pyrazolin-5-one,
3-Isopropoxy-4-[(pyrrol-3-yl)methylene]-2-pyrazolin-5-one,
4-[(8-Hydroxyquinolin-5-yl)methylene]-3-isopropoxy-2-pyrazolin-5-one,
4-{[4-(2-Diethylaminoethyl)-3,5-dimethylpyrrol-2-yl]methylene}-3-(2-pyrimidinyl)-2-pyrazolin-5-one,
4-{[4-(2-Diethylaminoethyl)-3,5-dimethylpyrrol-2-yl]methylene}-3-(3-pyridazinyl)-2-pyrazolin-5-one,
4-{[4-(2-Diethylaminoethyl)-3,5-dimethylpyrrol-2-yl]methylene}-3-(2-furyl)-2-pyrazolin-5-one,
4-{[4-(2-Diethylaminoethyl)-3,5-dimethylpyrrol-2-yl]methylene}-3-(2-thienyl)-2-pyrazolin-5-one,
4-{[4-(2-Diethylaminoethyl)-3,5-dimethylpyrrol-2-yl]methylene}-3-(4-pyrimidinyl)-2-pyrazolin-5-one,
4-{[4-(2-Diethylaminoethyl)-3,5-dimethylpyrrol-2-yl]methylene}-3-(5-pyrimidinyl)-2-pyrazolin-5-one,
4-{[4-(2-Diethylaminoethyl)-3,5-dimethylpyrrol-2-yl]methylene}-3-(4-pyridazinyl)-2-pyrazolin-5-one,
3-Cyclopropyl-4-[(3,5-dimethyl-4-(1-pyrrolidinylmethyl)pyrrol-2-yl)methylene]-2-pyrazolin-5-one,
3-Cyclopropyl-4-[(4-diethylaminomethyl-3,5-dimethylpyrrol-2-yl)methylene]-2-pyrazolin-5-one,
3-Cyclopropyl-4-[(4-(2-cyclopropylaminoethyl)-3,5-dimethylpyrrol-2-yl]methylene-2-pyrazolin-5-one,
3-Cyclopropyl-4-{[3,5-dimethyl-4-(2-phenylaminoethyl)pyrrol-2-yl]methylene}-2-pyrazolin-5-one,
3-Cyclopropyl-4-{{3,5-dimethyl-4-[2-(4-pyridylmethylamino)ethyl]pyrrol-2-yl}methylene}-2-pyrazolin-5-one, 4-{[4-(2-Carboxyethyl)-3,5-dimethylpyrrol-2-yl]methylene}-3-cyclopropyl-2-pyrazolin-5-one,
3-Cyclopropyl-4-[(4-diethylaminomethyl-3-isopropyl-5-methylpyrrol-2-yl)methylene]-2-pyrazolin-5-one,
3-Cyclopropyl-4-{[4-(1-pirrolidinylmethyl)-3-isopropyl-5-methylpyrrol-2-yl]methylene}-2-pyrazolin-5-one,
3-Cyclopropyl-4-{3-isopropyl-5-methyl-4-[2-(1-pyrrolidinylethyl)]pyrrol-2-yl}methylene}-2-pyrazolin-5-one,
3-Cyclopropyl-4-{[4-(2-cyclopropylaminoethyl)-3-isopropyl-5-methylpyrrol-2-yl]methylene}-2-pyrazolin-5-one,
3-Cyclopropyl-4-{{4-[3-(1-pyrrolidinyl)propyl]-3-isopropyl-5-methylpyrrol-2-yl}methylene}-2-pyrazolin-5-one,
3-Cyclopropyl-4-{[3-isopropyl-5-methyl-4-(4-piperidinobutyl)pyrrol-2-yl]methylene}-2-pyrazolin-5-one,
3-Cyclopropyl-4-{{4-[3-(4-pyridylmethylamino)propyl]-3-isopropyl-5-methylpyrrol-2-yl}methylene}-2-pyrazolin-5-one,
3-Cyclopropyl-4-{[4-(4-dimethylaminobutyl)-3-isopropyl-5-methylpyrrol-2-yl]methylene}-2-pyrazolin-5-one,
3-Cyclopropyl-4-[(3-cyclopropyl-4-diethylaminomethyl-5-methylpyrrol-2-yl)methylene]-2-pyrazolin-5-one,
3-Cyclopropyl-4-{[3-cyclopropyl-4-(1-pirrolidinylmethyl)-5-methylpyrrol-2-yl]methylene}-2-pyrazolin-5-one,
3-Cyclopropyl-4-{{3-cyclopropyl-5-methyl-4-[2-(1-pyrrolidinyl)ethyl]pyrrol-2-yl}methylene}-2-pyrazolin-5-one,
3-Cyclopropyl-4-{{3-cyclopropyl-4-[2-di(methoxyethyl)aminoethyl]-5-methylpyrrol-2-yl}methylene}-2-pyrazolin-5-one,
3-Cyclopropyl-4-{]3-cyclopropyl 4-(3-diethylaminopropyl)-5-methylpyrrol-2-yl]methylene}-2-pyrazolin-5-one,
3-Cyclopropyl-4-{{3-cyclopropyl-4-[3-(2,5-dimethyl-1-pyrrolidinyl)propyl]-5-methylpyrrol-2-yl}methylene}-2-pyrazolin-5-one,
3-Cyclopropyl-4-{]3-cyclopropyl-5-methyl-4-(3-phenylmethylaminopropyl)pyrrol-2-yl]methylene}-2-pyrazolin-5-one,
3-Cyclopropyl-4-{{3-cyclopropyl-5-methyl-4-[4-(1-pyrrolidinyl)butyl]pyrrol-2-yl}methylene}-2-pyrazolin-5-one,
3-Cyclopropyl-4-{]3-cyclopropyl-5-methyl-4-(4-cyclobutylaminobutyl)pyrrol-2-yl]methylene}-2-pyrazolin-5-one,
4-{[4-(2-Cyclopropylaminoethyl)-3,5-dimethylpyrrol-2-yl]methylene}-3-pyrazinyl-2-pyrazolin-5-one,
4-{[3,5-Dimethyl-4-(2-phenylaminoethyl)pyrrol-2-yl]methylene}-3-pyrazinyl-2-pyrazolin-5-one,
4-{{3,5-Dimethyl-4-[2-(4-pyridylmethylamino)ethyl]pyrrol-2-yl}methylene}-3-pyrazinyl-2-pyrazolin-5-one,
4-{[4-(2-Carboxyethyl)-3,5-dimethylpyrrol-2-yl]methylene}-3-pyrazinyl-2-pyrazolin-5-one,
4-[(4-Diethylaminomethyl-3-isopropyl-5-methylpyrrol-2-yl)methylene]-3-pyrazinyl-2-pyrazolin-5-one,
4-{[4-(1-Pirrolidinylmethyl)-3-isopropyl-5-methylpyrrol-2-yl]methylene}-3-pyrazinyl-2-pyrazolin-5-one,
4-{{3-Isopropyl-5-methyl-4-[2-(1-pyrrolidinylethyl)]pyrrol-2-yl}methylene}-3-pyrazinyl-2-pyrazolin-5-one,
4-{[4-(2-Cyclopropylaminoethyl)-3-isopropyl-5-methylpyrrol-2-yl]methylene}-3-pyrazinyl-2-pyrazolin-5-one,
3-Pyrazinyl-4-{{4-[3-(1-pyrrolidinyl)propyl]-3-isopropyl-5-methylpyrrol-2-yl}methylene}-2-pyrazolin-5-one,
4-{[3-Isopropyl-5-methyl-4-(4-piperidinobutyl)pyrrol-2-yl]methylene}-3-pyrazinyl-2-pyrazolin-5-one,
3-Pyrazinyl-4-{{4-[3-(4-pyridylmethylamino)propyl]-3-isopropyl-5-methylpyrrol-2-yl}methylene}-2-pyrazolin-5-one,
4-{[4-(4-Dimethylaminobutyl)-3-isopropyl-5-methylpyrrol-2-yl]methylene}-3-pyrazinyl-2-pyrazolin-5-one,
4-[(3-Cyclopropyl-4-diethylaminomethyl-5-methylpyrrol-2-yl)methylene]-3-pyrazinyl-2-pyrazolin-5-one,
4-{{3-Cyclopropyl-5-methyl-4-[2-(1-pyrrolidinyl)ethyl]pyrrol-2-yl}methylene}-3-pyrazinyl-2-pyrazolin-5-one,
4-{{3-Cyclopropyl-4-[2-di(methoxyethyl)aminoethyl]-5-methylpyrrol-2-yl}methylene}-2-pyrazinyl-2-pyrazolin-5-one,
4-{[3-Cyclopropyl-4-(3-diethylaminopropyl)-5-methylpyrrol-2-yl]methylene}-3-pyrazinyl-2-pyrazolin-5-one,
4-{{3-Cyclopropyl-4-[3-(2,5-dimethyl-1-pyrrolidinyl)propyl]-5-methylpyrrol-2-yl}methylene}-3-pyrazinyl-2-pyrazolin-5-one,
4-{[3-Cyclopropyl-5-methyl-4-(3-phenylmethylaminopropyl)pyrrol-2-yl]methylene}-3-pyrazinyl-2-pyrazolin-5-one,
4-{{3-Cyclopropyl-5-methyl-4-[4-(1-pyrrolidinyl)butyl]pyrrol-2-yl}methylene}-3-pyrazinyl-2-pyrazolin-5-one,
4-{[3-Cyclopropyl-5-methyl-4-(4-cyclobutylaminobutyl)pyrrol-2-yl]methylene}-3-pyrazinyl-2-pyrazolin-5-one,
4-[(3,5-Dimethyl-4-(1-pyrrolidinylmethylpyrrol-2-yl)methylene]-3-(2-furyl)-2-pyrazolin-5-one,
4-[(4-Diethylaminomethyl-3,5-dimethylpyrrol-2-yl)methylene]-3-(2-furyl)-2-pyrazolin-5-one,
4-{[4-(2-Cyclopropylaminoethyl)-3,5-dimethylpyrrol-2-yl]methylene}-3-(2-furyl)-2-pyrazolin-5-one,
4-{[3,5-Dimethyl-4-(2-ethylaminoethyl)-pyrrol-2-yl]methylene}-3-(2-furyl)-2-pyrazolin-5-one,
4-{[3,5-Dimethyl-4-(2-phenylaminoethyl)pyrrol-2-yl]methylene}-3-(2-furyl)-2-pyrazolin-5-one,
4-{{3,5-Dimethyl-4-[2-(4-pyridylmethylamino)ethyl]pyrrol-2-yl}methylene}-3-(2-furyl)-2-pyrazolin-5-one,
4-[(4-Diethylaminomethyl-3-isopropyl-5-methylpyrrol-2-yl)methylene]-3-(2-furyl)-2-pyrazolin-5-one,
4-{[4-(1-Pirrolidinylmethyl)-3-isopropyl-5-methylpyrrol-2-yl]methylene}-3-(2-furyl)-2-pyrazolin-5-one,
4-{[4-(2-Carboxyethyl)-3,5-dimethylpyrrol-2-yl]methylene}-3-(2-furyl)-2-pyrazolin-5-one,
4-{{3-Isopropyl-5-methyl-4-[2-(1-pyrrolidinylethyl)]pyrrol-2-yl}methylene}-3-(2-furyl)-2-pyrazolin-5-one,
4-{[4-(2-Cyclopropylaminoethyl)-3-isopropyl-5-methylpyrrol-2-yl]methylene}-3-(2-furyl)-2-pyrazolin-5-one,
3-(2-Furyl)-4-{{4-[3-(1-pyrrolidinyl)propyl]-3-isopropyl-5-methylpyrrol-2-yl}methylene}-2-pyrazolin-5-one,
3-(2-Furyl)-4-{[3-isopropyl-5-methyl-4-(4-piperidinobutyl)pyrrol-2-yl]methylene}-2-pyrazolin-5-one,
3-(2-Furyl)-4-{{4-[3-(4-pyridylmethylamino)propyl]-3-isopropyl-5-methylpyrrol-2-yl}methylene}-2-pyrazolin-5-one,
4-{[4-(4-Dimethylaminobutyl)-3-isopropyl-5-methylpyrrol-2-yl]methylene}-3-(2-furyl)-2-pyrazolin-5-one,
4-[(3-Cyclopropyl-4-diethylaminomethyl-5-methylpyrrol-2-yl)methylene]-3-(2-furyl)-2-pyrazolin-5-one,
4-{{3-Cyclopropyl-5-methyl-4-[2-(1-pyrrolidinyl)ethyl]pyrrol-2-yl}methylene}-3-(2-furyl)-2-pyrazolin-5-one,
4-{{3-Cyclopropyl-4-[2-di(methoxyethyl)aminoethyl]-5-methylpyrrol-2-yl}methylene}-3-(2-furyl)-2-pyrazolin-5-one,
4-{[3-Cyclopropyl-4-(3-diethylaminopropyl)-5-methylpyrrol-2-yl]methylene}-3-(2-furyl)-2-pyrazolin-5-one,
4-{{3-Cyclopropyl-4-[3-(2,5-dimethyl-1-pyrrolidinyl)propyl]-5-methylpyrrol-2-yl}methylene}-3-(2-furyl)-2-pyrazolin-5-one,
4-{[3-Cyclopropyl-5-methyl-4-(3-phenylmethylaminopropyl)pyrrol-2-yl]methylene}-3-(2-furyl)-2-pyrazolin-5-one,
4-{{3-Cyclopropyl-5-methyl-4-[4-(1-pyrrolidinyl)butyl]pyrrol-2-yl}methylene}-3-(2-furyl)-2-pyrazolin-5-one,
4-{[3-Cyclopropyl-5-methyl-4-(4-cyclobutylaminobutyl)pyrrol-2-yl]methylene}-3-(2-furyl)-2-pyrazolin-5-one, 4-[(3,5-Dimethyl-4-(1-pyrrolidinylmethylpyrrol-2-yl)methylene]-3-(2-thienyl)-2-pyrazolin-5-one,
4-[(4-Diethylaminomethyl-3,5-dimethylpyrrol-2-yl)methylene]-3-(2-thienyl)-2-pyrazolin-5-one,
4-{[4-(2-Cyclopropylaminoethyl)-3,5-dimethylpyrrol-2-yl]methylene}-3-(2-thienyl)-2-pyrazolin-5-one,
4-{[3,5-Dimethyl-4-(2-ethylaminoethyl)-pyrrol-2-yl]methylene}-3-(2-thienyl)-2-pyrazolin-5-one,
4-{[3,5-Dimethyl-4-(2-phenylaminoethyl)pyrrol-2-yl]methylene}-3-(2-thienyl)-2-pyrazolin-5-one,
4-{{3,5-Dimethyl-4-[2-(4-pyridylmethylamino)ethyl]pyrrol-2-yl}methylene}-3-(2-thienyl)-2-pyrazolin-5-one,
4-{[4-(2-Carboxyethyl)-3,5-dimethylpyrrol-2-yl]methylene}-3-(2-thienyl)-2-pyrazolin-5-one,
4-[(4-Diethylaminomethyl-3-isopropyl-5-methylpyrrol-2-yl)methylene]-3-(2-thienyl)-2-pyrazolin-5-one,
4-{[4-(1-Pirrolidinylmethyl)-3-isopropyl-5-methylpyrrol-2-yl]methylene}-3-(2-thienyl)-2-pyrazolin-5-one,
4-{{3-Isopropyl-5-methyl-4-[2-(1-pyrrolidinylethyl)]pyrrol-2-yl}methylene}-3-(2-thienyl)-2-pyrazolin-5-one,
4-{[4-(2-Cyclopropylaminoethyl)-3-isopropyl-5-methylpyrrol-2-yl]methylene}-3-(2-thienyl)-2-pyrazolin-5-one,
4-{{4-[3-(1-Pyrrolidinyl)propyl]-3-isopropyl-5-methylpyrrol-2-yl}methylene}-3-(2-thienyl)-2-pyrazolin-5-one,
4-{[3-Isopropyl-5-methyl-4-(4-piperidinobutyl)pyrrol-2-yl]methylene}-3-(2-thienyl)-2-pyrazolin-5-one,
4-{{4-[3-(4-Pyridylmethylamino)propyl]-3-isopropyl-5-methylpyrrol-2-yl}methylene}-3-(2-thienyl)-2-pyrazolin-5-one,
4-{[4-(4-Dimethylaminobutyl)-3-isopropyl-5-methylpyrrol-2-yl]methylene}-3-(2-thienyl)-2-pyrazolin-5-one,
4-[(3-Cyclopropyl-4-diethylaminomethyl-5-methylpyrrol-2-yl)methylene]-3-(2-thienyl)-2-pyrazolin-5-one,
4-{{3-Cyclopropyl-5-methyl-4-[2-(1-pyrrolidinyl)ethyl]pyrrol-2-yl}methylene}-3-(2-thienyl)-2-pyrazolin-5-one,
4-{{3-Cyclopropyl-4-[2-di(methoxyethyl)aminoethyl]-5-methylpyrrol-2-yl}methylene}-3-(2-thienyl)-2-pyrazolin-5-one,
4-{[3-Cyclopropyl-4-(3-diethylaminopropyl)-5-methylpyrrol-2-yl]methylene}-3-(2-thienyl)-2-pyrazolin-5-one,
4-{{3-Cyclopropyl-4-[3-(2,5-dimethyl-1-pyrrolidinyl)propyl]-5-methylpyrrol-2-yl}methylene}-3-(2-thienyl)-2-pyrazolin-5-one,
4-{[3-Cyclopropyl-5-methyl-4-(3-phenylmethylaminopropyl)pyrrol-2-yl]methylene}-3-(2-thienyl)-2-pyrazolin-5-one,
4-{{3-Cyclopropyl-5-methyl-4-[4-(1-pyrrolidinyl)butyl]pyrrol-2-yl}methylene}-3-(2-thienyl)-2-pyrazolin-5-one,
4-{[3-Cyclopropyl-5-methyl-4-(4-cyclobutylaminobutyl)pyrrol-2-yl]methylene}-3-(2-thienyl)-2-pyrazolin-5-one,
4-[(3,5-Dimethyl-4-(1-pyrrolidinylmethylpyrrol-2-yl)methylene]-3-(4-pyrimidinyl)-2-pyrazolin-5-one,
4-[(4-Diethylaminomethyl-3,5-dimethylpyrrol-2-yl)methylene]-3-(4-pyrimidinyl)-2-pyrazolin-5-one,
4-{[4-(2-Cyclopropylaminoethyl)-3,5-dimethylpyrrol-2-yl]methylene}-3-(4-pyrimidinyl)-2-pyrazolin-5-one,
4-{[3,5-Dimethyl-4-(2-ethylaminoethyl)-pyrrol-2-yl]methylene}-3-(4-pyrimidinyl)-2-pyrazolin-5-one,
4-{[3,5-Dimethyl-4-(2-phenylaminoethyl)pyrrol-2-yl]methylene}-3-(4-pyrimidinyl)-2-pyrazolin-5-one,
4-{{3,5-dimethyl-4-[2-(4-pyridylmethylamino)ethyl]pyrrol-2-yl}methylene}-3-(4-pyrimidinyl)-2-pyrazolin-5-one,
4-{[4-(2-Carboxyethyl)-3,5-dimethylpyrrol-2-yl]methylene}-3-(4-pyrimidinyl)-2-pyrazolin-5-one,
4-[(4-Diethylaminomethyl-3-isopropyl-5-methylpyrrol-2-yl)methylene]-3-(4-pyrimidinyl)-2-pyrazolin-5-one,
4-{[4-(1-Pirrolidinylmethyl)-3-isopropyl-5-methylpyrrol-2-yl]methylene}-3-(4-pyrimidinyl)-2-pyrazolin-5-one,
4-{{3-Isopropyl-5-methyl-4-[2-(1-pyrrolidinylethyl)]pyrrol-2-yl}methylene}-3-(4-pyrimidinyl)-2-pyrazolin-5-one,
4-{[4-(2-cyclopropylaminoethyl)-3-isopropyl-5-methylpyrrol-2-yl]methylene}-3-(4-pyrimidinyl)-2-pyrazolin-5-one,
3-(4-Pyrimidinyl)-4-{{4-[3-(1-pyrrolidinyl)propyl]-3-isopropyl-5-methylpyrrol-2-yl}methylene}-2-pyrazolin-5-one,
4-{[3-Isopropyl-5-methyl-4-(4-piperidinobutyl)pyrrol-2-yl]methylene}-3-(4-pyrimidinyl)-2-pyrazolin-5-one,
4-{{4-[3-(4-Pyridylmethylamino)propyl]-3-isopropyl-5-methylpyrrol-2-yl}methylene}-3-(4-pyrimidinyl)-2-pyrazolin-5-one,
4-{[4-(4-Dimethylaminobutyl)-3-isopropyl-5-methylpyrrol-2-yl]methylene}-3-(4-pyrimidinyl)-2-pyrazolin-5-one,
4-[(3-Cyclopropyl-4-diethylaminomethyl-5-methylpyrrol-2-yl)methylene]-3-(4-pyrimidinyl)-2-pyrazolin-5-one,
4-{(3-Cyclopropyl-5-methyl-4-[2-(1-pyrrolidinyl)ethyl]pyrrol-2-yl}methylene}-3-(4-pyrimidinyl)-2-pyrazolin-5-one,
4-{{3-Cyclopropyl-4-[2-di(methoxyethyl)aminoethyl]-5-methylpyrrol-2-yl}methylene}-3-(4-pyrimidinyl)-2-pyrazolin-5-one,
4-{[3-Cyclopropyl-4-(3-diethylaminopropyl)-5-methylpyrrol-2-yl]methylene}-3-(4-pyrimidinyl)-2-pyrazolin-5-one,
4-{{3-Cyclopropyl-4-[3-(2,5-dimethyl-1-pyrrolidinyl)propyl]-5-methylpyrrol-2-yl}methylene}-3-(4-pyrimidinyl)-2-pyrazolin-5-one,
4-{[3-Cyclopropyl-5-methyl-4-(3-phenylmethylaminopropyl)pyrrol-2-yl]methylene}-3-(4-pyrimidinyl)-2-pyrazolin-5-one,
4-{{3-Cyclopropyl-5-methyl-4-[4-(1-pyrrolidinyl)butyl]pyrrol-2-yl}methylene-3-(4-pyrimidinyl)-2-pyrazolin-5-one,
4-{[3-Cyclopropyl-5-methyl-4-(4-cyclobutylaminobutyl)pyrrol-2-yl]methylene}-3-(4-pyrimidinyl)-2-pyrazolin-5-one,
4-[(3,5-Dimethyl-4-(1-pyrrolidinylmethylpyrrol-2-yl)methylene]-3-(5-pyrimidinyl)-2-pyrazolin-5-one,
4-[(4-Diethylaminomethyl-3,5-dimethylpyrrol-2-yl)methylene]-3-(5-pyrimidinyl)-2-pyrazolin-5-one,
4-{[4-(2-Cyclopropylaminoethyl)-3,5-dimethylpyrrol-2-yl]methylene}-3-(5-pyrimidinyl)-2-pyrazolin-5-one,
4-{[3,5-Dimethyl-4-(2-ethylaminoethyl)-pyrrol-2-yl]methylene}-3-(5-pyrimidinyl)-2-pyrazolin-5-one,
4-{[3,5-Dimethyl-4-(2-phenylaminoethyl)pyrrol-2-yl]methylene}-3-(5-pyrimidinyl)-2-pyrazolin-5-one,
4-{{3,5-dimethyl-4-[2-(4-pyridylmethylamino)ethyl]pyrrol-2-yl}methylene}-3-(5-pyrimidinyl)-2-pyrazolin-5-one,
4-{[4-(2-Carboxyethyl)-3,5-dimethylpyrrol-2-yl]methylene}-3-(5-pyrimidinyl)-2-pyrazolin-5-one,
4-[(4-Diethylaminomethyl-3-isopropyl-5-methylpyrrol-2-yl)methylene]-3-(5-pyrimidinyl)-2-pyrazolin-5-one,
4-{[4-(1-Pirrolidinylmethyl)-3-isopropyl-5-methylpyrrol-2-yl]methylene}-3-(5-pyrimidinyl)-2-pyrazolin-5-one,
4-{{3-Isopropyl-5-methyl-4-[2-(1-pyrrolidinylethyl)]pyrrol-2-yl}methylene}-3-(5-pyrimidinyl)-2-pyrazolin-5-one, 4-{[4-(2-cyclopropylaminoethyl)-3-isopropyl-5-methylpyrrol-2-yl]methylene}-3-(5-pyrimidinyl)-2-pyrazolin-5-one, 3-(5-Pyrimidinyl)-4-{{4-[3-(1-pyrrolidinyl)propyl]-3-isopropyl-5-methylpyrrol-2-yl}methylene}-2-pyrazolin-5-one, 4-{[3-Isopropyl-5-methyl-4-(4-piperidinobutyl)pyrrol-2-yl]methylene}-3-(5-pyrimidinyl)-2-pyrazolin-5-one, 4-{4-[3-(4-Pyridylmethylamino)propyl]-3-isopropyl-5-methylpyrrol-2-yl}methylene}-3-(5-pyrimidinyl)-2-pyrazolin-5-one, 4-{[4-(4-Dimethylaminobutyl)-3-isopropyl-5-methylpyrrol-2-yl]methylene}-3-(5-pyrimidinyl)-2-pyrazolin-5-one, 4-[(3-Cyclopropyl-4-diethylaminomethyl-5-methylpyrrol-2-yl)methylene]-3-(5-pyrimidinyl)-2-pyrazolin-5-one, 4-{{3-Cyclopropyl-5-methyl-4-[2-(1-pyrrolidinyl)ethyl]pyrrol-2-yl}methylene}-3-(5-pyrimidinyl)-2-pyrazolin-5-one, 4-{{3-Cyclopropyl-4-[2-di(methoxyethyl)aminoethyl]-5-methylpyrrol-2-yl}methylene}-3-(5-pyrimidinyl)-2-pyrazolin-5-one, 4-{[3-Cyclopropyl-4-(3-diethylaminopropyl)-5-methylpyrrol-2-yl]methylene}-3-(5-pyrimidinyl)-2-pyrazolin-5-one, 4-{{3-Cyclopropyl-4-[3-(2,5-dimethyl-1-pyrrolidinyl)propyl]-5-methylpyrrol-2-yl}methylene}-3-(S-pyrimidinyl)-2-pyrazolin-5-one, 4-{[3-Cyclopropyl-{-methyl-4-(3-phenylmethylaminopropyl)pyrrol-2-yl]methylene}-3-(5-pyrimidinyl)-2-pyrazolin-5-one, 4-{{3-Cyclopropyl-5-methyl-4-[4-(1-pyrrolidinyl)butyl]pyrrol-2-yl}methylene}-3-(5-pyrimidinyl)-2-pyrazolin-5-one, 4-{[3-Cyclopropyl-5-methyl-4-(4-cyclobutylaminobutyl)pyrrol-2-yl]methylene}-3-(5-pyrimidinyl)-2-pyrazolin-5-one, 4-[(3,5-Dimethyl-4-(1-pyrrolidinylmethylpyrrol-2-yl)methylene]-3-(2-pyrimidinyl)-2-pyrazolin-5-one, 4-[(4-Diethylaminomethyl-3,5-dimethylpyrrol-2-yl)methylene]-3-(2-pyrimidinyl)-2-pyrazolin-5-one, 4-{[4-(2-Cyclopropylaminoethyl)-3,5-dimethylpyrrol-2-yl]methylene}-3-(2-pyrimidinyl)-2-pyrazolin-5-one, 4-{[3,5-Dimethyl-4-(2-ethylaminoethyl)-pyrrol-2-yl]methylene}-3-(2-pyrimidinyl)-2-pyrazolin-5-one, 4-{[3,5-Dimethyl-4-(2-phenylaminoethyl)pyrrol-2-yl]methylene}-3-(2-pyrimidinyl)-2-pyrazolin-5-one, 4-{3,5-dimethyl-4-[2-(4-pyridylmethylamino)ethyl]pyrrol-2-yl}methylene}-3-(2-pyrimidinyl)-2-pyrazolin-5-one, 4-{[4-(2-Carboxyethyl)-3,5-dimethylpyrrol-2-yl]methylene}-3-(2-pyrimidinyl)-2-pyrazolin-5-one, 4-[(4-Diethylaminomethyl-3-isopropyl-5-methylpyrrol-2-yl)methylene]-3-(2-pyrimidinyl)-2-pyrazolin-5-one, 4-{[4-(1-Pirrolidinylmethyl)-3-isopropyl-5-methylpyrrol-2-yl]methylene)-3-(2-pyrimidinyl)-2-pyrazolin-5-one, 4-{{3-Isopropyl-5-methyl-4-[2-(1-pyrrolidinylethyl)]pyrrol-2-yl}methylene}-3-(2-pyrimidinyl)-2-pyrazolin-5-one, 4-{[4-(2-cyclopropylaminoethyl)-3-isopropyl-5-methylpyrrol-2-yl]methylene}-3-(2-pyrimidinyl)-2-pyrazolin-5-one, 3-(2-Pyrimidinyl)-4-{{4-[3-(1-pyrrolidinyl)propyl]-3-isopropyl-5-methylpyrrol-2-yl}methylene}-2-pyrazolin-5-one, 4-{[3-Isopropyl-5-methyl-4-(4-piperidinobutyl)pyrrol-2-yl]methylene}-3-(2-pyrimidinyl)-2-pyrazolin-5-one, 4-{{4-[3-(4-Pyridylmethylamino)propyl]-3-isopropyl-5-methylpyrrol-2-yl}methylene}-3-(2-pyrimidinyl)-2-pyrazolin-5-one, 4-{[4-(4-Dimethylaminobutyl)-3-isopropyl-5-methylpyrrol-2-yl]methylene}-3-(2-pyrimidinyl)-2-pyrazolin-5-one, 4-[(3-Cyclopropyl-4-diethylaminomethyl-5-methylpyrrol-2-yl)methylene]-3-(2-pyrimidinyl)-2-pyrazolin-5-one, 4-{{3-Cyclopropyl-5-methyl-4-[2-(1-pyrrolidinyl)ethyl]pyrrol-2-yl}methylene}-3-(2-pyrimidinyl)-2-pyrazolin-5-one, 4-{{3-Cyclopropyl-4-[2-di(methoxyethyl)aminoethyl]-5-methylpyrrol-2-yl}methylene}-3-(2-pyrimidinyl)-2-pyrazolin-5-one, 4-{[3-Cyclopropyl-4-(3-diethylaminopropyl)-5-methylpyrrol-2-yl]methylene}-3-(2-pyrimidinyl)-2-pyrazolin-5-one, 4-{{3-Cyclopropyl-4-[3-(2,5-dimethyl-1-pyrrolidinyl)propyl]-5-methylpyrrol-2-yl}methylene}-3-(2-pyrimidinyl)-2-pyrazolin-5-one, 4-{[3-Cyclopropyl-5-methyl-4-(3-phenylmethylaminopropyl)pyrrol-2-yl]methylene}-3-(2-pyrimidinyl)-2-pyrazolin-5-one, 4-{{3-Cyclopropyl-5-methyl-4-[4-(1-pyrrolidinyl)butyl]pyrrol-2-yl}methylene}-3-(2-pyrimidinyl)-2-pyrazolin-5-one, 4-{[3-Cyclopropyl-5-methyl-4-(4-cyclobutylaminobutyl)pyrrol-2-yl]methylene}-3-(2-pyrimidinyl)-2-pyrazolin-5-one, 4-[(3,5-Dimethyl-4-(1-pyrrolidinylmethylpyrrol-2-yl)methylene]-3-(3-pyridazinyl)-2-pyrazolin-5-one, 4-[(4-Diethylaminomethyl-3,5-dimethylpyrrol-2-yl)methylene]-3-(3-pyridazinyl)-2-pyrazolin-5-one, 4-{[4-(2-Cyclopropylaminoethyl)-3,5-dimethylpyrrol-2-yl]methylene}-3-(3-pyridazinyl)-2-pyrazolin-5-one, 4-{[3,5-Dimethyl-4-(2-ethylaminoethyl)-pyrrol-2-yl]methylene}-3-(3-pyridazinyl)-2-pyrazolin-5-one, 4-{[3,5-Dimethyl-4-(2-phenylaminoethyl)pyrrol-2-yl]methylene}-3-(3-pyridazinyl)-2-pyrazolin-5-one, 4-{{3,5-dimethyl-4-[2-(4-pyridylmethylamino)ethyl]pyrrol-2-yl}methylene}-3-(3-pyridazinyl)-2-pyrazolin-5-one, 4-{[4-(2-Carboxyethyl)-3,5-dimethylpyrrol-2-yl]methylene}-3-(3-pyridazinyl)-2-pyrazolin-5-one, 4-[(4-Diethylaminomethyl-3-isopropyl-5-methylpyrrol-2-yl)methylene]-3-(3-pyridazinyl)-2-pyrazolin-5-one, 4-{[4-(1-Pirrolidinylmethyl)-3-isopropyl-5-methylpyrrol-2-yl]methylene)-3-(3-pyridazinyl)-2-pyrazolin-5-one, 4-{{3-Isopropyl-5-methyl-4-[2-(1-pyrrolidinylethyl)]pyrrol-2-yl}methylene}-3-(3-pyridazinyl)-2-pyrazolin-5-one, 4-{[4-(2-cyclopropylaminoethyl)-3-isopropyl-5-methylpyrrol-2-yl]methylene}-3-(3-pyridazinyl)-2-pyrazolin-5-one, 3-(3-Pyridazinyl)-4-{{4-[3-(1-pyrrolidinyl)propyl]-3-isopropyl-5-methylpyrrol-2-yl}methylene}-2-pyrazolin-5-one, 4-{[3-Isopropyl-5-methyl-4-(4-piperidinobutyl)pyrrol-2-yl]methylene}-3-(3-pyridazinyl)-2-pyrazolin-5-one, 4-{{4-[3-(4-Pyridylmethylamino)propyl]-3-isopropyl-5-methylpyrrol-2-yl}methylene}-3-(3-pyridazinyl)-2-pyrazolin-5-one, 4-{[4-(4-Dimethylaminobutyl)-3-isopropyl-5-methylpyrrol-2-yl]methylene}-3-(3-pyridazinyl)-2-pyrazolin-5-one, 4-[(3-Cyclopropyl-4-diethylaminomethyl-5-methylpyrrol-2-yl)methylene]-3-(3-pyridazinyl)-2-pyrazolin-5-one, 4-{{3-Cyclopropyl-5-methyl-4-[2-(1-pyrrolidinyl)ethyl]pyrrol-2-yl}methylene}-3-(3-pyridazinyl)-2-pyrazolin-5-one,
4-{{3-Cyclopropyl-4-[2-di(methoxyethyl)aminoethyl]-5-methylpyrrol-2-yl}methylene}-3-(3-pyridazinyl)-2-pyrazolin-5-one,
4-{[3-Cyclopropyl-4-(3-diethylaminopropyl)-5-methylpyrrol-2-yl]methylene}-3-(3-pyridazinyl)-2-pyrazolin-5-one,
4-{{3-Cyclopropyl-4-[3-(2,5-dimethyl-1-pyrrolidinyl)propyl]-5-methylpyrrol-2-yl}methylene}-3-(3-pyridazinyl)-2-pyrazolin-5-one,
4-{[3-Cyclopropyl-5-methyl-4-(3-phenylmethylaminopropyl)pyrrol-2-yl]methylene}-3-(3-pyridazinyl)-2-pyrazolin-5-one,
4-{{3-Cyclopropyl-5-methyl-4-[4-(1-pyrrolidinyl)butyl]pyrrol-2-yl}methylene}-3-(3-pyridazinyl)-2-pyrazolin-5-one,
4-{{3-Cyclopropyl-5-methyl-4-(4-cyclobutylaminobutyl)pyrrol-2-yl]methylene}-3-(3-pyridazinyl)-2-pyrazolin-5-one,
4-[(3,5-Dimethyl-4-(1-pyrrolidinylmethylpyrrol-2-yl)methylene]-3-(4-pyridazinyl)-2-pyrazolin-5-one,
4-[(4-Diethylaminomethyl-3,5-dimethylpyrrol-2-yl)methylene]-3-(4-pyridazinyl)-2-pyrazolin-5-one,
4-{[4-(2-Cyclopropylaminoethyl)-3,5-dimethylpyrrol-2-yl]methylene}-3-(4-pyridazinyl)-2-pyrazolin-5-one,
4-{[3,5-Dimethyl-4-(2-ethylaminoethyl)-pyrrol-2-yl]methylene}-3-(4-pyridazinyl)-2-pyrazolin-5-one,
4-{[3,5-Dimethyl-4-(2-phenylaminoethyl)pyrrol-2-yl]methylene}-3-(4-pyridazinyl)-2-pyrazolin-5-one,
4-{{3,5-dimethyl-4-[2-(4-pyridylmethylamino)ethyl]pyrrol-2-yl}methylene}-3-(4-pyridazinyl)-2-pyrazolin-5-one,
4-[(4-Diethylaminomethyl-3-isopropyl-5-methylpyrrol-2-yl)methylene]-3-(4-pyridazinyl)-2-pyrazolin-5-one,
4-{[4-(1-Pirrolidinylmethyl)-3-isopropyl-5-methylpyrrol-2-yl]methylene}-3-(4-pyridazinyl)-2-pyrazolin-5-one,
4-{[4-(2-Carboxyethyl)-3,5-dimethylpyrrol-2-yl]methylene}-3-(4-pyridazinyl)-2-pyrazolin-5-one,
4-{{3-Isopropyl-5-methyl-4-[2-(1-pyrrolidinylethyl)]pyrrol-2-yl}methylene}-3-(4-pyridazinyl)-2-pyrazolin-5-one,
4-{[4-(2-cyclopropylaminoethyl)-3-isopropyl-5-methylpyrrol-2-yl]methylene}-3-(4-pyridazinyl)-2-pyrazolin-5-one,
3-(4-Pyridazinyl)-4-{{4-[3-(1-pyrrolidinyl)propyl]-3-isopropyl-5-methylpyrrol-2-yl}methylene}-2-pyrazolin-5-one,
4-{[3-Isopropyl-5-methyl-4-(4-piperidinobutyl)pyrrol-2-yl]methylene}-3-(4-pyridazinyl)-2-pyrazolin-5-one,
4-{{4-[3-(4-Pyridylmethylamino)propyl]-3-isopropyl-5-methylpyrrol-2-yl}methylene}-3-(4-pyridazinyl)-2-pyrazolin-5-one,
4-{[4-(4-Dimethylaminobutyl)-3-isopropyl-5-methylpyrrol-2-yl]methylene}-3-(4-pyridazinyl)-2-pyrazolin-5-one,
4-[(3-Cyclopropyl-4-diethylaminomethyl-5-methylpyrrol-2-yl)methylene]-3-(4-pyridazinyl)-2-pyrazolin-5-one,
4-{{3-Cyclopropyl-5-methyl-4-[2-(1-pyrrolidinyl)ethyl]pyrrol-2-yl}methylene}-3-(4-pyridazinyl)-2-pyrazolin-5-one,
4-{{3-Cyclopropyl-4-[2-di(methoxyethyl)aminoethyl]-5-methylpyrrol-2-yl}methylene}-3-(4-pyridazinyl)-2-pyrazolin-5-one,
4-{[3-Cyclopropyl-4-(3-diethylaminopropyl)-5-methylpyrrol-2-yl]methylene}-3-(4-pyridazinyl)-2-pyrazolin-5-one,
4-{{3-Cyclopropyl-4-[3-(2,5-dimethyl-1-pyrrolidinyl)propyl]-5-methylpyrrol-2-yl}methylene}-3-(4-pyridazinyl)-2-pyrazolin-5-one,
4-{[3-Cyclopropyl-5-methyl-4-(3-phenylmethylaminopropyl)pyrrol-2-yl]methylene}-3-(4-pyridazinyl)-2-pyrazolin-5-one,
4-{{3-Cyclopropyl-5-methyl-4-[4-(1-pyrrolidinyl)butyl]pyrrol-2-yl}methylene}-3-(4-pyridazinyl)-2-pyrazolin-5-one,
4-{[3-Cyclopropyl-5-methyl-4-(4-cyclobutylaminobutyl)pyrrol-2-yl]methylene}-3-(4-pyridazinyl)-2-pyrazolin-5-one,
4-[(3,5-Dimethyl-4-(1-pyrrolidinylmethylpyrrol-2-yl)methylene]-3-(1,2,4-triazin-3-yl)-2-pyrazolin-5-one,
4-[(4-Diethylaminomethyl-3,5-dimethylpyrrol-2-yl)methylene]-3-(1,2,4-triazin-3-yl)-2-pyrazolin-5-one,
4-{[4-(2-Cyclopropylaminoethyl)-3,5-dimethylpyrrol-2-yl]methylene}-3-(1,2,4-triazin-3-yl)-2-pyrazolin-5-one,
4-{[3,5-Dimethyl-4-(2-ethylaminoethyl)-pyrrol-2-yl]methylene}-3-(1,2,4-triazin-3-yl)-2-pyrazolin-5-one,
4-{[3,5-Dimethyl-4-(2-phenylaminoethyl)pyrrol-2-yl]methylene}-3-(1,2,4-triazin-3-yl)-2-pyrazolin-5-one,
4-{{3,5-dimethyl-4-[2-(4-pyridylmethylamino)ethyl]pyrrol-2-yl}methylene}-3-(1,2,4-triazin-3-yl)-2-pyrazolin-5-one,
4-{[4-(2-Carboxyethyl)-3,5-dimethylpyrrol-2-yl]methylene}-3-(1,2,4-triazin-3-yl)-2-pyrazolin-5-one,
4-[(4-Diethylaminomethyl-3-isopropyl-5-methylpyrrol-2-yl)methylene]-3-(1,2,4-triazin-3-yl)-2-pyrazolin-5-one,
4-{[4-(1-Pirrolidinylmethyl)-3-isopropyl-5-methylpyrrol-2-yl]methylene}-3-(1,2,4-triazin-3-yl)-2-pyrazolin-5-one,
4-{{3-Isopropyl-5-methyl-4-[2-(1-pyrrolidinylethyl)]pyrrol-2-yl}methylene}-3-(1,2,4-triazin-3-yl)-2-pyrazolin-5-one,
4-{[4-(2-cyclopropylaminoethyl)-3-isopropyl-5-methylpyrrol-2-yl]methylene}-3-(1,2,4-triazin-3-yl)-2-pyrazolin-5-one,
4-{{4-[3-(1-Pyrrolidinyl)propyl]-3-isopropyl-5-methylpyrrol-2-yl}methylene}-3-(1,2,4-triazin-3-yl)-2-pyrazolin-5-one,
4-{[3-Isopropyl-5-methyl-4-(4-piperidinobutyl)pyrrol-2-yl]methylene}-3-(1,2,4-triazin-3-yl)-2-pyrazolin-5-one,
4-{{4-[3-(4-Pyridylmethylamino)propyl]-3-isopropyl-5-methylpyrrol-2-yl}methylene}-3-(1,2,4-triazin-3-yl)-2-pyrazolin-5-one,
4-{[4-(4-Dimethylaminobutyl)-3-isopropyl-5-methylpyrrol-2-yl]methylene}-3-(1,2,4-triazin-3-yl)-2-pyrazolin-5-one,
4-[(3-Cyclopropyl-4-diethylaminomethyl-5-methylpyrrol-2-yl)methylene]-3-(1,2,4-triazin-3-yl)-2-pyrazolin-5-one,
4-{{3-Cyclopropyl-5-methyl-4-[2-(1-pyrrolidinyl)ethyl]pyrrol-2-yl}methylene}-3-(1,2,4-triazin-3-yl)-2-pyrazolin-5-one,
4-{{3-Cyclopropyl-4-[2-di(methoxyethyl)aminoethyl]-5-methylpyrrol-2-yl}methylene}-3-(1,2,4-triazin-3-yl)-2-pyrazolin-5-one,
4-{[3-Cyclopropyl-4-(3-diethylaminopropyl)-5-methylpyrrol-2-yl]methylene}-3-(1,2,4-triazin-3-yl)-2-pyrazolin-5-one,
4-{{3-Cyclopropyl-4-[3-(2,5-dimethyl-1-pyrrolidinyl)propyl]-5-methylpyrrol-2-yl}methylene}-3-(1,2,4-triazin-3-yl)-2-pyrazolin-5-one,
4-{[3-Cyclopropyl-5-methyl-4-(3-phenylmethylaminopropyl)pyrrol-2-yl]methylene}-3-(1,2,4-triazin-3-yl)-2-pyrazolin-5-one, 4-{{3-Cyclopropyl-5-methyl-4-[4-(1-pyrrolidinyl)butyl]pyrrol-2-yl}methylene}-3-(1,2,4-triazin-3-yl)-2-pyrazolin-5-one, 4-{[3-Cyclopropyl-5-methyl-4-(4-cyclobutylaminobutyl)pyrrol-2-yl]methylene}-3-(1,2,4-triazin-3-yl)-2-pyrazolin-5-one, 4-{[4-(2-Diethylaminoethyl)-5-methyl-3-trifluoromethylpyrrol-2-yl]methylene}-3-pyrazinyl-2-pyrazolin-5-one, 4-{{5-Methyl-4-[2-(1-pyrrolidinylethyl)]-3-trifluoromethylpyrrol-2-yl}methylene}-3-pyrazinyl-2-pyrazolin-5-one, 4-{[4-(2-Ethylaminoethyl)-5-methyl-3-trifluoromethylpyrrol-2-yl]methylene}-3-pyrazinyl-2-pyrazolin-5-one, 4-{{5-Methyl-4-[2-(4-pyridiylmethylaminoethyl)]-3-trifluoromethylpyrrol-2-yl}methylene}-3-pyrazinyl-2-pyrazolin-5-one, 4-{{4-[2-(1-Imidazoyl)ethyl]-5-methyl-3-trifluoromethylpyrrol-2-yl}methylene}-3-pyrazinyl-2-pyrazolin-5-one, 4-{[4-(2-Aminoethyl)-5-methyl-3-trifluoromethylpyrrol-2-yl]methylene}-3-pyrazinyl-2-pyrazolin-5-one, 4-{[4-(2-Diethylaminoethyl)-5-methyl-3-tert-butylpyrrol-2-yl]methylene}-3-pyrazinyl-2-pyrazolin-5-one, 4-{{5-Methyl-4-[2-(1-pyrrolidinylethyl)]-3-tert-butylpyrrol-2-yl}methylene}-3-pyrazinyl-2-pyrazolin-5-one, 4-{[4-(2-Ethylaminoethyl)-5-methyl-3-tert-butylpyrrol-2-yl]methylene}-3-pyrazinyl-2-pyrazolin-5-one, 4-{{5-Methyl-4-[2-(4-pyridiylmethylaminoethyl)]-3-tert-butylpyrrol-2-yl}methylene}-3-pyrazinyl-2-pyrazolin-5-one, 4-{{4-[2-(1-Imidazoyl)ethyl]-5-methyl-3-tert-butylpyrrol-2-yl}methylene}-3-pyrazinyl-2-pyrazolin-5-one, 4-{[4-(2-Aminoethyl)-5-methyl-3-tert-butylylpyrrol-2-yl]methylene}-3-pyrazinyl-2-pyrazolin-5-one, 4-{[4-(2-Diethylaminoethyl)-3-ethyl-5-methylpyrrol-2-yl]methylene}-3-pyrazinyl-2-pyrazolin-5-one, 4-{{3-Ethyl-5-methyl-4-[2-(1-pyrrolidinylethyl)]pyrrol-2-yl}-methylene}-3-pyrazinyl-2-pyrazolin-5-one, 4-{[3-Ethyl-4-(2-ethylaminoethyl)-5-methylpyrrol-2-yl]methylene}-3-pyrazinyl-2-pyrazolin-5-one, 4-{{3-Ethyl-5-methyl-4-[2-(4-pyridiylmethylaminoethyl)]pyrrol-2-yl}methylene}-3-pyrazinyl-2-pyrazolin-5-one, 4-{{4-[2-(1-Imidazoyl)ethyl]-5-methyl-3-ethylpyrrol-2-yl}methylene}-3-pyrazinyl-2-pyrazolin-5-one, 4-{[4-(2-Aminoethyl)-5-methyl-3-ethylpyrrol-2-yl]methylene}-3-pyrazinyl-2-pyrazolin-5-one, 4-{[3-Cyclobutyl-4-(2-diethylaminoethyl)-5-methylpyrrol-2-yl]methylene}-3-pyrazinyl-2-pyrazolin-5-one, 4-{{3-Cyclobutyl-5-methyl-4-[2-(1-pyrrolidinylethyl)]pyrrol-2-yl}methylene}-3-pyrazinyl-2-pyrazolin-5-one, 4-{[3-Cyclobutyl-4-(2-ethylaminoethyl)-5-methylpyrrol-2-yl]methylene}-3-pyrazinyl-2-pyrazolin-5-one, 4-{{3-Cyclobutyl-5-methyl-4-[2-(4-pyridiylmethylaminoethyl)]pyrrol-2-yl}methylene}-3-pyrazinyl-2-pyrazolin-5-one, 4-{{4-[2-(1-Imidazoyl)ethyl]-5-methyl-3-cyclobutylpyrrol-2-yl}methylene}-3-pyrazinyl-2-pyrazolin-5-one, 4-{[4-(2-Aminoethyl)-5-methyl-3-cyclobutylpyrrol-2-yl]methylene}-3-pyrazinyl-2-pyrazolin-5-one, 4-{[3-Cyclopentyl-4-(2-diethylaminoethyl)-5-methylpyrrol-2-yl]methylene}-3-pyrazinyl-2-pyrazolin-5-one, 4-{{3-Cyclopentyl-5-methyl-4-[2-(1-pyrrolidinylethyl)]pyrrol-2-yl}methylene}-3-pyrazinyl-2-pyrazolin-5-one, 4-{[3-Cyclopentyl-4-(2-ethylaminoethyl)-5-methylpyrrol-2-yl]methylene}-3-pyrazinyl-2-pyrazolin-5-one, 4-{{3-Cyclopentyl-5-methyl-4-[2-(4-pyridiylmethylaminoethyl)]pyrrol-2-yl}methylene}-3-pyrazinyl-2-pyrazolin-5-one, 4-{{4-[2-(1-Imidazoyl)ethyl]-5-methyl-3-cyclopentylpyrrol-2-yl}methylene}-3-pyrazinyl-2-pyrazolin-5-one, 4-{[4-(2-Aminoethyl)-5-methyl-3-cyclopentylpyrrol-2-yl]methylene}-3-pyrazinyl-2-pyrazolin-5-one 4-{[3-Cyclohexyl-4-(2-diethylaminoethyl)-5-methylpyrrol-2-yl]methylene}-3-pyrazinyl-2-pyrazolin-5-one, 4-{{3-Cyclohexyl-5-methyl-4-[2-(1-pyrrolidinylethyl)]pyrrol-2-yl}methylene}-3-pyrazinyl-2-pyrazolin-5-one, 4-{[3-Cyclohexyl-4-(2-ethylaminoethyl)-5-methylpyrrol-2-yl]methylene}-3-pyrazinyl-2-pyrazolin-5-one, 4-{{3-Cyclohexyl-5-methyl-4-[2-(4-pyridiylmethylaminoethyl)]pyrrol-2-yl}methylene}-3-pyrazinyl-2-pyrazolin-5-one, 4-{{4-[2-(1-Imidazoyl)ethyl]-5-methyl-3-cyclohexylpyrrol-2-yl}methylene}-3-pyrazinyl-2-pyrazolin-5-one, 4-{[4-(2-Aminoethyl)-5-methyl-3-cyclohexylpyrrol-2-yl]methylene}-3-pyrazinyl-2-pyrazolin-5-one, 4-{[4-(2-Diethylaminoethyl)-5-methyl-3-phenylpyrrol-2-yl]methylene}-3-pyrazinyl-2-pyrazolin-5-one, 4-{{5-Methyl-3-phenyl-4-[2-(1-pyrrolidinylethyl)]pyrrol-2-yl}methylene}-3-pyrazinyl-2-pyrazolin-5-one, 4-{[4-(2-Ethylaminoethyl)-5-methyl-3-phenylpyrrol-2-yl]methylene}-3-pyrazinyl-2-pyrazolin-5-one, 4-{{5-Methyl-3-phenyl-4-[2-(4-pyridiylmethylaminoethyl)]pyrrol-2-yl}methylene}-3-pyrazinyl-2-pyrazolin-5-one, 4-{{4-[2-(1-Imidazoyl)ethyl]-5-methyl-3-phenylpyrrol-2-yl}methylene}-3-pyrazinyl-2-pyrazolin-5-one, 4-{[4-(2-Aminoethyl)-5-methyl-3-phenylpyrrol-2-yl]methylene}-3-pyrazinyl-2-pyrazolin-5-one, 4-{[4-(2-Diethylaminoethyl)-5-methyl-3-(4-methoxyphenyl)pyrrol-2-yl]methylene}-3-pyrazinyl-2-pyrazolin-5-one, 4-{{5-Methyl-3-(4-methoxyphenyl)-4-[2-(1-pyrrolidinylethyl)]pyrrol-2-yl}methylene}-3-pyrazinyl-2-pyrazolin-5-one, 4-{[4-(2-Ethylaminoethyl)-5-methyl-3-(4-methoxyphenyl)pyrrol-2-yl]methylene}-3-pyrazinyl-2-pyrazolin-5-one, 4-{{5-Methyl-3-(4-methoxyphenyl)-4-[2-(4-pyridiylmethylaminoethyl)]pyrrol-2-yl}methylene}-3-pyrazinyl-2-pyrazolin-5-one, 4-{{4-[2-(1-Imidazoyl)ethyl]-5-methyl-3-(4-methoxyphenyl)pyrrol-2-yl}methylene}-3-pyrazinyl-2-pyrazolin-5-one, 4-{[4-(2-Aminoethyl)-5-methyl-3-(4-methoxyphenyl)pyrrol-2-yl]methylene}-3-pyrazinyl-2-pyrazolin-5-one, 4-{[4-(2-Diethylaminoethyl)-5-methyl-3-(2-pyridyl)pyrrol-2-yl]methylene}-3-pyrazinyl-2-pyrazolin-5-one, 4-{{5-Methyl-3-(2-pyridyl)-4-[2-(1-pyrrolidinylethyl)]pyrrol-2-yl}methylene}-3-pyrazinyl-2-pyrazolin-5-one, 4-{[4-(2-Ethylaminoethyl)-5-methyl-3-(2-pyridyl)pyrrol-2-yl]methylene}-3-pyrazinyl-2-pyrazolin-5-one, 4-{{5-Methyl-3-(2-pyridyl)-4-[2-(4-pyridiylmethylaminoethyl)]pyrrol-2-yl}methylene}-3-pyrazinyl-2-pyrazolin-5-one, 4-{{4-[2-(1-Imidazoyl)ethyl]-5-methyl-3-(2-pyridyl)pyrrol-2-yl}methylene}-3-pyrazinyl-2-pyrazolin-5-one, 4-{[4-(2-Aminoethyl)-5-methyl-3-(2-pyridyl)pyrrol-2-yl]methylene}-3-pyrazinyl-2-pyrazolin-5-one, 4-{[4-(2-Diethylaminoethyl)-5-methyl-3-pyrazinylpyrrol-2-yl]methylene}-3-pyrazinyl-2-pyrazolin-5-one, 4-{{5-Methyl-3-pyrazinyl-4-[2-(1-pyrrolidinylethyl)]pyrrol-2-yl}methylene}-3-pyrazinyl-2-pyrazolin-5-one, 4-{[4-(2-Ethylaminoethyl)-5-methyl-3-pyrazinylpyrrol-2-yl]methylene}-3-pyrazinyl-2-pyrazolin-5-one,
4-{{5-Methyl-3-pyrazinyl-4-[2-(4-pyridiylmethylaminoethyl)]pyrrol-2-yl}methylene}-3-pyrazinyl-2-pyrazolin-5-one,
4-{{4-[2-(1-Imidazoyl)ethyl]-5-methyl-3-pyrazinylpyrrol-2-yl}methylene}-3-pyrazinyl-2-pyrazolin-5-one,
4-{[4-(2-Cyclopropylaminoethyl)-5-methyl-3-pyrazinylpyrrol-2-yl]methylene}-3-pyrazinyl-2-pyrazolin-5-one,
4-{[4-(2-Diethylaminoethyl)-5-methyl-3-(2-imidazoyl)pyrrol-2-yl]methylene}-3-pyrazinyl-2-pyrazolin-5-one,
4-{{5-Methyl-3-(2-imidazoyl)-4-[2-(1-pyrrolidinylethyl)]pyrrol-2-yl}methylene}-3-pyrazinyl-2-pyrazolin-5-one,
4-{[4-(2-Ethylaminoethyl)-5-methyl-3-(2-imidazoyl)pyrrol-2-yl]methylene}-3-pyrazinyl-2-pyrazolin-5-one,
4-{{5-Methyl-3-(2-imidazoyl)-4-[2-(4-pyridiylmethylaminoethyl)]pyrrol-2-yl}methylene}-3-pyrazinyl-2-pyrazolin-5-one,
4-{{4-[2-(1-Imidazoyl)ethyl]-5-methyl-3-(2-imidazoyl)pyrrol-2-yl}methylene}-3-pyrazinyl-2-pyrazolin-5-one,
4-{[4-(2-Cyclopropylaminoethyl)-5-methyl-3-(2-imidazoyl)pyrrol-2-yl]methylene}-3-pyrazinyl-2-pyrazolin-5-one,
4-{[4-(2-Diethylaminoethyl)-5-methyl-3-(2-pyrimidinyl)pyrrol-2-yl]methylene}-3-pyrazinyl-2-pyrazolin-5-one,
4-{{5-Methyl-3-(2-pyrimidinyl)-4-[2-(1-pyrrolidinylethyl)]pyrrol-2-yl}methylene}-3-pyrazinyl-2-pyrazolin-5-one,
4-{[4-(2-Ethylaminoethyl)-5-methyl-3-(2-pyrimidinyl)pyrrol-2-yl]methylene}-3-pyrazinyl-2-pyrazolin-5-one,
4-{{5-Methyl-3-(2-pyrimidinyl)-4-[2-(4-pyridiylmethylaminoethyl)]pyrrol-2-yl}methylene}-3-pyrazinyl-2-pyrazolin-5-one,
4-{{4-[2-(1-Imidazoyl)ethyl]-5-methyl-3-(2-pyrimidinyl)pyrrol-2-yl}methylene}-3-pyrazinyl-2-pyrazolin-5-one,
4-{[4-(2-Cyclopropylaminoethyl)-5-methyl-3-(2-pyrimidinyl)pyrrol-2-yl]methylene}-3-pyrazinyl-2-pyrazolin-5-one,
4-{[4-(2-Diethylaminoethyl)-5-methyl-3-(3-isoxazolyl)pyrrol-2-yl]methylene}-3-pyrazinyl-2-pyrazolin-5-one,
4-{{5-Methyl-3-(3-isoxazolyl)-4-[2-(1-pyrrolidinylethyl)]pyrrol-2-yl}methylene}-3-pyrazinyl-2-pyrazolin-5-one,
4-{[4-(2-Ethylaminoethyl)-5-methyl-3-(3-isoxazolyl)pyrrol-2-yl]methylene}-3-pyrazinyl-2-pyrazolin-5-one,
4-{{5-Methyl-3-(3-isoxazolyl)-4-[2-(4-pyridylmethylaminoethyl)]pyrrol-2-yl}methylene}-3-pyrazinyl-2-pyrazolin-5-one,
4-{{4-[2-(1-Imidazoyl)ethyl]-5-methyl-3-(3-isoxazolyl)pyrrol-2-yl}methylene}-3-pyrazinyl-2-pyrazolin-5-one,
4-{[4-(2-Cyclopropylaminoethyl)-5-methyl-3-(3-isoxazolyl)pyrrol-2-yl]methylene}-3-pyrazinyl-2-pyrazolin-5-one,
4-{([4-(2-Diethylaminoethyl)-5-methyl-3-(2-furyl)pyrrol-2-yl]methylene}-3-pyrazinyl-2-pyrazolin-5-one,
4-{{5-Methyl-3-(2-furyl)-4-[2-(1-pyrrolidinylethyl)]pyrrol-2-yl}methylene}-3-pyrazinyl-2-pyrazolin-5-one,
4-{[4-(2-Ethylaminoethyl)-5-methyl-3-(2-furyl)pyrrol-2-yl]methylene}-3-pyrazinyl-2-pyrazolin-5-one,
4-{{5-Methyl-3-(2-furyl)-4-[2-(4-pyridiylmethylaminoethyl)]pyrrol-2-yl}methylene}-3-pyrazinyl-2-pyrazolin-5-one,
4-{{4-[2-(1-Imidazoyl)ethyl]-5-methyl-3-(2-furyl)pyrrol-2-yl}methylene}-3-pyrazinyl-2-pyrazolin-5-one,
4-{[4-(2-Cyclopropylaminoethyl)-5-methyl-3-(2-furyl)pyrrol-2-yl]methylene}-3-pyrazinyl-2-pyrazolin-5-one,
4-{[4-(2-Diethylaminoethyl)-5-hydroxymethyl-3-isopropylpyrrol-2-yl]methylene}-3-pyrazinyl-2-pyrazolin-5-one,
4-{{5-Hydroxymethyl-3-isopropyl-4-[2-(1-pyrrolidinylethyl)]pyrrol-2-yl}methylene}-3-pyrazinyl-2-pyrazolin-5-one,
4-{[4-(2-Ethylaminoethyl)-5-hydroxymethyl-3-isopropylpyrrol-2-yl]methylene}-3-pyrazinyl-2-pyrazolin-5-one,
4-{{5-Hydroxymethyl-3-isopropyl-4-[2-(4-pyridiylmethylaminoethyl)]pyrrol-2-yl}methylene}-3-pyrazinyl-2-pyrazolin-5-one,
4-{{4-[2-(1-Imidazoyl)ethyl]-5-hydroxymethyl-3-isopropylpyrrol-2-yl}methylene}-3-pyrazinyl-2-pyrazolin-5-one,
4-{[4-(2-Cyclopropylaminoethyl)-5-hydroxymethyl-3-isopropylpyrrol-2-yl]methylene}-3-pyrazinyl-2-pyrazolin-5-one,
4-{[4-(2-Diethylaminoethyl)-3,5-dicyclopropylpyrrol-2-yl]methylene}-3-pyrazinyl-2-pyrazolin-5-one,
4-{{3,5-Dicyclopropyl-4-[2-(1-pyrrolidinylethyl)]pyrrol-2-yl}methylene}-3-pyrazinyl-2-pyrazolin-5-one,
4-{[4-(2-Ethylaminoethyl)-3,5-dicyclopropylpyrrol-2-yl]methylene}-3-pyrazinyl-2-pyrazolin-5-one,
4-{{3,5-Dicyclopropyl-4-[2-(4-pyridiylmethylaminoethyl)]pyrrol-2-yl}methylene}-3-pyrazinyl-2-pyrazolin-5-one,
4-{{4-[2-(1-Imidazoyl)ethyl]-3,5-dicyclopropylpyrrol-2-yl}methylene}-3-pyrazinyl-2-pyrazolin-5-one,
4-{[4-(2-Cyclopropylaminoethyl)-3,5-dicyclopropylpyrrol-2-yl]methylene}-3-pyrazinyl-2-pyrazolin-5-one,
4-{[4-(2-Diethylaminomethyl)-5-methyl-3-trifluoromethylpyrrol-2-yl]methylene}-3-pyrazinyl-2-pyrazolin-5-one,
4-{[4-(2-Dimethylaminomethyl)-5-methyl-3-trifluoromethylpyrrol-2-yl]methylene}-3-pyrazinyl-2-pyrazolin-5-one,
4-{{5-Methyl-4-[2-(1-pyrrolidinylmethyl)]-3-trifluoromethylpyrrol-2-yl}methylene}-3-pyrazinyl-2-pyrazolin-5-one,
4-{[4-(2-Ethylaminomethyl)-5-methyl-3-trifluoromethylpyrrol-2-yl]methylene}-3-pyrazinyl-2-pyrazolin-5-one,
4-{{5-Methyl-4-[2-(4-pyridiylmethylaminomethyl)]-3-trifluoromethylpyrrol-2-yl}methylene}-3-pyrazinyl-2-pyrazolin-5-one,
4-{{4-[2-(1-Imidazoyl)methyl]-5-methyl-3-trifluoromethylpyrrol-2-yl}methylene}-3-pyrazinyl-2-pyrazolin-5-one,
4-{[4-(2-Aminomethyl)-5-methyl-3-trifluoromethylpyrrol-2-yl]methylene}-3-pyrazinyl-2-pyrazolin-5-one,
4-{[4-(2-Diethylaminomethyl)-5-methyl-3-tert-butylpyrrol-2-yl]methylene}-3-pyrazinyl-2-pyrazolin-5-one,
4-{[4-(2-Dimethylaminomethyl)-5-methyl-3-tert-butylpyrrol-2-yl]methylene}-3-pyrazinyl-2-pyrazolin-5-one,
4-{{5-Methyl-4-[2-(1-pyrrolidinylmethyl)]-3-tert-butylpyrrol-2-yl}methylene}-3-pyrazinyl-2-pyrazolin-5-one,
4-{[4-(2-Ethylaminomethyl)-5-methyl-3-tert-butylpyrrol-2-yl]methylene}-3-pyrazinyl-2-pyrazolin-5-one,
4-{{5-Methyl-4-[2-(4-pyridiylmethylaminomethyl)]-3-tert-butylpyrrol-2-yl}methylene}-3-pyrazinyl-2-pyrazolin-5-one,
4-{{4-[2-(1-Imidazoyl)methyl]-5-methyl-3-tert-butylpyrrol-2-yl}methylene}-3-pyrazinyl-2-pyrazolin-5-one,
4-{[4-(2-Aminomethyl)-5-methyl-3-tert-butylylpyrrol-2-yl]methylene}-3-pyrazinyl-2-pyrazolin-5-one,
4-{[4-(2-Diethylaminomethyl)-3-ethyl-5-methylpyrrol-2-yl]methylene}-3-pyrazinyl-2-pyrazolin-5-one,
4-{[4-(2-Dimethylaminomethyl)-3-ethyl-5-methylpyrrol-2-yl]methylene}-3-pyrazinyl-2-pyrazolin-5-one,
4-{{3-Ethyl-5-methyl-4-[2-(1-pyrrolidinylmethyl)]pyrrol-2-yl}methylene}-3-pyrazinyl-2-pyrazolin-5-one,
4-{[3-Ethyl-4-(2-ethylaminomethyl)-5-methylpyrrol-2-yl]methylene}-3-pyrazinyl-2-pyrazolin-5-one, 4-{{3-Ethyl-5-methyl-4-[2-(4-pyridiylmethylaminomethyl)]pyrrol-2-yl]methylene}-3-pyrazinyl-2-pyrazolin-5-one,
4-{{4-[2-(1-Imidazoyl)methyl]-5-methyl-3-ethylpyrrol-2-yl}methylene}-3-pyrazinyl-2-pyrazolin-5-one,
4-{[4-(2-Aminomethyl)-5-methyl-3-ethylpyrrol-2-yl]methylene}-3-pyrazinyl-2-pyrazolin-5-one,
4-{[3-Cyclobutyl-4-(2-diethylaminomethyl)-5-methylpyrrol-2-yl]methylene}-3-pyrazinyl-2-pyrazolin-5-one,
4-{[3-Cyclobutyl-4-(2-dimethylaminomethyl)-5-methylpyrrol-2-yl]methylene}-3-pyrazinyl-2-pyrazolin-5-one,
4-{{3-Cyclobutyl-5-methyl-4-[2-(1-pyrrolidinylmethyl)]pyrrol-2-yl}methylene}-3-pyrazinyl-2-pyrazolin-5-one,
4-{[3-Cyclobutyl-4-(2-ethylaminomethyl)-5-methylpyrrol-2-yl]methylene}-3-pyrazinyl-2-pyrazolin-5-one,
4-{{3-Cyclobutyl-5-methyl-4-[2-(4-pyridiylmethylaminomethyl)]pyrrol-2-yl]methylene}-3-pyrazinyl-2-pyrazolin-5-one,
4-{{4-[2-(1-Imidazoyl)methyl]-5-methyl-3-cyclobutylpyrrol-2-yl}methylene}-3-pyrazinyl-2-pyrazolin-5-one,
4-{[4-(2-Aminomethyl)-5-methyl-3-cyclobutylpyrrol-2-yl]methylene}-3-pyrazinyl-2-pyrazolin-5-one,
4-{[3-Cyclopentyl-4-(2-diethylaminomethyl)-5-methylpyrrol-2-yl]methylene}-3-pyrazinyl-2-pyrazolin-5-one,
4-{[3-Cyclopentyl-4-(2-dimethylaminomethyl)-5-methylpyrrol-2-yl]methylene}-3-pyrazinyl-2-pyrazolin-5-one,
4-{{3-Cyclopentyl-5-methyl-4-[2-(1-pyrrolidinylmethyl)]pyrrol-2-yl}methylene}-3-pyrazinyl-2-pyrazolin-5-one,
4-{[3-Cyclopentyl-4-(2-ethylaminomethyl)-5-methylpyrrol-2-yl]methylene}-3-pyrazinyl-2-pyrazolin-5-one,
4-{{3-Cyclopentyl-5-methyl-4-[2-(4-pyridiylmethylaminomethyl)]pyrrol-2-yl]methylene}-3-pyrazinyl-2-pyrazolin-5-one,
4-{{4-[2-(1-Imidazoyl)methyl]-5-methyl-3-cyclopentylpyrrol-2-yl}methylene}-3-pyrazinyl-2-pyrazolin-5-one,
4-{[4-(2-Aminomethyl)-5-methyl-3-cyclopentylpyrrol-2-yl]methylene}-3-pyrazinyl-2-pyrazolin-5-one
4-{[3-Cyclohexyl-4-(2-diethylaminomethyl)-5-methylpyrrol-2-yl]methylene}-3-pyrazinyl-2-pyrazolin-5-one,
4-{[3-Cyclohexyl-4-(2-dimethylaminomethyl)-5-methylpyrrol-2-yl]methylene}-3-pyrazinyl-2-pyrazolin-5-one,
4-{{3-Cyclohexyl-5-methyl-4-[2-(1-pyrrolidinylmethyl)]pyrrol-2-yl}methylene}-3-pyrazinyl-2-pyrazolin-5-one,
4-{[3-Cyclohexyl-4-(2-ethylaminomethyl)-5-methylpyrrol-2-yl]methylene}-3-pyrazinyl-2-pyrazolin-5-one,
4-{{3-Cyclohexyl-5-methyl-4-[2-(4-pyridiylmethylaminomethyl)]pyrrol-2-yl}methylene}-3-pyrazinyl-2-pyrazolin-5-one,
4-{{4-[2-(1-Imidazoyl)methyl]-5-methyl-3-cyclohexylpyrrol-2-yl}methylene}-3-pyrazinyl-2-pyrazolin-5-one,
4-{[4-(2-Aminomethyl)-5-methyl-3-cyclohexylpyrrol-2-yl]methylene}-3-pyrazinyl-2-pyrazolin-5-one,
4-{[4-(2-Diethylaminomethyl)-5-methyl-3-phenylpyrrol-2-yl]methylene}-3-pyrazinyl-2-pyrazolin-5-one,
4-{[4-(2-Dimethylaminomethyl)-5-methyl-3-phenylpyrrol-2-yl]methylene}-3-pyrazinyl-2-pyrazolin-5-one,
4-{{5-Methyl-3-phenyl-4-[2-(1-pyrrolidinylmethyl)]pyrrol-2-yl}methylene}-3-pyrazinyl-2-pyrazolin-5-one,
4-{[4-(2-Ethylaminomethyl)-5-methyl-3-phenylpyrrol-2-yl]methylene}-3-pyrazinyl-2-pyrazolin-5-one,
4-{{5-Methyl-3-phenyl-4-[2-(4-pyridiylmethylaminomethyl)]pyrrol-2-yl}methylene}-3-pyrazinyl-2-pyrazolin-5-one,
4-{{4-[2-(1-Imidazoyl)methyl]-5-methyl-3-phenylpyrrol-2-yl}methylene}-3-pyrazinyl-2-pyrazolin-5-one,
4-{[4-(2-Aminomethyl)-5-methyl-3-phenylpyrrol-2-yl]methylene}-3-pyrazinyl-2-pyrazolin-5-one,
4-{[4-(2-Diethylaminomethyl)-5-methyl-3-(4-methoxyphenyl)pyrrol-2-yl]methylene}-3-pyrazinyl-2-pyrazolin-5-one,
4-{[4-(2-Dimethylaminomethyl)-5-methyl-3-(4-methoxyphenyl)pyrrol-2-yl]methylene}-3-pyrazinyl-2-pyrazolin-5-one,
4-{{5-Methyl-3-(4-methoxyphenyl)-4-[2-(1-pyrrolidinylmethyl)]pyrrol-2-yl}methylene}-3-pyrazinyl-2-pyrazolin-5-one,
4-{[4-(2-Ethylaminomethyl)-5-methyl-3-(4-methoxyphenyl)pyrrol-2-yl]methylene}-3-pyrazinyl-2-pyrazolin-5-one,
4-{{5-Methyl-3-(4-methoxyphenyl)-4-[2-(4-pyridiylmethylaminomethyl)]pyrrol-2-yl}methylene}-3-pyrazinyl-2-pyrazolin-5-one,
4-{{4-[2-(1-Imidazoyl)methyl]-5-methyl-3-(4-methoxyphenyl)pyrrol-2-yl}methylene}-3-pyrazinyl-2-pyrazolin-5-one,
4-{[4-(2-Aminomethyl)-5-methyl-3-(4-methoxyphenyl)pyrrol-2-yl]methylene}-3-pyrazinyl-2-pyrazolin-5-one,
4-{[4-(2-Diethylaminomethyl)-5-methyl-3-(2-pyridyl)pyrrol-2-yl]methylene}-3-pyrazinyl-2-pyrazolin-5-one,
4-{[4-(2-Dimethylaminomethyl)-5-methyl-3-(2-pyridyl)pyrrol-2-yl]methylene}-3-pyrazinyl-2-pyrazolin-5-one,
4-{{5-Methyl-3-(2-pyridyl)-4-[2-(1-pyrrolidinylmethyl)]pyrrol-2-yl}methylene}-3-pyrazinyl-2-pyrazolin-5-one,
4-{[4-(2-Ethylaminomethyl)-5-methyl-3-(2-pyridyl)pyrrol-2-yl]methylene}-3-pyrazinyl-2-pyrazolin-5-one,
4-{{5-Methyl-3-(2-pyridyl)-4-[2-(4-pyridylmethylaminomethyl)]pyrrol-2-yl}methylene}-3-pyrazinyl-2-pyrazolin-5-one,
4-{{4-[2-(1-Imidazoyl)methyl]-5-methyl-3-(2-pyridyl)pyrrol-2-yl}methylene}-3-pyrazinyl-2-pyrazolin-5-one,
4-{[4-(2-Aminomethyl)-5-methyl-3-(2-pyridyl)pyrrol-2-yl]methylene}-3-pyrazinyl-2-pyrazolin-5-one,
4-{[4-(2-Diethylaminomethyl)-5-methyl-3-pyrazinylpyrrol-2-yl]methylene}-3-pyrazinyl-2-pyrazolin-5-one,
4-{[4-(2-Dimethylaminomethyl)-5-methyl-3-pyrazinylpyrrol-2-yl]methylene}-3-pyrazinyl-2-pyrazolin-5-one,
4-{{5-Methyl-3-pyrazinyl-4-[2-(1-pyrrolidinylmethyl)]pyrrol-2-yl}methylene}-3-pyrazinyl-2-pyrazolin-5-one,
4-{[4-(2-Ethylaminomethyl)-5-methyl-3-pyrazinylpyrrol-2-yl]methylene}-3-pyrazinyl-2-pyrazolin-5-one,
4-{{5-Methyl-3-pyrazinyl-4-[2-(4-pyridiylmethylaminomethyl)]pyrrol-2-yl}methylene}-3-pyrazinyl-2-pyrazolin-5-one,
4-{{4-[2-(1-Imidazoyl)methyl]-5-methyl-3-pyrazinylpyrrol-2-yl}methylene}-3-pyrazinyl-2-pyrazolin-5-one,
4-{[4-(2-Cyclopropylaminomethyl)-5-methyl-3-pyrazinylpyrrol-2-yl]methylene}-3-pyrazinyl-2-pyrazolin-5-one,
4-{[4-(2-Diethylaminomethyl)-5-methyl-3-(2-imidazoyl)pyrrol-2-yl]methylene}-3-pyrazinyl-2-pyrazolin-5-one,
4-{[4-(2-Dimethylaminomethyl)-5-methyl-3-(2-imidazoyl)pyrrol-2-yl]methylene}-3-pyrazinyl-2-pyrazolin-5-one,
4-{{5-Methyl-3-(2-imidazoyl)-4-[2-(1-pyrrolidinylmethyl)]pyrrol-2-yl}methylene}-3-pyrazinyl-2-pyrazolin-5-one,
4-{[4-(2-Ethylaminomethyl)-5-methyl-3-(2-imidazoyl)pyrrol-2-yl]methylene}-3-pyrazinyl-2-pyrazolin-5-one,
4-{{5-Methyl-3-(2-imidazoyl)-4-[2-(4-pyridiylmethylaminomethyl)]pyrrol-2-yl}methylene}-3-pyrazinyl-2-pyrazolin-5-one,
4-{{4-[2-(1-Imidazoyl)methyl]-5-methyl-3-(2-imidazoyl)pyrrol-2-yl}methylene}-3-pyrazinyl-2-pyrazolin-5-one,
4-{[4-(2-Cyclopropylaminomethyl)-5-methyl-3-(2-imidazoyl)pyrrol-2-yl]methylene}-3-pyrazinyl-2-pyrazolin-5-one, 4-{[4-(2-Diethylaminomethyl)-5-methyl-3-(2-pyrimidinyl)pyrrol-2-yl]methylene}-3-pyrazinyl-2-pyrazolin-5-one,
4-{[4-(2-Dimethylaminomethyl)-5-methyl-3-(2-pyrimidinyl)pyrrol-2-yl]methylene}-3-pyrazinyl-2-pyrazolin-5-one,
4-{{5-Methyl-3-(2-pyrimidinyl)-4-[2-(1-pyrrolidinylmethyl)]pyrrol-2-yl}methylene}-3-pyrazinyl-2-pyrazolin-5-one,
4-{[4-(2-Ethylaminomethyl)-5-methyl-3-(2-pyrimidinyl)pyrrol-2-yl]methylene}-3-pyrazinyl-2-pyrazolin-5-one,
4-{{5-Methyl-3-(2-pyrimidinyl)-4-[2-(4-pyridiylmethylaminomethyl)]pyrrol-2-yl}methylene}-3-pyrazinyl-2-pyrazolin-5-one,
4-{{4-[2-(1-Imidazoyl)methyl]-5-methyl-3-(2-pyrimidinyl)pyrrol-2-yl}methylene}-3-pyrazinyl-2-pyrazolin-5-one,
4-{[4-(2-Cyclopropylaminomethyl)-5-methyl-3-(2-pyrimidinyl)pyrrol-2-yl]methylene}-3-pyrazinyl-2-pyrazolin-5-one,
4-{[4-(2-Diethylaminoethyl)-5-methyl-3-(3-isoxazolyl)pyrrol-2-yl]methylene}-3-pyrazinyl-2-pyrazolin-5-one,
4-{[4-(2-Dimethylaminoethyl)-5-methyl-3-(3-isoxazolyl)pyrrol-2-yl]methylene}-3-pyrazinyl-2-pyrazolin-5-one,
4-{{5-Methyl-3-(3-isoxazolyl)-4-[2-(1-pyrrolidinylmethyl)]pyrrol-2-yl}methylene}-3-pyrazinyl-2-pyrazolin-5-one,
4-{[4-(2-Ethylaminomethyl)-5-methyl-3-(3-isoxazolyl)pyrrol-2-yl]methylene}-3-pyrazinyl-2-pyrazolin-5-one,
4-{{5-Methyl-3-(3-isoxazolyl)-4-[2-(4-pyridylmethylaminomethyl)]pyrrol-2-yl}methylene}-3-pyrazinyl-2-pyrazolin-5-one,
4-{{4-[2-(1-Imidazoyl)methyl]-5-methyl-3-(3-isoxazolyl)pyrrol-2-yl}methylene}-3-pyrazinyl-2-pyrazolin-5-one,
4-{[4-(2-Cyclopropylaminomethyl)-5-methyl-3-(3-isoxazolyl)pyrrol-2-yl]methylene}-3-pyrazinyl-2-pyrazolin-5-one,
4-{[4-(2-Diethylaminomethyl)-5-methyl-3-(2-furyl)pyrrol-2-yl]methylene}-3-pyrazinyl-2-pyrazolin-5-one,
4-{[4-(2-Dimethylaminomethyl)-5-methyl-3-(2-furyl)pyrrol-2-yl]methylene}-3-pyrazinyl-2-pyrazolin-5-one,
4-{{5-Methyl-3-(2-furyl)-4-[2-(1-pyrrolidinylmethyl)]pyrrol-2-yl}methylene}-3-pyrazinyl-2-pyrazolin-5-one,
4-{[4-(2-Ethylaminomethyl)-5-methyl-3-(2-furyl)pyrrol-2-yl]methylene}-3-pyrazinyl-2-pyrazolin-5-one,
4-{{5-Methyl-3-(2-furyl)-4-[2-(4-pyridiylmethylaminomethyl)]pyrrol-2-yl}methylene}-3-pyrazinyl-2-pyrazolin-5-one,
4-{{4-[2-(1-Imidazoyl)methyl]-5-methyl-3-(2-furyl)pyrrol-2-yl}methylene}-3-pyrazinyl-2-pyrazolin-5-one,
4-{[4-(2-Cyclopropylaminomethyl)-5-methyl-3-(2-furyl)pyrrol-2-yl]methylene}-3-pyrazinyl-2-pyrazolin-5-one,
4-{[4-(2-Diethylaminomethyl)-5-hydroxymethyl-3-isopropylpyrrol-2-yl]methylene}-3-pyrazinyl-2-pyrazolin-5-one,
4-{[4-(2-Dimethylaminomethyl)-5-hydroxymethyl-3-isopropylpyrrol-2-yl]methylene}-3-pyrazinyl-2-pyrazolin-5-one,
4-{{5-Hydroxymethyl-3-isopropyl-4-[2-(1-pyrrolidinylmethyl)]pyrrol-2-yl}methylene}-3-pyrazinyl-2-pyrazolin-5-one,
4-{[4-(2-Ethylaminomethyl)-5-hydroxymethyl-3-isopropylpyrrol-2-yl]methylene}-3-pyrazinyl-2-pyrazolin-5-one,
4-{{5-Hydroxymethyl-3-isopropyl-4-[2-(4-pyridiylmethylaminomethyl)]pyrrol-2-yl}methylene}-3-pyrazinyl-2-pyrazolin-5-one,
4-{{4-[2-(1-Imidazoyl)methyl]-5-hydroxymethyl-3-isopropylpyrrol-2-yl}methylene}-3-pyrazinyl-2-pyrazolin-5-one,
4-{[4-(2-Cyclopropylaminomethyl)-5-hydroxymethyl-3-isopropylpyrrol-2-yl]methylene}-3-pyrazinyl-2-pyrazolin-5-one,
4-{[4-(2-Diethylaminomethyl)-3,5-dicyclopropylpyrrol-2-yl]methylene}-3-pyrazinyl-2-pyrazolin-5-one,
4-{[4-(2-Dimethylaminomethyl)-3,5-dicyclopropylpyrrol-2-yl]methylene}-3-pyrazinyl-2-pyrazolin-5-one,
4-{{3,5-Dicyclopropyl-4-[2-(1-pyrrolidinylmethyl)]pyrrol-2-yl}methylene}-3-pyrazinyl-2-pyrazolin-5-one,
4-{[4-(2-Ethylaminomethyl)-3,5-dicyclopropylpyrrol-2-yl]methylene}-3-pyrazinyl-2-pyrazolin-5-one,
4-{{3,5-Dicyclopropyl-4-[2-(4-pyridiylmethylaminomethyl)]pyrrol-2-yl}methylene}-3-pyrazinyl-2-pyrazolin-5-one,
4-{{4-[2-(1-Imidazoyl)methyl]-3,5-dicyclopropylpyrrol-2-yl}methylene}-3-pyrazinyl-2-pyrazolin-5-one,
4-[(4-Cyclopropylaminomethyl-3,5-dicyclopropylpyrrol-2-yl)methylene]-3-pyrazinyl-2-pyrazolin-5-one,
4-{[3-Cyclopropylaminomethyl-5-methyl-4-(2-diethylaminoethyl)pyrrol-2-yl]methylene}-3-pyrazinyl-2-pyrazolin-5-one,
4-{[3-Cyclopropylaminomethyl-5-methyl-4-(2-hydroxyethyl)pyrrol-2-yl]methylene}-3-pyrazinyl-2-pyrazolin-5-one,
4-{[3-dimethylaminomethyl-5-methyl-4-(2-diethylaminoethyl)pyrrol-2-yl]methylene}-3-pyrazinyl-2-pyrazolin-5-one, and
4-{[3-hydroxymethyl-5-methyl-4-(2-diethylaminoethyl)pyrrol-2-yl]methylene}-3-pyrazinyl-2-pyrazolin-5-one.

Compounds of formula I may exist as salts with pharmaceutically acceptable acids. The present invention includes such salts. Examples of such salts include hydrochlorides, hydrobromides, sulphates, methanesulphonates, nitrates, maleates, acetates, citrates, fumarates, tartrates [e.g., (+)-tartrates, (−)-tartrates or mixtures thereof including racemic mixtures], succinates, benzoates and salts with amino acids such as glutamic acid. These salts may be prepared by methods known to those skilled in the art.

Certain compounds of formula I which have acidic substituents may exist as salts with pharmaceutically acceptable bases. The present invention includes such salts. Example of such salts include sodium salts, potassium salts, lysine salts and arginine salts. These salts may be prepared by methods known to those skilled in the art.

Certain compounds of formula I and their salts may exist in more than one crystal form and the present invention includes each crystal form and mixtures thereof.

Certain compounds of formula I and their salts may also exist in the form of solvates, for example hydrates, and the present invention includes each solvate and mixtures thereof.

Certain compounds of formula I may contain one or more chiral centers, and exist in different optically active forms. When compounds of formula I contain one chiral center, the compounds exist in two enantiomeric forms and the present invention includes both enantiomers and mixtures of enantiomers. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent.

It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of formula I contains more than one chiral center it may exist in diastereoisomeric forms. The diastereoisomeric pairs may be separated by methods known to those skilled in the art, for example chromatography or crystallization and the individual enantiomers within each pair may be separated as described above. The present invention includes each diastereoisomer of compounds of formula I and mixtures thereof.

Certain compounds of formula I may exist in different tautomeric forms or as different geometric isomers, and the present invention includes each tautomer and/or geometric isomer of compounds of formula I and mixtures thereof.

Certain compounds of formula I may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of formula I and mixtures thereof.

Certain compounds of formula I may exist in zwitterionic form and the present invention includes each zwitterionic form of compounds of formula I and mixtures thereof.

The compounds of this invention are useful as inhibitors of serine/threonine and tyrosine kinases. In particular, compounds of this invention are useful as inhibitors of tyrosine kinases that are important in hyperproliferative diseases, especially in the process of angiogenesis. For example, certain of these compounds are inhibitors of such receptor kinases as KDR, Flt-1, FGFR, PDGFR, c-Met, or IGF-1-R. Since these compounds are anti-angiogenic, they are important substances for inhibiting the progression disease states where angiogenesis is an important component. Certain compounds of the invention are effective as inhibitors of such serine/threonine kinases as erk, MAP kinases, cdks, Plk-1 or Raf-1. These compounds are useful in the treatment of cancer, and hyperproliferative disorders. In addition, certain compounds are effective inhibitors of non-receptor kinases such as src, lyn, lck, fyn, blk, hck. These compounds are useful in the treatment of cancer, hyperproliferative disorders and immunologic diseases.

The present invention provides a method of inhibiting the kinase activity of tyrosine kinases and serine/threonine kinases comprising the administration of a compound represented by formula I to said kinase in sufficient concentration to inhibit the enzyme activity of said kinase.

The present invention further includes the use of these compounds in pharmaceutical compositions with a pharmaceutically effective amount of the above-described compounds and a pharmaceutically acceptable carrier or excipient. These pharmaceutical compositions can be administered to individuals to slow or halt the process of angiogenesis in angiogenesis-aided diseases, or to treat edema, effusions, exudates, or ascites and other conditions associated with vascular hyperpermeability. Certain pharmaceutical compositions can be administered to individuals to treat cancer and hyperproliferative disorders by inhibiting serine/threonine kinases such as cdk, Plk-1, erk, etc.

DETAILED DESCRIPTION OF THE INVENTION

The compounds of this invention have antiangiogenic properties. These antiangiogenic properties are due at least in part to the inhibition of protein tyrosine kinases essential for angiogenic processes. For this reason, these compounds can be used as active agents against such disease states as arthritis, atherosclerosis, psoriasis, hemangiomas, myocardial angiogenesis, coronary and cerebral collaterals, ischemic limb angiogenesis, wound healing, peptic ulcer *Helicobacter* related diseases, virally-induced angiogenic disorders, fractures, Crow-Fukase syndrome (POEMS), preeclampsia, menometrorrhagia, cat scratch fever, rubeosis, neovascular glaucoma and retinopathies such as those associated with diabetic retinopathy, retinopathy of prematurity, or age-related macular degeneration. In addition, some of these compounds can be used as active agents against solid tumors, malignant ascites, hematopoietic cancers and hyperproliferative disorders such as thyroid hyperplasia (especially Grave's disease), and cysts (such as hypervascularity of ovarian stroma characteristic of polycystic ovarian syndrome (Stein-Leventhal syndrome)) since such diseases require a proliferation of blood vessel cells for growth and/or metastasis.

Further, some of these compounds can be used as active agents against burns, chronic lung disease, stroke, polyps, anaphylaxis, chronic and allergic inflammation, delayed-type hypersensitivity, ovarian hyperstimulation syndrome, brain tumor-associated cerebral edema, high-altitude, trauma or hypoxia induced cerebral or pulmonary edema, ocular and macular edema, ascites, and other diseases where vascular hyperpermeability, effusions, exudates, protein extravasation, or edema is a manifestation of the disease. The compounds will also be useful in treating disorders in which protein extravasation leads to the deposition of fibrin and extracellular matrix, promoting stromal proliferation (e.g. keloid, fibrosis, cirrhosis and carpal tunnel syndrome). Increased VEGF production potentiates inflammatory processes such as monocyte recruitment and activation. The compounds of this invention will also be useful in treating inflammatory disorders such as inflammatory bowel disease (IBD) and Crohn's disease.

VEGF's are unique in that they are the only angiogenic growth factors known to contribute to vascular hyperpermeability and the formation of edema. Indeed, vascular hyperpermeability and edema that is associated with the expression or administration of many other growth factors appears to be mediated via VEGF production. Inflammatory cytokines stimulate VEGF production. Hypoxia results in a marked upregulation of VEGF in numerous tissues, hence situations involving infarct, occlusion, ischemia, anemia, or circulatory impairment typically invoke VEGF/VPF mediated responses. Vascular hyperpermeability, associated edema, altered transendothelial exchange and macromolecular extravasation, which is often accompanied by diapedesis, can result in excessive matrix deposition, aberrant stromal proliferation, fibrosis, etc. Hence, VEGF-mediated hyperpermeability can significantly contribute to disorders with these etiologic features.

It is envisaged that the disorders listed above are mediated to a significant extent by protein tyrosine kinase activity involving the KDR/VEGFR-2 and/or the Flt-1/VEGFR-1 tyrosine kinases. By inhibiting the activity of these tyrosine kinases, the progression of the listed disorders is inhibited because the angiogenic or vascular hyperpermeability component of the disease state is severely curtailed. The action of certain compounds of this invention, by their selectivity for specific tyrosine kinases, result in a minimization of side effects that would occur if less selective tyrosine kinase inhibitors were used. Certain compounds of the invention are also effective inhibitors of FGFR, PDGFR, c-Met and IGF-1-R. These receptor kinases can directly or indirectly potentiate angiogenic and hyperproliferative responses in various disorders, hence their inhibition can impede disease progression.

The compounds of this invention have inhibitory activity against protein kinases. That is, these compounds modulate signal transduction by protein kinases. Compounds of this invention inhibit protein kinases from serine/threonine and tyrosine kinase classes. In particular, these compounds selectively inhibit the activity of the KDR/FLK-1/VEGFR-2 tyrosine kinases. Certain compounds of this invention also inhibit the activity of additional tyrosine kinases such as Flt-1/VEGFR-1, FGFR, PDGFR, IGF-R, c-Met, Src-subfamily kinases such as Lck, Src, fyn, yes, etc. Additionally, some compounds of this invention significantly inhibit serine/threonine kinases such as PKC, MAP kinases, erk, CDKs, Plk-1, or Raf-1 which play an essential role in cell proliferation and cell-cycle progression. The potency and specificity of the generic compounds of this invention towards a particular protein kinase can often be altered and optimized by variations in the nature, number and arrangement of the substituents (i.e., $R_1$, $R_2$, $R_3$, $R_4$, $R_5$, $R_6$ and $R_7$) of and conformational restrictions. In addition the metabolites of certain compounds may also possess significant protein kinase inhibitory activity.

The compounds of this invention, when administered to individuals in need of such compounds, inhibit vascular hyperpermeability and the formation of edema in these individuals. These compounds act, it is believed, by inhibiting the activity of KDR tyrosine kinase which is involved in the process of vascular hyperpermeability and edema formation. The KDR tyrosine kinase may also be referred to as FLK-1 tyrosine kinase, NYK tyrosine kinase or VEGFR-2 tyrosine kinase. KDR tyrosine kinase is activated when vascular endothelial cell growth factor (VEGF) or another activating ligand (such as VEGF-C, VEGF-D, VEGF-E or HIV Tat protein) binds to a KDR tyrosine kinase receptor which lies on the surface of vascular endothelial cells. Following such KDR tyrosine kinase activation, hyperpermeability of the blood vessels occurs and fluid moves from the blood stream past the blood vessel walls into the interstitial spaces, thereby forming an area of edema. Diapedesis also often accompanies this response. Similarly, excessive vascular hyperpermeability can disrupt normal molecular exchange across the endothelium in critical tissues and organs (e.g., lung and kidney), thereby causing macromolecular extravasation and deposition. Following this acute response to KDR stimulation which is believed to facilitate the subsequent angiogenic process, prolonged KDR tyrosine kinase stimulation results in the proliferation and chemotaxis of vascular endothelial cells and formation of new vessels. By inhibiting KDR tyrosine kinase activity, either by blocking the production of the activating ligand, by blocking the activating ligand binding to the KDR tyrosine kinase receptor, by preventing receptor dimerization and transphosphorylation, by inhibiting the enzyme activity of the KDR tyrosine kinase (inhibiting the phosphorylation function of the enzyme) or by some other mechanism that interrupts its downstream signaling (D. Mukhopedhyay et al., *Cancer Res.* 58:1278–1284 (1998) and references therein), hyperpermeability, as well as associated extravasation, subsequent edema formation and matrix deposition, and angiogenic responses, may be inhibited and minimized.

One group of preferred compounds of this invention have the property of inhibiting KDR tyrosine kinase activity without significantly inhibiting Flt-1 tyrosine kinase activity (Flt-1 tyrosine kinase is also referred to as VEGFR-1 tyrosine kinase). Both KDR tyrosine kinase and Flt-1 tyrosine kinase are activated by VEGF binding to KDR tyrosine kinase receptors and to Flt-1 tyrosine kinase receptors, respectively. Since Flt-1 tyrosine kinase activity may mediate important events in endothelial maintenance and vascular function, an inhibition of this enzyme activity may lead to toxic or adverse effects. At the very least, such inhibition is unnecessary for blocking the angiogenic responses, induction of vascular hyperpermeability and the formation of edema, so it is wasteful and of no value to the individual. Certain preferred compounds of this invention are unique because they inhibit the activity of one VEGF-receptor tyrosine kinase (KDR) that is activated by activating ligands but do not inhibit other receptor tyrosine kinases, such as Flt-1, that are also activated by certain activating ligands. The preferred compounds of this invention are, therefore, selective in their tyrosine kinase inhibitory activity.

The compounds of the present invention are also useful in the treatment of ulcers—bacterial, fungal, Mooren ulcers and ulcerative colitis.

The compounds of the present invention are also useful in the treatment of conditions wherein undesired angiogenesis, edema, or stromal deposition occurs in viral infections such as Herpes simplex, Herpes Zoster, AIDS, parapoxvirus, psoriasis, Kaposi's sarcoma, protozoan infections and toxoplasmosis, endometriosis, ovarian hyperstimulation syndrome, preeclampsia, menometrorrhagia, systemic lupus, sarcoidosis, synovitis, inflammatory bowel disease, Crohn's disease, sickle cell anaemia, Lyme's disease, pemphigoid, Paget's disease, hyperviscosity syndrome, Osler-Weber-Rendu disease, chronic inflammation, chronic occlusive pulmonary disease, asthma, rheumatoid arthritis and osteoarthritis, and edema following burns, trauma, radiation, or stroke.

The compounds of the present invention are also useful in the treatment of ocular conditions such as ocular and macular edema, ocular neovascular disease, scleritis, radial keratotomy, uveitis, vitritis, myopia, optic pits, chronic retinal detachment, post-laser complications, conjunctivitis, Stargardt's disease and Eales disease in addition to retinopathy and macular degeneration.

The compounds of the present invention are also useful in the treatment of cardiovascular conditions such as atherosclerosis, restenosis, vascular occlusion and carotid obstructive disease.

The compounds of the present invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

The compounds of the present invention are also useful in the treatment of Crow-Fukase (POEMS) syndrome and diabetic conditions such as glaucoma, diabetic retinopathy and microangiopathy.

It is envisaged that the disorders listed above are mediated to a significant extent by protein tyrosine kinase activity involving the VEGF receptors (e.g. KDR and Flt-1). By inhibiting the activity of these receptor tyrosine kinases, the progression of the listed disorders is inhibited because the angiogenic component of the disease state is severely curtailed. The action of the compounds of this invention, by their selectivity for specific tyrosine kinases, result in a minimization of side effects that would occur if less selective tyrosine kinase inhibitors were used.

In another aspect the present invention provides compounds of formula I as defined initially above (including the provisos) for use as medicaments, particularly as inhibitors of protein kinase activity for example tyrosine kinase activity, serine kinase activity and threonine kinase activity. In yet another aspect the present invention provides the use of compounds of formula I as defined initially above (including the provisos) in the manufacture of a medicament for use in the inhibition of protein kinase activity.

In this invention, the following definitions are applicable:

"Physiologically acceptable salts" refers to those salts which retain the biological effectiveness and properties of the free bases and which are obtained by reaction with inorganic acids such as hydrochloric acid, hydrobromic acid, sulfuric acid, nitric acid, phosphoric acid or organic acids such as sulfonic acid, carboxylic acid, organic phosphoric acid, methanesulfonic acid, ethanesulfonic acid, p-toluenesulfonic acid, salicylic acid, lactic acid, tartaric acid and the like.

"Alkyl" refers to a saturated aliphatic hydrocarbon, including straight-chain and branched-chain groups having 1 to 6 carbons or cyclic hydrocarbons having 3 to 6 carbons.

"Alkoxy" refers to an "O-alkyl" group, where "alkyl" is defined as described above.

Pharmaceutical Formulations

The compounds of this invention can be administered to a human patient by themselves or in pharmaceutical compositions where they are mixed with suitable carriers or excipient(s) at doses to treat or ameliorate vascular hyperpermeability, edema and associated disorders. Mixtures of these compounds can also be administered to the patient as a simple mixture or in suitable formulated pharmaceutical compositions. A therapeutically effective dose further refers to that amount of the compound or compounds sufficient to result in the prevention or attenuation of inappropriate neovascularization, progression of hyperproliferative disorders, edema, VEGF-associated hyperpermeability and/or VEGF-related hypotension. Techniques for formulation and administration of the compounds of the instant application may be found in "Remington's Pharmaceutical Sciences," Mack Publishing Co., Easton, Pa., latest edition.

Routes of Administration

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into an edematous site, often in a depot or sustained release formulation.

Furthermore, one may administer the drug in a targeted drug delivery system, for example, in a liposome coated with endothelial cell-specific antibody.

Composition/Formulation

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. The compounds may be formulated for parenteral administration by injection, e.g. bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5 W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethysulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the organic molecule compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

For any compound used in the method of the invention, the therapeutically effective dose can be estimated initially from cellular assays. For example, a dose can be formulated in cellular and animal models to achieve a circulating concentration range that includes the $IC_{50}$ as determined in cellular assays (i.e., the concentration of the test compound which achieves a half-maximal inhibition of a given protein kinase activity). In some cases it is appropriate to determine the $IC_{50}$ in the presence of 3 to 5% serum albumin since such a determination approximates the binding effects of plasma protein on the compound. Such information can be used to more accurately determine useful doses in humans. Further, the most preferred compounds for systemic administration effectively inhibit protein kinase signaling in intact cells at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p 1). In the treatment of crises, the administration of an acute bolus or an infusion approaching the MTD may be required to obtain a rapid response.

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g. the concentration necessary to achieve 50–90% inhibition of protein kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10–90% of the time, preferably between 30–90% and most preferably between 50–90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

In some formulations it may be beneficial to use the compounds of the present invention in the form of particles of very small size, for example as obtained by fluid energy milling.

The use of compounds of the present invention in the manufacture of pharmaceutical compositions is illustrated by the following description. In this description the term "active compound" denotes any compound of the invention but particularly any compound which is the final product of one of the preceding Examples.

a) Capsules

In the preparation of capsules, 10 parts by weight of active compound and 240 parts by weight of lactose can be de-aggregated and blended. The mixture can be filled into hard gelatin capsules, each capsule containing a unit dose or part of a unit dose of active compound.

b) Tablets

Tablets can be prepared from the following ingredients.

|  | Parts by weight |
|---|---|
| Active compound | 10 |
| Lactose | 190 |
| Maize starch | 22 |
| Polyvinylpyrrolidone | 10 |
| Magnesium stearate | 3 |

The active compound, the lactose and some of the starch can be de-aggregated, blended and the resulting mixture can be granulated with a solution of the polyvinylpyrrolidone in ethanol. The dry granulate can be blended with the magnesium stearate and the rest of the starch. The mixture is then compressed in a tabletting machine to give tablets each containing a unit dose or a part of a unit dose of active compound.

c) Enteric Coated Tablets

Tablets can be prepared by the method described in (b) above. The tablets can be enteric coated in a conventional manner using a solution of 20% cellulose acetate phthalate and 3% diethyl phthalate in ethanol: dichloromethane (1:1).

d) Suppositories

In the preparation of suppositories, 100 parts by weight of active compound can be incorporated in 1300 parts by weight of triglyceride suppository base and the mixture formed into suppositories each containing a therapeutically effective amount of active ingredient.

In the compositions of the present invention the active compound may, if desired, be associated with other compatible pharmacologically active ingredients. For example, the compounds of this invention can be administered in combination with one or more additional pharmaceutical agents that inhibit or prevent the production of VEGF, attenuate intracellular responses to VEGF, block intracellular signal transduction, inhibit vascular hyperpermeability, reduce inflammation, or inhibit or prevent the formation of edema or neovascularization. The compounds of the invention can be administered prior to, subsequent to or simultaneously with the additional pharmaceutical agent, whichever course of administration is appropriate. The additional pharmaceutical agents include but are not limited to anti-edemic steroids, NSAIDS, ras inhibitors, anti-TNF agents, anti-IL-1 agents, antihistamines, PAF-antagonists, COX-1 inhibitors, COX-2 inhibitors, NO synthase inhibitors, PKC inhibitors and P13 kinase inhibitors. The compounds of the invention and the additional pharmaceutical agents act either additively or synergistically. Thus, the administration of such a combination of substances that inhibit angiogenesis, vascular hyperpermeability and/or inhibit the formation of edema can provide greater relief from the deleterious effects of a hyperproliferative disorder, angiogenesis, vascular hyperpermeability or edema than the administration of either substance alone. In the treatment of malignant disorders combinations with antiproliferative or cytotoxic chemotherapies or radiation are anticipated.

The present invention also comprises the use of a compound of formula I as a medicament.

Both the Src and Syk families of kinases play pivotal roles in the regulation of immune function. The Src family currently includes Fyn, Lck, Fgr, Fes, Lyn, Src, Yes, Hck, and Blk. The Syk family is currently understood to include only Zap and Syk. The Janus family of kinases is involved in the transduction of growth factor and pro-inflammatory cytokine signals through a number of receptors. Although BTK and ITK, members of the Tec family of kinases, play a less well understood role in immunobiology, their modulation by an inhibitor may prove therapeutically beneficial. The kinases RIP, IRAK-1, IRAK-2, NIK, TPL-2/COT, IKK-1 and IKK-2 are involved in the signal transduction pathways for the key pro-inflammatory cytokines TNF and IL-1. By virtue of their ability to inhibit one or more of these kinases, compounds of formula I may function as immunomodulatory agents useful for the maintenance of allografts and the treatment of autoimmune disorders. Through their ability to regulate T cell activation or the potentiation of an inflammatory process, these compounds could be used to treat such autoimmune diseases. Transplants due to rejection phenomena, either host versus graft for solid organs or graft versus host for bone marrow, are limited by the toxicity of currently available immunosuppressive agents and would benefit from an efficacious drug with improved therapeutic index. Gene targeting experiments have demonstrated the essential role of Src in the biology of osteoclasts, the cells responsible for bone resorption. Compounds of formula I, through their ability to regulate Src, may also be useful in the treatment of osteoporosis, osteopetrosis, Paget's disease, tumor-induced hypercalcemia and in the treatment of bone metastases.

A number of protein kinases have been demonstrated to be protooncogenes. Chromosome breakage (at the ltk kinase break point on chromosome 5), translocation as in the case of the Abl gene with BCR (Philadelphia chromosome), truncation in instances such as c-Kit or EGFR, or mutation (e.g., Met) result in the creation of dysregulated proteins converting them from protooncogene to oncogene products. In other tumors, oncogenesis is driven by an autocrine or paracrine ligand/growth factor receptor interactions. Members of the src-family kinases are typically involved in downstream signal transduction thereby potentiating the oncogenesis and themselves may become oncogenic by over-expression or mutation. By inhibiting the protein kinase activity of these proteins the disease process may be disrupted. Vascular restenosis may involve process of FGF and/or PDGF-promoted smooth muscle and endothelial cell proliferation. The ligand stimulation of FGFR, PDGFR, IGF1-R and c-Met in vivo is proangiogenic, and potentiates angiogenesis dependent disorders. Inhibition of FGFr, PDGFr, c-Met, or IGF1-R kinase activity may be an efficacious strategy for inhibiting these phenomena. Thus compounds of formula I which inhibit the kinase activity of normal or aberrant c-kit, c-met, c-fms, src-family members, EGFr, erbB2, erbB4, BCR-Abl, PDGFr, FGFr, IGF1-R and other receptor or cytosolic tyrosine kinases may be of value in the treatment of benign and neoplastic proliferative diseases.

In many pathological conditions (for example, solid primary tumors and metastases, Kaposi's sarcoma, rheumatoid arthritis, blindness due to inappropriate ocular neovascularization, psoriasis and atherosclerosis) disease progression is contingent upon persistent angiogenesis. Polypeptide growth factors often produced by the disease tissue or associated inflammatory cells, and their corresponding endothelial cell specific receptor tyrosine kinases (e.g., KDR/VEGFR-2, Flt-1/VEGFR-1, Tie-2/Tek and Tie) are essential for the stimulation of endothelial cell growth, migration, organization, differentiation and the establishment of the requisite new functional vasculature. As a result of the "vascular permeability factor" activity of VEGF in mediating vascular hyperpermeability, VEGF-stimulation of a VEGFR kinase is also believed to play an important role in the formation of tumor ascites, cerebral and pulmonary edema, pleural and pericardial effusions, delayed-type hypersensitivity reactions, tissue edema and organ dysfunction following trauma, burns, ischemia, diabetic complications, endometriosis, adult respiratory distress syndrome (ARDS), post-cardiopulmonary bypass-related hypotension and hyperpermeability, and ocular edema leading to glaucoma or blindness due to inappropriate neovascularization. In addition to VEGF, recently identified VEGF-C and VEGF-D, and virally-encoded VEGF-E or HIV-Tat protein can also cause a vascular hyperpermeability response through the stimulation of a VEGFR kinase. Tie-2 is expressed also in a select population of hematopoietic stem cells in which it may play a role in their recruitment, adhesion, regulation and differentiation (*Blood,* 4317–4326 (1997)); this Tie-2 expressing population may serve as circulating angiogenic endothelial progenitors. Certain agents according to formula I capable of blocking the kinase activity of endothelial cell specific kinases could therefore inhibit disease progression involving these situations.

The compounds of formula I or a salt thereof or pharmaceutical compositions containing a therapeutically effective amount thereof may be used in the treatment of benign and neoplastic proliferative diseases and disorders of the immune system. Such diseases include autoimmune diseases, such as rheumatoid arthritis, thyroiditis, type 1 diabetes, multiple sclerosis, sarcoidosis, inflammatory bowel disease, Crohn's disease, myasthenia gravis and systemic lupus erythematosus; psoriasis, organ transplant rejection (eg. kidney rejection, graft versus host disease), benign and neoplastic proliferative diseases, human cancers such as lung, breast, stomach, bladder, colon, pancreas, ovarian, prostate and rectal cancer and hematopoietic malignancies (leukemia and lymphoma), and diseases involving inappropriate vascularization for example diabetic retinopathy, retinopathy of prematurity, choroidal neovascularization due to age-related macular degeneration, and infantile hemangiomas in human beings. In addition, such inhibitors may be useful in the treatment of disorders involving VEGF mediated edema, ascites, effusions, and exudates, including for example macular edema, cerebral edema, acute lung injury and adult respiratory distress syndrome (ARDS).

The compounds of the present invention may also be useful in the prophylaxis of the above diseases.

A further aspect of the present invention provides the use of a compound of formula I or a salt thereof in the manufacture of a medicament for treating vascular hyperpermeability, angiogenesis-dependent disorders, proliferative diseases and/or disorders of the immune system in mammals, particularly human beings.

The present invention also provides a method of treating vascular hyperpermeability, inappropriate neovascularization, proliferative diseases and/or disorders of the immune system which comprises the administration of a therapeutically effective amount of a compound of formula I to a mammal, particularly a human being, in need thereof.

The in vitro potency of compounds in inhibiting these protein kinases may be determined by the procedures detailed below.

The potency of compounds can be determined by the amount of inhibition of the phosphorylation of an exogenous substrate (e.g., synthetic peptide (Z. Songyang et al., *Nature.* 373:536-539) by a test compound relative to control.

KDR Tyrosine Kinase Production Using Baculovirus System:

The coding sequence for the human KDR intra-cellular domain (aa789–1354) was generated through PCR using cDNAs isolated from HUVEC cells. A poly-His6 sequence was introduced at the N-terminus of this protein as well. This fragment was cloned into transfection vector pVL1393 at the Xba 1 and Not 1 site. Recombinant baculovirus (BV) was generated through co-transfection using the BaculoGold Transfection reagent (PharMingen). Recombinant BV was plaque purified and verified through Western analysis. For protein production, SF-9 cells were grown in SF-900-II medium at 2×106/ml, and were infected at 0.5 plaque forming units per cell (MOI). Cells were harvested at 48 hours post infection.

Purification of KDR

SF-9 cells expressing $(His)_6$ KDR(aa789–1354) were lysed by adding 50 ml of Triton x-100 lysis buffer (20 mM Tris, pH 8.0, 137 mM NaCl, 10% glycerol, 1% Triton x-100, 1 mM PMSF, 10 µg/ml aprotinin, 1 µg/ml leupeptin) to the cell pellet from IL of cell culture. The lysate was centrifuged at 19,000 rpm in a Sorval SS-34 rotor for 30 min at 4° C. The cell lysate was applied to a 5 ml $NiCl_2$ chelating sepharose column, equilibrated with 50 mM HEPES, pH7.5, 0.3 M NaCl. KDR was eluted using the same buffer containing 0.25 M imidazole. Column fractions were analyzed using SDS-PAGE and an ELISA assay (below) which measures kinase activity. The purified KDR was exchanged into 25 mM HEPES, pH7.5, 25 mM NaCl, 5 mM DTT buffer and stored at 80° C.

Human Tie-2 Kinase Production and Purification

The coding sequence for the human Tie-2 intra-cellular domain (aa775-1124) was generated through PCR using cDNAs isolated from human placenta as a template. A poly-$His_6$ sequence was introduced at the N-terminus and this construct was cloned into transfection vector pVL 1939 at the Xba 1 and Not 1 site. Recombinant BV was generated through co-transfection using the BaculoGold Transfection reagent (PharMingen). Recombinant BV was plaque purified and verified through Western analysis. For protein production, SF-9 insect cells were grown in SF-900-II medium at 2×106/ml, and were infected at MOI of 0.5. Purification of the His-tagged kinase used in screening was analogous to that described for KDR.

Human Flt-1 Tyrosine Kinase Production and Purification

The baculoviral expression vector pVL1393 (Phar Mingen, Los Angeles, Calif.) was used. A nucleotide sequence encoding poly-His6 was placed 5' to the nucleotide region encoding the entire intracellular kinase domain of human Flt-1 (amino acids 786–1338). The nucleotide sequence encoding the kinase domain was generated through PCR using cDNA libraries isolated from HUVEC cells. The histidine residues enabled affinity purification of the protein as a manner analogous to that for KDR and ZAP70. SF-9 insect cells were infected at a 0.5 multiplicity and harvested 48 hours post infection.

EGFR Tyrosine Kinase Source

EGFR was purchased from Sigma (Cat # E-3641; 500 units/50 µl) and the EGF ligand was acquired from Oncogene Research Products/Calbiochem (Cat # PF011-100).

Expression of ZAP70

The baculoviral expression vector used was pVL1393. (Pharmingen, Los Angeles, Calif.) The nucleotide sequence encoding amino acids M(H)6 $LVPR_9S$ was placed 5' to the region encoding the entirety of ZAP70 (amino acids 1–619). The nucleotide sequence encoding the ZAP70 coding region was generated through PCR using cDNA libraries isolated from Jurkat immortalized T-cells. The histidine residues enabled affinity purification of the protein (vide infra). The $LVPR_9S$ bridge constitutes a recognition sequence for proteolytic cleavage by thrombin, enabling removal of the affinity tag from the enzyme. SF-9 insect cells were infected at a multiplicity of infection of 0.5 and harvested 48 hours post infection.

Extraction and purification of ZAP70

SF-9 cells were lysed in a buffer consisting of 20 mM Tris, pH 8.0, 137 mM NaCl, 10% glycerol, 1% Triton x-100, 1 mM PMSF, 1 µg/ml leupeptin, 10 µg/ml aprotinin and 1 mM sodium orthovanadate. The soluble lysate was applied to a chelating sepharose HiTrap column (Pharmacia) equilibrated in 50 mM HEPES, pH 7.5, 0.3 M NaCl. Fusion protein was eluted with 250 mM imidazole. The enzyme was stored in buffer containing 50 mM HEPES, pH 7.5, 50 mM NaCl and 5 mM DTT.

Lck source

Lck or truncated forms of Lck may be commercially obtained (e.g. from Upstate Biotechnology Inc. (Saranac Lake, N.Y.) and Santa Cruz Biotechnology Inc. (Santa Cruz, Ca.)) or purified from known natural or recombinant sources using conventional methods.

Enzyme Linked Immunosorbent Assay (ELISA) For PTKs

Enzyme linked immunosorbent assays (ELISA) were used to detect and measure the presence of tyrosine kinase activity. The ELISA were conducted according to known protocols which are described in, for example, Voller, et al., 1980, "Enzyme-Linked Immunosorbent Assay," In: *Manual of Clinical Immunology*, 2d ed., edited by Rose and Friedman, pp 359–371 Am. Soc. of Microbiology, Washington, D.C.

The disclosed protocol was adapted for determining activity with respect to a specific PTK. For example, preferred protocols for conducting the ELISA experiments is provided below. Adaptation of these protocols for determining a compound's activity for other members of the receptor PTK family, as well as non-receptor tyrosine kinases, are well within the abilities of those in the art. For purposes of determining inhibitor selectivity, a universal PTK substrate (e.g., random copolymer of poly($Glu_4$ Tyr), 20,000–50,000 MW) was employed together with ATP (typically 5 µM) at concentrations approximately twice the apparent Km in the assay.

The following procedure was used to assay the inhibitory effect of compounds of this invention on KDR, Flt-1, Flt-4/VEGFR-3, Tie-2, EGFR, FGFR, PDGFR, IGF-1-R, c-Met and ZAP70 tyrosine kinase activity:

Buffers and Solutions:
PGTPoly (Glu, Tyr) 4:1
Store powder at −20° C. Dissolve powder in phosphate buffered saline (PBS) for 50 mg/ml solution. Store 1 ml aliquots at −20° C. When making plates dilute to 250 µg/ml in Gibco PBS.
Reaction Buffer: 100 mM Hepes, 20 mM $MgCl_2$, 4 mM $MnCl_2$, 5 mM DTT, 0.02% BSA, 200 µM $NaVO_4$, pH 7.10
ATP: Store aliquots of 100 mM at −20° C. Dilute to 20 µM in water
Washing Buffer: PBS with 0.1% Tween 20
Antibody Diluting Buffer: 0.1% bovine serum albumin (BSA) in PBS
TMB Substrate: mix TMB substrate and Peroxide solutions 9:1 just before use or use K-Blue Substrate from Neogen
Stop Solution: 1M Phosphoric Acid Procedure 1. Plate Preparation:
Dilute PGT stock (50 mg/ml, frozen) in PBS to a 250 µg/ml. Add 125 µl per well of Corning modified flat bottom high affinity ELISA plates (Corning #25805-96). Add 125 µl PBS to blank wells. Cover with sealing tape and incubate overnight 37° C. Wash 1× with 250 µl washing buffer and dry for about 2 hrs in 37° C. dry incubator. Store coated plates in sealed bag at 4° C. until used.

2. Tyrosine Kinase Reaction:
   Prepare inhibitor solutions at a 4× concentration in 20% DMSO in water.
   Prepare reaction buffer
   Prepare enzyme solution so that desired units are in 50 µl, e.g. for KDR make to 1 ng/µl for a total of 50 ng per well in the reactions. Store on ice.
   Make 4×ATP solution to 20 µM from 100 mM stock in water. Store on ice
   Add 50 µl of the enzyme solution per well (typically 5–50 ng enzyme/well depending on the specific activity of the kinase)
   Add 25 µl 4× inhibitor
   Add 25 µl 4× ATP for inhibitor assay
   Incubate for 10 minutes at room temperature
   Stop reaction by adding 50 µl 0.05N HCl per well
   Wash plate
**Final Concentrations for Reaction: 5 µM ATP, 5% DMSO 3. Antibody Binding
   Dilute 1 mg/ml aliquot of PY20-HRP (Pierce) antibody (a phosphotyrosine antibody) to 50 ng/ml in 0.1% BSA in PBS by a 2 step dilution (100×, then 200×)
   Add 100 µl Ab per well. Incubate 1 hr at room temp.
   Incubate 1 hr at 4 C.
   Wash 4× plate 4. Color reaction
   Prepare TMB substrate and add 100 µl per well
   Monitor OD at 650 nm until 0.6 is reached
   Stop with 1M Phosphoric acid. Shake on plate reader.
   Read OD immediately at 450 nm Optimal incubation times and enzyme reaction conditions vary slightly with enzyme preparations and are determined empirically for each lot. For Lck, the Reaction Buffer utilized was 100 mM MOPSO, pH 6.5, 4 mM MnCl$_2$, 20 mM MgCl$_2$, 5 mM DTT, 0.2% BSA, 200 mM NaVO$_4$ under the analogous assay conditions.

Compounds of formula I may have therapeutic utility in the treatment of diseases involving both identified, including those not mentioned herein, and as yet unidentified protein tyrosine kinases which are inhibited by compounds of formula I. All compounds exemplified herein significantly inhibit KDR kinase at concentrations of 50 micromolar or below. Some compounds of this invention also significantly inhibit other PTKs such as lck at concentrations of 50 micromolar or below.

Cdc2 Source

The human recombinant enzyme and assay buffer may be obtained commercially (New England Biolabs, Beverly, Mass. USA) or purified from known natural or recombinant sources using conventional methods.

Cdc2 Assay

The protocol used was that provided with the purchased reagents with minor modifications. In brief, the reaction was carried out in a buffer consisting of 50 mM Tris pH 7.5, 100 mM NaCl, 1 mM EGTA, 2 mM DTT, 0.01% Brij, 5% DMSO and 10 mM MgCl$_2$ (commercial buffer) supplemented with fresh 300 µM ATP (31 µCi/ml) and 30 µg/ml histone type IIIss final concentrations. A reaction volume of 80 µL, containing units of enzyme, was run for 20 minutes at 25 degrees C. in the presence or absence of inhibitor. The reaction was terminated by the addition of 120 µL of 10% acetic acid. The substrate was separated from unincorporated label by spotting the mixture on phosphocellulose paper, followed by 3 washes of 5 minutes each with 75 mM phosphoric acid. Counts were measured by a betacounter in the presence of liquid scintillant.

Certain compounds of this invention significantly inhibit cdc2 at concentrations below 50 uM.

PKC Kinase Source

The catalytic subunit of PKC may be obtained commercially (Calbiochem).

PKC Kinase Assay

A radioactive kinase assay was employed following a published procedure (Yasuda, I., Kirshimoto, A., Tanaka, S., Tominaga, M., Sakurai, A., Nishizuka, Y. *Biochemical and Biophysical Research Communication* 3:166, 1220–1227 (1990)). Briefly, all reactions were performed in a kinase buffer consisting of 50 mM Tris-HCl pH7.5, 10 mM MgCl$_2$, 2 mM DTT, 1 mM EGTA, 100 µM ATP, 8 µM peptide, 5% DMSO and $^{33}$P ATP (8 Ci/mM). Compound and enzyme were mixed in the reaction vessel and the reaction initiated by addition of the ATP and substrate mixture. Following termination of the reaction by the addition of 10 µL stop buffer (5 mM ATP in 75 mM phosphoric acid), a portion of the mixture was spotted on phosphocellulose filters. The spotted samples were washed 3 times in 75 mM phosphoric acid at room temperature for 5 to 15 minutes. Incorporation of radiolabel was quantified by liquid scintillation counting.

Erk2 Enzyme Source

The recombinant murine enzyme and assay buffer may be obtained commercially (New England Biolabs, Beverly Mass. USA) or purified from known natural or recombinant sources using conventional methods.

Erk2 Enzyme Assay

In brief, the reaction was carried out in a buffer consisting of 50 mM Tris pH 7.5, 1 mM EGTA, 2 mM DTT, 0.01% Brij, 5% DMSO and 10 mM MgCl$_2$ (commercial buffer) supplemented with fresh 100 µM ATP (31 µCi/ml) and 30 µM myelin basic protein under conditions recommended by the supplier. Reaction volumes and method of assaying incorporated radioactivity were as described for the PKC assay (vide supra).

In Vitro Models for T-cell Activation

Upon activation by mitogen or antigen, T-cells are induced to secrete IL-2, a growth factor that supports their subsequent proliferative phase. Therefore, one may measure either production of IL-2 from or cell proliferation of, primary T-cells or appropriate T-cell lines as a surrogate for T-cell activation. Both of these assays are well described in the literature and their parameters well documented (in Current Protocols in Immunology, Vol 2, 7.10.1–7.11.2).

In brief, T-cells may be activated by co-culture with allogenic stimulator cells, a process termed the one-way mixed lymphophocyte reaction. Responder and stimulator peripheral blood mononuclear cells are purified by Ficoll-Hypaque gradient (Pharmacia) per directions of the manufacturer. Stimulator cells are mitotically inactivated by treatment with mitomycin C (Sigma) or gamma irradiation. Responder and stimulator cells are co-cultured at a ratio of two to one in the presence or absence of the test compound. Typically $10^5$ responders are mixed with $5 \times 10^4$ stimulators and plated (200 µl volume) in a U bottom microtiter plate (Costar Scientific). The cells are cultured in RPMI 1640 supplemented with either heat inactivated fetal bovine serum (Hyclone Laboratories) or pooled human AB serum from male donors, $5\times10^{-5}$ M 2-mercaptoethanol and 0.5% DMSO, The cultures are pulsed with 0.5 µCi of $^3$H thymidine (Amersham) one day prior to harvest (typically day three). The cultures are harvested (Betaplate harvester, Wallac) and isotope uptake assessed by liquid scintillation (Betaplate, Wallac).

The same culture system may be used for assessing T-cell activation by measurement of IL-2 production. Eighteen to twenty-four hours after culture initiation, the supernatants are removed and the IL-2 concentration is measured by ELISA (R and D Systems) following the directions of the manufacturer.

In-Vivo Models of T-Cell Activation

The in vivo efficacy of compounds can be tested in animal models known to directly measure T-cell activation or for which T-cells have been proven the effectors. T-cells can be activated in vivo by ligation of the constant portion of the T-cell receptor with a monoclonal anti-CD3 antibody (Ab). In this model, BALB/c mice are given 10 µg of anti-CD3 Ab intraperitoneally two hours prior to exsanguination. Animals to receive a test drug are pre-treated with a single dose of the compound one hour prior to anti-CD3 Ab administration. Serum levels of the proinflammatory cytokines interferon-γ (IFN-γ) and tumor necrosis factor-α (TNF-α), indicators of T-cell activation, are measured by ELISA. A similar model employs in vivo T-cell priming with a specific antigen such as keyhole limpet hemocyanin (KLH) followed by a secondary in vitro challenge of draining lymph node cells with the same antigen. As previously, measurement of cytokine production is used to assess the activation state of the cultured cells. Briefly, C57BL/6 mice are immunized subcutaneously with 100 µg KLH emulsified in complete Freund's adjuvant (CFA) on day zero. Animals are pre-treated with the compound one day prior to immunization and subsequently on days one, two and three post immunization. Draining lymph nodes are harvested on day 4 and their cells cultured at $6\times10^6$ per ml in tissue culture medium (RPMI 1640 supplemented with heat inactivated fetal bovine serum (Hyclone Laboratories) $5\times10^{-5}$ M 2-mercaptoethanol and 0.5% DMSO) for both twenty-four and forty-eight hours. Culture supernatants are then assessed for the autocrine T-cell growth factor Interleukin-2 (IL-2) and/or IFN-γ levels by ELISA.

Lead compounds can also be tested in animal models of human disease. These are exemplified by experimental autoimmune encephalomyelitis (EAE) and collagen-induced arthritis (CIA). EAE models which mimic aspects of human multiple sclerosis have been described in both rats and mice (reviewed FASEB J. 5:2560–2566, 1991; murine model: Lab. Invest. 4(3):278, 1981; rodent model: J. Immunol 146(4): 1163–8, 1991). Briefly, mice or rats are immunized with an emulsion of myelin basic protein (MBP), or neurogenic peptide derivatives thereof, and CFA. Acute disease can be induced with the addition of bacterial toxins such as *bordetella pertussis*. Relapsing/remitting disease is induced by adoptive transfer of T-cells from MBP/peptide immunized animals.

CIA may be induced in DBA/1 mice by immunization with type II collagen (J. Immunol: 142(7):2237–2243). Mice will develop signs of arthritis as early as ten days following antigen challenge and may be scored for as long as ninety days after immunization. In both the EAE and CIA models, a compound may be administered either prophylactically or at the time of disease onset. Efficacious drugs should reduce severity and/or incidence.

Certain compounds of this invention which inhibit one or more angiogenic receptor PTK, and/or a protein kinase such as lck involved in mediating inflammatory responses can reduce the severity and incidence of arthritis in these models.

Compounds can also be tested in mouse allograft models, either skin (reviewed in Ann. Rev. Immunol., 10:333–58, 1992; Transplantation: 57(12): 1701–17D6, 1994) or heart (Am. J. Anat.:113:273, 1963). Briefly, full thickness skin grafts are transplanted from C57BL/6 mice to BALB/c mice. The grafts can be examined daily, beginning at day six, for evidence of rejection. In the mouse neonatal heart transplant model, neonatal hearts are ectopically transplanted from C57BL/6 mice into the ear pinnae of adult CBA/J mice. Hearts start to beat four to seven days post transplantation and rejection may be assessed visually using a dissecting microscope to look for cessation of beating.

Cellular Receptor PTK Assays

The following cellular assay was used to determine the level of activity and effect of the different compounds of the present invention on KDR/VEGFR2. Similar receptor PTK assays employing a specific ligand stimulus can be designed along the same lines for other tyrosine kinases using techniques well known in the art.

VEGF-Induced KDR Phosphorylation in Human Umbilical Vein Endothelial Cells (HUVEC) as Measured by Western Blots:

1. HUVEC cells (from pooled donors) were purchased from Clonetics (San Diego, Calif.) and cultured according to the manufacturer directions. Only early passages (3-8) were used for this assay. Cells were cultured in 100 mm dishes (Falcon for tissue culture; Becton Dickinson; Plymouth, England) using complete EBM media (Clonetics).

2. For evaluating a compound's inhibitory activity, cells were trypsinized and seeded at $0.5–1.0\times10^5$ cells/well in each well of 6-well cluster plates (Costar; Cambridge, Mass.).

3. 3–4 days after seeding, plates were 90–100% confluent. Medium was removed from all the wells, cells were rinsed with 5–10 ml of PBS and incubated 18–24 h with 5 ml of EBM base media with no supplements added (i.e., serum starvation).

4. Serial dilutions of inhibitors were added in 1 ml of EBM media (25 µM, 5 µM, or 1 µM final concentration to cells and incubated for one hour at 37 C. Human recombinant VEGF$_{165}$ (R & D Systems) was then added to all the wells in 2 ml of EBM medium at a final concentration of 50 ng/ml and incubated at 37 C for 10 minutes. Control cells untreated or treated with VEGF only were used to assess background phosphorylation and phosphorylation induction by VEGF.

All wells were then rinsed with 5-10 ml of cold PBS containing 1 mM Sodium Orthovanadate (Sigma) and cells were lysed and scraped in 200 µl of RIPA buffer (50 mM Tris-HCl) pH7, 150 mM NaCl, 1% NP-40, 0.25% sodium deoxycholate, 1 mM EDTA) containing protease inhibitors (PMSF 1 mM, aprotinin 1 µg/ml, pepstatin 1 µg/ml, leupeptin 1 µg/ml, Na vanadate 1 mM, Na fluoride 1 mM) and 1 µg/ml of Dnase (all chemicals from Sigma Chemical Company, St Louis, Mo.). The lysate was spun at 14,000 rpm for 30 min, to eliminate nuclei.

Equal amounts of proteins were then precipitated by addition of cold (−20 C) Ethanol (2 volumes) for a minimum of 1 hour or a maximum of overnight. Pellets were reconstituted in Laemli sample buffer containing 5%-mercaptoethanol (BioRad; Hercules, Calif.) and boiled for 5 min. The proteins were resolved by polyacrylamide gel electrophoresis (6%, 1.5 mm Novex, San Deigo, Calif.) and transferred onto a nitrocellulose membrane using the Novex system. After blocking with bovine serum albumin (3%), the proteins were probed overnight with anti-KDR polyclonal antibody (C20, Santa Cruz Biotechnology; Santa Cruz, Calif.) or with anti-phosphotyrosine monoclonal antibody (4G10, Upstate Biotechnology, Lake Placid, N.Y.) at 4 C. After washing and incubating for 1 hour with HRP-conjugated F(ab)$_2$ of goat anti-rabbit or goat-anti-mouse IgG the bands were visualized using the emission chemiluminescience (ECL) system (Amersham Life Sciences, Arlington Height, Ill.).

Certain examples of the present invention significantly inhibit cellular VEGF-induced KDR tyrosine kinase phosphorylation at concentrations of less than 50 μM.

In Vivo Uterine Edema Model

This assay measures the capacity of compounds to inhibit the acute increase in uterine weight in mice which occurs in the first few hours following estrogen stimulation. This early onset of uterine weight increase is known to be due to edema caused by increased permeability of uterine vasculature. Cullinan-Bove and Koss (*Endocrinology* (1993), 133:829–837) demonstrated a close temporal relationship of estrogen-stimulated uterine edema with increased expression of VEGF mRNA in the uterus. These results have been confirmed by the use of neutralizing monoclonal antibody to VEGF which significantly reduced the acute increase in uterine weight following estrogen stimulation (WO 97/42187). Hence, this system can serve as a model for in vivo inhibition of VEGF signaling and the associated hyperpermeability and edema.

Materials: All hormones were purchased from Sigma (St. Louis, Mo.) or Cal Biochem (La Jolla, Calif.) as lyophilized powders and prepared according to supplier instructions.

Vehicle components (DMSO, Cremaphor EL) were purchased from Sigma (St. Louis, Mo.).

Mice (Balb/c, 8–12 weeks old) were purchased from Taconic (Germantown, N.Y.) and housed in a pathogen-free animal facility in accordance with institutional Animal Care and Use Committee Guidelines.

Method:

Day 1: Balb/c mice were given an intraperitoneal (i.p.) injection of 12.5 units of pregnant mare's serum gonadotropin (PMSG).

Day 3: Mice received 15 units of human chorionic gonadotropin (hCG) i.p.

Day 4: Mice were randomized and divided into groups of 5–10. Test compounds were administered by i.p., i.v. or p.o. routes depending on solubility and vehicle at doses ranging from 1–100 mg/kg. Vehicle control group received vehicle only and two groups were left untreated.

Thirty minutes later, experimental, vehicle and 1 of the untreated groups were given an i.p. injection of 17-estradiol (500 μg/kg). After 2–3 hours, the animals were sacrificed by CO$_2$ inhalation. Following a midline incision, each uterus was isolated and removed by cutting just below the cervix and at the junctions of the uterus and oviducts. Fat and connective tissue were removed with care not to disturb the integrity of the uterus prior to weighing (wet weight). Uteri were blotted to remove fluid by pressing between two sheets of filter paper with a one liter glass bottle filled with water. Uteri were weighed following blotting (blotted weight). The difference between wet and blotted weights was taken as the fluid content of the uterus. Mean fluid content of treated groups was compared to untreated or vehicle treated groups. Significance was determined by Student's test. Non-stimulated control group was used to monitor estradiol response.

Results demonstrate that certain compounds of the present invention inhibit the formation of edema when administered systemically by various routes.

Certain compounds of this invention which are inhibitors of angiogenic receptor tyrosine kinases can also be shown active in a Matrigel implant model of neovascularization. The Matrigel neovascularization model involves the formation of new blood vessels within a clear "marble" of extracellular matrix implanted subcutaneously which is induced by the presence of proangiogenic factor producing tumor cells (for examples see: Passaniti, A., et al, Lab. Investig. (1992), 67(4), 519–528; Anat. Rec. (1997), 249(1), 63–73; Int. J. Cancer (1995), 63(5), 694–701; Vasc. Biol. (1995), 15(11), 1857–6). The model preferably runs over 3–4 days and endpoints include macroscopic visual/image scoring of neovascularization, microscopic microvessel density determinations, and hemoglobin quantitation (Drabkin method) following removal of the implant versus controls from animals untreated with inhibitors. The model may alternatively employ bFGF or HGF as the stimulus.

Certain compounds of this invention which inhibit one or more oncogenic, protooncogenic, or proliferation-dependent protein kinases, or angiogenic receptor PTK also inhibit the growth of primary murine, rat or human xenograft tumors in mice, or inhibit metastasis in murine models.

EXEMPLIFICATION

The core structure of the compounds of the invention was synthesized via a base catalyzed aldol condensation followed by an elimination reaction. Scheme I is a general representation of this reaction. The appropriate starting materials, II and III, for making the compounds of general formula IV of the present invention synthesized in accordance with general Scheme I are commercially available and/or can be made according to methods well-known in the art and/or are enabled by the description provided herein.

Scheme I: General synthesis of 4-[(substituted) methylene]-2-pyrazolin-5-ones.

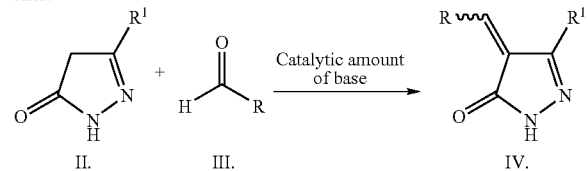

I. 4-[(Pyrrol-2-yl)methylene]-2-pyrazolin-5-ones (V).

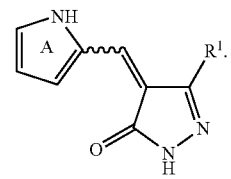

Example 1

3-Cyclopropyl-4-[(4,5-dimethylpyrrol-2-yl)methylene]-2-pyrazolin-5-one

A reaction mixture of 3-cyclopropyl-2-pyrazolin-5-one (790 mg, 6.3 mmol), 4,5-dimethylpyrrole-2-carboxaldehyde (800 mg, 6.5 mmol), and piperidine 100 mg, in ethanol 50 mL was stirred at 90° C. for 3.5 h. The solvent was removed under reduced pressure. The solid residue was purified by flash column chromatography using (3:7) ethyl acetate: hexane as the mobile phase, then further purified by recrystallization from toluene.

Example 40

3-Tert-butylureido-4-[(pyrrol-2-yl)methylene]-2-pyrazolin-5-one

A reaction mixture of 3-amino-4-[(pyrrol-2-yl)methylene]-2-pyrazoline-5-one (1.7 mmol) and tert-butylisocyanate (1 mL) in ethyl acetate 5 mL was stirred at 80° C. for 2 h. The product was collected by filtration and recrystallized from ethanol.

Example 88

4-{[4-(2-Dimethylaminoethoxycarbonyl)-3,5-dimethylpyrrol-2-yl]methylene}-3-isopropoxy-2-pyrazolin-5-one A mixture of 4-[(4-carboxy-3,5-dimethylpyrrol-2-yl)methylene]-3-isopropoxy-2-pyrazolin-5-one (200 mg, 0.68 mmol) in dichloromethane (20 ml) and a drop of DMF, was treated with oxalyldichloride (0.2 ml). The stirring was continued for 24 h and a solution of dimethylaminoethanol (0.6 g, 6.7 mmol) in dichloromethane (5 ml) was added. The stirring was continued for 24 h. The solvent was evaporated to dryness, the solid residue was treated with $NaHCO_3$ (5%) and extracted with dichloromethane. The solid obtained after elimination of the solvent was recrystallized from n-heptane.

Example 194

4-{[4-(2-Diethylaminoethyl)-3,5-dimethylpyrrole-2-yl]methylene}-3-pyrazinyl-2-pyrazolin-5-one N-oxide A mixture of Example 176 (0.2 g, 0.54 mmol) and m-chloroperbenzoic acid (0.2 g, 1.1 mmol) in chloroform (50 ml) was stirred at room temperature over 48 hrs. The solvent was removed to dryness and the residue purified by flash chromatography (dichloromethane/ethanol 9:1). Yield 30%, mp 192° C. (ethanol)

TABLE 1

Other compounds synthesized having structural formula V.

| Example | Substituent on Ring A | $R^1$ | Recrystallization Solvent | % Yield | Method |
|---|---|---|---|---|---|
| 1 | 4,5-dimethyl | cyclopropyl | toluene | 30 | see Example 1 |
| 2 | none | benzyl | toluene:heptane | 64 | see Example 1 |
| 3 | none | 4-methoxy-phenyloxymethyl | methanol | 36 | see Example 1 |
| 4 | none | phenyloxymethyl | NA | 33 | see Example 1 |
| 5 | none | 4-chloro-phenyloxymethyl | ethanol | 33 | see Example 1 |
| 6 | none | 4-methoxybenzyl | ethanol | 21 | see Example 1 |
| 7 | 4-(2-carboxyethyl)-3-methyl | benzyl | NA | | see Example 1 |
| 8 | 3-(2-carboxyethyl)-4-methyl | benzyl | isopropanol | | see Example 1 |
| 9 | none | 4-methyl-phenyloxymethyl | methanol | 42 | see Example 1 |
| 10 | none | amino | isopropanol | 90 | see Example 1 |
| 11 | none | isopropoxy | isopropanol | 52 | see Example 1 |
| 12 | none | phenylethyl | NA | 86 | see Example 1 |
| 13 | none | phenylamino | isopropanol | 86 | see Example 1 |
| 14 | none | 4-methylbenzyl | methanol | 60 | see Example 1 |
| 15 | none | 4-methylphenylamino | methanol | 86 | see Example 1 |
| 16 | none | 4-methoxyphenylamino | DMF:water | 92 | see Example 1 |
| 17 | none | 4-chlorobenzyl | ethanol | 56 | see Example 1 |
| 18 | none | 4-chlorophenylamino | ethanol | 90 | see Example 1 |
| 19 | none | 3-chlorophenyloxymethyl | NA | 50 | see Example 1 |
| 20 | none | indol-3-yl | ethanol | 90 | see Example 1 |
| 21 | none | 3-methoxybenzyl | methanol | 21 | see Example 1 |
| 22 | none | 3,4-dimethoxybenzyl | ethanol | 83 | see Example 1 |
| 23 | none | 4-methoxyphenylethyl | ethanol | 91 | see Example 1 |
| 24 | none | 4-phenylphenyloxymethyl | methanol | 72 | see Example 1 |
| 25 | none | 2-phenylpropyl | heptane | 10 | see Example 1 |

TABLE 1-continued

Other compounds synthesized having structural formula V.

| Example | Substituent on Ring A | R¹ | Recrystallization Solvent | % Yield | Method |
|---|---|---|---|---|---|
| 26 | none | 3-phenylpropyl | toluene:heptane | 60 | see Example 1 |
| 27 | none | 4-hydroxy-phenylethyl | methanol | 76 | see Example 1 |
| 28 | 3,5-dimethyl | phenylethyl | methanol | 51 | see Example 1 |
| 29 | none | 4-methyl-phenylethyl | ethanol | 53 | see Example 1 |
| 30 | 3,5-dimethyl | isopropoxy | heptane | 55 | see Example 1 |
| 31 | none | ethoxy | ethanol | 76 | see Example 1 |
| 32 | none | 4-nitro-phenylethyl | toluene | 48 | see Example 1 |
| 33 | none | 4-fluoro-phenylamino | isopropanol | 66 | see Example 1 |
| 34 | none | 4-chloro-phenylethyl | ethanol | 60 | see Example 1 |
| 35 | 4,5-dimethyl | isopropoxy | methanol | 55 | see Example 1 |
| 36 | 3,5-dimethyl-4-ethyl | isopropoxy | toluene | 47 | see Example 1 |
| 37 | 3,5-dimethyl-4-ethyl | phenylethyl | heptane | 49 | see Example 1 |
| 38 | 1-(4-hydroxy-butyl) | isopropoxy | NA | 80 | see Example 1 |
| 39 | none | cyclopentyloxy | methanol | 75 | see Example 1 |
| 40 | none | tert-butylureido | ethanol | 87 | see Example 40 |
| 41 | 4-methyl | isopropoxy | toluene | 34 | see Example 1 |
| 42 | 4-methyl | 4-amino-phenylethyl | NA | 27 | see Example 1 |
| 43 | 1-methyl | isopropoxy | toluene | 55 | see Example 1 |
| 44 | 5-methyl | isopropoxy | methanol:water | 30 | see Example 1 |
| 45 | 3,5-dimethyl-4-ethyl | 4-aminophenyl ethyl | toluene | 50 | see Example 1 |
| 46 | 5-methyl | ethoxy | methanol | 58 | see Example 1 |
| 47 | 3,5-dimethyl-4-ethyl | 4-carbamoyl-phenylethyl | DMF:water | 82 | see Example 1 |
| 48 | 3,5-dimethyl-4-ethyl | 4-methoxy carbonyl-phenylethyl | methanol | 70 | see Example 1 |
| 49 | 3,5-dimethyl-4-ethoxycarbonyl | isopropoxy | ethanol | 81 | see Example 1 |
| 50 | 3,5-dimethyl-4-ethoxycarbonyl | 4-amino-phenylethyl | ethanol | 62 | see Example 1 |
| 51 | 5-ethyl | isopropoxy | heptane | 48 | see Example 1 |
| 52 | 3,5-dimethyl-4-ethyl | 4-hydroxy-phenylethyl | isopropanol | 35 | see Example 1 |
| 53 | none | ethoxycarbonyl-methyl | ethanol | 35 | see Example 1 |
| 54 | none | 4-methoxy-phenylamino-carbonylmethyl | methanol | 46 | see Example 1 |
| 55 | 3(2-carboxyethyl)-4-methyl | isopropyl | ethanol | 32 | see Example 1 |
| 56 | none | cyclopropyl | ethanol | 50 | see Example 1 |
| 57 | none | cyclobutyl | ethanol | 65 | see Example 1 |
| 58 | none | 3-pyridyl | ethanol | 50 | see Example 1 |
| 59 | 1-(3,5-dichloro-phenyl) | cyclopropyl | ethanol | 30 | see Example 1 |
| 60 | none | 2,2,3,3-tetramethyl-cyclopropyl | toluene | 55 | see Example 1 |
| 61 | 3,5-dimethyl | cyclopropyl | toluene | 33 | see Example 1 |
| 62 | none | cyclopentyl | toluene | 66 | see Example 1 |
| 63 | none | 2-methyl cyclopropyl | hexane | 44 | see Example 1 |
| 64 | none | benzothiazol-2-yl | DMF:water | 60 | see Example 1 |
| 65 | 4,5-dimethyl | 3-pyridyl | ethanol | 35 | see Example 1 |
| 66 | 3,5-dimethyl-4-ethyl | cyclopropyl | ethanol | 50 | see Example 1 |
| 67 | none | pyrrol-2-yl | methanol | 88 | see Example 1 |
| 68 | 4-methyl | cyclopropyl | ethanol | 35 | see Example 1 |
| 69 | 4-methyl | benzothiazol-2-yl | ethanol | 48 | see Example 1 |
| 70 | 3,5-dimethyl | 3-pyridyl | ethanol | 24 | see Example 1 |

TABLE 1-continued

Other compounds synthesized having structural formula V.

| Example | Substituent on Ring A | R¹ | Recrystallization Solvent | % Yield | Method |
|---|---|---|---|---|---|
| 71 | 3,5-dimethyl-4-ethyl | 3-pyridyl | ethanol | 51 | see Example 1 |
| 72 | 5-methyl | cyclopropyl | ethanol | 50 | see Example 1 |
| 73 | 5-methyl | 3-pyridyl | ethanol | 47 | see Example 1 |
| 74 | 5-ethyl | cyclopropyl | ethanol:water | 21 | see Example 1 |
| 75 | 3,5-dimethyl-4-ethoxycarbonyl | cyclopropyl | ethanol | 83 | see Example 1 |
| 76 | 5-phenyl | isopropoxy | methanol | 66 | see Example 1 |
| 77 | none | propyl | NA | 49 | see Example 1 |
| 78 | none | methyl | NA | 6 | see Example 1 |
| 79 | none | 4-isopropyl-phenylamino | NA | 50 | see Example 1 |
| 80 | none | 3-phenylamino | NA | 80 | see Example 1 |
| 81 | 1-(4-hydroxy-butyl) | cyclopropyl | ethanol | 34 | see Example 1 |
| 82 | 4-(2-carboxyethyl)-3-methyl | isopropoxy | ethanol | 46 | see Example 1 |
| 83 | 4-carboxy-3,5-dimethyl | isopropoxy | NA | 41 | see Example 1 |
| 84 | 4,5-tetramethylene | isopropoxy | ethanol | 77 | see Example 1 |
| 85 | 3,4-dimethyl-4-morpholino methyl | isopropoxy | NA | 30 | see Example 1 |
| 86 | 3,5-dimethyl-4-dimethylamino methyl | isopropoxy | heptane | 30 | see Example 1 |
| 87 | 4-acetyl-3,5-dimethyl | isopropoxy | ethanol | 62 | see Example 1 |
| 88 | 3,5-dimethyl-4-(2-dimethyl aminoethyloxy carbonyl) | isopropoxy | heptane | 40 | See Example 88 |
| 89 | 3,5-dimethyl-4-(2-dimethyl aminoethyl aminocarbonyl) | isopropoxy | toluene:heptane | 41 | See Example 88 |
| 90 | 5-ethoxy carbonyl | isopropoxy | methanol | 79 | see Example 1 |
| 91 | 5-carboxy | isopropoxy | toluene | 83 | see Example 1 |
| 92 | none | 4-chlorophenyl aminocarbonyl methyl | DMF/water | 50 | see Example 1 |
| 93 | 5-phenyl | cyclopropyl | ethanol | 72 | see Example 1 |
| 94 | 3,5-dimethyl-4-ethyl | tetrahydrofuran-3-yl | toluene | 44 | see Example 1 |
| 95 | 4-carboxy-3,5-dimethyl | cyclopropyl | ethanol | 69 | see Example 1 |
| 96 | 3,5-dimethyl-4-ethoxycarbonyl | 3-pyridyl | ethanol | 86 | see Example 1 |
| 97 | 3,5-dimethyl-4-morpholino methyl | cyclopropyl | NA | 34 | see Example 1 |
| 98 | 3,4-dimethyl | pyrazinyl | methanol | 60 | see Example 1 |
| 99 | 4-(2-carboxy ethyl)-3-methyl | cyclopropyl | methanol | 51 | see Example 1 |
| 100 | 3,5-dimethyl-4-dimethylamino methyl | cyclopropyl | NA | 67 | see Example 1 |
| 101 | 5-ethoxy carbonyl | cyclopropyl | ethanol | 91 | see Example 1 |
| 102 | 4,5-tetramethylene | cyclopropyl | ethanol | 84 | see Example 1 |
| 103 | none | 2-methoxy carbonyl ethyl | ethanol | 56 | see Example 1 |
| 104 | none | ethoxycarbonyl | NA | 40 | see Example 1 |
| 105 | none | isopropyl | NA | 44 | see Example 1 |
| 106 | none | trans-2-phenyl cyclopropyl | toluene | 46 | see Example 1 |
| 107 | none | cyclohexyl | toluene | 32 | see Example 1 |
| 108 | 4,5-tetramethylene | cyclopropyl amino | ethanol | 50 | see Example 1 |

TABLE 1-continued

Other compounds synthesized having structural formula V.

| Example | Substituent on Ring A | R[1] | Recrystallization Solvent | % Yield | Method |
|---|---|---|---|---|---|
| 109 | 5-morpholino methyl | cyclopropyl | ethylacetate | 72 | see Example 1 |
| 110 | 5-carboxy | cyclopropyl | ethanol | 50 | see Example 1 |
| 111 | 4-chloro | ethoxy | ethanol | 88 | see Example 1 |
| 112 | 4-bromo | ethoxy | ethanol | 70 | see Example 1 |
| 113 | 5-chloro | ethoxy | NA | 37 | see Example 1 |
| 114 | 4-chloro | cyclopropyl | ethanol | 42 | see Example 1 |
| 115 | 4-bromo | cyclopropyl | ethanol | 50 | see Example 1 |
| 116 | 4,5-tetramethylene | pyrazinyl | ethanol | 85 | see Example 1 |
| 117 | 4,5-tetramethylene | 3-pyridyl | ethanol | 84 | see Example 1 |
| 118 | 4-carboxy-3,5-dimethyl | pyrazinyl | DMF | 66 | see Example 1 |
| 119 | 3,5-dimethyl-4-(2-dimethylamino ethyloxycarbonyl) | cyclopropyl | NA | 71 | see Example 88 |
| 120 | 3,5-dimethyl-4-(2-dimethylamino ethyloxycarbonyl) | pyrazinyl | NA | 20 | see Example 88 |
| 121 | 3,5-dimethyl-4-dimethylamino methyl | pyrazinyl | toluene | 76 | see Example 1 |
| 122 | 3,5-dimethyl-4-dimethylamino methyl maleate | pyrazinyl | ethanol | 98 | Maleate salt formed from free base of Example 121. (See footnote) |
| 123 | 3,5-dimethyl-4-(2-morpholino ethylamino carbonyl) | pyrazinyl | toluene | 20 | see Example 1 |
| 124 | 3,5-dimethyl | 2-pyridyl | ethanol | 36 | see Example 1 |
| 125 | 3,5-dimethyl-4-ethyl | 2-pyridyl | ethanol | 50 | see Example 1 |
| 126 | 4,5-tetramethylene | 2-pyridyl | ethanol | 58 | see Example 1 |
| 127 | 3,5-dimethyl | 2-furyl | ethanol | 51 | see Example 1 |
| 128 | 3,5-dimethyl-4-morpholino methyl | pyrazinyl | NA | 28 | see Example 1 |
| 129 | 3,5-dimethyl | 2-thienyl | ethanol | 25 | see Example 1 |
| 130 | 4-ethoxycarbonyl | cyclopropyl | ethanol | 68 | see Example 1 |
| 131 | 3,5-dimethyl-4-trifluoro acetamidomethyl | cyclopropyl | ethanol | 70 | see Example 1 |
| 132 | 4-aminomethyl-3,5-dimethyl | cyclopropyl | ethanol | 30 | see Example 1 |
| 133 | 3,5-dimethyl | benzothiazol-2-yl | ethanol | 40 | see Example 1 |
| 134 | 3,5-dimethyl-4-morpholino methyl | benzothiazol-2-yl | ethanol | 40 | see Example 1 |
| 135 | 3,5-dimethyl-4-ethyl | pyrazinyl | ethanol | 74 | see Example 1 |
| 136 | 4-ethoxycarbonyl | pyrazinyl | toluene | 26 | see Example 1 |
| 137 | 4-carboxy | pyrazinyl | methanol | 70 | see Example 1 |
| 138 | 3,5-dimethyl-4-diethanolamino methyl | pyrazinyl | ethanol | 50 | see Example 1 |
| 139 | 3,5-dimethyl-4-trifluoro acetamidomethyl | pyrazinyl | NA | 78 | see Example 1 |
| 140 | 4-ethoxycarbonyl-3-phenyl | cyclopropyl | ethanol | 68 | see Example 1 |
| 141 | 3,5-dimethyl-4-(1-pyrrolidinyl methyl) | pyrazinyl | toluene | 23 | see Example 1 |
| 142 | 3,5-dimethyl-4-dimethylamino methyl | 2-furyl | toluene | 20 | see Example 1 |
| 143 | 3,5-dimethyl-4-dimethylamino methyl | 2-thienyl | toluene | 48 | see Example 1 |

TABLE 1-continued

Other compounds synthesized having structural formula V.

| Example | Substituent on Ring A | R¹ | Recrystallization Solvent | % Yield | Method |
|---|---|---|---|---|---|
| 144 | 3,5-dimethyl-4-dimethylamino methyl | 3-pyridyl | toluene | 51 | see Example 1 |
| 145 | 3,5-dimethyl-4-ethoxycarbonyl | phenyl | ethanol | 89 | see Example 1 |
| 146 | 3,5-dimethyl-4-ethyl | phenyl | methanol | 34 | see Example 1 |
| 147 | 3,4-di(ethoxy carbonyl) | ethoxy | ethanol | 54 | see Example 1 |
| 148 | 4-ethoxycarbonyl | ethoxy | methanol | 30 | see Example 1 |
| 149 | 3,5-dimethyl-4-ethoxycarbonyl | 2-(3-pyridyl)ethyl | ethanol | 81 | see Example 1 |
| 150 | 3,5-dimethyl-4-ethoxycarbonyl | 1-methyl-2-phenylethyl | ethanol | 52 | see Example 1 |
| 151 | 4-carboxy-3,5-dimethyl | ethoxy | DMF:water | 81 | see Example 1 |
| 152 | 5-nitro | ethoxy | ethanol | 64 | see Example 1 |
| 153 | 4-nitro | ethoxy | toluene | 95 | see Example 1 |
| 154 | 4-carboxy | ethoxy | NA | 40 | see Example 1 |
| 155 | 3,5-dimethyl-4-(2-dimethyl aminoethyl amino carbonyl) | ethoxy | heptane | 86 | see Example 88 |
| 156 | 5-chloro-3-methoxycarbonyl-4-methoxy carbonylmethyl | ethoxy | ethanol | 46 | see Example 1 |
| 157 | 3-(2-carboxyethyl)-4-methyl | ethoxy | NA | 54 | see Example 1 |
| 158 | 3,5-dimethyl-4-ethoxycarbonyl | ethoxy | ethanol | 82 | see Example 1 |
| 159 | 4,5-tetramethylene | ethoxy | heptane | 80 | see Example 1 |
| 160 | 3,5-dimethyl-4-ethoxycarbonyl | trifluoro-methyl | ethanol | 45 | see Example 1 |
| 161 | 3,5-dimethyl-4-ethoxycarbonyl | 5-isoxazolyl | DMF:water | 74 | see Example 1 |
| 162 | 3,5-dimethyl-4-ethoxycarbonyl | 3-amino-phenyl | ethanol | 76 | see Example 1 |
| 163 | 4-morpholino ethyl aminocarbonyl | ethoxy | NA | 30 | see Example 88 |
| 164 | 4-ethoxycarbonyl-3-phenyl | pyrazinyl | toluene | 70 | see Example 1 |
| 165 | 4-(4-methyl-1-pyperazinyl methyl)-3,5-dimethyl | pyrazinyl | DMF | 58 | see Example 1 |
| 166 | 4-diethylamino methyl-3,5-dimethyl | pyrazinyl | NA | 20 | see Example 1 |
| 167 | 3,5-dimethyl-4-piperidino methyl | pyrazinyl | toluene | 25 | see Example 1 |
| 168 | 3,5-dimethyl-4-piperidinomethyl | 5-isoxazolyl | NA | 35 | see Example 1 |
| 169 | 3,5-dimethyl-4-dimethylamino methyl | 5-isoxazolyl | NA | 30 | see Example 1 |
| 170 | 5-methyl-4-dimethylamino methyl | pyrazinyl | toluene-heptane | 75 | see Example 1 |
| 171 | 3,5-Dimethyl-4-[N-(2-dimethyl-aminoethyl)-N-methylaminomethyl] | pyrazinyl | methanol | 40 | See example 1 |
| 172 | 3-dimethylamino-methyl-4,5-tetramethylene | cyclopropyl | NA | 30 | See example 1 |
| 173 | 3-dimethylamino-methyl-4,5-tetramethylene | pyrazinyl | NA | 30 | See example 1 |
| 174 | 3,5-dimethyl-4-dimethylamino-methyl maleate | cyclopropyl | Ethanol | 90 | Maleate salt form from free base of Example 100. (See footnote) |

TABLE 1-continued

Other compounds synthesized having structural formula V.

| Example | Substituent on Ring A | R[1] | Recrystallization Solvent | % Yield | Method |
|---|---|---|---|---|---|
| 175 | 4-(3-chloro propionyl)-3,5-dimethyl | pyrazinyl | Toluene | 88 | See example 1 |
| 176 | 4-(2-diethylamino-ethyl)-3,5-dimethyl | pyrazinyl | ethanol | 95 | See example 1 |
| 177 | 3,5-dimethyl-4-(dimethylamino-methyl) | 5-methyl-3-xazolyl | toluene/heptane | 40 | See example 1 |
| 178 | 3,5-Dimethyl-4-(4-hydroxypiperidinomethyl) | pyrazinyl | methanol | 40 | See example 1 |
| 179 | 4-Aminomethyl-3,5-dimethyl maleate | pyrazinyl | methanol | 76 | See example 1 |
| 180 | 4-(4-Benzylpiperidinomethyl)-3,5-dimethyl | pyrazinyl | toluene | 80 | See example 1 |
| 181 | 3,5-Dimethyl-4-(2-hydroxyethyl) | pyrazinyl | NA | 80 | See example 1 |
| 182 | 3,5-Dimethyl-4-[2-(1-pyrrolidinylethyl)] | pyrazinyl | toluene | 67 | See example 1 |
| 183 | 3,5-Dimethyl-4-[2-(1-pyrrolidinylethyl)] | cyclopropyl | toluene | 20 | See example 1 |
| 184 | 3,5-Dimethyl-4-(2-hydroxyethyl) | cyclopropyl | NA | 23 | See example 1 |
| 185 | 3,5-Dimethyl-4-(2-ethylaminoethyl) | pyrazinyl | NA | 35 | See example 1 |
| 186 | 4-(3-Diethyl aminopropyl)-3,5-dimethyl | pyrazinyl | ethanol | 52 | See example 1 |
| 187 | 3,5-Dimethyl-4-(3-hydroxypropyl) | pyrazinyl | ethanol | 82 | See example 1 |
| 188 | 3,5-Dimethyl-4-dimethylaminoacetyl hydrochloride | pyrazinyl | ethanol/ethy ether | 51 | See example 1 |
| 189 | 3,5-Dimethyl-4-dimethylaminoacetyl | ethoxy | ethanol/ylether | 44 | See example 1 |
| 190 | 4-(2-diethylaminoethyl)-3,5-Dimethyl | cyclopropyl | heptane | 54 | See example 1 |
| 191 | 3,5-Dimethyl-4-(2-dimethylaminoethyl) | pyrazinyl | toluene | 48 | See example 1 |
| 192 | 3,5-Dimethyl-4-(4-hydroxybutyl) | pyrazinyl | methanol | 58 | See example 1 |
| 193 | 4-(4-Diethylaminobutyl)-3,5-dimethyl | pyrazinyl | toluene | 60 | See example 1 |
| 194 | 4-(2-Diethylamino-ethyl-N-oxide)-3,5 dimethyl | pyrazinyl | Ethanol | 30 | See example 194 |
| 195 | 3,5-Dimethyl-4-(1-pyrrolidinylacetyl) | pyrazinyl | NA | 57 | See example 1 |
| 196 | 4-Diethylaminoacetyl-3,5-dimethyl | pyrazinyl | NA | 52 | See example 1 |
| 197 | 3-Isopropyl-5-methyl | pyrazinyl | Ethanol | 44 | See example 1 |
| 198 | 3,5-Dimethyl-4-[3-(1-pyrrolidinylpropyl)] | pyrazinyl | Ethanol | 30 | See example 1 |
| 199 | 4-Dimethyl aminomethyl-3-isopropyl-5-methyl | pyrazinyl | Toluene | 40 | See example 1 |
| 200 | 4-Dimethyl aminomethyl-3-isopropyl-5-methyl | cyclopropyl | Toluene | 40 | See example 1 |
| 201 | 3,5-Dimethyl-4-(2-ethoxyoxalyl) | pyrazinyl | Ethanol | 40 | See example 1 |
| 202 | 3,5-Dimethyl-4-(2-ethylaminoethyl) | cyclopropyl | NA | 60 | See example 1 |
| 203 | 3,5-Dimethyl-4-(2-cyclopropylaminoethyl) | pyrazinyl | Toluene | 40 | See example 1 |
| 204 | 3,5-Dimethyl-4-[2-(4-pyridyl-methylamino)ethyl] | pyrazinyl | NA | 40 | See example 1 |
| 205 | 3,5-Dimethyl-4-(2-cyclopropylaminoethyl) | cyclopropyl | Toluene | 36 | See example 1 |
| 206 | 3,5-Dimethyl-4-(2-diethylaminoethyl) | 2-pyrimidinyl | Toluene | 35 | See example 1 |
| 207 | 3,5-Dimethyl-4-(2-diethylaminoethyl) | 3-pyridazinyl | Toluene | 40 | See example 1 |
| 208 | 3,5-Dimethyl-4-(2-diethylaminoethyl) | 4-pyrimidinyl | Toluene | 50 | See example 1 |
| 209 | 3,5-Dimethyl-4-(2-diethylaminoethyl | 4-pyridazinyl | Toluene | 30 | See example 1 |

TABLE 1A

Physical data for compounds synthesized having structural formula V.

| | | Elemental Analysis | | | | | |
|---|---|---|---|---|---|---|---|
| | | Carbon | | Hydrogen | | Nitrogen | |
| Example | Mp. (° C.) | Calculated | Found | Calculated | Found | Calculated | Found |
| 1 | 220–222 | 68.10 | 68.27 | 6.59 | 6.61 | 18.32 | 18.30 |
| 2 | 182–184 | 71.69 | 72.00 | 5.21 | 5.40 | 16.72 | 16.47 |
| 3 | 177–180 | 64.63 | 64.06 | 5.08 | 5.02 | 14.13 | 14.00 |
| 4 | 163–165 | 67.40 | 66.88 | 4.90 | 4.88 | 15.72 | 15.53 |
| 5 | 218–222 | 59.71 | 59.87 | 4.00 | 4.24 | 13.92 | 13.85 |
| 6 | 179–180 | 68.55 | 68.45 | 5.03 | 5.44 | 14.99 | 14.99 |
| 7 | 270–272 | 67.64 | 67.17 | 5.67 | 5.82 | 12.45 | 12.38 |
| 8 (0.3 $H_2O$)* | 226–228 | 66.58 | 66.10 | 5.72 | 5.65 | 12.26 | 12.27 |
| 9 | 207–210 | 68.31 | 68.20 | 5.37 | 5.44 | 14.93 | 14.96 |
| 10 | 265–270 | 54.53 | 55.07 | 4.57 | 4.47 | 31.80 | 31.98 |
| 11 | 172–174 | 60.26 | 60.37 | 5.97 | 5.80 | 19.16 | 18.97 |
| 12 | 145–147 | 72.43 | 72.29 | 5.69 | 5.70 | 15.83 | 16.17 |
| 13 | 285–287 | 66.65 | 66.66 | 4.79 | 4.71 | 22.20 | 22.12 |
| 14 | 254–255 | 72.43 | 72.36 | 5.69 | 5.53 | 15.83 | 15.84 |
| 15 | 256–258 | 67.65 | 67.31 | 5.29 | 5.12 | 21.03 | 20.96 |
| 16 | 288–290 | 63.81 | 63.90 | 4.99 | 4.53 | 19.84 | 19.75 |
| 17 | 178–180 | 63.05 | 63.26 | 4.23 | 4.10 | 14.70 | 14.59 |
| 18 (0.25 $H_2O$)* | 245–247 | 57.74 | 57.69 | 3.97 | 3.81 | 19.23 | 18.95 |
| 19 | 165–167 | 59.71 | 59.69 | 4.00 | 4.05 | 13.92 | 13.80 |
| 20 | 300–305 | 69.55 | 69.67 | 4.37 | 4.61 | 20.27 | 20.39 |
| 21 | 169–171 | 68.31 | 68.27 | 5.37 | 5.36 | 14.93 | 14.92 |
| 22 | 164–165 | 65.58 | 65.58 | 5.50 | 5.63 | 13.49 | 13.44 |
| 23 | 137–139 | 69.13 | 69.15 | 5.80 | 5.69 | 14.22 | 14.30 |
| 24 (0.25 $H_2O$)* | 192–194 | 72.50 | 72.56 | 5.07 | 5.36 | 12.07 | 12.02 |
| 25 | 130–131 | 73.09 | 73.16 | 6.13 | 6.25 | 15.04 | 14.83 |
| 26 | 169–170 | 73.09 | 73.46 | 6.13 | 6.32 | 15.04 | 14.42 |
| 27 | 253–255 | 68.31 | 68.48 | 5.37 | 5.01 | 14.93 | 14.74 |
| 28 | 186–187 | 73.69 | 73.89 | 6.52 | 6.49 | 14.32 | 14.25 |
| 29 | 153–154 | 73.09 | 73.38 | 6.13 | 5.95 | 15.04 | 14.85 |
| 30 | 176–177 | 63.14 | 63.20 | 6.93 | 6.77 | 16.99 | 16.98 |
| 31 | 211–213 | 58.53 | 58.81 | 5.40 | 5.27 | 20.48 | 20.52 |
| 32 | 224–226 | 61.92 | 62.02 | 4.54 | 4.75 | 18.05 | 18.31 |
| 33 | 272–273 | 62.21 | 62.45 | 4.10 | 4.33 | 20.73 | 20.81 |
| 34 | 193–194 | 64.11 | 64.27 | 4.71 | 4.85 | 14.02 | 14.07 |
| 35 | 195–197 | 63.14 | 63.26 | 6.93 | 6.76 | 16.99 | 17.04 |
| 36 | 188–190 | 65.43 | 65.59 | 7.68 | 7.00 | 15.26 | 15.29 |
| 37 | 168–170 | 74.73 | 74.40 | 7.21 | 7.10 | 13.07 | 13.11 |
| 38 | 138–140 | 61.84 | 61.87 | 7.27 | 7.17 | 14.42 | 14.31 |
| 39 | 201–203 | 63.65 | 63.65 | 6.16 | 6.19 | 17.13 | 17.24 |
| 40 | 266–268 | 56.71 | 57.04 | 6.22 | 6.06 | 25.43 | 25.69 |
| 41 | 215–217 | 61.78 | 61.77 | 6.48 | 6.40 | 18.01 | 17.96 |
| 42 (0.75 $H_2O$)* | 178–180 | 66.32 | 66.78 | 6.33 | 6.01 | 18.19 | 17.85 |
| 43 | 199–201 | 61.78 | 61.97 | 6.48 | 6.36 | 18.01 | 17.91 |
| 44 | 128–130 | 61.78 | 61.42 | 6.48 | 6.32 | 18.01 | 17.78 |
| 45 | 183–185 | 71.40 | 71.38 | 7.19 | 7.28 | 16.65 | 16.62 |
| 46 | 197–199 | 64.35 | 64.69 | 7.33 | 6.96 | 16.08 | 16.03 |
| 47 | 297–299 | 69.21 | 69.08 | 6.64 | 6.68 | 15.37 | 15.31 |
| 48 | 177–179 | 60.94 | 69.70 | 6.64 | 6.57 | 11.07 | 11.10 |
| 49 | 226–228 | 60.18 | 60.06 | 6.63 | 6.46 | 13.16 | 13.02 |
| 50 | 186–188 | 66.30 | 66.20 | 6.36 | 6.25 | 14.73 | 14.68 |
| 51 | 119–121 | 63.14 | 63.14 | 6.93 | 6.95 | 16.99 | 17.00 |
| 52 | 260–262 | 71.19 | 71.01 | 6.87 | 6.96 | 12.45 | 12.36 |
| 53 | 124–126 | 58.29 | 58.49 | 5.29 | 5.04 | 16.99 | 16.99 |
| 54 | 240–242 | 62.95 | 62.96 | 4.97 | 5.00 | 17.27 | 17.11 |
| 55 | 229–231 | 62.26 | 62.20 | 6.62 | 6.37 | 14.52 | 14.36 |
| 56 | 158–160 | 65.65 | 65.78 | 5.51 | 5.50 | 20.88 | 20.78 |
| 57 | 150–152 | 66.95 | 67.09 | 6.08 | 5.76 | 19.52 | 19.45 |
| 58 | 222–224 | 65.53 | 65.57 | 4.23 | 4.29 | 25.51 | 23.62 |
| 59 | 188–190 | 58.97 | 59.06 | 3.78 | 3.92 | 12.13 | 11.98 |
| 60 | 160–162 | 70.01 | 70.28 | 7.44 | 7.35 | 16.33 | 16.22 |
| 61 | 193–195 | 68.09 | 68.34 | 6.59 | 6.39 | 18.32 | 18.18 |
| 62 (0.2 toluene)* | 127–129 | 69.82 | 69.73 | 6.75 | 6.64 | 16.96 | 17.20 |
| 63 | 132–133 | 66.95 | 67.11 | 6.08 | 6.03 | 19.52 | 19.73 |
| 64 | 340–342 | 61.20 | 61.38 | 3.42 | 3.70 | 19.03 | 19.19 |
| 65 | 220(d) | 67.65 | 67.47 | 5.29 | 5.30 | 21.04 | 20.94 |
| 66 | 206–210 | 70.01 | 69.65 | 7.44 | 7.46 | 16.33 | 16.23 |

TABLE 1A-continued

Physical data for compounds synthesized having structural formula V.

| | | Elemental Analysis | | | | | |
|---|---|---|---|---|---|---|---|
| | | Carbon | | Hydrogen | | Nitrogen | |
| Example | Mp. (° C.) | Calculated | Found | Calculated | Found | Calculated | Found |
| 67 | 245–247 | 63.70 | 63.76 | 4.45 | 4.64 | 24.76 | 24.64 |
| 68 | 212–215 | 66.95 | 66.72 | 6.08 | 5.63 | 19.52 | 19.29 |
| 69 (0.5 H₂O)* | 327–329 | 60.55 | 60.90 | 4.12 | 4.09 | 17.65 | 17.42 |
| 70 | 235–238 | 67.65 | 67.66 | 5.29 | 5.40 | 21.04 | 20.98 |
| 71 | 270–272 | 69.36 | 69.41 | 6.16 | 6.21 | 19.03 | 18.98 |
| 72 | 170–172 | 66.95 | 67.05 | 6.08 | 6.08 | 19.52 | 19.42 |
| 73 | 210–212 | 66.65 | 66.73 | 4.79 | 4.82 | 22.21 | 22.10 |
| 74 | 163–165 | 68.10 | 68.15 | 6.59 | 6.63 | 18.32 | 18.27 |
| 75 | 240–242 | 63.77 | 63.77 | 6.35 | 6.35 | 13.94 | 13.90 |
| 76 | 212–214 | 69.14 | 69.27 | 5.80 | 5.88 | 14.23 | 14.20 |
| 77–80 | | ¹³C and ¹H NMR and analytical LC/MS data consistent with assigned structure | | | | | |
| 81 | 134–136 | 65.91 | 65.60 | 7.00 | 6.99 | 15.37 | 15.03 |
| 82 | 267–269 | 59.01 | 59.12 | 6.27 | 6.22 | 13.76 | 13.66 |
| 83 | >300 | 57.72 | 57.81 | 5.88 | 5.84 | 14.42 | 14.25 |
| 84 | 206–207 | 65.91 | 66.04 | 7.01 | 6.78 | 15.37 | 15.34 |
| 85 | 162–164 | 62.41 | 62.36 | 7.56 | 7.46 | 16.17 | 15.94 |
| 86 | 173–175 | 63.13 | 63.27 | 7.95 | 7.73 | 18.41 | 18.34 |
| 87 | 209–210 | 62.27 | 61.86 | 6.62 | 6.58 | 14.52 | 14.25 |
| 88 | 165–167 | 59.65 | 59.82 | 7.23 | 7.05 | 15.46 | 15.34 |
| 89 | 192–194 | 59.82 | 59.92 | 7.53 | 7.26 | 19.38 | 19.21 |
| 90 | 205–207 | 57.72 | 57.96 | 5.88 | 5.62 | 14.42 | 14.43 |
| 91 | 235–237 | 51.24 | 51.78 | 5.38 | 5.49 | 14.94 | 14.95 |
| 92 | 240–242 | 58.45 | 58.07 | 3.98 | 3.96 | 17.04 | 16.64 |
| 93 | 208–210 | 73.62 | 73.60 | 5.45 | 5.62 | 15.15 | 15.14 |
| 94 | 163–165 | 66.87 | 66.70 | 7.36 | 7.10 | 14.62 | 14.59 |
| 95 | 312(d) | 61.53 | 61.08 | 5.53 | 5.38 | 15.37 | 15.11 |
| 96 | 247–249 | 63.89 | 64.05 | 5.36 | 5.48 | 16.56 | 16.70 |
| 97 | 175–177 | 65.82 | 65.62 | 7.36 | 7.43 | 17.06 | 16.75 |
| 98 | 245–250 | 62.91 | 63.30 | 4.90 | 5.10 | 26.20 | 26.29 |
| 99 | 290(d) | 62.70 | 62.66 | 5.96 | 5.83 | 14.62 | 14.47 |
| 100 | 176–178 | 67.10 | 67.21 | 7.74 | 7.49 | 19.56 | 19.53 |
| 101 | 250–152 | 61.52 | 61.73 | 5.53 | 5.46 | 15.37 | 15.40 |
| 102 | 227–230 | 70.56 | 70.62 | 6.71 | 6.61 | 16.46 | 16.52 |
| 103 | 134–136 | 58.29 | 58.71 | 5.29 | 5.44 | 16.99 | 17.03 |
| 104 | 177–179 | 56.64 | 56.85 | 4.75 | 4.56 | 18.01 | 17.56 |
| 105 | 120–122 | 65.01 | 65.12 | 6.44 | 6.44 | 20.67 | 20.59 |
| 106 | 173–175 | 74.42 | 74.20 | 5.60 | 5.77 | 14.46 | 14.77 |
| 107 | 176–178 | 69.11 | 69.21 | 7.04 | 7.08 | 17.27 | 17.24 |
| 108 | 240–243 | 66.64 | 66.62 | 6.71 | 6.39 | 20.72 | 20.80 |
| 109 | 184–186 | 63.98 | 64.21 | 6.71 | 6.69 | 18.65 | 18.74 |
| 110 | 220(d) | 54.75 | 55.17 | 4.97 | 4.90 | 15.96 | 16.21 |
| 111 | 237–239 | 50.12 | 50.54 | 4.21 | 3.90 | 17.53 | 17.59 |
| 112 | 242–244 | 42.28 | 42.45 | 3.55 | 3.39 | 14.79 | 14.58 |
| 113 | 170–172 | 50.12 | 49.98 | 4.21 | 4.21 | 17.53 | 18.10 |
| 114 | 220(d) | 56.06 | 56.46 | 4.27 | 4.37 | 17.83 | 17.54 |
| 115 | 210(d) | 47.16 | 47.60 | 3.59 | 3.85 | 15.00 | 14.57 |
| 116 | 253–255 | 65.51 | 65.83 | 5.15 | 5.25 | 23.87 | 23.86 |
| 117 | 264–267 | 69.84 | 69.61 | 5.51 | 5.53 | 19.16 | 19.13 |
| 118 | 225–228 | 56.71 | 56.59 | 4.94 | 4.79 | 22.00 | 21.94 |
| 119 | 172–174 | 62.77 | 62.61 | 7.02 | 6.71 | 16.26 | 16.06 |
| 120 | 223–225 | 58.30 | 58.79 | 5.92 | 6.10 | 21.47 | 20.89 |
| 121 | 220–222 | 63.50 | 63.57 | 6.26 | 6.25 | 25.39 | 25.55 |
| 122 | 206–210 | 55.01 | 54.51 | 5.71 | 5.64 | 18.32 | 18.30 |
| 123 | 178–180 | 59.56 | 60.03 | 5.95 | 5.82 | 23.15 | 22.87 |
| 124 | 228–230 | 67.65 | 68.00 | 5.29 | 5.46 | 21.04 | 21.12 |
| 125 | 184–186 | 69.36 | 69.19 | 6.16 | 6.09 | 19.03 | 19.33 |
| 126 | 214–216 | 69.84 | 69.94 | 5.51 | 5.41 | 19.16 | 19.33 |
| 127 | 235–237 | 65.87 | 65.88 | 5.13 | 5.24 | 16.46 | 16.51 |
| 128 | 274–277 | 62.28 | 62.26 | 6.05 | 5.90 | 22.93 | 22.94 |
| 129 | 235–237 | 61.96 | 62.01 | 4.82 | 4.91 | 15.48 | 15.44 |
| 130 | 192–194 | 61.52 | 61.73 | 5.53 | 5.53 | 15.37 | 15.43 |
| 131 | 278–280 | 54.23 | 54.40 | 4.83 | 4.92 | 15.81 | 15.68 |
| 132 | 217–219 | 63.61 | 63.84 | 7.11 | 6.90 | 21.19 | 21.22 |
| 133 | 295–297 | 63.33 | 63.55 | 4.37 | 4.45 | 17.38 | 17.44 |
| 134 | 285(d) | 62.15 | 62.03 | 5.54 | 6.02 | 16.47 | 16.91 |
| 135 | 264–267 | 65.06 | 65.10 | 5.80 | 5.71 | 23.71 | 23.51 |
| 136 | 155–157 | 59.74 | 59.30 | 4.46 | 4.40 | 21.24 | 21.20 |
| 137 | 230–232 | 54.26 | 54.58 | 3.77 | 3.34 | 24.34 | 23.99 |
| 138 | 242–244 | 58.44 | 58.81 | 6.36 | 6.28 | 21.52 | 21.84 |

TABLE 1A-continued

Physical data for compounds synthesized having structural formula V.

|  |  | Elemental Analysis | | | | | |
|---|---|---|---|---|---|---|---|
|  |  | Carbon | | Hydrogen | | Nitrogen | |
| Example | Mp. (° C.) | Calculated | Found | Calculated | Found | Calculated | Found |
| 139 | 302–305 | 51.45 | 51.30 | 3.93 | 4.26 | 21.17 | 20.88 |
| 140 | 218–220 | 68.75 | 69.07 | 5.48 | 5.53 | 12.02 | 11.96 |
| 141 | 235–237 | 64.02 | 64.11 | 6.41 | 6.54 | 23.58 | 23.01 |
| 142 | 209–211 | 65.36 | 65.37 | 6.45 | 6.89 | 17.93 | 16.53 |
| 143 | 208–210 | 61.32 | 61.43 | 6.20 | 6.18 | 16.83 | 16.64 |
| 144 | 220–224 | 66.85 | 67.24 | 6.54 | 6.54 | 21.65 | 21.11 |
| 145 | 216–217 | 67.64 | 67.71 | 5.68 | 5.80 | 12.45 | 12.53 |
| 146 | 274–275 | 73.70 | 73.80 | 6.53 | 6.53 | 14.32 | 14.39 |
| 147 | 132–134 | 55.01 | 55.24 | 5.48 | 5.32 | 12.03 | 12.03 |
| 148 | 212–216 | 56.31 | 56.25 | 5.45 | 5.20 | 15.15 | 15.02 |
| 149 | 180–182 | 65.56 | 65.10 | 6.05 | 5.96 | 15.29 | 15.20 |
| 150 | 168–170 | 69.64 | 69.91 | 6.64 | 6.43 | 11.07 | 11.10 |
| 151 | 310–312 | 56.31 | 56.30 | 5.45 | 5.15 | 15.15 | 15.17 |
| 152 | 208–210 | 48.00 | 48.37 | 4.03 | 4.19 | 22.39 | 22.65 |
| 153 | 287–289 | 48.00 | 48.37 | 4.03 | 4.04 | 22.39 | 22.64 |
| 154 | 290–293 | 53.01 | 52.63 | 4.45 | 4.47 | 16.86 | 16.59 |
| 155 | 158–160 | 58.61 | 58.82 | 6.94 | 6.48 | 16.08 | 16.05 |
| 156 | 225–227 | 48.72 | 49.00 | 4.36 | 4.18 | 11.36 | 11.35 |
| 157 | 255–257 | 57.72 | 57.65 | 5.88 | 5.97 | 14.42 | 14.32 |
| 158 | 232–234 | 59.01 | 59.06 | 6.27 | 6.30 | 13.76 | 13.68 |
| 159 | 178–180 | 64.85 | 64.61 | 6.61 | 6.95 | 16.20 | 15.99 |
| 160 | 252–254 | 51.07 | 51.17 | 4.29 | 4.34 | 12.76 | 12.60 |
| 161 | 255–257 | 58.53 | 58.63 | 4.91 | 5.08 | 17.06 | 16.96 |
| 162 | 214–216 | 64.76 | 64.91 | 5.72 | 5.74 | 15.90 | 15.74 |
| 163 | 197–199 | 56.50 | 56.22 | 6.41 | 6.37 | 19.38 | 18.96 |
| 164 | 255–257 | 65.11 | 65.37 | 4.42 | 4.49 | 18.08 | 18.11 |
| 165 | 295–297 | 63.31 | 63.62 | 6.64 | 6.66 | 25.84 | 25.96 |
| 166 | 242–244 | 64.75 | 64.66 | 6.86 | 6.73 | 23.85 | 23.74 |
| 167 | 240–242 | 65.91 | 65.61 | 6.64 | 6.74 | 23.06 | 22.69 |
| 168 | 215–217 | 63.79 | 63.57 | 6.44 | 6.56 | 19.38 | 19.82 |
| 169 | 161–163 | 56.45 | 56.96 | 6.51 | 6.45 | 20.57 | 20.29 |
| 170 | 193–195 | 61.92 | 62.18 | 5.85 | 5.74 | 27.08 | 26.80 |
| 171 | 205–207 | 62.96 | 62.48 | 7.13 | 6.73 | 25.70 | 25.40 |
| 172 | 182–185 | 69.20 | 69.21 | 7.74 | 7.82 | 17.93 | 17.41 |
| 173 | 210–212 | 65.12 | 64.66 | 6.33 | 6.02 | 23.98 | 23.50 |
| 174 | 199–201 | 59.68 | 59.31 | 6.51 | 6.37 | 13.92 | 14.42 |
| 175 | 213(d) | 57.92 | 58.32 | 4.61 | 4.82 | 19.08 | 19.26 |
| 176 | 210–212 | 65.55 | 65.24 | 7.15 | 7.18 | 22.93 | 22.94 |
| 177 | 242–244 | 62.37 | 61.87 | 6.47 | 6.55 | 21.39 | 21.06 |
| 178 (0.5 H$_2$O)* | 255–57 | 61.68 | 61.48 | 6.47 | 6.45 | 21.58 | 21.68 |
| 179 (0.5 H$_2$O) | 205–8 | 54.15 | 54.27 | 5.02 | 4.97 | 19.94 | 19.63 |
| 180 (0.25) | 211–14 | 70.64 | 70.56 | 6.69 | 7.06 | 18.30 | 17.93 |
| 181 | 306–8 | 61.72 | 61.64 | 5.50 | 5.45 | 22.49 | 22.41 |
| 182 (0.17 H$_2$O) | 190–92 | 65.36 | 64.97 | 6.67 | 6.55 | 22.86 | 23.20 |
| 183 | 197–200 | 69.90 | 69.87 | 8.02 | 8.12 | 17.16 | 16.86 |
| 184 | 244–46 | 65.91 | 65.52 | 7.00 | 6.98 | 15.37 | 15.05 |
| 185 | 192–94 | HRMN and EM data consistent with assigned structure | | | | | |
| 186 (3.H$_2$O) | 208.10 | 58.05 | 58.21 | 7.88 | 7.39 | 19.73 | 19.47 |
| 187 | 273–75 | 62.75 | 63.01 | 5.88 | 5.76 | 21.52 | 21.33 |
| 188 (ClH.2 H$_2$O) | >300(d) | 50.83 | 51.14 | 5.88 | 5.70 | 19.76 | 20.10 |
| 189 | 198 | 60.36 | 59.86 | 6.97 | 6.90 | 17.60 | 17.36 |
| 190 | 133 | 69.48 | 69.19 | 8.59 | 8.47 | 17.06 | 16.74 |
| 191 | 216 | 60.60 | 60.43 | 6.73 | 6.32 | 23.56 | 23.14 |
| 192 | 222 | 63.70 | 63.85 | 6.24 | 6.23 | 20.63 | 20.53 |
| 193 | 184 | 66.98 | 66.70 | 7.66 | 7.40 | 21.30 | 20.85 |
| 194 | 192 | 62.75 | 62.46 | 6.79 | 6.73 | 21.96 | 21.64 |
| 195 (0.5 H$_2$O) | 220 | 61.94 | 61.66 | 5.93 | 5.72 | 21.68 | 21.54 |
| 196 (0.5 H$_2$O) | 199 | 61.62 | 61.78 | 6.41 | 6.13 | 21.56 | 22.06 |
| 197 | 244 | 65.07 | 65.02 | 5.80 | 5.79 | 23.71 | 23.99 |
| 198 | 202–04 | 66.64 | 66.24 | 6.92 | 6.99 | 22.20 | 22.00 |
| 199 | 227 | 64.75 | 64.90 | 6.86 | 6.99 | 23.85 | 23.88 |
| 200 | 190–92 | 68.75 | 68.86 | 8.33 | 8.46 | 17.82 | 17.51 |
| 201 | 223 | 58.85 | 58.96 | 4.66 | 4.73 | 19.06 | 19.03 |

TABLE 1A-continued

Physical data for compounds synthesized having structural formula V.

| | | Elemental Analysis | | | | | |
|---|---|---|---|---|---|---|---|
| | | Carbon | | Hydrogen | | Nitrogen | |
| Example | Mp. (° C.) | Calculated | Found | Calculated | Found | Calculated | Found |
| 202 (0.4 H$_2$O) | 150 | 66.37 | 66.46 | 8.12 | 7.90 | 18.21 | 17.80 |
| 203 | 210–218 | 63.81 | 63.95 | 6.42 | 6.45 | 23.50 | 23.12 |
| 204 (0.2 H$_2$O) | 203–205 | 65.23 | 65.05 | 5.82 | 5.84 | 24.20 | 23.77 |
| 205 (0.4 H$_2$O) | 158–160 | 67.64 | 67.93 | 7.81 | 7.74 | 17.53 | 17.40 |
| 206 (0.2 H$_2$O) | 144–146 | 64.91 | 64.87 | 7.19 | 7.30 | 22.71 | 22.53 |
| 207 (0.2 H$_2$O) | 218–220 | 64.91 | 64.79 | 7.19 | 7.00 | 22.71 | 22.78 |
| 208 | 220 | 65.55 | 65.45 | 7.15 | 7.13 | 22.93 | 22.53 |
| 209 | 212–216 | 65.55 | 65.49 | 7.15 | 7.38 | 22.93 | 22.31 |

*The molecular weight calculated for the elemental analysis includes the solvent in the amount indicated.
Footnote: Maleate salts were formed by the addition of an ethanolic solution of maleic acid to the free base in ethanol at room temperature, followed by cooling, and filtration of the crystalline product.

II. 4-[(Indol-3-yl)methylene]-2-pyrazolin-5-ones
(VI)

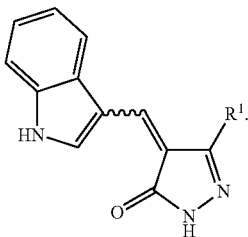

VI

Example 210

3-Benzyl-4-[(indol-3-yl)methylene]-2-pyrazolin-5-one

A reaction mixture of 3-benzyl-2-pyrazoline-5-one (905 mg, 5.2 mmol), 3-indole carboxaldehyde (800 mg, 5.6 mmol) and piperidine (100 mg) in ethanol (50 mL) was stirred at 90° C. for 3 h. After cooling overnight, the product was collected by filtration, then purified by recrystallization from ethanol.

TABLE 2

Other compounds synthesized having structural formula VI.

| Example | Substituent on Indole | R$^1$ | Recrystallization Solvent | % Yield | Method |
|---|---|---|---|---|---|
| 210 | none | benzyl | ethanol | 76 | see Example 210 |
| 211 | 1-(4-hydroxybutyl) | benzyl | methanol | 51 | see Example 210 |
| 212 | none | 4-methoxyphenyloxymethyl | isopropanol | 67 | see Example 210 |
| 213 | none | phenyloxymethyl | isopropanol | 94 | see Example 210 |
| 214 | none | 4-chlorophenyloxymethyl | ethanol | 65 | see Example 210 |
| 215 | none | 4-methoxybenzyl | ethanol | 90 | see Example 210 |
| 216 | none | 4-methylphenyloxymethyl | ethanol | 93 | see Example 210 |
| 217 | none | phenylethyl | ethanol | 84 | see Example 210 |
| 218 | none | isopropoxy | methanol | 81 | see Example 210 |
| 219 | none | 4-methylbenzyl | ethanol | 95 | see Example 210 |
| 220 | none | phenylamino | isopropanol | 52 | see Example 210 |
| 221 | none | 4-methylphenylamino | methanol | 60 | see Example 210 |
| 222 | none | 4-methoxyphenylamino | ethanol | 96 | see Example 210 |
| 223 | none | 4-chlorobenzyl | ethanol | 77 | see Example 210 |
| 224 | 1-(4-hydroxybutyl) | 4-methoxybenzyl | DMF:water | 89 | see Example 210 |
| 225 | none | 4-chlorophenylamino | DMF:water | 86 | see Example 210 |
| 226 | none | 3-methoxybenzyl | DMF:water | 99 | see Example 210 |
| 227 | none | 3,4-dimethoxybenzyl | DMF:water | 88 | see Example 210 |
| 228 | none | 4-hydroxybenzyl | DMF:water | 56 | see Example 210 |
| 229 | none | 3-chlorophenyloxymethyl | isopropanol | 89 | see Example 210 |
| 230 | none | indol-3-yl | methanol | 58 | see Example 210 |
| 231 | none | 4-methoxyphenylethyl | isopropanol | 88 | see Example 210 |
| 232 | none | 4-phenylphenyloxymethyl | NA | 91 | see Example 210 |
| 233 | none | 2-phenylpropyl | methanol | 60 | see Example 210 |
| 234 | none | 3-phenylpropyl | ethanol | 76 | see Example 210 |

TABLE 2-continued

Other compounds synthesized having structural formula VI.

| Example | Substituent on Indole | R¹ | Recrystallization Solvent | % Yield | Method |
|---|---|---|---|---|---|
| 235 | none | 4-hydroxyphenylethyl | methanol | 51 | see Example 210 |
| 236 | none | 4-methylphenylethyl | ethanol | 86 | see Example 210 |
| 237 | none | ethoxy | ethanol | 90 | see Example 210 |
| 238 | 1-(4-hydroxybutyl) | isopropoxy | toluene:heptane | 43 | see Example 210 |
| 239 | 1-(4-hydroxybutyl) | phenylethyl | methanol | 80 | see Example 210 |
| 240 | none | 4-nitrophenylethyl | isopropanol | 83 | see Example 210 |
| 241 | none | propoxy | DMF:water | 43 | see Example 210 |
| 242 | none | 4-fluorophenylamino | ethyl acetate | 65 | see Example 210 |
| 243 | none | 4-aminophenylethyl | methanol:water | 74 | see Example 210 |
| 244 | 2-methyl | isopropoxy | methanol | 40 | see Example 210 |
| 245 | 7-methyl | isopropoxy | ethanol | 98 | see Example 210 |
| 246 | 7-methyl | phenylethyl | DMF:water | 97 | see Example 210 |
| 247 | none | cyclopentyl | ethanol | 56 | see Example 210 |
| 248 | 1-methyl | isopropoxy | ethanol | 81 | see Example 210 |
| 249 | none | 4-methoxycarbonylphenylethyl | ethanol | 77 | see Example 210 |
| 250 | 1-isopropyl | isopropoxy | toluene:heptane | 71 | see Example 210 |
| 251 | 1-methyl | 4-hydroxyphenylethyl | ethanol | 50 | see Example 210 |
| 252 | none | isopropyl | ethanol | 76 | see Example 210 |
| 253 | none | 4-chlorophenylaminocarbonylmethyl | DMF:water | 40 | see Example 210 |
| 254 | none | ethoxycarbonylmethyl | methanol | 40 | see Example 210 |
| 255 | none | 4-methoxyphenylaminocarbonylmethyl | DMF:water | 40 | see Example 210 |
| 256 | none | cyclopropyl | DMF:water | 50 | see Example 210 |
| 257 | none | 3-pyridyl | ethanol | 50 | see Example 210 |
| 258 | none | 2-aminocarbonylethyl | methanol | 55 | see Example 210 |
| 259 | none | cyclobutyl | ethanol | 79 | see Example 210 |
| 260 | none | 2-(dimethylaminocarbonyl)ethyl | ethanol | 97 | see Example 210 |
| 261 | 1-(4-hydroxybutyl) | cyclopropyl | ethanol | 80 | see Example 210 |
| 262 | none | 4-pyridyl | ethanol | 91 | see Example 210 |
| 263 | none | cyclopentyl | ethanol | 75 | see Example 210 |
| 264 | none | 2,2,3,3-tetramethylcyclopropyl | ethanol | 32 | see Example 210 |
| 265 | none | 2-methylcyclopropyl | ethanol | 34 | see Example 210 |
| 266 | 1-(4-hydroxybutyl) | cyclohexyl | toluene | 41 | see Example 210 |
| 267 | 1-(4-hydroxybutyl) | 4-pyridyl | ethanol | 50 | see Example 210 |
| 268 | none | benzothiazol-2-yl | ethanol | 50 | see Example 210 |
| 269 | none | 2-pyridyl |  | 67 | see Example 210 |
| 270 | none | dimethylamino | ethanol | 77 | see Example 210 |
| 271 | none | pyrrol-2-yl | ethanol | 83 | see Example 210 |
| 272 | none | 6-methoxybenzothiazol-2-yl | ethanol | 60 | see Example 210 |
| 273 | 1-methyl | cyclopropyl | ethanol | 76 | see Example 210 |
| 274 | 7-methyl | cyclopropyl | ethanol | 60 | see Example 210 |
| 275 | 1-methyl | 3-pyridyl | ethanol | 64 | see Example 210 |
| 276 | none | propyl | NA | 63 | see Example 210 |
| 277 | none | methyl | NA | 68 | see Example 210 |
| 278 | none | trifluoromethyl | NA | 14 | see Example 210 |
| 279 | 1-(4-hydroxybutyl) | hydrogen | NA | 62 | see Example 210 |
| 280 | 1-(4-hydroxybutyl) | methyl | NA | 36 | see Example 210 |
| 281 | 1-(4-hydroxybutyl) | trifluoromethyl | NA | 7 | see Example 210 |
| 282 | 1-(4-hydroxybutyl) | Tert-butyl | NA | 50 | see Example 210 |
| 283 | none | ethoxycarbonyl | ethanol | 74 | see Example 210 |
| 284 | none | 2-methoxy | ethanol | 79 | see Example 210 |
| 285 | none | trans-2-phenyl-1-cyclopropyl | ethanol | 92 | see Example 210 |
| 286 | 1-(4-hydroxybutyl) | cyclobutyl | ethanol | 26 | see Example 210 |
| 287 | 6-carboxy-1-methyl | cyclopropyl | ethanol | 26 | see Example 210 |
| 288 | 5-methoxy-1-methyl | cyclopropyl | ethanol | 75 | see Example 210 |
| 289 | 1-methyl | pyrazinyl | ethanol | 82 | see Example 210 |
| 290 | 1,7-dimethyl | cyclopropyl | ethanol | 97 | see Example 210 |
| 291 | 1-methyl | tetrahydrofuran-3-yl | ethanol | 78 | see Example 210 |
| 292 | 1-methyl | cyclopropylamino | ethanol | 54 | see Example 210 |
| 293 | 6-carboxy-1-methyl | isopropoxy | DMF:water | 45 | see Example 210 |
| 294 | 1,7-dimethyl | isopropoxy | methanol | 53 | see Example 210 |
| 295 | 5-methoxy-1-methyl | isopropoxy | ethanol | 72 | see Example 210 |
| 296 | 1-methyl | 4-fluorophenylamino | methanol | 80 | see Example 210 |
| 297 | 1-methyl | trifluoroacetamido | methanol | 70 | see Example 210 |
| 298 | 1-methyl | 4-aminophenylethyl | toluene | 64 | see Example 210 |
| 299 | 1-methyl | amino | ethanol | 80 | see Example 210 |
| 300 | none | 4-chlorophenylethyl | ethanol | 85 | see Example 210 |
| 301 | 1-methyl | ethoxy | ethanol | 80 | see Example 210 |
| 302 | 1-methyl | 5-isoxazolyl | DMF:water | 83 | see Example 210 |
| 303 | 1-methyl | tertbutyl | ethanol | 92 | see Example 210 |
| 304 | 6-carboxy-1-methyl | pyrazinyl | DMF | 98 | see Example 210 |

TABLE 2-continued

Other compounds synthesized having structural formula VI.

| Example | Substituent on Indole | R¹ | Recrystallization Solvent | % Yield | Method |
|---|---|---|---|---|---|
| 305 | 1-methyl-6-[2-(4-morpholino)ethyl]-aminocarbonyl | pyrazinyl | NA | 20 | see Example 210 |

TABLE 2A

Physical data for compounds synthesized having structural formula VI.

| | | Elemental Analysis | | | | |
|---|---|---|---|---|---|---|
| | | Carbon | | Hydrogen | | Nitrogen |
| Example | Mp. (° C.) | Calculated | Found | Calculated | Found | Calculated | Found |
|---|---|---|---|---|---|---|---|
| 210 | 292–295 | 75.73 | 75.74 | 5.02 | 5.28 | 13.94 | 13.85 |
| 211 | 217–220 | 73.97 | 73.93 | 6.20 | 6.14 | 11.25 | 11.18 |
| 212 | 266–268 | 69.35 | 69.23 | 4.65 | 5.05 | 12.13 | 12.03 |
| 213 | 284–286 | 71.91 | 71.86 | 4.76 | 4.78 | 13.24 | 13.34 |
| 214 | 264–267 | 64.87 | 64.78 | 4.01 | 4.12 | 11.94 | 11.93 |
| 215 | 265–270 | 72.49 | 72.64 | 5.17 | 5.21 | 12.68 | 12.72 |
| 216 | 288–291 | 72.49 | 72.52 | 5.17 | 5.36 | 12.68 | 12.74 |
| 217 | 268–270 | 76.17 | 76.12 | 5.43 | 5.55 | 13.32 | 13.59 |
| 218 | 263–265 | 66.90 | 66.75 | 5.61 | 5.46 | 15.60 | 15.48 |
| 219 | 280–282 | 76.17 | 76.34 | 5.43 | 5.23 | 13.32 | 13.30 |
| 220 | 265–267 | 71.50 | 71.48 | 4.66 | 4.62 | 18.53 | 18.35 |
| 221 (0.75 $H_2O$)* | 255–257 | 69.11 | 69.30 | 5.30 | 5.07 | 16.98 | 16.99 |
| 222 | 265–267 | 68.66 | 68.65 | 4.85 | 4.98 | 16.85 | 16.67 |
| 223 | 274–277 | 67.96 | 67.77 | 4.20 | 4.39 | 12.51 | 12.33 |
| 224 | 204–206 | 71.44 | 71.39 | 6.24 | 6.14 | 10.41 | 10.32 |
| 225 | 248–250 | 64.19 | 64.01 | 3.89 | 4.15 | 16.63 | 16.59 |
| 226 | 288–290 | 72.49 | 72.46 | 5.17 | 5.16 | 12.68 | 12.81 |
| 227 | 282–284 | 69.79 | 69.68 | 5.29 | 5.29 | 11.62 | 11.75 |
| 228 | 295–300 | 71.91 | 71.20 | 4.76 | 4.76 | 13.24 | 13.44 |
| 229 | 265–268 | 64.87 | 64.91 | 4.01 | 4.16 | 11.94 | 11.92 |
| 230 (0.5 $CH_3OH$)* | 288–292 | 71.91 | 71.45 | 4.71 | 4.69 | 16.36 | 13.36 |
| 231 | 266–268 | 73.02 | 72.78 | 5.54 | 5.70 | 12.16 | 12.09 |
| 232 (0.75 $H_2O$)* | 295–296 | 73.78 | 73.58 | 5.07 | 5.21 | 10.32 | 10.20 |
| 233 | 253–255 | 76.57 | 76.06 | 5.81 | 6.09 | 12.75 | 12.60 |
| 234 | 218–220 | 76.57 | 76.52 | 5.81 | 5.93 | 12.75 | 12.62 |
| 235 (1.0 $CH_3OH$)* | 271–275 | 69.40 | 69.40 | 5.82 | 5.72 | 11.56 | 11.38 |
| 236 | 244–245 | 76.57 | 76.73 | 5.81 | 5.72 | 12.75 | 12.64 |
| 237 | 248–250 | 65.87 | 65.94 | 5.13 | 5.01 | 16.46 | 16.45 |
| 238 | 210–212 | 66.84 | 66.76 | 6.79 | 6.83 | 12.30 | 12.21 |
| 239 | 205–207 | 74.39 | 74.32 | 6.50 | 6.58 | 10.84 | 10.92 |
| 240 | 295–297 | 66.65 | 66.65 | 4.47 | 4.85 | 15.54 | 15.75 |
| 241 | 246–247 | 66.90 | 66.95 | 5.61 | 5.56 | 15.60 | 15.61 |
| 242 (0.75 Ethyl Acetate)* | 251–252 | 65.28 | 64.88 | 4.92 | 4.91 | 14.50 | 14.53 |
| 243 | 244–246 | 72.70 | 72.45 | 5.49 | 5.67 | 16.95 | 16.71 |
| 244 (0.25 $CH_3OH$)* | 262–264 | 66.99 | 66.78 | 6.22 | 6.09 | 14.42 | 14.46 |
| 245 | 254–256 | 67.82 | 67.78 | 6.04 | 5.76 | 14.83 | 14.82 |
| 246 | 302–304 | 76.57 | 75.96 | 5.81 | 5.59 | 12.75 | 12.84 |
| 247 | 277–279 | 69.13 | 68.95 | 5.80 | 5.79 | 14.22 | 14.36 |
| 248 | 239–240 | 67.82 | 67.75 | 6.04 | 6.10 | 14.83 | 14.77 |
| 249 | 259–260 | 70.76 | 70.62 | 5.13 | 5.43 | 11.25 | 11.24 |
| 250 | 161–163 | 69.43 | 69.40 | 6.75 | 6.80 | 13.49 | 13.48 |
| 251 | 255–257 | 73.04 | 72.89 | 5.50 | 5.72 | 12.17 | 12.11 |
| 252 | 264–266 | 71.12 | 71.17 | 5.96 | 5.87 | 16.58 | 16.65 |
| 253 | 305–307 | 63.41 | 63.17 | 3.99 | 4.07 | 14.79 | 14.57 |
| 254 | 235–237 | 64.63 | 64.81 | 5.08 | 5.04 | 14.13 | 14.22 |
| 255 (0.5 $H_2O$)* | >300 | 65.78 | 65.64 | 4.99 | 4.81 | 14.61 | 14.61 |
| 256 | 300–305 | 71.69 | 71.39 | 5.21 | 5.22 | 16.72 | 16.75 |
| 257 | 305–307 | 70.82 | 70.71 | 4.36 | 4.36 | 19.43 | 19.50 |
| 258 | 280–281 | 61.58 | 61.86 | 5.29 | 5.44 | 18.36 | 18.12 |
| 259 | >300 | 72.43 | 72.30 | 5.69 | 5.71 | 15.84 | 15.85 |
| 260 | 258–260 | 65.79 | 65.66 | 5.84 | 5.50 | 18.05 | 17.82 |
| 261 | 215–216 | 70.56 | 70.29 | 6.54 | 6.45 | 12.99 | 12.99 |

TABLE 2A-continued

Physical data for compounds synthesized having structural formula VI.

| Example | Mp. (° C.) | Elemental Analysis | | | | | |
|---|---|---|---|---|---|---|---|
| | | Carbon | | Hydrogen | | Nitrogen | |
| | | Calculated | Found | Calculated | Found | Calculated | Found |
| 262 | >300 | 70.82 | 70.76 | 4.19 | 4.78 | 19.43 | 19.29 |
| 263 | 300–304 | 73.09 | 72.79 | 6.13 | 6.06 | 15.04 | 14.98 |
| 264 (0.25 H$_2$O)* | 296–298 | 73.16 | 73.43 | 6.86 | 6.89 | 13.47 | 13.36 |
| 265 | 294–296 | 72.43 | 72.57 | 5.69 | 5.73 | 15.84 | 15.85 |
| 266 | 226–227 | 72.29 | 72.10 | 7.44 | 7.56 | 11.49 | 11.54 |
| 267 | 224–225 | 68.27 | 68.65 | 5.73 | 5.91 | 15.16 | 15.25 |
| 268 | >300 | 66.26 | 65.96 | 3.51 | 3.64 | 16.27 | 16.25 |
| 269 | 278–280 | 70.82 | 71.07 | 4.19 | 4.35 | 19.43 | 19.53 |
| 270 | 258–260 | 66.12 | 66.26 | 5.54 | 5.50 | 22.03 | 21.87 |
| 271 | 300–302 | 69.55 | 68.91 | 4.37 | 4.54 | 20.28 | 20.23 |
| 272 | >300 | 64.16 | 64.20 | 3.77 | 3.94 | 14.96 | 14.69 |
| 273 | 245–247 | 72.43 | 72.34 | 5.69 | 5.72 | 15.83 | 15.78 |
| 274 | 286–288 | 72.73 | 72.14 | 5.69 | 5.91 | 15.83 | 15.60 |
| 275 (0.5 H$_2$O)* | 230–232 | 69.44 | 69.89 | 4.85 | 4.84 | 17.99 | 18.10 |
| 276–282 | | $^{13}$C and $^1$H NMR and analytical LC/MS data consistent with assigned structure | | | | | |
| 283 | 250(d) | 63.59 | 63.42 | 4.62 | 5.00 | 14.83 | 14.83 |
| 284 | 267–269 | 64.63 | 64.58 | 5.08 | 5.29 | 14.13 | 14.14 |
| 285 | 280–282 | 75.99 | 76.11 | 5.31 | 5.32 | 12.66 | 12.65 |
| 286 | 220–222 | 71.19 | 71.16 | 6.87 | 6.85 | 12.45 | 12.46 |
| 287 | 237–240(d) | 66.00 | 66.00 | 4.88 | 4.85 | 13.58 | 13.43 |
| 288 | 236–238 | 67.09 | 67.48 | 5.96 | 6.00 | 13.80 | 13.76 |
| 289 | 263–265 | 67.31 | 67.58 | 4.32 | 4.48 | 23.09 | 23.31 |
| 290 | 258–260 | 72.15 | 72.33 | 6.22 | 6.06 | 14.85 | 15.11 |
| 291 | 208–210 | 69.13 | 69.18 | 5.80 | 5.85 | 14.23 | 14.25 |
| 292 | 160–164(d) | 68.55 | 68.25 | 5.75 | 5.86 | 19.98 | 19.71 |
| 293 | 330–332 | 62.38 | 62.37 | 5.23 | 5.31 | 12.84 | 12.87 |
| 294 | 245–247 | 68.67 | 68.86 | 6.44 | 6.21 | 14.13 | 14.14 |
| 295 | 238–239 | 65.16 | 65.31 | 6.11 | 6.10 | 13.41 | 13.46 |
| 296 | 218–219 | 67.09 | 66.65 | 4.82 | 4.99 | 16.12 | 16.10 |
| 297 | 252–253 | 53.58 | 53.80 | 3.30 | 3.51 | 16.66 | 16.67 |
| 298 | 192–193 | 74.29 | 74.26 | 5.98 | 5.85 | 15.27 | 15.38 |
| 299 | 246–247 | 63.73 | 63.51 | 5.10 | 5.32 | 22.88 | 22.54 |
| 300 | 271–272 | 68.67 | 68.59 | 4.61 | 5.04 | 12.01 | 11.81 |
| 301 | 194–196 | 66.90 | 66.94 | 5.61 | 5.72 | 15.60 | 15.62 |
| 302 | 271–272 | 65.75 | 66.02 | 4.14 | 4.34 | 19.17 | 19.00 |
| 303 | 201–203 | 70.28 | 70.02 | 7.44 | 7.41 | 13.29 | 13.17 |
| 304 | >300 | 60.47 | 60.96 | 4.54 | 4.33 | 20.02 | 19.85 |
| 305 | 240–241 | 61.52 | 61.67 | 5.59 | 5.67 | 20.92 | 20.91 |

*The molecular weight calculated for the elemental analysis includes the solvent in the amount indicated.
Footnote: Maleate salts were formed by the addition of an ethanolic solution of maleic acid to the free base in ethanol at room temperature, followed by cooling, and filtration of the crystalline product.

III. 4-[(Indol-2-yl)methylene]-2-pyrazolin-5-one (VII)

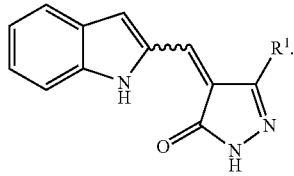

VII

TABLE 3

Compounds synthesized having structural formula VII.

| Example | Substituent on Indole | R$^1$ | Recrystallization Solvent | % Yield | Method |
|---|---|---|---|---|---|
| 306 | none | isopropoxy | ethanol | 81 | see Example 210 |
| 307 | none | 4-hydroxyphenylethyl | ethanol | 45 | see Example 210 |

TABLE 3-continued

Compounds synthesized having structural formula VII.

| Example | Substituent on Indole | R¹ | Recrystallization Solvent | % Yield | Method |
|---|---|---|---|---|---|
| 308 | none | 4-aminophenylethyl | NA | 20 | see Example 210 |
| 309 | none | 4-methoxycarbonylphenylethyl | toluene | 75 | see Example 210 |
| 310 | none | 4-carbamoylphenylethyl | DMF:water | 90 | see Example 210 |
| 311 | none | cyclopropyl | ethanol | 35 | see Example 210 |
| 312 | 3-dimethylaminomethyl | cyclopropyl | NA | 20 | see Example 210 |
| 313 | none | 3-pyridyl | ethanol | 62 | see Example 210 |
| 314 | 5-methoxy | isopropoxy | methanol | 78 | see Example 210 |
| 315 | 1-methyl | isopropoxy | DMF:water | 89 | see Example 210 |
| 316 | none | tetrahydrofuran-3-yl | ethylacetate | 30 | see Example 210 |
| 317 | 5-methoxy | cyclopropyl | ethanol | 33 | see Example 210 |
| 318 | 5-nitro | cyclopropyl | DMF | 84 | see Example 210 |
| 319 | none | isopropyl | methanol | 80 | see Example 210 |
| 320 | none | 4-carboxyphenylethyl | DMF:water | 65 | see Example 210 |
| 321 | none | phenyl | ethanol | 55 | see Example 210 |
| 322 | 3-methyl | isopropoxy | methanol | 76 | see Example 210 |
| 323 | 3-(2-methoxycarbonyl-2-acetamidoethyl) | isopropoxy | toluene:heptane | 40 | see Example 210 |
| 324 | none | ethoxy | ethanol | 55 | see Example 210 |
| 325 | 3-(4-morpholinomethyl) | ethoxy | ethanol | 65 | see Example 210 |
| 326 | 3-(4-morpholinomethyl) | cyclopropyl | ethylacetate | 46 | see Example 210 |
| 327 | 5-methoxy | pyrazinyl | NA | 91 | see Example 210 |
| 328 | 5-methoxy | 2-pyridyl | NA | 90 | see Example 210 |
| 329 | 4-chloro-6,7-dihydro | ethoxy | ethanol | 54 | see Example 210 |
| 330 | 4-chloro-6,7-dihydro | pyrazinyl | toluene | 83 | see Example 210 |
| 331 | 4-oxo-1,5,6,7-tetrahydro | pyrazinyl | toluene | 40 | see Example 210 |
| 332 | 3-dimethylaminomethyl | ethoxy | toluene-heptane | 41 | see Example 210 |

TABLE 3A

Physical data for compounds synthesized having structural formula VII.

| | | Elemental Analysis | | | | | |
|---|---|---|---|---|---|---|---|
| | | Carbon | | Hydrogen | | Nitrogen | |
| Example | Mp. (° C.) | Calculated | Found | Calculated | Found | Calculated | Found |
| 306 | 221–223 | 66.90 | 67.11 | 5.61 | 5.53 | 15.60 | 15.68 |
| 307 | 242–245 | 72.49 | 72.34 | 5.17 | 5.15 | 12.68 | 12.36 |
| 308 | 187–189 | 72.71 | 72.99 | 5.49 | 5.48 | 16.96 | 16.35 |
| 309 | 210–212 | 70.76 | 70.99 | 5.13 | 5.00 | 11.25 | 11.11 |
| 310 (0.25 H₂O)* | 263–265 | 69.44 | 69.51 | 5.09 | 5.05 | 15.43 | 15.21 |
| 311 (0.75 H₂O)* | 238–240 | 68.04 | 67.68 | 5.55 | 5.11 | 15.87 | 15.75 |
| 312 (0.25 H₂O)* | 202(d) | 69.10 | 69.13 | 6.60 | 6.46 | 17.91 | 17.56 |
| 313 (0.5 H₂O)* | 155–157 | 68.67 | 68.68 | 4.40 | 4.48 | 18.84 | 18.56 |
| 314 | 219–220 | 64.20 | 64.48 | 5.72 | 5.76 | 14.04 | 14.08 |
| 315 | 254–255 | 67.83 | 67.89 | 6.05 | 6.09 | 14.83 | 14.83 |
| 316 | 180–183 | 68.31 | 68.49 | 5.37 | 5.57 | 14.94 | 14.80 |
| 317 | 221–224 | 68.31 | 68.34 | 5.37 | 5.35 | 14.94 | 14.82 |
| 318 | 316–320 | 60.80 | 60.70 | 4.08 | 4.35 | 18.91 | 19.01 |
| 319 | 245–247 | 67.14 | 67.08 | 6.01 | 6.03 | 20.88 | 20.94 |
| 320 | >300 | 70.18 | 69.87 | 4.77 | 4.87 | 11.69 | 11.76 |
| 321 | 210–211 | 75.25 | 75.17 | 4.56 | 4.75 | 14.62 | 14.62 |
| 322 | 241–243 | 67.83 | 67.97 | 6.05 | 6.05 | 14.83 | 14.89 |
| 323 | 205–206 | 61.16 | 61.51 | 5.87 | 5.93 | 13.58 | 13.27 |
| 324 | 265–267 | 65.87 | 65.91 | 5.13 | 5.27 | 16.46 | 16.52 |
| 325 | 205–206 | 64.39 | 64.64 | 6.26 | 6.35 | 15.81 | 15.82 |
| 326 | 203–180 | 68.55 | 68.53 | 6.32 | 6.31 | 15.99 | 15.80 |
| 327 | 272–274 | 63.94 | 64.29 | 4.10 | 4.00 | 21.93 | 22.10 |
| 328 | 170–172 | 67.91 | 68.06 | 4.43 | 4.43 | 17.60 | 17.74 |
| 329 | 177–203 | 57.64 | 57.87 | 4.84 | 4.79 | 14.40 | 14.35 |
| 330 (0.4 toluene)* | 206–209 | 62.27 | 62.20 | 4.22 | 4.47 | 19.31 | 19.27 |
| 331 (0.1 toluene)* | 300–303 | 63.36 | 63.49 | 4.36 | 4.41 | 22.12 | 21.96 |
| 332 | 185–187 | 65.37 | 65.13 | 6.45 | 6.35 | 17.94 | 17.70 |

*The molecular weight calculated for the elemental analysis includes the solvent in the amount indicated.

IV. 4-[(7-Azaindol-3-yl)methylene]-2-pyrazolin-5-ones (VIII)

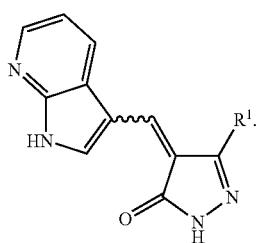

VIII

TABLE 4

Compounds synthesized having structural formula VIII.

| Example | Substituent on azaindole | R¹ | Recrystallization Solvent | % Yield | Method |
|---|---|---|---|---|---|
| 333 | none | benzyl | DMF:water | 71 | see Example 210 |
| 334 | 1-(4-hydroxybutyl) | benzyl | ethyl acetate | 30 | see Example 210 |
| 335 | none | 4-methoxyphenyloxymethyl | DMF:water | 80 | see Example 210 |
| 336 | none | isopropoxy | methanol | 61 | see Example 210 |
| 337 | none | amino | DMF:water | 92 | see Example 210 |
| 338 | none | 4-methoxybenzyl | DMF:water | 96 | see Example 210 |
| 339 | none | phenylamino | DMF:water | 77 | see Example 210 |
| 340 | none | 4-methylbenzyl | ethanol | 95 | see Example 210 |
| 341 | none | 4-hydroxyphenylethyl | ethanol | 84 | see Example 210 |
| 342 | 1-(4-hydroxybutyl) | 4-hydroxyphenylethyl | methanol | 80 | see Example 210 |
| 343 | none | isopropyl | ethanol | 30 | see Example 210 |
| 344 | none | cyclopropyl | ethanol | 50 | see Example 210 |
| 345 | none | cyclobutyl | ethanol | 74 | see Example 210 |
| 346 | none | 3-pyridyl | ethanol | 40 | see Example 210 |
| 347 | none | phenyl | NA | 56 | see Example 210 |
| 348 | none | 4-fluorophenylamino | NA | 14 | see Example 210 |
| 349 | none | propyl | NA | 24 | see Example 210 |
| 350 | none | methyl | NA | 77 | see Example 210 |
| 351 | none | trifluoromethyl | NA | 17 | see Example 210 |
| 352 | none | tert-butyl | NA | 80 | see Example 210 |
| 353 | 1-(4-hydroxybutyl) | trifluoromethyl | NA | 6 | see Example 210 |
| 354 | none | 4-isopropylphenylamino | NA | 30 | see Example 210 |
| 355 | none | 3-methylphenylamino | NA | 70 | see Example 210 |
| 356 | 1-(4-hydroxybutyl) | 3-methylphenylamino | NA | 30 | see Example 210 |
| 357 | none | phenylethyl | DMF:water | 63 | see Example 210 |

TABLE 4A

Physical data for compounds synthesized having structural formula VIII.

| | | Elemental Analysis | | | | | |
|---|---|---|---|---|---|---|---|
| | | Carbon | | Hydrogen | | Nitrogen | |
| Example | Mp. (° C.) | Calculated | Found | Calculated | Found | Calculated | Found |
| 333 | 274–277 | 71.50 | 71.63 | 4.66 | 4.88 | 18.53 | 18.17 |
| 334 | 176–179 | 70.56 | 70.67 | 5.92 | 5.87 | 14.96 | 14.78 |
| 335 | 300–302 | 65.69 | 65.62 | 4.35 | 4.85 | 16.12 | 15.77 |
| 336 | 258–260 | 62.21 | 61.57 | 5.22 | 5.12 | 20.72 | 20.57 |
| 337 (1 H₂O)* | >300 | 53.82 | 53.92 | 4.48 | 4.34 | 28.54 | 28.22 |
| 338 | 273–276 | 68.66 | 68.05 | 4.85 | 4.89 | 16.85 | 16.67 |
| 339 (1 H₂O)* | 249–252 | 63.54 | 63.45 | 4.70 | 4.75 | 21.79 | 21.68 |
| 340 (0.5 H₂O)* | >300 | 70.07 | 70.54 | 5.22 | 5.07 | 17.21 | 17.24 |
| 341 | 270–272 | 68.66 | 68.25 | 4.85 | 5.04 | 16.86 | 16.71 |
| 342 | 211–212 | 68.30 | 67.97 | 5.98 | 6.11 | 13.85 | 13.80 |
| 343 | 300(d) | 66.12 | 65.91 | 5.54 | 5.57 | 22.03 | 21.89 |
| 344 (0.25 H₂O)* | 245–246 | 65.48 | 65.20 | 4.90 | 4.76 | 21.82 | 21.47 |
| 345 | 300–302 | 66.52 | 66.51 | 5.39 | 5.22 | 20.69 | 20.88 |
| 346 | 212–215 | 66.50 | 65.84 | 3.83 | 4.07 | 24.20 | 23.93 |
| 347 | 280–282 | 70.80 | 70.50 | 4.20 | 4.10 | 19.40 | 19.10 |

TABLE 4A-continued

Physical data for compounds synthesized having structural formula VIII.

| | | Elemental Analysis | | | | | |
|---|---|---|---|---|---|---|---|
| | | Carbon | | Hydrogen | | Nitrogen | |
| Example | Mp. (° C.) | Calculated | Found | Calculated | Found | Calculated | Found |
| 348–356 | $^{13}$C and $^1$H NMR and analytical LC/MS data consistent with assigned structure | | | | | | |
| 357 | 317–319 | 72.13 | 71.69 | 5.09 | 5.04 | 17.70 | 17.65 |

*The molecular weight calculated for the elemental analysis includes the solvent in the amount indicated.
Footnote: Maleate salts were formed by the addition of an ethanolic solution of maleic acid to the free base in ethanol at room temperature, followed by cooling, and filtration of the crystalline product.

V. 4-(Phenylmethylene)-2-pyrazolin-5-ones (IX)

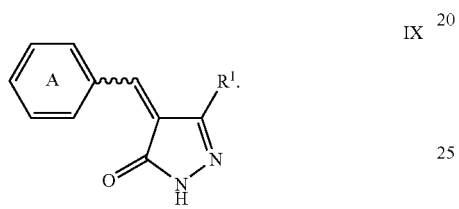

IX

TABLE 5

Compounds synthesized having structural formula IX.

| Example | Substituent on Ring A | R[1] | Recrystallization Solvent | % Yield | Method |
|---|---|---|---|---|---|
| 358 | 4-dimethylamino | benzyl | ethanol | 32 | see Example 210 |
| 359 | 4-dimethylamino | isopropoxy | toluene:heptane | 51 | see Example 210 |
| 360 | 4-dimethylamino | phenylethyl | NA | 45 | see Example 210 |
| 361 | 4-dimethylamino | cyclopropyl | ethanol | 77 | see Example 210 |

TABLE 5A

Physical data for compounds synthesized having structural formula IX.

| | | Elemental Analysis | | | | | |
|---|---|---|---|---|---|---|---|
| | | Carbon | | Hydrogen | | Nitrogen | |
| Example | Mp. (° C.) | Calculated | Found | Calculated | Found | Calculated | Found |
| 358 | 253–255 | 74.73 | 74.20 | 6.27 | 6.13 | 13.75 | 13.34 |
| 359 | 197–198 | 65.91 | 66.33 | 7.01 | 6.86 | 15.37 | 15.27 |
| 360 | 224–225 | 75.20 | 75.08 | 6.62 | 6.56 | 13.15 | 13.19 |
| 361 | 280–289 | 70.56 | 70.33 | 6.71 | 6.80 | 16.46 | 16.20 |

VI. 4-[(Pyrazol-4-yl)methylene]-2-pyrazolin-5-ones (X)

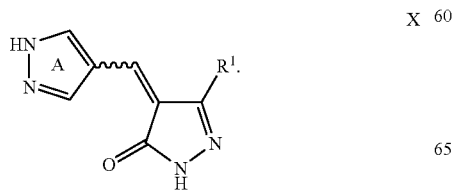

X

TABLE 6

Compounds synthesized having structural formula X.

| Example | Substituent on Ring A | $R^1$ | Recrystallization Solvent | % Yield | Method |
|---|---|---|---|---|---|
| 362 | 3-methyl | isopropoxy | ethyl acetate | 80 | see Example 210 |
| 363 | 3-methyl | cyclopropyl | toluene | 51 | see Example 210 |

TABLE 6A

Physical data for compounds synthesized having structural formula X.

| | | Elemental Analysis | | | | |
|---|---|---|---|---|---|---|
| | | Carbon | | Hydrogen | | Nitrogen |
| Example | Mp. (° C.) | Calculated | Found | Calculated | Found | Calculated | Found |
| 362 | 228–230 | 56.39 | 56.06 | 6.02 | 5.91 | 23.91 | 23.77 |
| 363 | 265–267 | 61.09 | 61.30 | 5.59 | 5.83 | 25.91 | 25.71 |

VII. 4-[(Imidazol-2-yl)methylene]-2-pyrazolin-5-ones (XI)

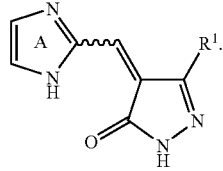

XI

VIII. 4-[(Imidazol-4-yl)methylene]-2-pyrazolin-5-ones (XII)

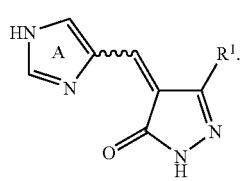

XII

TABLE 7

Compounds synthesized having structural formula XI.

| Example | Substituent on Ring A | $R^1$ | Recrystallization Solvent | % Yield | Method |
|---|---|---|---|---|---|
| 364 | none | isopropoxy | toluene | 45 | see Example 210 |
| 365 | none | cyclopropyl | ethanol | 42 | see Example 210 |

TABLE 8

Compound synthesized having structural formula XII.

| Example | Substituent on Ring A | $R^1$ | Recrystallization Solvent | % Yield | Method |
|---|---|---|---|---|---|
| 366 | none | isopropoxy | ethanol | 81 | see Example 210 |

TABLE 7A

Physical data for compounds synthesized having structural formula XI.

| | | Elemental Analysis | | | | |
|---|---|---|---|---|---|---|
| | | Carbon | | Hydrogen | | Nitrogen |
| Example | Mp. (° C.) | Calculated | Found | Calculated | Found | Calculated | Found |
| 364 | 212–214 | 54.53 | 54.96 | 5.49 | 4.61 | 25.43 | 25.67 |
| 365 | 264–266 | 59.39 | 59.52 | 4.98 | 5.00 | 27.71 | 27.37 |

TABLE 8A

Physical data for compounds synthesized having structural formula XII.

| Example | Mp. (° C.) | Carbon Calculated | Carbon Found | Hydrogen Calculated | Hydrogen Found | Nitrogen Calculated | Nitrogen Found |
|---|---|---|---|---|---|---|---|
| 366 | 259–260 | 54.53 | 54.84 | 5.49 | 5.68 | 25.43 | 25.37 |

IX. 4-[(Thien-2-yl)methylene]-2-pyrazolin-5-ones (XIII)

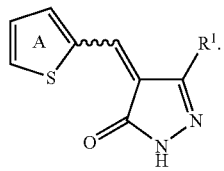

XIII

TABLE 9

Compound synthesized having structural formula XIII.

| Example | Substituent on Ring A | $R^1$ | Recrystallization Solvent | % Yield | Method |
|---|---|---|---|---|---|
| 367 | none | cyclopropyl | ethanol | 20 | see Example 210 |

TABLE 9A

Physical data for compounds synthesized having structural formula XIII.

| Example | Mp. (° C.) | Carbon Calculated | Carbon Found | Hydrogen Calculated | Hydrogen Found | Nitrogen Calculated | Nitrogen Found |
|---|---|---|---|---|---|---|---|
| 367 | 275–277 | 60.53 | 60.68 | 4.61 | 4.74 | 12.83 | 12.50 |

TABLE 10

Compound synthesized having structural formula XIV.

| Example | Substituent on indole | $R^1$ | Recrystallization Solvent | % Yield | Method |
|---|---|---|---|---|---|
| 368 | none | isopropyl | ethanol | 54 | see Example 210 |

X. 4-[(Indol-3-yl)methylene]-1-methyl-2-pyrazolin-5-ones (XIV)

XIV

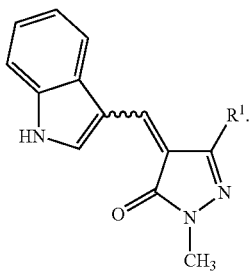

TABLE 10A

Physical data for compounds synthesized having structural formula XIV.

| Example | Mp. (° C.) | Elemental Analysis | | | | | |
|---|---|---|---|---|---|---|---|
| | | Carbon | | Hydrogen | | Nitrogen | |
| | | Calculated | Found | Calculated | Found | Calculated | Found |
| 368 | 241–242 | 71.88 | 71.73 | 6.41 | 6.47 | 15.72 | 15.71 |

XI. 4-[(Pyrrol-3-yl)methylene]-2-pyrazoline-5-ones (XV)

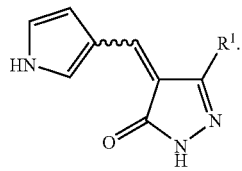

XV

TABLE 11

Compound synthesized having structural formula XV.

| Example | Substituent on pyrrole | $R^1$ | Recrystallization Solvent | % Yield | Method |
|---|---|---|---|---|---|
| 369 | none | isopropoxy | methanol | 70 | see Example 210 |

TABLE 11A

Physical data for compounds synthesized having structural formula XV.

| Example | Mp. (° C.) | Elemental Analysis | | | | | |
|---|---|---|---|---|---|---|---|
| | | Carbon | | Hydrogen | | Nitrogen | |
| | | Calculated | Found | Calculated | Found | Calculated | Found |
| 369 | 252–255 | 60.26 | 60.35 | 5.98 | 5.82 | 19.17 | 19.13 |

TABLE 12

Compound synthesized having structural formula XVI.

| Example | Subst. on quinoline | $R^1$ | Recrystallization Solvent | % Yield | Method |
|---|---|---|---|---|---|
| 370 | 8-hydroxy | isopropoxy | methanol | 40 | see Example 210 |

XII. 4-[(Quinolin-5-yl)methylene]-2-pyrazoline-5-ones (XVI)

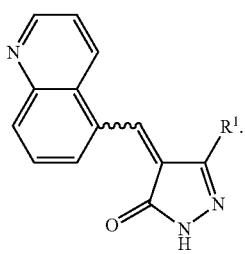

XVI

TABLE 12A

Physical data for compounds synthesized having structural formula XVI.

| | | Elemental Analysis | | | | |
|---|---|---|---|---|---|---|
| | | Carbon | | Hydrogen | | Nitrogen |
| Example | Mp., ° C. | Calculated | Found | Calculated | Found | Calculated | Found |
| 370 | >300 | 64.64 | 64.43 | 5.09 | 5.01 | 14.13 | 13.98 |

X. Synthesis of Starting Materials.

A. Synthesis of 3-ketoesters (XIX).

The general method used to synthesize 3-ketoesters is shown in Scheme II.

Scheme II: Synthesis of 3-ketoesters

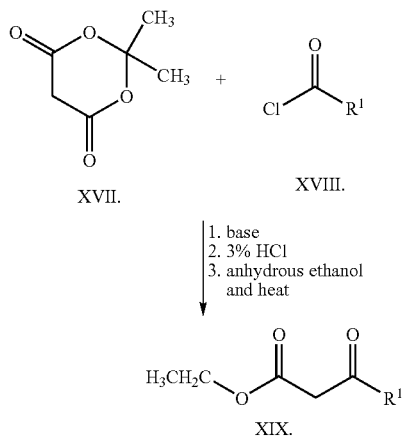

Example 371

Ethyl 3-(2,2,3,3-tetramethylcyclopropyl)-3-oxopropionate

Pyridine (5 g, 0.063 mol) and 2,2,3,3-tetramethylcyclopropyl carbonyl chloride (5 g, 0.031 mol) were added to an ice-cold solution of 2,2-dimethyl-1,3-dioxane-4,7-dione (4.7 g, 0.032 mol) in anhydrous dichloromethane (37 ML) under a nitrogen atmosphere. The temperature was maintained at 0° C. for 1 h, then was allowed to raise to room temperature overnight. The mixture was then transferred to a separatory funnel, washed twice with 3% hydrochloric acid and twice with water. The organic layer was dried over magnesium sulfate, then filtered and concentrated under reduced pressure to give 5 g of a dark red oil. The oil was refluxed for 3 h in anhydrous ethanol (60 mL). The solvent was evaporated and the product was purified by distillation.

Example 377

Ethyl 3-(6-methoxybenzothiazol-2-yl)-3-oxopropionate

Ethyl acetate (7.2 g, 0.082 mol) was added to sodium hydride (1.5 g of a 50% dispersion in oil, 0.032 mol), keeping the temperature below 25° C. 2-Ethoxycarbony-2-(6-methoxy)benzothiazole (5.25 g, 0.022 mol) was added. The mixture was warmed to reflux gently and then stirred at room temperature overnight. The reaction was quenched with ice water (50 mL) and the pH was adjusted to 7.7 with concentrated hydrochloric acid. The product precipitated out and was collected by filtration, washed with water, then dried.

Example 378

Ethyl 4-(4-phenylphenyloxy)-3-oxobutanoate

Sodium hydride (5.0 g, 0.114 mole) and 4-phenylphenol (15.3 g, 0.09 mol) were stirred at 0° C. in 75 mL of dimethyl formamide (hereinafter "DMF") for 2 h. Ethyl 4-chloroacetoacetate (5.0 g, 0.03 mol) in DMF (75 mL) was added. The mixture was stirred for 1 h at 0° C. and for 12 h at room temperature, then neutralized with 50% phosphoric acid and extracted with dichloromethane. The product was purified by silica gel chromatography using (8:2) toluene:ethanol as the mobile phase.

TABLE 13

Compounds synthesized having structural formula XIX.

| Example | $R^1$ | % Yield | b.p. (° C.) | m.p. (° C.) | Method |
|---|---|---|---|---|---|
| 371 | 2,2,3,3-tetramethyl-cyclopropyl | 67 | 68 (0.2 mmHg) | NA | see Example 371 |
| 372 | 2-methylcyclopropyl | 50 | 62–4 (0.2 mmHg) | NA | see Example 371 |
| 373 | trans-2-phenyl-cyclopropyl | 64 | 138–40 (0.2 mmHg) | NA | see Example 371 |
| 374 | tetrahydrofuran-3-yl | 60 | 82–6 (0.2 mmHg) | NA | see Example 371 |
| 375 | 3-methoxy-phenylmethyl | 62 | 132 (0.2 mmHg) | NA | see Example 371 |
| 376 | phenylethyl | 55 | 110 (0.2 mmHg) | NA | see Example 371 |
| 377 | 6-methoxy-benxothiazol-2-yl | 65 | NA | 160 | see Example 377 |
| 378 | 4-phenylphenoxy-methyl | 33 | NA | 83 | see Example 378 |
| 379 | 3-chloro-phenoxymethyl | 32 | 147 (8 mmHg) | NA | see Example 378 |
| 380 | pyrazinyl | 71 | NA | 82 | see Example 377 |

B. Synthesis of Ethyl Cyclopentyloxythiocarbonylacetate acidified with concentrated hydrochloric acid and extracted with diethyl ether. The ethereal phase was washed with water, dried and purified by distillation.

Yield 15 g, (75%) b.p. 140–142° C. (15 mm Hg).

C. Synthesis of 2-pyrazolin-5-ones

2-Pyrazolin-5-ones were synthesized by the following four methods.

Scheme III: Synthesis of ethyl alkyloxy or aryloxy carbonimidoyl acetate hydrochloride ($R^9$ is a substituted or unsubstituted aliphatic or aromatic group).

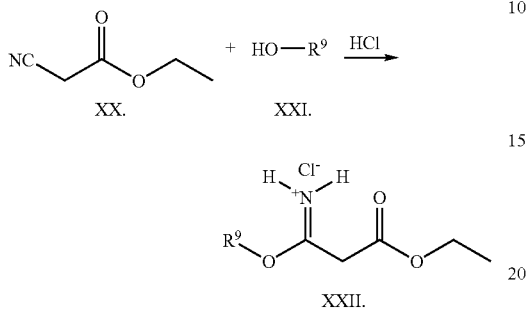

Scheme V: Method 1 for synthesizing 2-pyrazolin-5-ones.

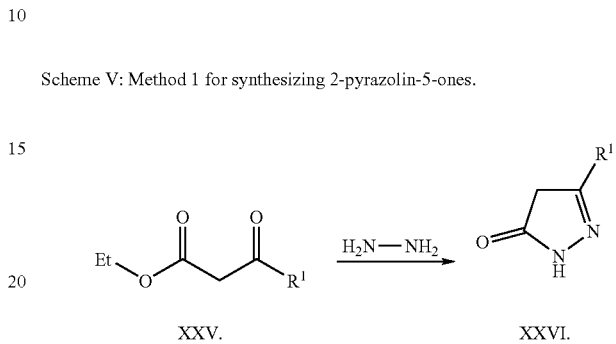

Example 381

Synthesis of ethyl cyclopentyloxycarbonimidoyl acetate hydrochloride (XXII)

A mixture of dry ethyl cyanoacetate (14 g, 0.12 mol) and dry cyclopentanol (12 g, 0.15 mol) was saturated at 0° C. with hydrogen chloride gas for 3 hours, kept at 0° C. overnight, then diluted with diethylether. The product precipitated out and was collected by filtration and washed with ether.

Yield 22.4 g, (77%) m.p. 110–112° C.

Scheme VI: Method 2 for synthesizing 2-pyrazolin-5-ones.

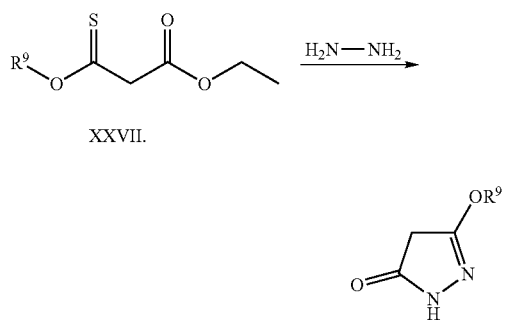

Scheme IV: Synthesis of ethyl alkyloxythio or aryloxythio carbonylacetate.

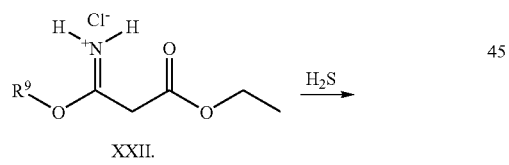

Scheme VII: Method 3 for synthesizing 2-pyrazolin-5-ones.

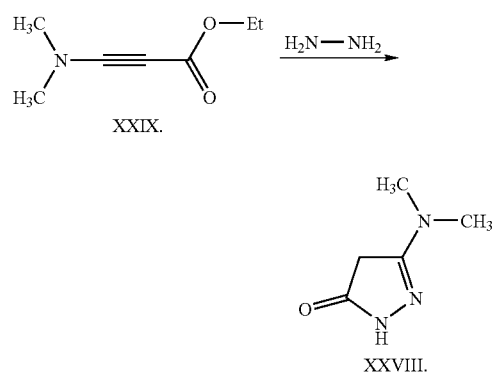

Example 382

Ethyl cyclopentyloxythiocarbonylacetate (XXIV)

A mixture of ethyl cyclopentyloxycarbonimidoyl acetate hydrochloride (22 g 0.09 mol) in anhydrous pyridine (150 ml) is treated with hydrogen sulfide for 8 hours and kept at room temperature for 48 hours. The mixture reaction was Scheme VIII: Method 4 for synthesizing 2-pyrazolin-5-ones.

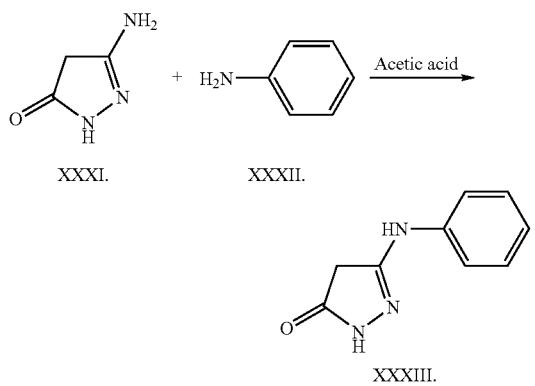

Example 383

3-(2,2,3,3-Tetramethylcyclopropyl)-2-pyrazolin-5-one

Hydrazine hydrate (1.1 g, 0.024 mol) was added to a solution of ethyl 3-(2,2,3,3-tetramethylcyclopropyl-3-oxopropionate (4.41 g, 0.020 mol) in anhydrous ethanol (60 ml). The reaction mixture refluxed for 3 h. After cooling, the solvent was evaporated, and the residue was triturated with hexane to give a white solid.

Example 411

3-(4-Hydroxybenzyl)-2-pyrazolin-5-one

A stirred suspension of 3-(4-methoxybenzyl)-2-pyrazolin-5-one 2.5 mmol in dichloromethane 100 ml cooled at −78° C., was treated with boron tribromide 7.5 ml (1M in dichloromethane). After 1 hour at −78° C. the reaction mixture was stirred at room temperature for 12 hours. The mixture was quenched with water 50 ml. The aqueous phase was separated out, and basified with 5% sodium bicarbonate solution. The formed precipitate was filtered and crystallized from methanol.

Example 413

3-(4-Carbamoylphenylethyl)-2-pyrazolin-5-one

A mixture of 3-(4-methoxycarbonylphenylethyl)-2-pyrazolin-5-one (7.7 mmol) in ammonium hydroxide 25% (30 ml), was stirred at room temperature for 12 hours. The solvent was concentrated in vacuo and the solid product formed was filtered and dried.

Example 414

3-(2-Aminocarbonylethyl)-2-pyrazolin-5-one

A mixture of 3-(ethoxycarbonylmethyl)-2-pyrazolin-5-one (1 g, 5.8 mmol) and NaCN (28 mg, 0.58 mmol) in 30 ml of 9M ammonia in MeOH was heated to 45° C. in sealed tube for 3 days. After cooling, the solvent was evaporated and the residue was suspended in water. The precipitated solid was collected by filtration.

Example 416

3-(4-Methoxyphenylamino)-2-pyrazolin-5-one

A mixture of 3-amino-2-pyrazolin-5-one (20 mmol), 4-methoxyaniline (25 mol) in 50 ml of acetic acid was refluxed for 4 hours. The solvent was evaporated, the residue was suspended in water. The solid was filtered and crystallized from methanol.

TABLE 14

Compounds synthesized having structural formula XXVI.

| Example | $R^1$ | % Yield | M.p. (° C.) | Recrystallization Solvent | Method |
|---|---|---|---|---|---|
| 383 | 2,2,3,3-tetramethyl-cyclopropyl | 44 | 195–7 | NA | see Example 383 |
| 384 | ethoxycarbonylmethyl | 44 | 115–6 | toluene | see Example 383 |
| 385 | pyrrol-2-yl | 30 | 205–8 | NA | see Example 383 |
| 386 | indol-3-yl | 69 | 250–3 | NA | see Example 383 |
| 387 | 6-methoxybenzothiazol-2-yl | 40 | 269–70 | NA | see Example 383 |
| 388 | 2-methylcyclopropyl | 70 | 196–7 | water | see Example 383 |
| 389 | trans-2-phenyl-cyclopropyl | 65 | 194–5 | ethanol | see Example 383 |
| 390 | tetrahydrofuran-3-yl | 36 | 204–5 | ethanol | see Example 383 |
| 391 | 4-methoxybenzyl | 73 | 192–5 | NA | see Example 383 |
| 392 | 4-methylbenzyl | 80 | 212–4 | ethanol:water | see Example 383 |
| 393 | 4-chlorobenzyl | 67 | 206–8 | ethanol | see Example 383 |
| 394 | 3-methoxybenzyl | 72 | 163–5 | NA | see Example 383 |
| 395 | 3,4-dimethoxybenzyl | 69 | 193–5 | NA | see Example 383 |

TABLE 14-continued

Compounds synthesized having structural formula XXVI.

| Example | R¹ | % Yield | M.p. (° C.) | Recrystallization Solvent | Method |
|---|---|---|---|---|---|
| 396 | phenylethyl | 72 | 204–7 | NA | see Example 383 |
| 397 | 2-phenylpropyl | 72 | 215 | NA | see Example 383 |
| 398 | 3-phenylpropyl | 76 | 200–1 | ethanol | see Example 383 |
| 399 | 4-methoxyphenylethyl | 85 | 230 | ethanol | see Example 383 |
| 400 | 4-methylphenylethyl | 90 | 251–2 | NA | see Example 383 |
| 401 | 4-chlorophenylethyl | 63 | 243 | NA | see Example 383 |
| 402 | 4-nitrophenylethyl | 69 | 247 | DMF:water | see Example 383 |
| 403 | 4-aminophenylethyl | 61 | 220–2 | NA | see Example 383 |
| 404 | 4-methoxy-carbonylphenylethyl | 77 | 259–60 | ethanol | see Example 383 |
| 405 | 4-phenylphenyloxymethyl | 50 | 250 | ethanol | see Example 383 |
| 406 | 4-methoxy-phenyloxymethyl | 70 | 216–8 | ethanol | see Example 383 |
| 407 | 4-chloro-phenyloxymethyl | 38 | 224–6 | ethanol | see Example 383 |
| 408 | 3-chloro-phenyloxymethyl | 40 | 232–4 | ethanol | see Example 383 |
| 409 | 4-methylphenyloxymethyl | 77 | 207–10 | methanol | see Example 383 |
| 410 | cyclopentyloxy | 75 | 180–1 | toluene | see Example 383 |
| 411 | 4-hydroxybenzyl | 75 | 233 | methanol | see Example 411 |
| 412 | 4-hydroxyphenylethyl | 70 | 205–6 | water | see Example 411 |
| 413 | 4-carbamoylphenylethyl | 90 | >270 | DMF:water | see Example 413 |
| 414 | 2-aminocarbonylethyl | 66 | 193–6 | NA | see Example 414 |
| 415 | 2-dimethylamino-carbonylethyl | 38 | 203–9 | NA | see Example 414 |
| 416 | 4-methoxyphenylamino | 30 | 232–4 | methanol | see Example 416 |
| 417 | 4-chlorophenylamino | 28 | 262–4 | ethanol | see Example 416 |
| 418 | 4-fluorophenylamino | 35 | 259–60 | NA | see Example 416 |
| 419 | cyclopropylamino | 82 | 155–158 | NA | see Example 383 |
| 420 | pyrazinyl | 86 | 193(d) | ethanol | see Example 383 |
| 421 | isopropylamino | 20 | 123–25 | ethanol | see Example 383 |
| 422 | 2-pyrimidinyl | 55 | 278–80 | ethanol | see Example 383 |
| 423 | 3-pyridazinyl | 83 | 294–95 | ethanol | see Example 383 |
| 424 | 4-pyrimidinyl | 72 | 290–300 | ethanol | see Example 383 |
| 425 | 4-pyrimidinyl | 60 | 288–291 | ethanol | see Example 383 |

D. Synthesis of Aldehydes

Example 426

1-(4-Acetoxybutyl)-azaindole-3-carboxaldehyde

A solution of 7-azaindole-3-carboxaldehyde (4.19 g, 28 mmol) in dry N,N dimehylformamide (50 ml) was added dropwise, keeping the temperature between 5–10° C., to a stirring suspension of 60% sodium hydride (oil dispersion) (1.2 g, 30 mmol) in dry DMF (65 ml) under nitrogen atmosphere. After addition was completed, stirring was continued at the same temperature for 30 min., then a solution of 4-bromobutylacetate (6.16 g, 31 mmol) in dry N,N-dimethylformamide (15 ml) was added dropwise, and the mixture was allowed to warm to room temperature. The reaction mixture was stirred at room temperature for 137 h, then water (100 ml) was added, and the mixture extracted with dichloromethane (2×100 ml). The organic phase was washed with water (3×100 ml), dried over anhydrous magnesium sulfate, filtered and the solvent removed under reduce pressure to give an oil (6.8 g, 93%) which was used without further purification.

Example 427

1-(4-Hydroxybutyl)-7-azaindole-3-carboxaldehyde

A solution of sodium hydroxide (0.2 g, 17.5 mmol) in water (35 ml) was added to a solution of 1-(4-acetoxybutyl)-7-azaindole-3-carboxaldehyde (2.3 g, 8.8 mmol) in methanol (40 ml). The mixture was heated at 60° C. for 0.5 h, then the solvent was evaporated to dryness. The residue was dissolved in a mixture of ethyl acetate and water (50 ml:50 ml) and the water layer was separated out. The organic phase was washed with water, dried over magnesium sulfate, filtered and evaporated to dryness. The residue was used without further purification. Yield 78%. m.p. 90° C.

Example 428

1-(4-Hydroxybutyl)pyrrole-2-carboxaldehyde

The product was obtained following the procedure in Example 51 except that pyrrole-2-carboxaldehyde was used instead of 7-azaindole-3-carboxaldehyde. The product was purified by silica gel chromatography using (5:5) ethyl acetate:hexane. Yield 67%.

Example 429

3-Isopropyl-5-methylpyrrole-2-carboxaldehyde

To a solution of anhydrous DMF (2.1 ml, 27 mmol) in anhydrous dichloroethane (50 ml) at 0° C. under nitrogen, POCl$_3$ (2.1 ml, 23 mmol) was added dropwise. The solution was allowed to warm at room temperature for 1 h. Then, the suspension was cooled at 0° C. and a solution of 3-isopropyl-5-methylpyrrole (2 g, 16 mmol) in dichloroethane (20 ml) was added dropwise over 20 min. After stirring at room temperature for 24 h, water followed by NaOH were added to pH: 8. The organic layer was extracted, dried and the solvent removed to dryness. The residue was purified by flash chromatography. Yield 67%, m.p. 90–93° C.

Example 430

3,5-Dimethyl-4-morpholinomethylpyrrole-2-carboxaldehyde 3,5-Dimethylpyrrole-2-carboxaldehyde (0.5 g, 4 mmole) was added to a solution of morpholine (0.35 g, 4 mmol), formaldehyde 37% (0.32 g, 4 mmol) and acetic acid (2 ml). The mixture was stired overnight at room temperature under nitrogen, then the reaction was diluted with NaHCO$_3$ to pH 8. The aqueous solution was extracted with ethylacetate and the organic layer was dried over Mg SO$_4$. The ethylacetate was evaporated in vacuo to give 0.4 g of pure solid.

The following compounds were synthesized by a method analogous to the method described in Example 430:
3,5-Dimethyl-4-dimethylaminomethylpyrrole-2-carboxaldehyde, 3-(4-morpholino)methyl-indole-2-carboxaldehyde,
3,5-dimethyl-4-diethylaminomethylpyrrole-2-carboxaldehyde,
3,5-dimethyl-4-piperidinomethylpyrrole-2-carboxaldehyde,
3,5-dimethyl-4-[(4-methyl-1-piperazinyl)methyl]pyrrole-2-carboxaldehyde,
3,5-dimethyl-4-(1-pyrrolidinylmethyl)pyrrole-2-carboxaldehyde,
5-methyl-4-dimethylaminomethylpyrrole-2-carboxaldehyde,
3,5-dimethyl-4-[N-methyl-N-(2-dimethylaminoethyl)aminomethyl]pyrrole-2-carboxaldehyde,
3,5-dimethyl-4-diethanolaminomethylpyrrole-2-carboxaldehyde,
4-(4-benzylpiperidinomethyl)-3,5-dimethylpyrrole-2-carboxaldehyde,
4-dimethylaminomethyl-3-isopropyl-5-methylpyrrole-2-carboxaldehyde,
3,5-dimethyl-4-(4-hydroxypiperidinomethyl) pyrrole-2-carboxaldehyde, and
3-dimethylaminomethyl-4,5-tetramethylenepyrrole-2-carboxaldehyde.

Example 431

3,5-Dimethyl-4-trifluoroacetamidomethylpyrrole-2-carboxaldehyde

A mixture of 3,5-dimethylpyrrole-2-carboxaldehyde (2.6 g, 0.02 mol) and N-(hydroxymethyl)trifluoroacetamide (3 g, 0.02 mol) was added in portionwise to sulfuric acid (15 ml) keeping the temperature below 10° C. The mixture of reaction was allowed to warm at room temperature for 4 h. The reaction was poured into ice-water (100 ml), the precipitated solid was filtered and washed with water. The white solid (yield, 78%) was used without further purification. M.p. 200° C.

Example 432

4-Aminomethyl-3,5-dimethylpyrrole-2-carboxaldehyde

A mixture of 3,5-dimethyl-4-trifluoroacetamidomethylpyrrole-2-carboxaldehyde (3.9 g, 15.7 mmol), NaOH 10% (19 ml) and methanol (100 ml) was heated to reflux for 1 h. The solution was concentrated to half volume under reduced pressure. Water was added and the precipitated solid was filtered. Yield 72%, m.p. 210–20° C. (d).

Example 433

3-Acetyl-4-oxopentylacetate

A mechanically stirred mixture of pentane-2,4-dione (60 g, 0.6 mol), 2-bromoethylacetate (100 g, 0.6 mol), anhydrous potassium carbonate (83 g, 0.6 mol), IK (99.6 g, 0.6 mol) and dry acetone (500 ml) was heated under reflux for 24 h. The mixture was concentrated under reduced pressure and poured into hydrochloric acid (1.7 M, 400 ml). The product was isolated by successive extractions with ether, ethyl acetate and dichloromethane. The combined organic extracts were washed with brine, the solvent removed to dryness and the residue distilled to give 38 g of the acetate b.p. 75–80° C. (0.1 mm Hg).

4-Acetyl-5-oxohexyl acetate [yield 60%, b.p. 110° C. (0.2 mm Hg)], and 5-Acetyl-6-oxoheptyl acetate [yield 77%, b.p. 102° C. (0.2 mm Hg)] were prepared by the method described in Example 433.

Example 434 tert-Butyl 4-(2-acetoxyethyl)-3,5-dimethylpyrrole-2-carboxylate

A stirred solution of tert-butylacetoacetate (26 g, 0.165 mol) in acetic acid (48 ml) was treated below 20° C. by the dropwise addition of sodium nitrite (11.3 g, 0.165 mol) in water (17 ml) and left to stand overnight.

A solution of 3-acetyl-4-oxopentylacetate (30 g, 0.161 mol) in acetic acid (56 ml) was heated to 80° C. when a mixture of zinc dust (26.2 g, 0.40 mol), and sodium acetate (26.3 g, 0.32 mol) was added portionwise while the above hydroximino derivative (97 ml, 0.165 mol) was added dropwise. The reaction mixture was stirred vigorously during the addition which was regulated so that zinc was always in excess and the temperature remained between 90–100° C. When the addition was complete the mixture was boiled gently for 15 min and stirred to room temperature overnight. The reaction mixture was poured into ice-water and allowed to stand over 2 hr. The solid was filtered and washed with water and recrystallized from aqueous ethanol. Yield 78%, m.p. 92° C.

tert-Butyl 4-(3-acetoxypropyl)-3,5-dimethylpyrrole-2-carboxylate [yield 60%, m.p. 73° C. (hexane)] and tert-Butyl 4-(4-acetoxybutyl)-3,5-dimethylpyrrole-2-carboxylate [yield 52%, m.p. 62° C. (hexane)] were prepared by the method described in Example 434.

Example 435

3,5-Dimethyl-4-(2-hydroxyethyl)pyrrole-2-carboxaldehyde tert-Butyl 4-(2-acetoxyethyl)-3,5-dimethylpyrrole-2-carboxylate (15 g, 53 mmol) was dissolved in TFA (40 ml) and the solution was stirred at 40° C. under nitrogen for 10 min. The reaction mixture was then cooled to 0° C. and triethylorthoformate (9.6 ml, 58 mmol) was added dropwise. The mixture was allowed to warm up to 20° C. and was stirred for 1 hr before being poured into ice water. This was extracted with dichloromethane and the extracts were washed successively with 10% aqueous ammonia and water and dried over $MgSO_4$. 4-(2-acetoxyethyl)-3,5-dimethylpyrrole-2-carboxaldehyde was purified by silica gel chromatography using (7:3) ethyl acetate:hexane. Yield 45%, m.p. 125–27° C. (water).

To a solution of the above compound (5 g, 23 mmol) in ethanol (20 ml), NaOH 10% (10 ml) was added. The mixture was stirred at room temperature for 30 min., and the final solution was concentrated, diluted with water and extracted with dichloromethane. The organic extracts were dried and the solvent was removed to dryness. Yield 98%, m.p. 100° C. (ethyl acetate).

3,5-Dimethyl-4-(3-hydroxypropyl)pyrrole-2-carboxaldehyde [yield 60%, m.p. 85° C. (ethyl acetate/hexane)] and 3,5-Dimethyl-4-(4-hydroxybutyl)pyrrole-2-carboxaldehyde [yield 38%, m.p. 99° C. (hexane)] were prepared by the method described in Example 435.

Example 436

4-(2-Diethylaminoethyl)-3,5-dimethylpyrrol-2-carboxaldehyde

Methanesulfonyl chloride (4 ml, 51 mmol) in THF anhydrous (4 ml) was added to a stirred solution of 3,5-dimethyl-4-(2-hydroxyethyl)pyrrole-2-carboxaldehyde (4.3 g, 25.7 mmol) and triethylamine (5.2 g, 51 mmol) in THF anhydrous (60 ml) at 0–5° C. and the mixture was stirred for 1 h at room temperature. Water was then added to the mixture and the precipitated solid was filtered. Yield 89%, m.p. 142–44° C.

A mixture of the above mesilate (23 mmol), $K_2CO_3$ (23 mmol), diethylamine (90 mmol) and 2-propanol (70 ml) was heated to 100° C. for 0.5 h. The solvent was removed to dryness and the residue treated with water and extracted with methylenehloride. The organic extracts were dried and the solvent evaporated to dryness. Yield 70%, m.p. 70° C. (n-heptane).

3,5-Dimethyl-4-[2-(1-pyrrolidinylethyl)]pyrrole-2-carboxaldehyde, 3,5-Dimethyl-4-(2-ethylaminoethyl)pyrrole-2-carboxaldehyde, 4-(3-Diethylaminopropyl)-3,5-dimethylpyrrole-2-carboxaldehyde, 4-(4-Diethylaminobutyl)-3,5-dimethylpyrrole-2-carboxaldehyde, 3,5-Dimethyl-4-[3-(1-pyrrolidinylpropyl)]pyrrole-2-carboxaldehyde were isolated as oils and were prepared by a method analogous to the method described in Example 436.

Example 437

4-(2-Chloroacetyl)-3,5-dimethylpyrrole-2-carboxaldehyde

Anhydrous aluminum chloride (42 g, 315 mmol) was added portionwise over 30 min to a room temperature solution of 3,5-dimethylpyrrol-2-carboxaldehyde (5 g, 40 mmol) in 1,2-dichloroethane (50 ml) under nitrogen. After stirring for 15 min, chloroacetyl chloride (17 g, 150 mmol) was added dropwise over 1 h. After addition was complete, the mixture was stirred at room temperature for 16 h. The mixture was poured onto crushed ice and the organic layer separated, dried over anhydrous sodium sulfate, and the solvent removed under reduced pressure. Yield 57%, m.p. 205–09° C. (toluene).

Example 438

3,5-Dimethyl-4-(2-diethylaminoacetyl)pyrrole-2-carboxaldehyde

Diethylamine (5 ml) was added to a solution of 4-(2-Chloroacetyl)-3,5-dimethylpyrrole-2-carboxaldehyde (1 g, 5 mmol) in THF (20 ml). The mixture was stirred at room temperature for 24 h. The solvent was removed under reduced pressure and the residue was treated with water, $NaHCO_3$ (5%) and extracted with dichloromethane. After drying and filtering, the solvent was removed and the residue was used without further purification.

3,5-Dimethyl-4-(2-dimethylaminoacetyl)pyrrole-2-carboxaldehyde, 3,5-Dimethyl-4-[2-(1-pyrrolidinyl)acetyl]pyrrole-2-carboxaldehyde were synthesized by a method analogous to the method described in Example 438.

Example 439

3,5-Dimethyl-4-ethoxyoxalylpyrrole-2-carboxaldehyde

Anhydrous aluminum chloride (37 g, 277 mmol) was added portionwise over 30 min to a room temperature solution of 3,5-dimethylpyrrol-2-carboxaldehyde (7.6 g, 62 mmol) in 1,2-dichloroethane (140 ml) under nitrogen. After stirring for 30 min, nitromethane (11.2 ml, 179 mmol) was added. The mixture was cooled at 0° C. and ethyl chlorooxoacetate (12.8 g, 94 mmol) was added dropwise over 1 h. After addition was complete, the mixture was stirred at room temperature for 4 h. The mixture was poured onto crushed ice and the organic layer separated, dried, and the evaporation afforded a white solid. Yield 45%, m.p. 125–127° C. (toluene).

All compounds of the foregoing Examples had NMR spectral data that were consistent with the respective chemical structures.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A compound represented by the following structural formula:

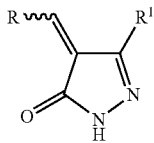

or physiologically acceptable salts thereof, wherein:

R is selected from the group consisting of substituted pyrrolyl;

wherein R is substituted by one or more halogen, lower alkyl group, $R^3O$—, hydroxyl, $HOC(O)$, $R^3OC(O)$—, $R^3OC(O)R^6$—, $R^3OR^6$—, trihalomethyl, trihalomethylcarbonyl, nitro, —$C(O)NR^4R^5$, —$NR^4R^5$, $R^3CO$—, —$(CH_2)_nR^7$, —$C(O)(CH_2)_n$—$R^7$, —$C(O)(CH_2)_n$—$C(O)$—$R^7$, —$O(CH_2)_nR^7$, —$C(O)NR^4(CH_2)_nR^7$, —$C(O)O(CH_2)_nR^7$, —$OC(O)(CH_2)_nR^7$, —$NR^4C(O)(CH_2)_nR^7$, —$R^6NR^4R^5$, —$R^6N(R^4)$—$R^6$—$R^7$, —$R^6N(R^6$—$R^7)_2$, —$R^6C(O)NR^4(CH_2)_nR^7$, —$R^6C(O)O(CH_2)_nR^7$, —$R^6OC(O)(CH_2)_nR^7$, —$R^6NR^4C(O)(CH_2)_{nR^7}$, —$R^6CH(C(O)OR^4(NR^5C(O)R^4)$ or a substituted aryl or aralkyl group, wherein the substituent is selected from the group consisting of halogen, trihalomethyl, hydroxy, —$NR^4R^5$, nitro, —$CONR^4R^5$, lower alkyl group, $R^3O$—, —$C(O)OR^4$ or —$OC(O)R^3$;

wherein $R^6$ is a lower alkyl group or an aryl group;

wherein $R^7$ is alkoxy, haloalkyl, lower alkyl piperazine, hydroxyl, $R^3O$—, $R^3C(O)$— or —$NR^4R^5$;

wherein suitable substituents for $R^3$, $R^4$ and $R^5$ can be one or more moieties selected from the group consisting of halogens, lower alkyl, hydroxy, lower alkoxy, carboxy, lower alkyl ester, trihalomethyl, nitro, phenyl, phenyl-lower alkyl, $(C_3-C_6)$cycloalkyl, $(C_3-C_6)$cycloalkyl-alkyl, CN, amino, alkylamino, dialkylamino, —$C(O)NH_2$, —$C(O)NH(alkyl)$ and —$C(O)N(alkyl)_2$;

$R^1$ is hydrogen or -A-Z;

A is —$(CH_2)_n$;

Z is a ring system selected from the group consisting of phenyl and pyrazinyl, wherein said ring system can be optionally substituted with one or more moieties selected from the group consisting of halogens, lower alkyl, $R^3O$—, HO—, $HOC(O)$—, $R^3OC(O)$—, trihalomethyl, nitro, an aromatic group, a $(C_3-C_6)$cycloalkyl group, a heterocyclic group, an aralkyl group, a $(C_3-C_6)$cycloalkyl-alkyl group, a heterocyclyl-alkyl group, —CN, —$C(O)NR^4R^5$ or —$NR^4R^5$;

$R^3$ for each occurrence is, independently selected from the group consisting of substituted or unsubstituted: lower alkyl group, lower alkoxy lower alkyl group, aromatic group, $(C_3-C_6)$cycloalkyl group, heterocyclic group, aralkyl group, a $(C_3-C_6)$cycloalkyl-alkyl group, and heterocyclyl-alkyl group;

$R^4$ and $R^5$ for each occurrence are each, independently, hydrogen, or are selected from the group consisting of substituted or unsubstituted: lower alkyl group, aromatic group, $(C_3-C_6)$cycloalkyl group, heterocyclic group, aralkyl group, a $(C_3-C_6)$cycloalkyl-alkyl group, and heterocyclyl-alkyl group;

optionally, $R^4$ and $R^5$ together with the nitrogen to which they are attached represent morpholino, pyrrolidino, piperidino, imidazol-1-yl, piperazino, thiamorpholino, azepino or perhydro-1,4-diazepin-1-yl groups each optionally substituted by one or more moieties selected from the group consisting of lower alkyl, hydroxy, lower alkoxy lower alkyl, an aromatic group, a $(C_3-C_6)$ cycloalkyl group, a heterocyclic group, an aralkyl group, a $(C_3-C_6)$cycloalkyl-alkyl group, and a heterocyclyl-alkyl group; and n is 0.

2. The compound of claim 1 wherein the compound is a mixture of stereoisomers.

3. The compound of claim 2 wherein the stereoisomers are enantiomers.

4. The compound of claim 3 wherein the stereoisomers are E and Z isomers.

5. The compound of claim 1 wherein the compound is a mixture of structural isomers.

6. The compound of claim 5 wherein the structural isomers are tautomers.

7. A compound according to claim 1 wherein R is substituted with one or more substituents, each independently selected from the group consisting of halogens, lower alkyl groups, $R^3O$—, hydroxyl, $HOC(O)$, $R^3OC(O)$—, $R^3OC(O)R^6$—, $R^3OR^6$—, trihalomethyl, trihalomethylcarbonyl, nitro, —$C(O)NR^4R^5$, —$NR^4R^5$, $R^3CO$—, $(CH_2)_n$—$R^7$, —$C(O)(CH_2)_nR^7$, —$O(CH_2)_nR^7$, —$C(O)NR^4(CH_2)_nR^7$, —$C(O)O(CH_2)_nR^7$, —$OC(O)(CH_2)_nR^7$, —$NR^4C(O)(CH_2)_nR^7$, —$R^6NR^4R^5$, —$R^6N(R^4)$—$R^6$—$R^7$, —$R^6N(R^6$—$R^7)_2$, —$R^6C(O)NR^4(CH_2)_nR^7$, —$R^6C(O)O(CH_2)_nR^7$, —$R^6OC(O)(CH_2)_nR^7$, —$R^6NR^4C(O)(CH_2)_nR^7$, —$R^6CH(C(O)OR^4)(NR^5C(O)R^4)$, an optionally substituted aryl and an optionally substituted aralkyl group;

wherein the optionally substituted aryl and optionally substituted aralkyl groups are optionally substituted with one or more substituents selected from the group consisting of halogen, trihalomethyl, hydroxyl, —$NR^4R^5$, nitro, —$CONR^4R^5$, lower alkyl group, $R^3O$—, —$C(O)OR4$ and —$OC(O)R^3$;

$R^6$ is a lower alkyl group or an aryl group; and $R^7$ is alkoxy, haloalkyl, loweralkyl piperazine, hydroxyl, $R^3O$—, $R^3C(O)$— or —$NR^4R^5$.

8. A compound of claim 7, wherein R is a substituted pyrrol-2-yl or a substituted pyrrol-3-yl.

9. A compound of claim 8, wherein R is substituted with one or more moieties selected from the group consisting of Br, Cl, F, aminomethyl, N,N-dimethylaminomethyl, carboxy, carboxymethyl, carboxyethyl, carbonylmethyl, carbonylethyl, methoxycarbonyl, ethoxycarbonyl, phenyl, 4-morpholinomethyl, —$C(O)$—$O$—$(CH_2)_2$—$N(Me)_2$, —$C(O)$—

O—(CH$_2$)$_2$—N(Et)$_2$, —C(O)—O—CH$_2$—N(Me)$_2$, —C(O)—O—(CH$_2$)$_2$—N(Me)$_2$, —C(O)—NH—(CH$_2$)$_2$—N(Me)$_2$, —CH$_2$—NH—C(O)—CF$_3$, (CH$_2$)$_n$—R$^7$ and an optionally substituted moiety selected from the group consisting of methyl, ethyl, propyl, isopropyl, butyl and phenyl, where said optionally substituted moiety is optionally substituted with one or more of Br, Cl, F, hydroxyl, nitro, amino or lower alkyl.

10. A compound of claim 1 wherein R$^1$ is pyrazinyl or phenyl and R is pyrrolyl substituted by one or more methyl and diethylaminoethyl.

11. A compound of claim 10 wherein the compound is 4-[4-(2-diethylamino-ethyl)-3,5-dimethyl-1H-pyrrol-2-ylmethylene]-5-pyrazin-2-yl-2,4-dihydropyrazol-3-one.

* * * * *